US008486671B2

(12) United States Patent
Renz et al.

(10) Patent No.: US 8,486,671 B2
(45) Date of Patent: *Jul. 16, 2013

(54) METHOD FOR THE PRODUCTION OF POLYUNSATURATED FATTY ACIDS

(75) Inventors: Andreas Renz, Limburgerhof (DE); Ernst Heinz, Hamburg (DE); Amine Abbadi, Hamburg (DE); Frederic Domergue, Hamburg (DE); Thorsten Zank, Mannheim (DE)

(73) Assignee: BASF Plant Science GmbH, Ludwigshafen (DE)

( * ) Notice: Subject to any disclaimer, the term of this patent is extended or adjusted under 35 U.S.C. 154(b) by 428 days.

This patent is subject to a terminal disclaimer.

(21) Appl. No.: 12/417,171

(22) Filed: Apr. 2, 2009

(65) Prior Publication Data

US 2009/0209774 A1  Aug. 20, 2009

Related U.S. Application Data

(62) Division of application No. 10/547,477, filed as application No. PCT/EP2004/000771 on Jan. 29, 2004, now Pat. No. 7,537,920.

(30) Foreign Application Priority Data

Feb. 27, 2003 (DE) .................. 103 08 836

(51) Int. Cl.
*C12P 7/64* (2006.01)
*C12N 9/12* (2006.01)

(52) U.S. Cl.
USPC .......................... 435/134; 435/194

(58) Field of Classification Search
USPC ........................ 435/194; 536/23.2
See application file for complete search history.

(56) References Cited

U.S. PATENT DOCUMENTS

| 5,614,393 A | 3/1997 | Thomas et al. |
| 5,968,791 A | 10/1999 | Davies et al. |
| 6,043,411 A | 3/2000 | Nishizawa et al. |
| 2004/1011176 | 6/2004 | Heinz et al. |

FOREIGN PATENT DOCUMENTS

| EP | 0 550 162 A1 | 7/1993 |
| EP | 0 794 250 A1 | 9/1997 |
| WO | WO-91/13972 | 9/1991 |
| WO | WO-93/06712 | 4/1993 |
| WO | WO-93/11245 | 6/1993 |
| WO | WO-94/11516 | 5/1994 |
| WO | WO-94/18337 | 8/1994 |
| WO | WO-95/18222 | 7/1995 |
| WO | WO-96/21022 | 7/1996 |
| WO | WO-97/21340 | 6/1997 |
| WO | WO-97/30582 | 8/1997 |
| WO | WO-98/27203 | 6/1998 |
| WO | WO-98/46763 | 10/1998 |
| WO | WO-98/46764 | 10/1998 |
| WO | WO-98/46765 | 10/1998 |
| WO | WO-98/46776 | 10/1998 |
| WO | WO-98/55625 | 12/1998 |
| WO | WO-99/27111 | 6/1999 |
| WO | WO-99/64616 | 12/1999 |
| WO | WO-00/18889 | 4/2000 |
| WO | WO-00/21557 | 4/2000 |
| WO | WO-00/42195 | 7/2000 |
| WO | WO-01/59128 | 8/2001 |
| WO | WO-02/072742 | 9/2002 |

OTHER PUBLICATIONS

Sigma catalog (1993), pp. 1745-1746.*
Abbadi, A. et al., "Transgenic Oilseeds as Sustainable Source of Nutritionally Relevant C20 and C22 Polyunsaturated Fatty Acids?", Eur. J. Lipid Sci. Technol. 103 (2001), pp. 106-113.
Akermoun, M. et al., "Complex Lipid Biosynthesis: Phospholipid Synthesis", Biochemical Society Transactions 28 (2000), pp. 713-715.
Cases, S. et al., "Identification of a Gene Encoding an Acyl CoA:diacylglycerol Acyltransferase, a Key Enzyme in Triacylglycerol Synthesis", Proc. Natl. Acad. Sci., USA, 95 (1998), pp. 13018-13023.
Fraser, T. et al., "Partial Purification and Photoaffinity Labelling of Sunflower Acyl-CoA:lysophosphatidycholine Acyltransferase", Biochemical Society Transactions 28 (2000), pp. 715-718.
Frentzen, M., "Acyltransferases From Basic Science to Modified Seed Oils", Fett/Lipid 100, 4-5 (1998), pp. 161-166.
Huang, Y.-S. et al., "Cloning of 12- and 6-Desaturases From *Mortierella alpina* and Recombinant Production of -Linolenic Acid in *Saccharomyces cerevisiae*", Lipids 34, 7 (1999), pp. 649-659.
Knutzon, D. S. et al., "Cloning of a Coconut Endosperm cDNA Encoding A 1-Acyl-*sn*- Glycerol-3-Phosphate Acyltransferase That Accepts Medium-Chain-Length Substrates", Plant Physiol. 109 (1995), pp. 999-1006.
Lands, W. E., "Metabolism of Glycerolipids", The Journal of Biological Chemistry 235, 8 (1960), pp. 2233-2237.
Lopez Alonso, D. et al., "Plants as 'Chemical Factories' for the Production of Polyunsaturated Fatty Acids", Biotechnology Advances 18 (2000), pp. 481-497.
McKeon, T. et al., "Acyl-Acyl Carrier Protein Thioesterase From Safflower", Methods in Enzymology 71 (1981), pp. 178-180.

(Continued)

*Primary Examiner* — Tekchand Saidha
(74) *Attorney, Agent, or Firm* — Novak Druce Connolly Bove + Quigg LLP

(57) ABSTRACT

The present invention relates to a process for producing polyunsaturated fatty acids in an organism by introducing nucleic acids into the organism which code for polypeptides having acyl-CoA:lysophospholipid a cyltransferase activity. Advantageously, these nucleic acid sequences may, if appropriate together with further nucleic acid sequences coding for biosynthesis polypeptides of the fatty acid or lipid metabolism, be expressed in the transgenic organism. The invention furthermore relates to the nucleic acid sequences, to nucleic acid constructs comprising the nucleic acid sequences of the invention, to vectors comprising the nucleic acid sequences and/or the nucleic acid constructs and to transgenic organisms comprising the abovementioned nucleic acid sequences, nucleic acid constructs and/or vectors. A further part of the invention relates to oils, lipids and/or fatty acids produced by the process of the invention and to their use.

20 Claims, 12 Drawing Sheets

OTHER PUBLICATIONS

Mikolajczak, K. L. et al., "Search for New Industrial Oils v. Oils of Cruciferae", Journal of the American Oil Chemists' Society 38 (1961), pp. 678-681.

Mishra, S. et al., "Purification and Characterization of Thiol-Reagent-Sensitive Glycerol-3-Phosphate Acyltransferase From the Membrane Fraction of An Oleaginous Fungus", Biochem, J. 355 (2001), pp. 315-322.

Slabas, A. R. et al., "Acyltransferases and Their Role in the Biosynthesis of Lipids—Opportunities for New Oils", J. Plant Physiol. 158 (2001), pp. 505-513.

Stukey, J. E. et al., "The *OLE1* Gene of *Saccharomyces cerevisiae* Encodes the 9 Fatty Acid Desaturase and Can be Functionally Replaced by the Rat Stearoyl-CoA Desaturase Gene", The Journal of Biological Chemistry, 265, 33 (1990), pp. 20144-20149.

Stymne, S. et al., "Evidence for the Reversibility of the Acyl-CoA:lysophosphatidylcholine Acyltransferases in Microsomal Preparations From Developing Safflower (*Carthamus tinctorius*L.) Cotyledons and Rat Liver", Biochem. J. 223 (1984), pp. 305-314.

Metz, J. G. et al., "Production of Polyunsaturated Fatty Acids by Polyketide Synthases in Both Prokaryotes and Eukaryotes", Science 293 (2001), pp. 290-293.

Stymne S. et al., "Triacylglycerol Biosynthesis", The Biochemistry of Plants: a Comprehensive Treatise, 9 (1987), Stumpf, P. K., Ed., Academic Press: NY, pp. 175-214.

Tumaney, A. W. et al. "Synthesis of Azidophospholipids and Labeling of Lysophosphatidylcholine Acyltransferase From Developing Soybean Cotyledons", Biochimica et Biophysica Acta 1439 (1999), pp. 47-56.

Wada, H. et al., "Enhancement of Chilling Tolerance of a Cyanobacterium by Genetic Manipulation of Fatty Acid Desaturation", Nature 347 (1990), pp. 200-203.

Wang, X. M. et al., "Biosynthesis and Regulation of Linolenic Acid in Higher Plants", Plant Physiol. Biochem. 26, 6 (1988), pp. 777-792.

Yamashita, A. et al., "ATP-Independent Fatty Acyl-Coenzyme A Synthesis From Phospholipid, Coenzyme A-Dependent Transacylation Activity Toward Lysophosphatidic Acid Catalyzed by Acyl-Coenzyme A:Lysophosphatidic Acid Acyltransferase", The Journal of Biological Chemistry 276, 29 (2001), pp. 26745-26752.

Wilkinson, J., Putativel-Acyl-sn-glycerol-3-phosphate acyltransferase T0638.1 (EC2.3.1.51) (1-AGP acyltransferase) (1-AGPAT) (Lysophosphatidic acid acyltransferase) (LPAAT), Uniprot Database Accession No. Q22267, Dec. 15, 1998.

Wilkinson, J., "Genome sequence of the nematode *C. elegans*: a platform for investigating biology", EBI Database Accession No. Z73975, Jun. 9, 1996.

Zank, T.K., et al., "Cloning and functional expression of the first plant fatty acid elongase specific for Δ6-polyunsaturated fatty acids", Biochemical Society Tranbsactions, 28, 6 (2000), pp. 654-658.

Ucciani, E., Nouveau Dictionnaire des Huiles Vegetales. Technique & Documentation, Lavoisier, 1995, ISBN: 2-7430-0009-0, pp. 577-578, 582.

Suggs, S. V. et al., "Use of synthetic oligonucleotides as hybridization probes: isolation of cloned cDNA sequences for human beta 2-microglobulin", Proc. Natl. Acad. Sci., U. S. A. 78, 11 (1981), pp. 6613-6617.

\* cited by examiner

Figure 1: Amino acid sequence comparison of C. elegans LPLATs (Ce-T06E8.1 and Ce-F59F4.4) with M. musculus LPAAT (Mm-NP061350).

```
              1                                                             50
Mm-NP061350   MELWPGAWTA LLLLLILLLS TLWFCSSSAK YFFKMAFYNG WLLFLAILAI
Ce-T06E8.1    ...MENFWSI VVFFLLSILF ILYNISTVCH YYMRISFYYF TTLLHGMEVC
Ce-F59F4.4    .......MTF LAILFVIAVL LLLAQLPVIG FYIRAVYFGM CLIIGGFLGG 51                                                            100
Mm-NP061350   PVCAVRGRNV ENMKILRLLL LHAKYLYGLR VEVRGAHHFP PTQPYVVVSN
Ce-T06E8.1    VTMIPSWLNC KCADYYFHSF FYWCKWTCVH TTVYGYEKTQ VEGPAWWICN
Ce-F59F4.4    LASIPFGKSP NNHFRMFKIF QAMTWPMGVR FELRNSEILH DKKPYLLLAN 101                                                           150
Mm-NP061350   HQSSLDILGM MEVLPDRCVP IAKRELLWAG SAGLACWLAG IIFIDRKRTG
Ce-T06E8.1    HQSSLDILSM ASIWPKNCVV MMKRILAYVP FFNLGAYFSN IIFIDRYNRE
Ce-F59F4.4    HQSALDVLGM SFAWPVDCVV MLKSSLKYLP GFNLCAYLCD SVYINRFSKE 151                                                           200
Mm-NP061350   DALSVMSEVA QTLLTQDVRV WVFPEGTRNH NGSMLPFKRG ARLLAVQAQV
Ce-T06E8.1    RAMASVDYCA SEMKNRNLKL WVFPEGTRNR EGGELPFKKG ADNLAVRAQI
Ce-F59F4.4    KALKTVDTTL HELVTKKRKV WIYPEGTRNA EPELLPFKKG ARILAKQAKI 201                                                           250
Mm-NP061350   PILPIVMSSY QDFYSKKEFR FTSPGRCQVR VLPPVSTEGL TPDDVPALAD
Ce-T06E8.1    PILPVVFSDY RDFYSKPGRY FKNDGEVVLR VLDATPTKGL TLDDVSELSD
Ce-F59F4.4    PIVPCVFSSH KFFYSHAEKR LTS.GNCILD ILPEVDSS.. KFDSIDDLSA 251                  285
Mm-NP061350   SVRHSMLTIF RELSTDGLGG GDCLKKPGGA GEARL
Ce-T06E8.1    MCRDVMLAAY KEVTLEAQQR NATRRGETKD GKKSE
Ce-F59F4.4    HCRKIMQAHR EKLDAEAANL NI........ .....
```

Figure 2: Fatty acid profiles of transgenic C13ABYS86 S. cerevisiae cells
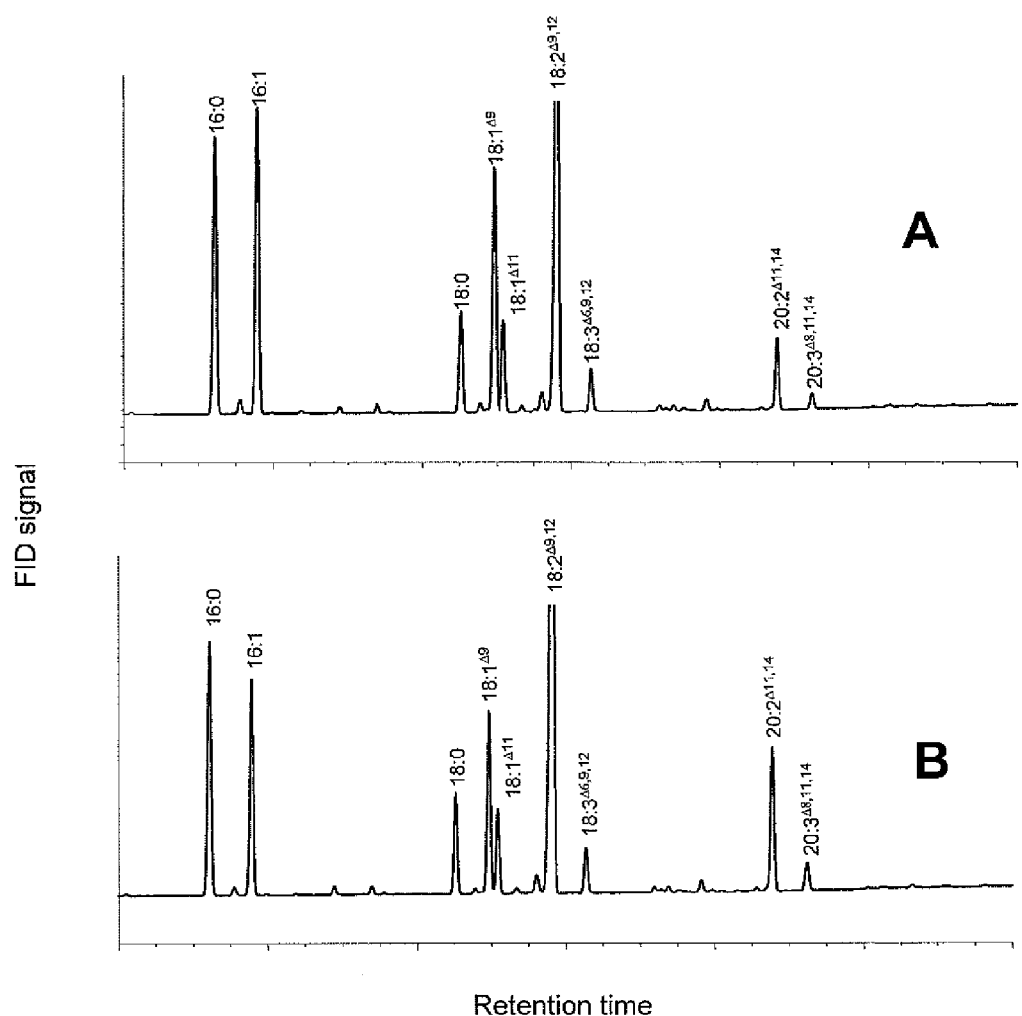

Figure 3: Fatty acid profiles of transgenic C13ABYS86 S. cerevisiae cells
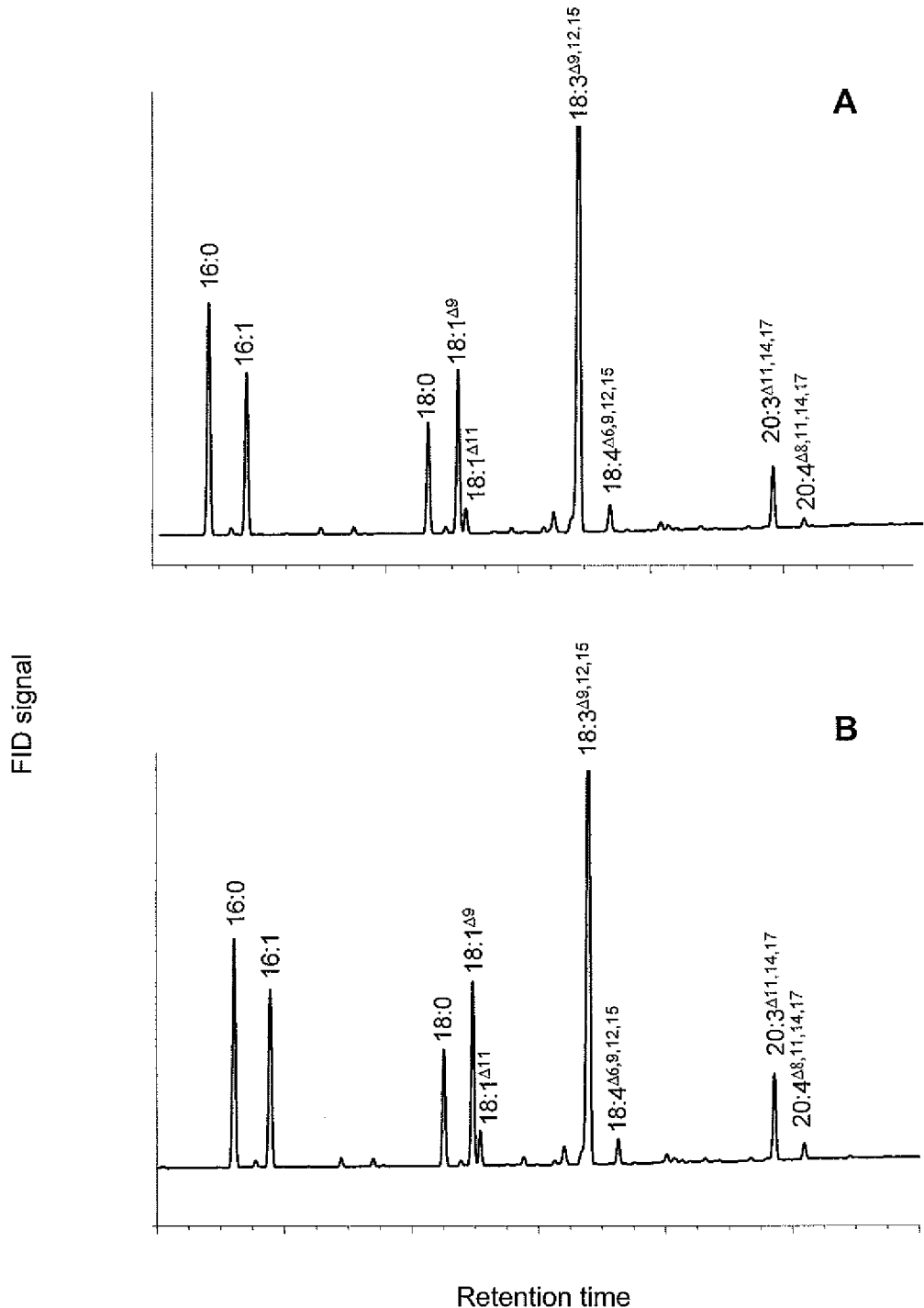

Figure 4: Elongation of exogenously applied $18:2^{\Delta 9,12}$ and $18:3^{\Delta 9,12,15}$, following their endogenous Δ6-desaturation (data of figs. 2 and 3).
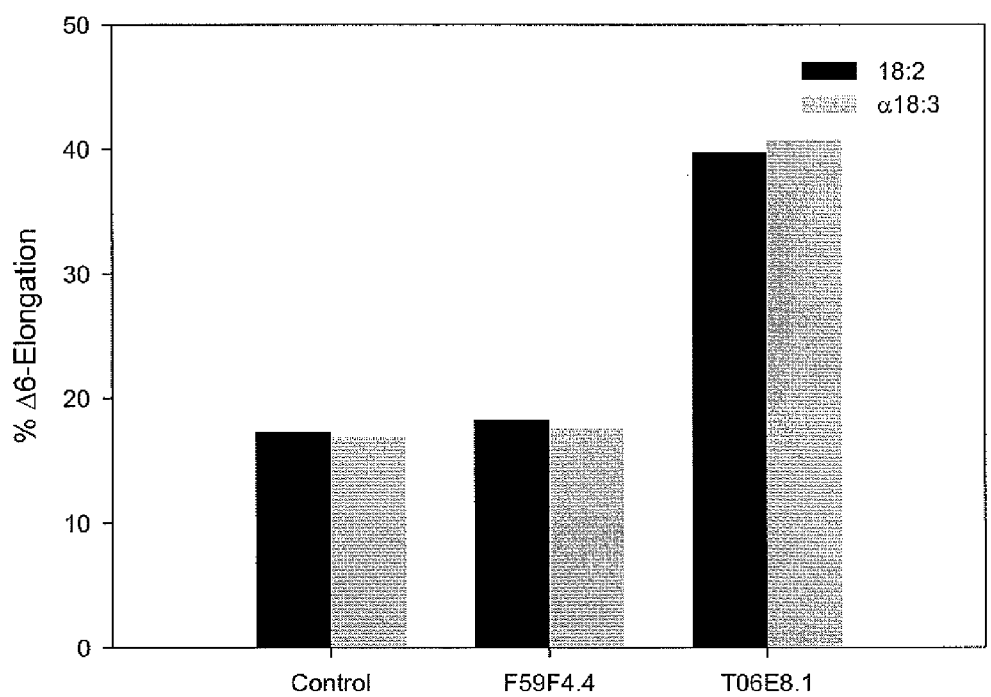

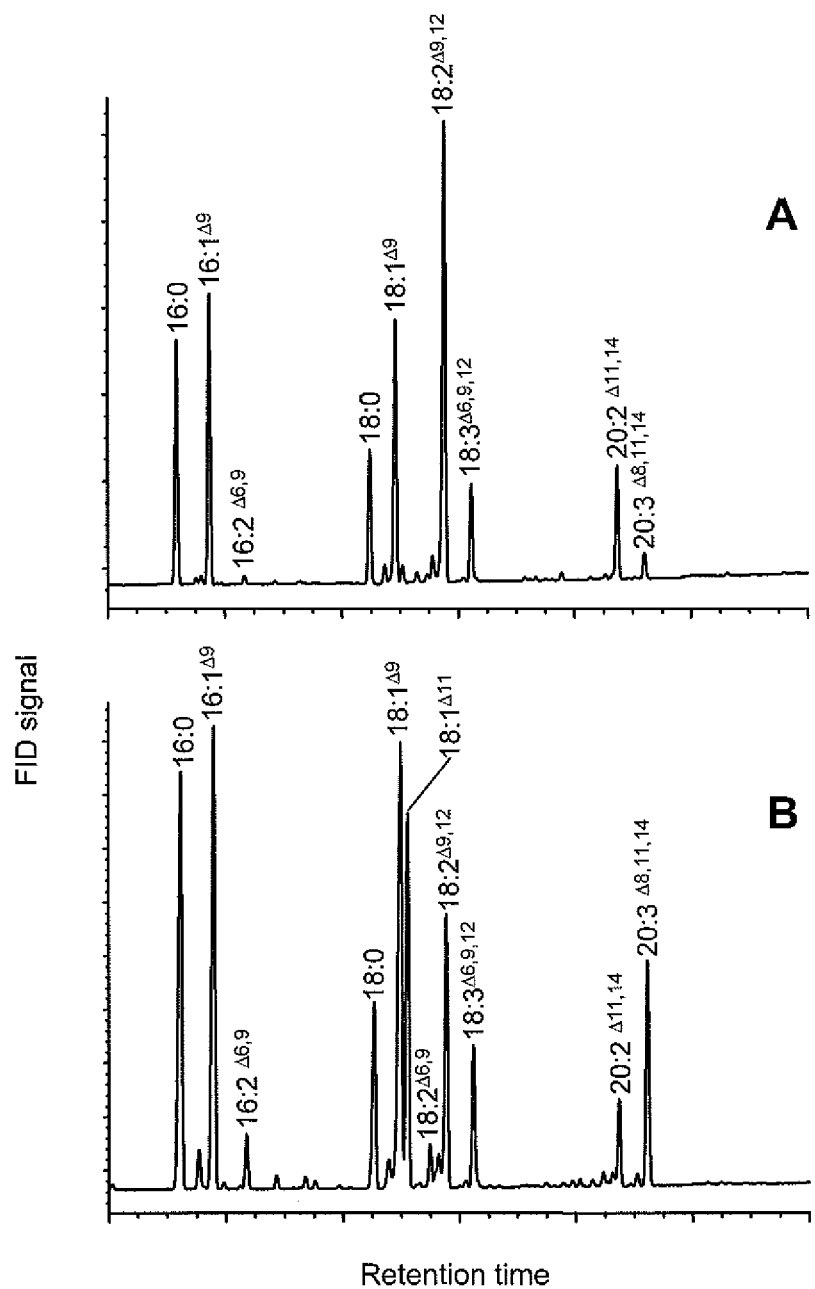
Figure 5: Fatty acid profiles of transgenic INVSc1 *S. cerevisiae* cells

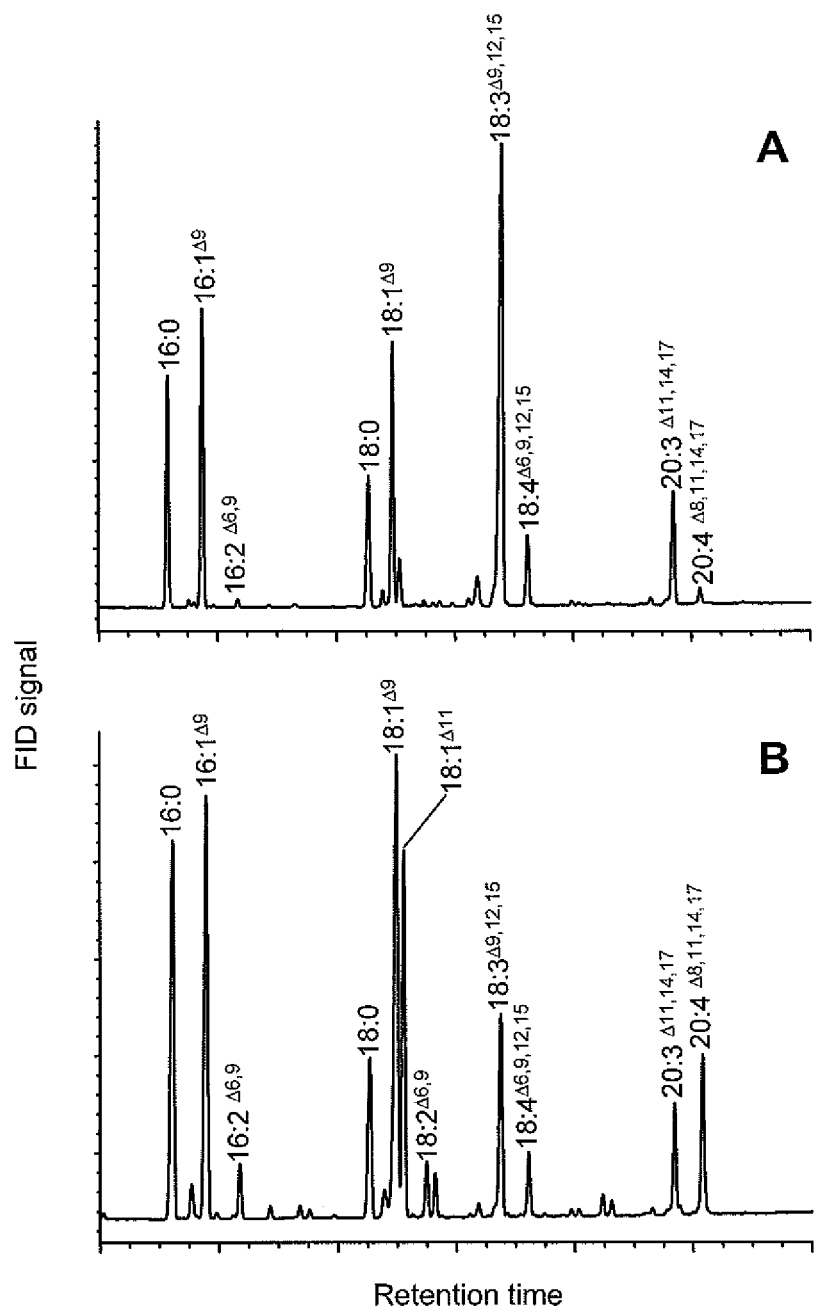
Figure 6: Fatty acid profiles of transgenic INVSc1 *S. cerevisiae* cells Figure 7: Acyl-CoA composition of transgenic INVSc1 yeasts transformed with the vectors pESCLeu PpD6Pse1/pYes2 (A) or pESCLeu-PpD6-Pse1/pYes2-T06E8.1 (B).
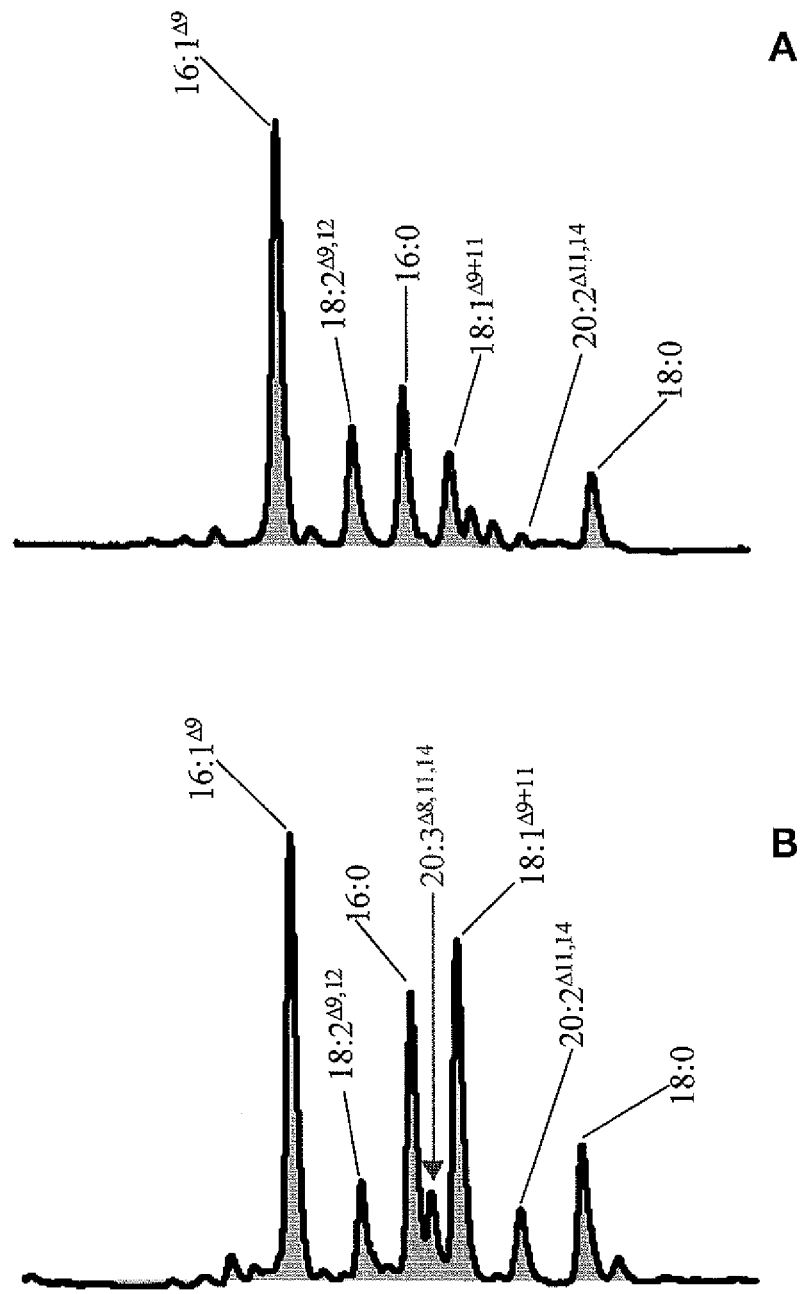

Figure 8: Vector map of pSUN3CeLPLAT
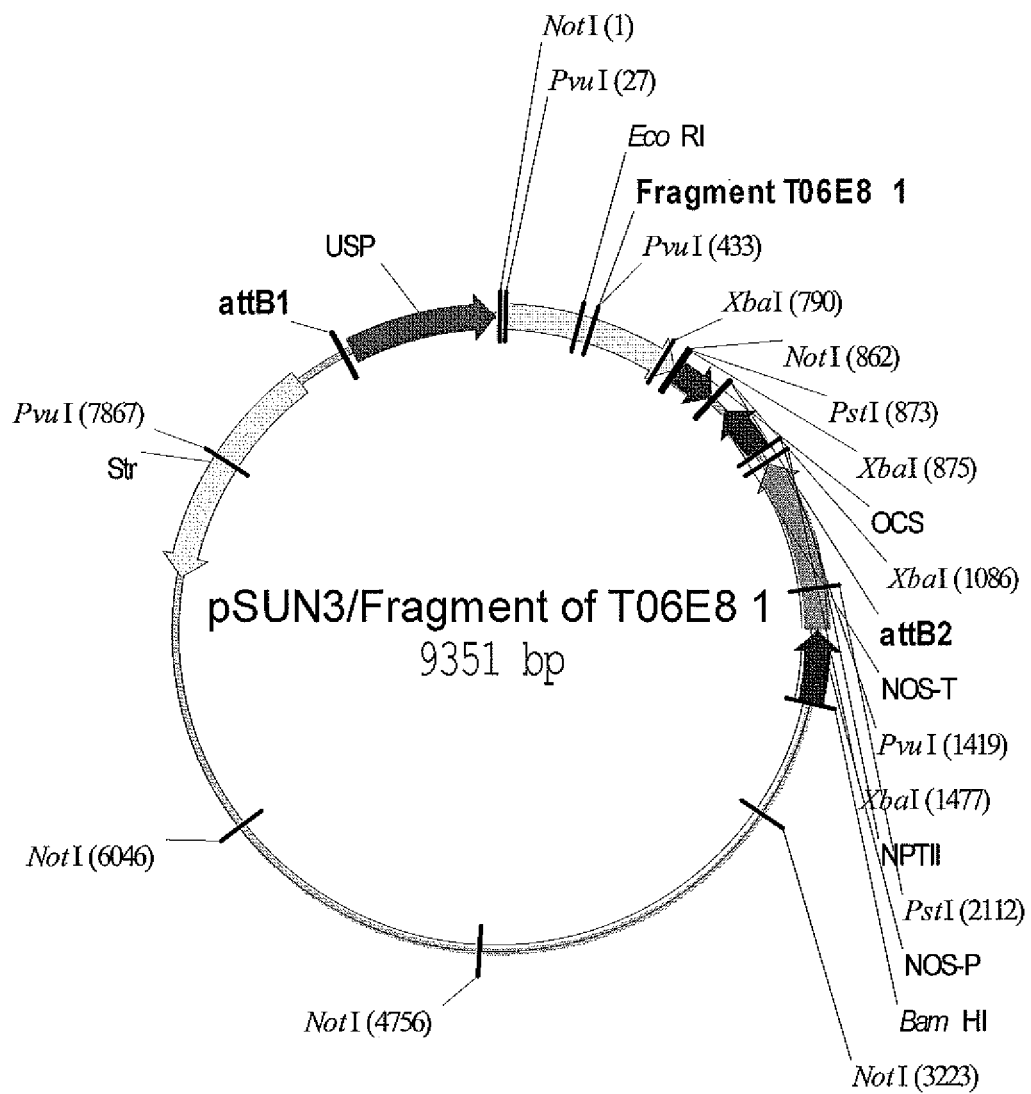

Figure 9A: Vector map of pGPTV LeB4-700 + T06E8.1
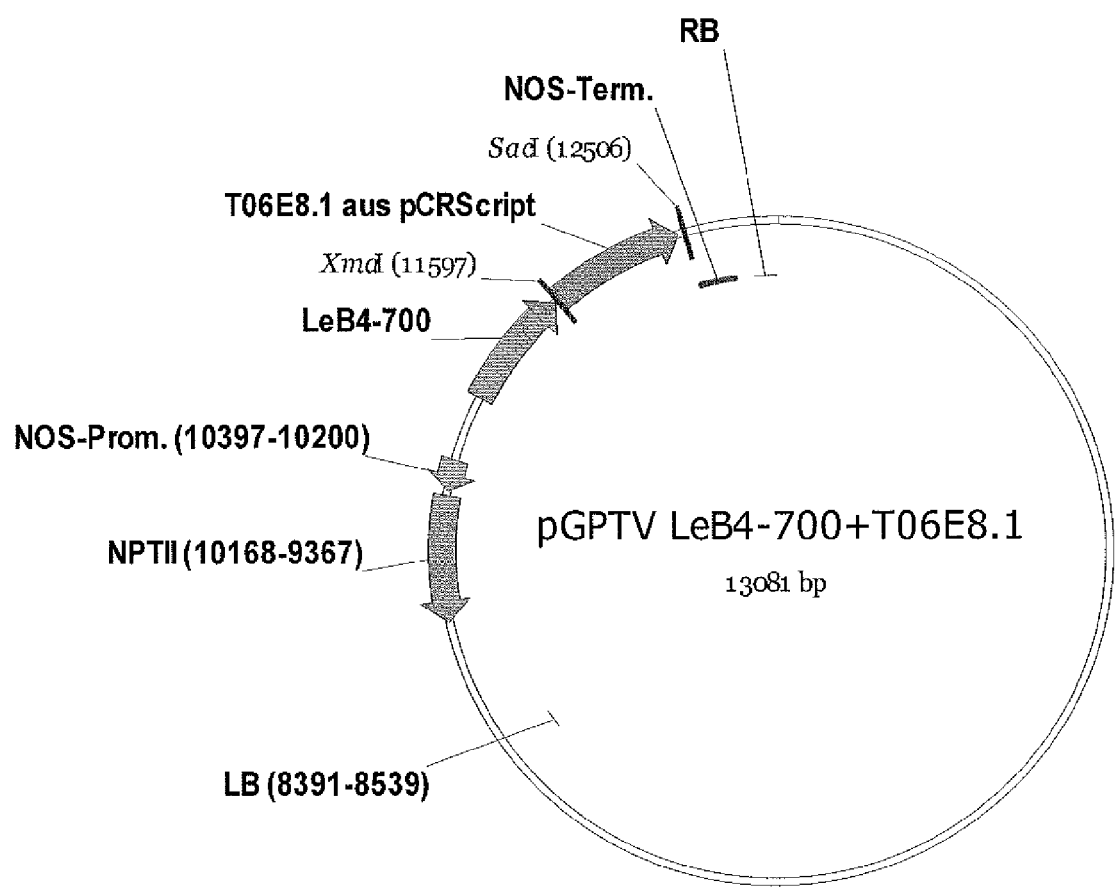

Figure 9B: Vector map of pGPTV USP/OCS-1,2,3 PSE1(Pp)+D6-Des(Pt)+2AT (T06E8-1)
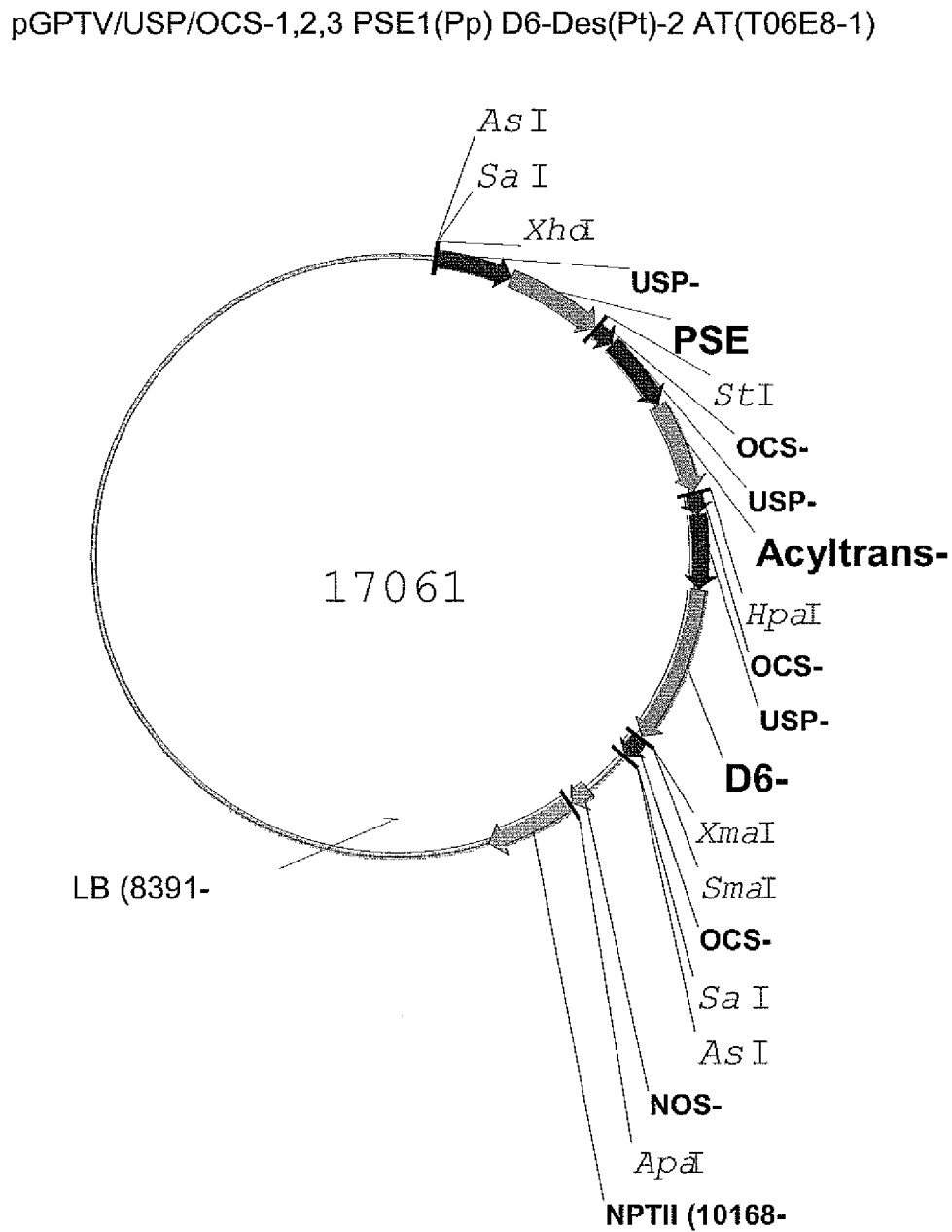

Figure 10A: Biosynthetic pathway of LCPUFAs
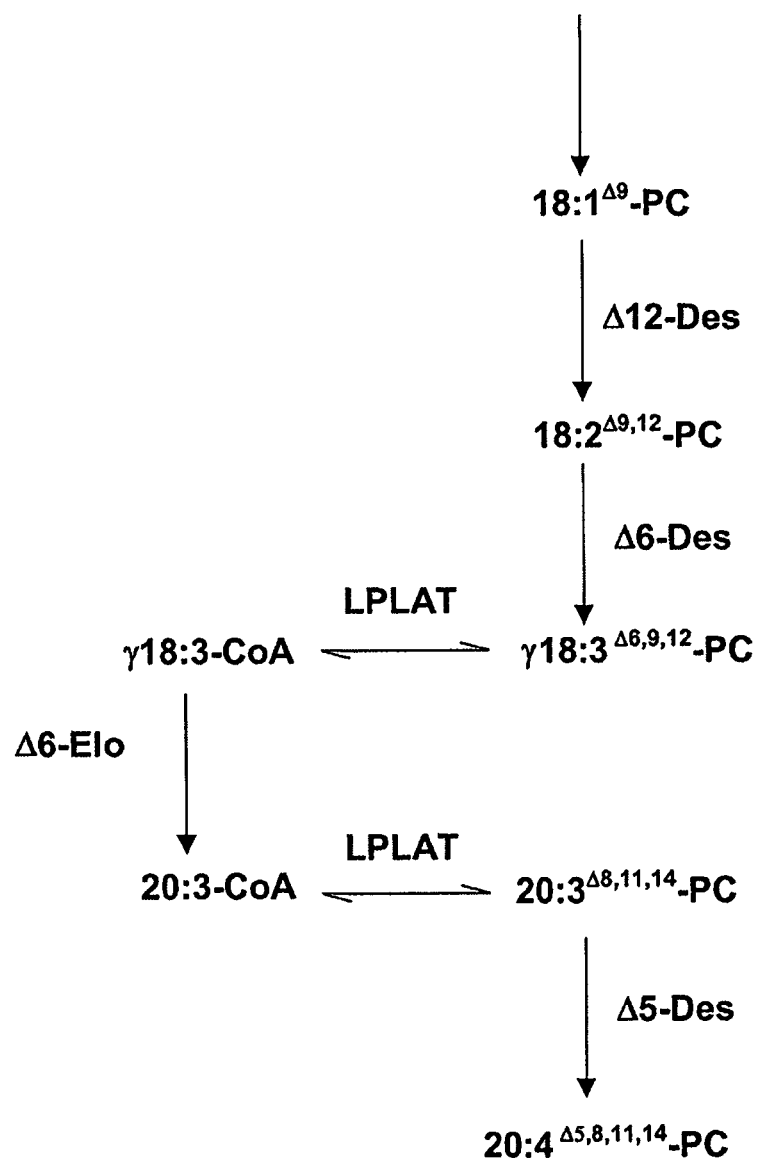

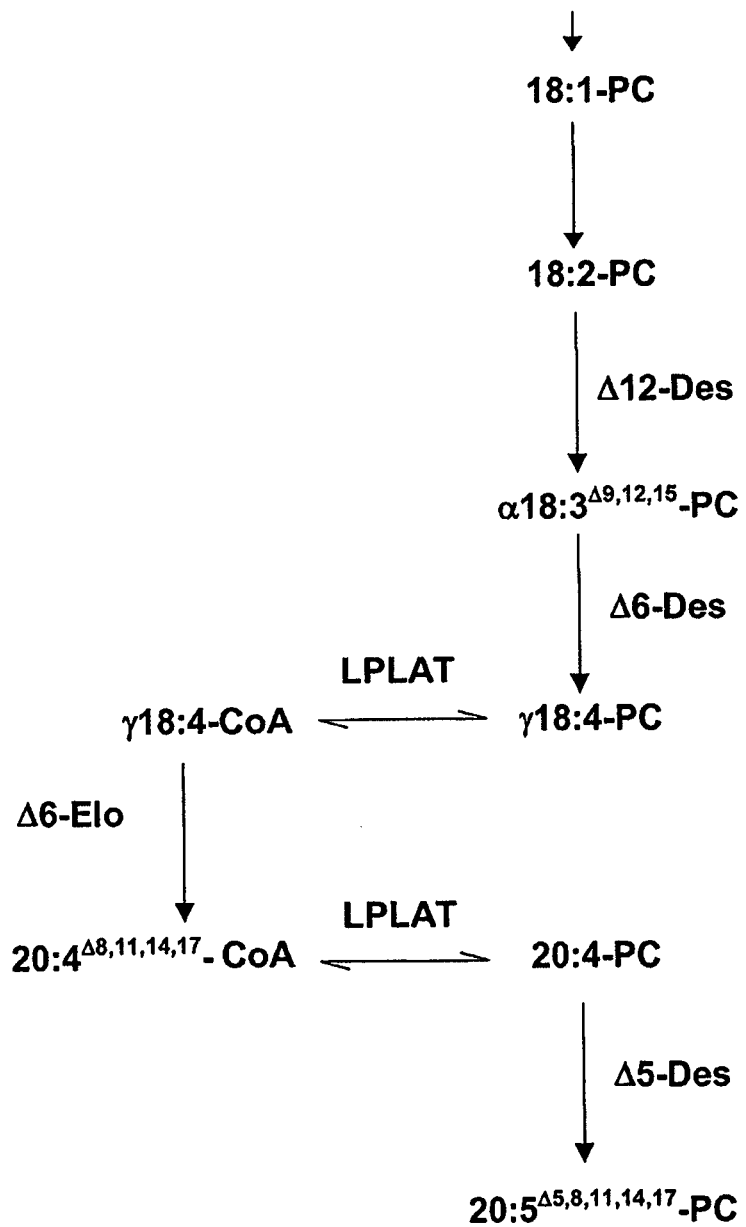
Figure 10B: Biosynthetic pathway of LCPUFAs

METHOD FOR THE PRODUCTION OF POLYUNSATURATED FATTY ACIDS

RELATED APPLICATIONS

This application is a continuation of U.S. patent application Ser. No. 10/547,447, filed Aug. 26, 2005, which is a national stage application (under 35 U.S.C. 371) of PCT/EP20041000771 filed Jan. 29, 2004, which claims benefit to German application 10308836.9 filed Feb. 27, 2003.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_12810_00882. The size of the text file is 273 KB, and the text file was created on Apr. 1, 2009.

BACKGROUND OF THE INVENTION

The present invention relates to a process for producing polyunsaturated fatty acids in an organism by introducing nucleic acids into said organism which code for polypeptides having acyl-CoA:lysophospholipid-acyltransferase activity. Advantageously, these nucleic acid sequences may, if appropriate together with further nucleic acid sequences coding for biosynthesis polypeptides of the fatty acid or lipid metabolism, be expressed in the transgenic organism.

The invention furthermore relates to the nucleic acid sequences, to nucleic acid constructs comprising the nucleic acid sequences of the invention, to vectors comprising said nucleic acid sequences and/or said nucleic acid constructs and to transgenic organisms comprising the abovementioned nucleic acid sequences, nucleic acid constructs and/or vectors.

A further part of the invention relates to oils, lipids and/or fatty acids produced by the process of the invention and to their use.

Fatty acids and triglycerides have a multiplicity of applications in the food industry, in animal nutrition, in cosmetics and in the pharmacological sector. Depending on whether they are free saturated or unsaturated fatty acids or else triglycerides with an elevated content of saturated or unsaturated fatty acids, they are suitable for very different applications; thus, for example, polyunsaturated fatty acids are added to baby food to improve the nutritional value. Polyunsaturated ω-3-fatty acids and ω-6-fatty acids are, in this connection, an important constituent of animal and human food. Owing to the composition of human food, which is customary today, an addition of polyunsaturated ω-3-fatty acids which are preferably present in fish oils to the food is particularly important. Thus, for example, polyunsaturated fatty acids such as docosahexaenoic acid (=DHA, $C22:6^{\Delta4,7,10,13,16,19}$) or eisosapentaenoic acid (=EPA, $C20:5^{\Delta5,8,11,14,17}$) are added to baby food to improve the nutritional value. The unsaturated fatty acid DHA is said to have a positive effect on brain development.

Hereinbelow, polyunsaturated fatty acids are referred to as PUFA, PUFAs, LCPUFA or LCPUFAs (poly unsaturated fatty acids, PUFA, long chain poly unsaturated fatty acids, LCPUFA).

The various fatty acids and triglycerides are obtained, usually in the form of their triacylglycerides (=triglycerides=triglycerols), mainly from microorganisms such as *Mortierella* or *Schizochytrium* or from oil-producing plants such as soybean, oilseed rape, algae such as *Crypthecodinium* or *Phaeodactylum* and others. However, they may also be obtained from animals such as, for example, fish. The free fatty acids are advantageously prepared by hydrolysis. Higher polyunsaturated fatty acids such as DHA, EPA, arachidonic acid (=ARA, $C20:4\Delta5,8,11,14$), dihomo-γ-linolenic acid ($C20:3^{\Delta8,11,14}$) or docosapentaenoic acid (DPA, $C22:5^{\Delta7,10,13,16,19}$) cannot be isolated from oil crops, such as oilseed rape, soybean, sunflower, safflower or others. Conventional natural sources of these fatty acids are fish such as herring, salmon, sardine, red fish, eel, carp, trout, halibut, mackerel, zander or tuna, or algae.

Depending on the intended application, preference is given to oils with saturated or unsaturated fatty acids; thus, for example, lipids with unsaturated fatty acids, especially polyunsaturated fatty acids, are preferred in human nutrition. The polyunsaturated ω-3-fatty acids are said to have in this connection a positive effect on the cholesterol level in the blood and thus on the possibility of preventing heart disease. The risk of heart disease, stroke or hypertension may be reduced markedly by adding these ω-3-fatty acids to food. ω-3-fatty acids can also have a positive effect on inflammatory, especially chronically inflammatory, processes in connection with immunological disorders such as rheumatoid arthritis. They are therefore added to food, especially dietetic food, or are applied in medicaments. ω-6-fatty acids such as arachidonic acid tend to have a negative effect on these diseases in connection with said rheumatic disorders, due to our customary foodstuff composition.

ω-3- and ω-6-fatty acids are precursors of tissue hormones, the "eicosanoides, such as the prostaglandins, which are derived from dihomo-γ-linolenic acid, arachidonic acid and eicosapentaenoic acid, the thromoxanes and leukotrienes which are derived from arachidonic acid and eicosapentaenoic acid. Eicosanoides ("$PG_2$ series") which are formed from ω-6-fatty acids normally promote inflammatory reactions, while eicosanoides ("$PG_3$ series") from ω-3-fatty acids have little or no proinflammatory effect.

Owing to their positive properties, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 and Huang et al., Lipids 34, 1999: 649-659. However, the biochemical characterization of the various desaturases has been insufficient to date since the enzymes, being membrane-bound proteins, can be isolated and characterized only with great difficulty (McKeon et al., Methods in Enzymol. 71, 1981: 12141-12147, Wang et al., Plant Physiol. Biochem., 26, 1988: 777-792). Membrane-bound desaturases are normally characterized by being introduced into a suitable organism which is subsequently studied for enzyme activity by analyzing reactants and products. Δ6-desaturases are described in WO 93/06712, U.S. Pat. No. 5,614,393, U.S. Pat. No. 5,614, 393, WO 96/21022, WO 00/21557 and WO 99/27111, as is the application for production in transgenic organisms, namely in WO 98/46763, WO 98/46764, WO 9846765. The expression of various desaturases such as those in WO 99/64616 or WO 98/46776 and the formation of polyunsaturated fatty acids are also described and claimed in this connection. Regarding the efficacy of desaturase expression and its influence on the formation of polyunsaturated fatty acids, it should be noted that expression of a single desaturase, as described previously, has resulted in only low contents of unsaturated fatty acids/lipids such as, for example, γ-linolenic acid and stearidonic acid. Furthermore, a mixture of ω-3- and ω-6-fatty acids was usually obtained.

Particularly suitable microorganisms for producing PUFAs are microorganisms such as *Thraustochytrium* or *Schizochytrium* strains, algae such as *Phaeodactylum tricornutum* or *Crypthecodinium* species, ciliates, such as *Stylonychia* or *Colpidium*, fungi such as *Mortierella, Entomophthora* or *Mucor*. Strain selection has resulted in the development of a number of mutant strains of the corresponding microorganisms, which produce a series of desirable compounds including PUFAs. However, the mutation and selection of strains with improved production of a particular molecule such as the polyunsaturated fatty acids is a time-consuming and difficult process. Therefore, preference is given, whenever possible, to genetic engineering processes, as described above. However, only limited amounts of the desired polyunsaturated fatty acids such as DPA, EPA or ARA can be produced with the aid of the abovementioned microorganisms, and, depending on the microorganism used, the former are usually obtained as fatty acid mixtures of, for example, EPA, DPA and DHA.

Alternatively, fine chemicals may be produced advantageously on a large scale via production in plants which are developed so as to produce the abovementioned PUFAs. Plants which are particularly well suited for this purpose are oil crops which contain large amounts of lipid compounds, such as oilseed rape, canola, linseed, soybean, sunflower, borage and evening primrose. However, other crop plants containing oils or lipids and fatty acids are also well suited, as mentioned in the detailed description of the present invention. Conventional breeding has been used to develop a number of mutant plants which produce a spectrum of desirable lipids and fatty acids, cofactors and enzymes. However, the selection of new plant cultivars with improved production of a particular molecule is a time-consuming and difficult process or even impossible if the compound does not naturally occur in the respective plant, as is the case with polyunsaturated $C_{18}$-, $C_{20}$-fatty acids and $C_{22}$-fatty acids and those having longer carbon chains.

Owing to the positive properties of unsaturated fatty acids, there has been no lack of attempts in the past to make available these genes which are involved in the synthesis of fatty acids or triglycerides for the production of oils in various plants with a modified content of polyunsaturated fatty acids. Previously, however, it was not possible to produce longer-chain polyunsaturated $C_{20}$- and/or $C_{22}$-fatty acids such as EPA or ARA in plants.

However, in other organisms as well as microorganisms such as algae or fungi too, genetically engineered modifications of the fatty acid metabolic pathway via introducing and expressing, for example, desaturases resulted only in relatively small increases in productivity in these organisms. One reason for this may be the high complexity of the fatty acid metabolism. Thus, incorporation of polyunsaturated fatty acids into membrane lipids and/or into triacylglycerides and their degradation and conversion are very complex and, even now, has still not been fully elucidated and understood biochemically and, especially genetically.

The biosynthesis of LCPUFAs and incorporation of LCPUFAs into membranes or triacylglycerides are carried out via various metabolic pathways (Abbadi et al. (2001) European Journal of Lipid Science & Technology 103:106-113). In bacteria such as *Vibrio* and microalgae such as *Schizochytrium*, malonyl-CoA is converted via a LCPUFA-producing polyketide synthase to give LCPUFAs (Metz et al. (2001) Science 293: 290-293; WO 00/42195; WO 98/27203; WO 98/55625). In microalgae such as *Phaeodactylum* and mosses such as *Physcomitrelia*, unsaturated fatty acids such as linoleic acid or linolenic acid are converted in the form of their acyl-CoAs in multiple desaturation and elongation steps to give LCPUFAs (Zank et al. (2000) Biochemical Society Transactions 28: 654-658). In mammals, the biosynthesis of DHA includes β-oxidation, in addition to desaturation and elongation steps.

In microorganisms and lower plants, LCPUFAs are present either exclusively in the form of membrane lipids, as is the case in *Physcomitrella* and *Phaeodactylum*, or in membrane lipids and triacylglycerides, as is the case in *Schizochytrium* and *Mortierella*. Incorporation of LCPUFAs into lipids and oils is catalyzed by various acyltransferases and transacylases. These enzymes are already known to carry out the incorporation of saturated and unsaturated fatty acids [Slabas (2001) J. Plant Physiology 158: 505-513; Frentzen (1998) Fett/Lipid 100: 161-166); Cases et al. (1998) Proc. Nat. Acad. Sci. USA 95: 13018-13023]. The acyltransferases are enzymes of the "Kennedy pathway", which are located on the cytoplasmic side of the membrane system of the endoplasmic reticulum, referred to as "ER" hereinbelow. ER membranes may be isolated experimentally as "microsomal fractions" from various organisms (Knutzon et al. (1995) Plant Physiology 109: 999-1006; Mishra & Kamisaka (2001) Biochemistry 355: 315-322; U.S. Pat. No. 5,968,791). These ER-bound acyltransferases in the microsomal fraction use acyl-CoA as the activated form of fatty acids. Glycerol-3-phosphate acyltransferase, referred to as GPAT hereinbelow, catalyzes the incorporation of acyl groups at the sn-1 position of glycerol 3-phosphate. 1-Acylglycerol-3-phosphate acyltransferase (E.C. 2.3.1.51), also known as lysophosphatidic-acid acyltransferase and referred to as LPAAT hereinbelow, catalyzes the incorporation of acyl groups at the sn-2 position of lysophosphatidic acid, abbreviated as LPA hereinbelow. After dephosphorylation of phosphatidic acid by phosphatidic-acid phosphatase, diacylglycerol acyltransferase, referred to as DAGAT hereinbelow, catalyzes the incorporation of acyl groups at the sn-3 position of diacylglycerols. Apart from these Kennedy pathway enzymes, further enzymes capable of incorporating acyl groups from membrane lipids into triacylglycerides are involved in the incorporation of fatty acids into triacylglycerides, namely phospholipid diacylglycerol acyltransferase, referred to as PDAT hereinbelow, and lysophosphatidylcholine acyltransferase, referred to as LPCAT.

The enzymic activity of an LPCAT was first described in rats [Land (1960) Journal of Biological Chemistry 235: 2233-2237]. A plastic LPCAT isoform [Akermoun et al. (2000) Biochemical Society Transactions 28: 713-715] and an ER-bound isoform [Tumaney and Rajasekharan (1999) Biochimica et Biophysica Acta 1439: 47-56; Fraser and Stobart, Biochemical Society Transactions (2000) 28: 715-7718] exist in plants. LPCAT is involved in the biosynthesis and transacylation of polyunsaturated fatty acids in animals as well as in plants [Stymne and Stobart (1984) Biochem. J. 223: 305-314; Stymne und Stobart (1987) in 'The Biochemistry of Plants: a Comprehensive Treatise', Vol. 9 (Stumpf, P. K. ed.) pp. 175-214, Academic Press, New York]. An important function of LPCAT or, more generally, of an acyl-CoA:lysophospholipid acyltransferase, referred to as LPLAT hereinbelow, in the ATP-independent synthesis of acyl-CoA from phospholipids has been described by Yamashita et al. (2001; Journal of Biological Chemistry 276: 26745-26752).

Despite many biochemical data, no genes coding for LPCAT have been identified previously. Genes of various other plant acyltransferases have been isolated and are described in WO 00/18889 (Novel Plant Acyltransferases).

Higher plants comprise polyunsaturated fatty acids such as linoleic acid (C18:2) and linolenic acid (C18:3). Arachidonic acid (ARA), eicosapentaenoic acid (EPA) and docosahexaenoic acid (DHA) are, as described above, found not at all in the seed oil of higher plants, or only in traces (E. Ucciani: Nouveau Dictionnaire des Huiles Végétales. Technique & Documentation—Lavoisier, 1995. ISBN: 2-7430-0009-0). It is advantageous to produce LCPUFAs in higher plants, preferably in oil seeds such as oilseed rape, linseed, sunflower and soybean, since large amounts of high-quality LCPUFAs for the food industry, animal nutrition and pharmaceutical purposes may be obtained at low costs in this way. To this end, it is advantageous to introduce into and express in oil seeds genes coding for enzymes of the biosynthesis of LCPUFAs by genetic engineering methods. Said genes encode, for example, Δ6-desaturase, Δ6-elongase, Δ5-desaturase, Δ5-elongase and Δ4-desaturase. These genes may advantageously be isolated from microorganisms, animals and lower plants which produce LCPUFAs and incorporate them in the membranes or triacylglycerides. Thus, Δ6-desaturase genes have already been isolated from the moss *Physcomitrella patens* and Δ6-elongase genes have already been isolated from *P. patens* and the nematode *C. elegans*.

First transgenic plants which comprise and express genes coding for enzymes of the LCPUFA biosynthesis and produce LCPUFAs have been described for the first time, for example, in DE 102 19 203 (process for the production of polyunsaturated fatty acids in plants). However, these plants produce LCPUFAs in amounts which require further optimization for processing the oils present in said plants.

In order to enable food and feed to be enriched with these polyunsaturated fatty acids, there is therefore a great need for a simple, inexpensive process for producing said polyunsaturated fatty acids, especially in eukaryotic systems.

BRIEF SUMMARY OF THE INVENTION

It was therefore the object to develop a process for producing polyunsaturated fatty acids in a eukaryotic organism. This object was achieved by the process according to the invention for producing polyunsaturated fatty acids in an organism, wherein said process comprises the following steps:
a) introducing into the organism at least one nucleic acid sequence having the sequence depicted in SEQ ID NO: 1, SEQ ID NO: 3, SEQ ID NO: 5 or SEQ ID NO: 7, which sequence codes for a polypeptide having an acyl-CoA:lysophospholipid-acyltransferase activity; or
b) introducing into said organism at least one nucleic acid sequence which can be derived, as a result of the degenerated genetic code, from the coding sequence comprised in SEQ ID NO: 1, SEQ ID NO: 3, SEQ ID NO: 5 or SEQ ID NO: 7, or
c) introducing into said organism at least one derivative of the nucleic acid sequence depicted in SEQ ID NO: 1, SEQ ID NO: 3, SEQ ID NO: 5 or SEQ ID NO: 7, which code for polypeptides having the amino acid sequence depicted in SEQ ID NO: 2, SEQ ID NO: 4, SEQ ID NO: 6 or SEQ ID NO: 8 and which are at least 40% homologous at the amino acid level to SEQ ID NO: 2, SEQ ID NO: 4, SEQ ID NO: 6 or SEQ ID NO: 8 and have an equivalent acyl-CoA:lysophospholipid-acyltransferase activity, and
d) culturing and harvesting said organism.

BRIEF DESCRIPTION OF THE DRAWINGS

FIG. 1 shows the amino acid sequence comparison of *C. elegans* LPLATs (Ce-T06E8.1, SEQ ID NO: 36, and Ce-F59F4.4, SEQ ID NO: 59) with *M. musculus* LPAAT (Mm-NP061350, SEQ ID NO: 58).

FIG. 2 shows the fatty acid profiles of transgenic C13ABYS86 *S. cerevisiae* cells.

FIG. 3 shows the fatty acid profiles of transgenic C13ABYS86 *S. cerevisiae* cells.

FIG. 4 shows the elongation of exogenously applied $18:2^{6,9,12}$ and $18:3^{\Delta 9,12,15}$, following their endogenous Δ6-desaturation (data of FIGS. 2 and 3).

FIG. 5 shows the fatty acid profiles of transgenic INVSc1 *S. cerevisiae* cells.

FIG. 6 shows the fatty acid profiles of transgenic INVSc1 *S. cerevisiae* cells.

FIG. 7 shows the acyl-CoA composition of transgenic INVSc1 yeasts transformed with the vectors pESCLeu PpD6Pse1/pYes2 (A) or pESCLeu-PpD6-Pse1/pYes2-T06E8.1 (B).

FIG. 8 shows the vector map of pSUN3CeLPLAT.

FIG. 9A shows the vector map of pGPTVLeB4-700+T06E8.1.

FIG. 9B shows the vector map of pGPTVUSP/OCS-1,2,3 PSE1(Pp)+D6-Des(Pt)+2AT (T06E8-1).

FIG. 10A shows the biosynthetic pathway of LCPUFAs.

FIG. 10B shows the biosynthetic pathway of LCPUFAs.

DETAILED DESCRIPTION OF THE INVENTION

Advantageously, the polyunsaturated fatty acids produced in the process of the invention comprise at least two, advantageously three, double bonds. The fatty acids particularly advantageously comprise four or five double bonds. Fatty acids produced in the process advantageously have 16, 18, 20 or 22 carbon atoms in the fatty acid chain. These fatty acids which have been produced may be produced in said process as a single product or be present in a fatty acid mixture.

The nucleic acid sequences used in the process of the invention are isolated nucleic acid sequences which code for polypeptides having acyl-CoA:lysophospholipid-acyltransferase activity.

The polyunsaturated fatty acids produced in the process are advantageously bound in membrane lipids and/or triacylglycerides but may also occur in the organisms as free fatty acids or else bound in the form of other fatty acid esters. In this context, they may be present as "pure products" or else advantageously in the form of mixtures of various fatty acids or mixtures of different glycerides. The various fatty acids bound in the triacylglycerides can be derived here from short-chain fatty acids having from 4 to 6 carbon atoms, medium-chain fatty acids having from 8 to 12 carbon atoms or long-chain fatty acids having from 14 to 24 carbon atoms, with preference being given to the long-chain fatty acids and particular preference being given to the long-chain fatty acids, LCPUFAs, of $C_{18}$-, $C_{20}$- and/or $C_{22}$-fatty acids.

The process of the invention advantageously produces fatty acid esters with polyunsaturated $C_{16}$-, $C_{18}$-, $C_{20}$- and/or $C_{22}$-fatty acid molecules, with at least two double bonds being present in the fatty acid ester. These fatty acid molecules preferably comprise three, four or five double bonds and advantageously lead to the synthesis of hexadecadienoic acid ($C16:2^{\Delta 9,12}$), γ-linolenic acid (=GLA, $C18:3^{6,9,12}$), stearidonic acid (=SDA, $C18:4^{\Delta 6,9,12,15}$), dihomo-γ-linolenic acid (=DGLA, $20:3^{\Delta 8,11,14}$), eicosatetraenoic acid (=ETA, $C20:4^{\Delta 5,8,11,14}$), arachidonic acid (ARA), eicosapentaenoic acid (EPA) or mixtures thereof, preferably EPA and/or ARA.

The fatty acid esters with polyunsaturated $C_{16}$-, $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipid, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetylcoenzyme A esters which comprise the polyunsaturated fatty acids with at least two, preferably three double bonds, from the organisms which have been used for the preparation of the fatty acid esters. In addition to these esters, the polyunsaturated fatty acids are also present in the organisms, advantageously the plants as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPUFAs produced in a content of at least 3% by weight, advantageously at least 5% by weight, preferably at least 8% by weight, especially preferably at least 10% by weight, most preferably at least 15% by weight, based on the total fatty acids in the transgenic organisms, preferably in a transgenic plant. Since a plurality of reaction steps are performed by the starting compounds hexadecadienoic acid (C16:2), linoleic acid (C18:2) and linolenic acid (C18:3) in the process according to the invention, the end products of the process such as, for example, arachidonic acid (ARA) or eicosapentaenoic acid (EPA) are not obtained as absolutely pure products; minor traces of the precursors are always present in the end product. If, for example, both linoleic acid and linolenic acid are present in the starting organism and the starting plant, the end products such as ARA and EPA are present as mixtures. The precursors should advantageously not amount to more than 20% by weight, preferably not to more than 15% by weight, especially preferably not to more than 10% by weight, most preferably not to more than 5% by weight, based on the amount of the end product in question. Advantageously, only ARA or only EPA, bound or as free acids, are produced as end products in a transgenic plant owing to the process according to the invention. If both compounds (ARA and EPA) are produced simultaneously, they are advantageously produced in a ratio of at least 1:2 (EPA:ARA), advantageously of at least 1:3, preferably 1.4, especially preferably 1:5.

Owing to the nucleic acid sequences according to the invention, an increase in the yield of polyunsaturated fatty acids of at least 50%, advantageously of at least 80%, especially advantageously of at least 100%, very especially advantageously of at least 150%, in comparison with the nontransgenic starting organism, can be obtained by comparison in GC analysis (see examples).

Chemically pure polyunsaturated fatty acids or fatty acid compositions can also be synthesized by the processes described above. To this end, the fatty acids or the fatty acid compositions are isolated from the organism, such as the microorganisms or the plants or the culture medium in or on which the organisms have been grown, or from the organism and the culture medium, in the known manner, for example via extraction, distillation, crystallization, chromatography or combinations of these methods. These chemically pure fatty acids or fatty acid compositions are advantageous for applications in the food industry sector, the cosmetics sector and especially the pharmacological industry sector.

Suitable organisms for the production in the process according to the invention are, in principle, any organisms such as fungi, such as *Mortierella* or *Thraustrochytrium*, yeasts such as *Saccharomyces* or *Schizosaccharomyces*, mosses such as *Physcomitrella* or *Ceratodon*, nonhuman animals such as *Caenorhabditis*, algae such as *Crypthecodinium* or *Phaeodactylum* or plants such as dicotyledonous or monocotyledonous plants. Organisms which are especially advantageously used in the process according to the invention are organisms which belong to the oil-producing organisms, that is to say which are used for the production of oils, such as fungi, such as *Mortierella* or *Thraustrochytrium*, algae such as *Crypthecodinium, Phaeodactylum*, or plants, in particular plants, preferably oil crop plants which comprise large amounts of lipid compounds, such as peanut, oilseed rape, canola, sunflower, safflower, poppy, mustard, hemp, castor-oil plant, olive, sesame, *Calendula, Punica*, evening primrose, verbascum, thistle, wild roses, hazelnut, almond, macadamia, avocado, bay, pumpkin/squash, linseed, soybean, pistachios, borage, trees (oil palm, coconut or walnut) or arable crops such as maize, wheat, rye, oats, triticale, rice, barley, cotton, cassaya, pepper, *Tagetes, Solanaceae* plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:2- and/or C18:3-fatty acids, such as sunflower, safflower, tobacco, verbascum, sesame, cotton, pumpkin/squash, poppy, evening primrose, walnut, linseed, hemp, thistle or safflower. Very especially preferred plants are plants such as safflower, sunflower, poppy, evening primrose, walnut, linseed or hemp.

It is advantageous to the inventive process described to introduce, in addition to the nucleic acids introduced in steps (a) to (c) of the process, further nucleic acids which encode enzymes of the fatty acid or lipid metabolism.

In principle, all genes of the fatty acid or lipid metabolism can be used in the process for the production of polyunsaturated fatty acids, advantageously in combination with the inventive acyl-CoA:lysophospholipid acyltransferase. Genes of the fatty acid or lipid metabolism selected from the group consisting of acyl-CoA dehydrogenase(s), acyl-ACP [=acyl carrier protein] desaturase(s), acyl-ACP thioesterase(s), fatty acid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) are advantageously used in combination with the acyl-CoA:lysophospholipid acyl-transferase. Genes selected from the group of the Δ4-desaturases, Δ5-desaturases, Δ6-desaturases, Δ8-desaturases, Δ9-desaturases, Δ12-desaturases, Δ5-elongases, Δ6-elongases or Δ9-elongases are especially preferably used in combination with the acyl-CoA:lysophospholipid acyltransferase in the process of the invention.

Owing to the enzymatic activity of the nucleic acids used in the process according to the invention which encode polypeptides with acyl-CoA:lysophospholipid acyltransferase activity, advantageously in combination with nucleic acid sequences which encode polypeptides of the fatty acid or lipid metabolism, such as Δ4-, Δ5-, Δ6-, Δ8-desaturase or Δ5-, Δ6- or Δ9-elongase activity, a wide range of polyunsaturated fatty acids can be produced in the process according to the invention. Depending on the choice of the organisms, such as the advantageous plants, used for the process according to the invention, mixtures of the various polyunsaturated fatty acids or individual polyunsaturated fatty acids, such as EPA or ARA, can be produced in free or bound form. Depending on the prevailing fatty acid composition in the starting plant (C18:2- or C18:3-fatty acids), fatty acids which are derived from C18:2-fatty acids, such as GLA, DGLA or ARA, or fatty acids which are derived from C18:3-fatty acids, such as SDA, ETA or EPA, are thus obtained. If only linoleic acid (=LA, $C18:2^{\Delta9,12}$) is present as unsaturated fatty acid in the plant used for the process, the process can only afford GLA, DGLA and ARA as products, all of which can be present as free fatty acids or in bound form. If only α-linolenic acid (=ALA, $C18:3^{\Delta9,12,15}$) is present as unsaturated fatty acid in the plant used for the process, as is the case, for example, in linseed, the process can only afford SDA, ETA and EPA as products, all of which can be present as free fatty acids or in bound form, as described above. Owing to the modification of the activity of the enzymes involved in the synthesis, acyl-CoA:lysophospholipid acyltransferase, advantageously in combination with Δ5-, Δ6-desaturase and Δ6-elongase or with Δ5-Δ8-desaturase and Δ9-elongase or in combination with only the first two genes, Δ6-desaturase and Δ6-elongase or Δ8-desaturase and Δ9-elongase, of the synthesis cascade, it is possible to produce, in a targeted fashion, only individual products in the abovementioned organisms, advantageously in the abovementioned plants. Owing to the activity of Δ6-desaturase and Δ6-elongase, for example, GLA and DGLA, or SDA and ETA, are formed, depending on the starting plant and unsaturated fatty acid. DGLA or ETA or mixtures of these are preferably formed. If Δ5-desaturase is additionally introduced into the organisms, advantageously into the plant, ARA or EPA is additionally formed. This also applies to organisms into which Δ8-desaturase and Δ9-elongase have been introduced previously. Advantageously, only ARA or EPA or mixtures of these are synthesized, depending on the fatty acid present in the organism, or in the plant, which acts as starting substance for the synthesis. Since biosynthetic cascades are involved, the end products in question are not present in pure form in the organisms. Small amounts of the precursor compounds are always additionally present in the end product. These small amounts amount to less than 20% by weight, advantageously less than 15% by weight, especially advantageously less than 10% by weight, most advantageously less than 5, 4, 3, 2 or 1% by weight, based on the end products DGLA, ETA or their mixtures, or ARA, EPA or their mixtures.

To increase the yield in the above-described process for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which encodes a polypeptide with Δ12-desaturase activity. This is particularly advantageous in oil-producing organisms such as oilseed rape which are high in oleic acid. Since these organisms are only low in linoleic acid (Mikoklajczak et al., Journal of the American Oil Chemical Society, 38, 1961, 678-681), the use of the abovementioned Δ12-desaturases for producing the starting material linoleic acid is advantageous.

Nucleic acids used in the process according to the invention are advantageously derived from plants such as algae such as lsochrysis or *Crypthecodinium*, algae/diatoms such as *Phaeodactylum*, mosses such as *Physcomitrella* or *Ceratodon*, or higher plants such as the *Primulaceae* such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, yeasts or animals such as nematodes such as *Caenorhabditis*, insects or humans. The nucleic acids are advantageously derived from fungi, animals, or from plants such as algae or mosses, preferably from nematodes such as *Caenorhabditis*.

The process according to the invention advantageously employs the abovementioned nucleic acid sequences or their derivatives or homologs which encode polypeptides which retain the enzymatic activity of the proteins encoded by nucleic acid sequences. These sequences, individually or in combination with the nucleic acid sequence which encode acyl-CoA:lysophospholipid acyltransferase, are cloned into expression constructs and used for the introduction into, and expression in, organisms. Owing to their construction, these expression constructs make possible an advantageous optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the organism is transformed with the nucleic acid sequence according to the invention which encodes the acyl-CoA:lysophospholipid acyltransferase, a gene construct or a vector as described above, alone or in combination with further nucleic acid sequences which encode proteins of the fatty acid or lipid metabolism. In a further preferred embodiment, this process furthermore comprises the step of obtaining the fine chemical from the culture. The culture can, for example, take the form of a fermentation culture, for example in the case of the cultivation of microorganisms, such as, for example, *Mortierella, Saccharomyces* or *Thraustochytrium*, or a greenhouse- or field-grown culture of a plant. The cell or the organism produced thus is advantageously a cell of an oil-producing organism, such as an oil crop, such as, for example, peanut, oilseed rape, canola, linseed, hemp, soybean, safflower, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

For the purposes of the invention, "transgenic" or "recombinant" means with regard to, for example, a nucleic acid sequence, an expression cassette (=gene construct) or a vector comprising the nucleic acid sequence or an organism transformed with the nucleic acid sequences, expression cassette or vector according to the invention, all those constructions brought about by recombinant methods in which either
a) the nucleic acid sequence according to the invention, or
b) a genetic control sequence which is operably linked with the nucleic acid sequence according to the invention, for example a promoter, or
c) (a) and (b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original organism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the inventive nucleic acid sequence with the corresponding acyl-CoA:lysophospholipid acyltransferase gene—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic organism or transgenic plant for the purposes of the invention is understood as meaning, as above, that the nucleic acids used in the process are not at their natural locus in the genome of an organism, it being possible for the nucleic acids to be expressed homologously or heterologously. However, as mentioned, transgenic also means that, while the nucleic acids according to the invention are at their natural position in the genome of an organism, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic organisms are fungi such as *Mortierelia* or plants such as the oil crops.

Organisms or host organisms for the nucleic acids, the expression cassette or the vector used in the process according to the invention are, in principle, advantageously all organisms which are capable of synthesizing fatty acids, specifically unsaturated fatty acids, and/or which are suitable for the expression of recombinant genes. Examples which may be mentioned are plants such as *Arabidopsis, Asteraceae* such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Saprolegnia,* or *Pythium,* bacteria, such as the genus *Escherichia,* yeasts, such as the genus *Saccharomyces,* cyanobacteria, ciliates, algae or protozoans such as dinoflagellates, such as *Crypthecodinium*. Preferred organisms are those which are naturally capable of synthesizing substantial amounts of oil, such as fungi, such as *Mortierella alpina, Pythium insidiosum,* or plants such as soybean, oilseed rape, coconut, oil palm, safflower, flax, hemp, castor-oil plant, *Calendula*, peanut, cacao bean or sunflower, or yeasts such as *Saccharomyces cerevisiae* with soybean, flax, oilseed rape, safflower, sunflower, *Calendula, Mortierella* or *Saccharomyces cerevisiae* being especially preferred. In principle, host organisms are, in addition to the abovementioned transgenic organisms, also transgenic animals, advantageously nonhuman animals, for example *C. elegans.*

Further utilizable host cells are detailed in: Goeddel, Gene Expression Technology: Methods in Enzymology 185, Academic Press, San Diego, Calif. (1990).

Expression strains which can be used, for example those with a lower protease activity, are described in: Gottesman, S., Gene Expression Technology: Methods in Enzymology 185, Academic Press, San Diego, Calif. (1990) 119-128.

These include plant cells and certain tissues, organs and parts of plants in all their phenotypic forms such as anthers, fibers, root hairs, stalks, embryos, calli, cotyledons, petioles, harvested material, plant tissue, reproductive tissue and cell cultures which are derived from the actual transgenic plant and/or can be used for bringing about the transgenic plant.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotyledons, petioles, harvested material, plant tissue, reproductive tissue and cell cultures which are derived from the actual transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fat, lipids and/or free fatty acids. Polyunsaturated fatty acids produced by this process can be obtained by harvesting the organisms, either from the crop in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat by pressing. To allow for greater ease of disruption of the plant parts, specifically the seeds, they are previously comminuted, steamed or roasted. The seeds which have been pretreated in this manner can subsequently be pressed or extracted with solvents such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, substances such as the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigments remaining in the product, the products are subjected to bleaching, for example using filler's earth or active charcoal. At the end, the product is deodorized, for example using steam.

The PUFAs or LCPUFAs produced by this process are advantageously $C_{18}$-, $C_{20}$- or $C_{22}$-fatty acid molecules with at least two double bonds in the fatty acid molecule, preferably three, four, five or six double bonds. These $C_{18}$-, $C_{20}$- or $C_{22}$-fatty acid molecules can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids or fractions thereof which have been produced by the above-described process, especially preferably oil, lipid or a fatty acid composition comprising PUFAs and being derived from transgenic plants.

A further embodiment according to the invention is the use of the oil, lipid, the fatty acids and/or the fatty acid composition in feedstuffs, foodstuffs, cosmetics or pharmaceuticals.

The term "oil", "lipid" or "fat" is understood as meaning a fatty acid mixture comprising unsaturated or saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. The content of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least two double bonds which are produced in the process are, as described above, for example sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least two double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or integrated into the genome of the host cell. In the case of integration into the genome, integration can be random or else be effected by recombination such that the native gene is replaced by the copy introduced, whereby the production of the desired compound by the cell is modulated, or by the use of a gene in trans, so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains which also accumulate PUFAs in the triacylglycerol fraction are particularly advantageous for the process according to the invention and thus for the modification of the lipid and PUFA production system in a host, in particular plants such as oil crops, for example oilseed rape, canola, linseed, hemp, soybeans, sunflowers and borage. They can therefore be used advantageously in the process according to the invention.

Substrates of the acyl-CoA:lysophospholipid acyltransferase(s) which are advantageously used are $C_{16}$-, $C_{18}$-, $C_{20}$- or $C_{22}$-fatty acids.

To produce the long-chain PUFAs according to the invention, the polyunsaturated $C_{16}$- or $C_{18}$-fatty acids must first be desaturated by the enzymatic activity of a desaturase and subsequently be elongated by at least two carbon atoms via an elongase. After one elongation cycle, this enzyme activity gives $C_{18}$- or $C_{20}$-fatty acids and after two or three elongation cycles $C_{22}$- or $C_{24}$-fatty acids. The activity of the desaturases and elongases used in the process according to the invention preferably leads to $C_{18}$-, $C_{20}$- and/or $C_{22}$-fatty acids, advantageously with at least two double bonds in the fatty acid molecule, preferably with three, four or five double bonds, especially preferably to give $C_{20}$- and/or $C_{22}$-fatty acids with at least two double bonds in the fatty acid molecule, preferably with three, four or five double bonds in the molecule. After a first desaturation and the elongation have taken place, further desaturation steps such as, for example, one in the Δ5 position may take place. Products of the process according to the invention which are especially preferred are dihomo-γ-linolenic acid, arachidonic acid, eicosapentaenoic acid, docosapentaenoic acid and/or docosahexaenoic acid. The $C_{18}$-fatty acids with at least two double bonds in the fatty acid can be elongated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of the fatty acids, oils, lipids or fats in the plants which are advantageously used is, for example, in general the seed or cell strata of the seed, so that seed-specific expression of the nucleic acids used in the process makes sense. However, it is obvious that the biosynthesis of fatty acids, oils or lipids need not be limited to the seed tissue, but can also take place in a tissue-specific manner in all the other parts of the plant, for example in epidermal cells or in the tubers.

If microorganisms such as yeasts, such as *Saccharomyces* or *Schizosaccharomyces*, fungi such as *Mortierella, Aspergillus, Phytophtora, Entomophthora, Mucor* or *Thraustochytrium*, algae such as lsochrysis, *Phaeodactylum* or *Crypthecodinium* are used as organisms in the process according to the invention, these organisms are advantageously grown in fermentation cultures.

Owing to the use of the nucleic acids according to the invention which encode acyl-CoA:lysophospholipid acyltransferase(s), the polyunsaturated fatty acids produced in the process can be increased by at least 10%, preferably by at least 15%, especially preferably by at least 20%, very especially preferably by at least 50% in comparison with the wild type of the organisms which do not comprise the nucleic acids recombinantly.

In principle, the polyunsaturated fatty acids produced by the process according to the invention in the organisms used in the process can be increased in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic organisms is enlarged by the process according to the invention.

If microorganisms are used as organisms in the process according to the invention, they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while passing in oxygen. The pH of the liquid medium can either be kept constant, that is to say regulated during the culturing period, or not. The cultures can be grown batchwise, semi-batchwise or continuously. Nutrients can be provided at the beginning of the fermentation or fed in semicontinuously or continuously. The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semibatchwise or continuously. An overview over known cultivation methods can be found in the textbook by Chmiel (Bioprozeβtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents include dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° to 45° C. and preferably 25° C. to 40° C. The culture is continued until formation of the desired product is at a maximum. This aim is normally achieved within 10 to 160 hours.

The fermentation broths obtained in this way, in particular those containing polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The fatty acids obtained in the process are also suitable as starting material for the chemical synthesis of further products of interest. For example, they can be used in combination with one another or alone for the preparation of pharmaceuticals, foodstuffs, animal feeds or cosmetics.

The invention furthermore relates to isolated nucleic acid sequences coding for polypeptides having acyl-CoA:lysophospholipid acyltransferase activity wherein the acyl-CoA:lysophospholipid acyltransferases encoded by said nucleic acid sequences specifically convert $C_{16}$-, $C_{18}$-, $C_{20}$- or $C_{22}$-fatty acids having at least one double bond in the fatty acid molecule.

Advantageous isolated nucleic acid sequences are sequences selected from the group consisting of:
a) a nucleic acid sequence having the sequence depicted in SEQ ID NO: 1, SEQ ID NO: 3, SEQ ID NO: 5 or SEQ ID NO: 7,
b) nucleic acid sequences which can be derived from the coding sequence comprised in SEQ ID NO: 1, SEQ ID NO: 3, SEQ ID NO: 5 or SEQ ID NO: 7 as a result of the degenerated genetic code
c) derivatives of the nucleic acid sequence depicted in SEQ ID NO: 1, SEQ ID NO: 3, SEQ ID NO: 5 or SEQ ID NO: 7 which code for polypeptides having the amino acid sequence depicted in SEQ ID NO: 2, SEQ ID NO: 4, SEQ ID NO: 6 or SEQ ID NO: 8 and are at least 40% homologous at the amino acid level to SEQ ID NO: 2, SEQ ID NO: 4, SEQ ID NO: 6 or SEQ ID NO: 8 and have an acyl-CoA:lysophospholipid-acyltransferase activity.

The abovementioned nucleic acid sequences are advantageously derived from a eukaryotic organism.

The nucleic acid sequences used in the process which code for proteins with acyl-CoA:lysophospholipid acyltransferase activity or for proteins of the fatty acid or lipid metabolism are advantageously introduced in an expression cassette (=nucleic acid construct) which makes possible the expression of the nucleic acids in an organism, advantageously a plant or a microorganism.

To introduce the nucleic acids used in the process, the latter are advantageously amplified and ligated in the known manner. Preferably, a procedure following the protocol for Pfu DNA polymerase or a Pfu/Taq DNA polymerase mixture is followed. The primers are selected taking into consideration the sequence to be amplified. The primers should advantageously be chosen in such a way that the amplificate comprises the entire codogenic sequence from the start codon to the stop codon. After the amplification, the amplificate is expediently analyzed. For example, a gel-electrophoretic separation can be carried out, which is followed by a quantitative and a qualitative analysis. Thereafter, the amplificate can be purified following a standard protocol (for example Qiagen). An aliquot of the purified amplificate is then available for the subsequent cloning step. Suitable cloning vectors are generally known to the skilled worker. These include, in particular, vectors which are capable of replication in microbial systems, that is to say mainly vectors which ensure efficient cloning in yeasts or fungi and which make possible the stable transformation of plants. Those which must be mentioned in particular are various binary and cointegrated vector systems which are suitable for the T-DNA-mediated transformation. Such vector systems are, as a rule, characterized in that they comprise at least the vir genes required for the *Agrobacterium*-mediated transformation and the T-DNA-delimiting sequences (T-DNA border). These vector systems advantageously also comprise further cis-regulatory regions such as promoters and terminator sequences and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small, easy to manipulate and to replicate both in *E. coli* and in *Agrobacterium*. These binary vectors include vectors from the series pBIB-HYG, pPZP, pBecks, pGreen. In accordance with the invention, pBin19, pB101, pBinAR, pGPTV and pCAMBIA are used by preference. An overview of the binary vectors and their use is found in Hellens et al, Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is ligated with vector fragments which have been prepared in a similar manner, using ligase. In this context, a particular nucleic acid construct, or vector or plasmid construct, can have one or else more than one codogenic gene segment. The codogenic gene segments in these constructs are preferably linked operably with regulatory sequences. The regulatory sequences include, in particular, plant sequences such as the above-described promoters and terminator sequences. The constructs can advantageously be stably propagated in microorganisms, in particular in *Escherichia coli* and *Agrobacterium tumefaciens*, under selective conditions and make possible the transfer of heterologous DNA into plants or microorganisms.

The nucleic acids used in the process, the inventive nucleic acids and nucleic acid constructs, can be introduced into organisms such as microorganisms or advantageously plants, advantageously using cloning vectors, and thus be used in the transformation of plants such as those which are published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, the inventive nucleic acids and nucleic acid constructs, and/or vectors used in the process can be used for the recombinant modification of a broad spectrum of organisms, advantageously plants, so that the latter become better and/or more efficient PUFA producers.

A series of mechanisms exists by which the modification of an acyl-CoA:lysophospholipid acyltransferase protein can influence directly the yield, production and/or production efficiency of a fine chemical from an oil crop plant or a microorganism, owing to a modified protein. The number or activity of the acyl-CoA:lysophospholipid acyltransferase protein or gene and also of gene combinations of acyl-CoA:

lysophospholipid acyltransferases, desaturases and/or elongases may have increased, so that greater amounts of the compounds produced are produced de novo, since the organisms lacked this activity and ability to biosynthesize prior to introduction of the corresponding gene(s). This applies analogously to the combination with further desaturases or elongases or further enzymes of the fatty acid and lipid metabolism. The use of various divergent sequences, i.e. sequences which differ at the DNA sequence level, may also be advantageous in this context, or else the use of promoters for gene expression which makes possible a different gene expression in the course of time, for example as a function of the degree of maturity of a seed or an oil-storing tissue.

Owing to the introduction of one or more acyl-CoA:lysophospholipid acyltransferase, desaturase and/or elongase genes into an organism, alone or in combination with other genes in a cell, it is not only possible to increase biosynthesis flux towards the end product, but also to increase, or to create de novo the corresponding triacylglycerol composition. Likewise, the number or activity of other genes which are involved in the import of nutrients which are required for the biosynthesis of one or more fine chemicals (e.g. fatty acids, polar and/or neutral lipids), can be increased, so that the concentration of these precursors, cofactors or intermediates within the cells or within the storage compartment is increased, whereby the ability of the cells to produce PUFAs as described below is enhanced further. Fatty acids and lipids are themselves desirable fine chemicals; by optimizing the activity or increasing the number of one or more acyl-CoA:lysophospholipid acyltransferases, desaturases and/or elongases which are involved in the biosynthesis of these compounds, or by destroying the activity of one or more desaturases which are involved in the degradation of these compounds, an enhanced yield, production and/or efficiency of production of fatty acid and lipid molecules in organisms, advantageously in plants, is made possible.

The isolated nucleic acid molecules used in the process according to the invention encode proteins or parts of these, where the proteins or the individual protein or parts thereof comprise(s) an amino acid sequence with sufficient homology to an amino acid sequence which is shown in the sequence SEQ ID NO: 2, SEQ ID NO: 4, SEQ ID NO: 6 or SEQ ID NO: 8, so that the protein or part thereof retains an acyl-CoA:lysophospholipid acyltransferase activity. The protein or part thereof which is encoded by the nucleic acid molecule preferably retains its essential enzymatic activity and the ability to participate in the metabolism of compounds required for the synthesis of cell membranes or lipid bodies in organisms, advantageously in plants, or in the transport of molecules across these membranes. Advantageously, the protein encoded by the nucleic acid molecules is at least approximately 40%, preferably at least approximately 60% and more preferably at least approximately 70%, 80% or 90% and most preferably at least approximately 95%, 96%, 97%, 98%, 99% or more homologous to the amino acid sequences shown in SEQ ID NO: 2, SEQ ID NO: 4, SEQ ID NO: 6 or SEQ ID NO: 8. Advantageous embodiments of the inventive amino acid sequence of the sequence SEQ ID NO: 2 are amino acid sequences which have a valine residue instead of the methionine at position 30 of SEQ ID NO: 2 or have a glycine residue instead of the serine at position 100 or have a serine residue instead of the phenylalanine at position 170. These are indicated in SEQ ID NO: 4, SEQ ID NO: 6 and SEQ ID NO: 8, respectively.

Essential enzymatic activity of the acyl-CoA:lysophospholipid acyltransferases used is understood as meaning that they retain at least an enzymatic activity of at least 10%, preferably 20%, especially preferably 30% and very especially 40% in comparison with the proteins/enzymes encoded by the sequence with SEQ ID NO: 1, SEQ ID NO: 3, SEQ ID NO: 5 or SEQ ID NO: 7 and their derivatives and can thus participate in the metabolism of compounds required for the synthesis of fatty acids in an organism, advantageously a plant cell, or in the transport of molecules across membranes, meaning desaturated $C_{16}$-, $C_{18}$- or $C_{20-24}$-carbon chains with double bonds at least two, advantageously three, four or five positions.

Nucleic acids which can advantageously be used in the process are derived from fungi or plants such as algae or mosses, such as the genera *Physcomitrella, Thraustochytrium, Phytophthora, Ceratodon, Isochrysis, Aleurita, Muscarioides, Mortierella, Borago, Phaeodactylum, Crypthecodinium* or from nematodes such as *Caenorhabditis*, specifically from the genera and species *Physcomitrella patens, Phytophtora infestans, Ceratodon purpureus, Isochrysis galbana, Aleurita farinosa, Muscarioides viallii, Mortierella alpina, Borago officinalis, Phaeodactylum tricornutum*, or especially advantageously from *Caenorhabditis elegans*.

Alternatively, the isolated nucleotide sequences used may encode acyl-CoA:lysophospholipid acyltransferases which hybridize with a nucleotide sequence of SEQ ID NO: 1, SEQ ID NO: 3, SEQ ID NO: 5 or SEQ ID NO: 7, for example under stringent conditions.

The nucleic acid sequences used in the process are advantageously introduced into an expression cassette which makes possible the expression of the nucleic acids in organisms such as microorganisms or plants.

In doing so, the nucleic acid sequences which encode the acyl-CoA:lysophospholipid acyltransferases of the invention, the desaturases used and/or the elongases are linked operably with one or more regulatory signals, advantageously for enhancing gene expression. These regulatory sequences are intended to make possible the specific expression of the genes and proteins. Depending on the host organism, this may mean, for example, that the gene is expressed and/or overexpressed only after induction has taken place, or else that it expresses and/or overexpresses immediately. For example, these regulatory sequences take the form of sequences to which inductors or repressors bind, thus controlling the expression of the nucleic acid. In addition to these novel regulatory sequences, or instead of these sequences, the natural regulation of these sequences may still be present before the actual structural genes and, if appropriate, may have been genetically modified in such a way that natural regulation has been eliminated and expression of the genes has been enhanced. However, the expression cassette (=expression construct=gene construct) can also be simpler in construction, that is to say no additional regulatory signals have been inserted before the nucleic acid sequence or its derivatives, and the natural promoter together with its regulation was not removed. Instead, the natural regulatory sequence has been mutated in such a way that regulation no longer takes place and/or gene expression is enhanced. These modified promoters can also be positioned on their own before the natural gene in the form of part-sequences (=promoter with parts of the nucleic acid sequences used in accordance with the invention) in order to enhance the activity. Moreover, the gene construct may advantageously also comprise one or more what are known as enhancer sequences in operable linkage with the promoter, which make possible an enhanced expression of the nucleic acid sequence. Additional advantageous sequences, such as further regulatory elements or terminator sequences, may also be inserted at the 3' end of the DNA sequences. The acyl-CoA:lysophospholipid acyltransferase genes and the advantageously used Δ4-desaturase, Δ5-desaturase, Δ6-desaturase and/or A8-desaturase genes and/or Δ5-elongase, Δ6-elongase and/or Δ9-elongase genes may be present in one or more copies in the expression cassette (=gene construct). Preferably, only one copy of the genes is present in each expression cassette. This gene construct or the gene constructs can be expressed together in the host organism. In this context, the gene construct(s) can be inserted in one or more vectors and be present in the cell in free form, or else be inserted in the genome. It is advantageous for the insertion of further genes in the host genome when the genes to be expressed are present together in one gene construct.

In this context, the regulatory sequences or factors can, as described above, preferably have a positive effect on the gene expression of the genes introduced, thus enhancing it. Thus, an enhancement of the regulatory elements, advantageously at the transcriptional level, may take place by using strong transcription signals such as promoters and/or enhancers. In addition, however, enhanced translation is also possible, for example by improving the stability of the mRNA.

A further embodiment of the invention is one or more gene constructs which comprise one or more sequences which are defined by SEQ ID NO: 1, SEQ ID NO: 3, SEQ ID NO: 5 or SEQ ID NO: 7 or its derivatives and which encode polypeptides as shown in SEQ ID NO: 2, SEQ ID NO: 4, SEQ ID NO: 6 or SEQ ID NO: 8. The abovementioned acyl-CoA:lysophospholipid acyltransferases lead advantageously to an exchange of fatty acids between the mono-, di- and/or triglyceride pool of the cell and the CoA-fatty acid ester pool, the substrate advantageously having one, two, three, four or five double bonds and advantageously 16, 18, 20, 22 or 24 carbon atoms in the fatty acid molecule. The same applies to their homologs, derivatives or analogs, which are linked operably with one or more regulatory signals, advantageously for enhancing gene expression.

Advantageous regulatory sequences for the novel process are present for example in promoters such as the cos, tac, trp, tet, trp-tet, lpp, lac, lpp-lac, lacIq, T7, T5, T3, gal, trc, ara, SP6, λ-PR or λ-PL promoter and are advantageously employed in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscissic acid-inducible) or WO 93/21334 (ethanol- or cyclohexenol-inducible) promoters. Further suitable plant promoters are the cytosolic FBPase promoter or the ST-LSI promoter of potato (Stockhaus et al., EMBO J. 8, 1989, 2445), the *glycine max* phosphoribosylpyrophosphate amidotransferase promoter (Genbank Accession No. U87999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter as described, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arabidopsis oleosin* promoter), U.S. Pat. No. 5,504,200 (*Phaseolus vulgaris* phaseolin promoter), WO 91/13980 (Brassica Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890.

In principle, it is possible to use all natural promoters together with their regulatory sequences, such as those mentioned above, for the novel process. It is also possible and advantageous to use synthetic promoters, either in addition or alone, in particular when they mediate seed-specific expression, such as those described in WO 99/16890.

In order to achieve a particularly high PUFA content, especially in transgenic plants, the PUFA biosynthesis genes should advantageously be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Preferred promoters are listed hereinbelow: USP (=unknown seed protein) and vicilin (*Vicia faba*) [Baumlein et al., Mol. Gen Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumines B4 (LegB4 promoter) [Bäumlein et al., Plant J., 2,2, 1992], Lpt2 and lpt1 (barley) [WO 95/15389 and WO 95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic-acid-inducible promoter (WO 95/19443), a tetracycline-inducible promoter (Gatz et al. (1992) Plant J. 2, 397-404) and an ethanol-inducible promoter.

To ensure the stable integration of the biosynthesis genes into the transgenic plant over a plurality of generations, each of the nucleic acids which encode acyl-CoA:lysophospholipid acyltransferase, the advantageous Δ4-desaturase, Δ5-desaturase, Δ6-desaturase, Δ8-desaturase and/or Δ5-elongase, Δ6-elongase and/or Δ9-elongase and which are used in the process should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and, if appropriate, a terminator sequence is positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via the suitable cleavage site, for example in the polylinker. Advantageously, each nucleic acid sequence has its own promoter and, if appropriate, its own terminator sequence. However, it is also possible to insert a plurality of nucleic acid sequences behind a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminator sequences can be used in the expression cassette. However, it is also possible to use only one type of promoter in the cassette. This, however, may lead to undesired recombination events.

As described above, the transcription of the genes which have been introduced should advantageously be terminated by suitable terminator sequences at the 3' end of the biosynthesis genes which have been introduced (behind the stop codon). An example of a sequence which can be used in this context is the OCS1 terminator sequence. As is the case with the promoters, different terminator sequences should be used for each gene.

As described above, the gene construct can also comprise further genes to be introduced into the organisms. It is possible and advantageous to introduce into the host organisms, and to express therein, regulatory genes such as genes for inductors, repressors or enzymes which, owing to their enzyme activity, engage in the regulation of one or more genes of a biosynthesis pathway. These genes can be of heterologous or of homologous origin. Moreover, further biosynthesis genes of the fatty acid or lipid metabolism can advantageously be present in the nucleic acid construct, or gene construct; however, these genes can also be positioned on one or more further nucleic acid constructs. Biosynthesis genes of the fatty acid or lipid metabolism which are preferably used are a gene selected from the group consisting of acyl-CoA dehydrogenase(s), acyl-ACP [=acyl carrier protein] desaturase(s), acyl-ACP thioesterase(s), fatty acid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) or combinations thereof. Especially advantageous nucleic acid sequences are biosynthesis genes of the fatty acid or lipid metabolism selected from the group of the Δ4-desaturase, Δ5-desaturase, Δ6-desaturase, Δ8-desaturase, Δ9-desaturase, Δ12-desaturase, Δ5-elongase, Δ6-elongase or Δ9-elongase.

In this context, the abovementioned desaturases can be cloned into expression cassettes of the invention in combination with other elongases and desaturases and used for transforming plants with the aid of *Agrobacterium*.

Here, the regulatory sequences or factors can, as described above, preferably have a positive effect on, and thus enhance, the expression of the genes which have been introduced. Thus, enhancement of the regulatory elements can advantageously take place at the transcriptional level by using strong transcription signals such as promoters and/or enhancers. However, an enhanced translation is also possible, for example by improving the stability of the mRNA. In principle, the expression cassettes can be used directly for introduction into the plants or else be introduced into a vector.

These advantageous vectors, preferably expression vectors, comprise the nucleic acids which encode acyl-CoA: lysophospholipid acyltransferases and which are used in the process, or else a nucleic acid construct which comprises the nucleic acid used either alone or in combination with further biosynthesis genes of the fatty acid or lipid metabolism such as Δ4-desaturase, Δ5-desaturase, Δ6-desaturase, Δ8-desaturase, Δ9-desaturase, Δ12-desaturase, Δ5-elongase, Δ6-elongase and/or Δ9-elongase. As used in the present context, the term "vector" refers to a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids. In the present description, "plasmid" and "vector" can be used exchangeably since the plasmid is the form of vector which is most frequently used. However, the invention is also intended to cover other forms of expression vectors, such as viral vectors, which exert similar functions. Furthermore, the term "vector" is also intended to encompass other vectors with which the skilled worker is familiar, such as phages, viruses such as SV40, CMV, TMV, transposons, IS elements, phasmids, phagemids, cosmids, linear or circular DNA.

The recombinant expression vectors advantageously used in the process comprise the nucleic acids described below or the above-described gene construct in a form which is suitable for expressing the nucleic acids used in a host cell, which means that the recombinant expression vectors comprise one or more regulatory sequences, selected on the basis of the host cells used for the expression, which regulatory sequence(s) is/are linked operably with the nucleic acid sequence to be expressed. In a recombinant expression vector, "linked operably" means that the nucleotide sequence of interest is bound to the regulatory sequencers) in such a way that the expression of the nucleotide sequence is possible and they are bound to each other in such a way that both sequences carry out the predicted function which is ascribed to the sequence (for example in an in-vitro transcription/translation system, or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnology, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the desired expression level of the protein and the like.

The recombinant expression vectors used can be designed for the expression of acyl-CoA:lysophospholipid acyltransferases, desaturases and elongases in prokaryotic or eukaryotic cells. This is advantageous since intermediate steps of the vector construction are frequently carried out in microorganisms for the sake of simplicity. For example, acyl-CoA:lysophospholipid acyltransferase, desaturase and elongase genes can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or non-fusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRITS (Pharmacia, Piscataway, N.J.), where glutathione S-transferase (GST), maltose-E binding protein and protein A, respectively, is fused with the recombinant target protein.

Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter.

Other vectors which are suitable for prokaryotic organisms are known to the skilled worker, these vectors are, for example in *E. coli* pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-111113-B1, λgt11 or pBdC1, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples for vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, acyl-CoA:lysophospholipid acyltransferases, desaturases and/or elongases can be expressed in insect cells using Baculovirus expression vectors. Baculovirus vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

The abovementioned vectors offer only a small overview over suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018). For further suitable expression systems for prokaryotic and eukaryotic cells, see the Chapters 16 and 17 in Sambrook, J., Fritsch, E. F., and Maniatis, T., Molecular Cloning: A Laboratory Manual, 2nd edition, Cold Spring Harbor Laboratory, Cold Spring Harbor Laboratory Press, Cold Spring Harbor, N.Y., 1989.

In a further embodiment of the process, the acyl-CoA: lysophospholipid acyltransferases, desaturases and elongases can be expressed in single-celled plant cells (such as algae), see Falciatore et al., 1999, Marine Biotechnology 1 (3):239-251 and references cited therein, and in plant cells from higher plants (for example spermatophytes such as arable crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38.

A plant expression cassette preferably comprises regulatory sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but all other terminator sequences which are functionally active in plants are also suitable.

Since plant gene expression is very often not limited to the transcriptional level, a plant expression cassette preferably comprises other sequences which are linked operably, such as translation enhancers, for example the overdrive sequence, which enhances the tobacco mosaic virus 5'-untranslated leader sequence, which increases the protein/RNA ratio (Gallie et al., 1987, Nucl. Acids Research 15:8693-8711).

As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CaMV (Franck et al., Cell 21 (1980) 285-294), 19S CaMV (see also U.S. Pat. No. 5,352,605 and WO 84/02913), or plant promoters, such as the promoter of the small rubisco subunit, which is described in U.S. Pat. No. 4,962,028.

Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmid reticulum, elaioplasts, peroxisomes and other compartments of plant cells.

As described above, plant gene expression can also be achieved via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley lpt2 or lpt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890.

In particular, it may be desired to bring about the multiparallel expression of the acyl-CoA:lysophospholipid acyltransferases used in the process alone or in combination with desaturases and/or elongases. Such expression cassettes can be introduced via the simultaneous transformation of a plurality of individual expression constructs or, preferably, by combining a plurality of expression cassettes on one construct. Also, a plurality of vectors can be transformed with in each case a plurality of expression cassettes and then transferred into the host cell.

Other promoters which are likewise especially suitable are those which bring about plastid-specific expression, since plastids constitute the compartment in which the precursors and some end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

Vector DNA can be introduced into prokaryotic or eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

Host cells which are suitable in principle for taking up the nucleic acid according to the invention, the gene product according to the invention or the vector according to the invention are all prokaryotic or eukaryotic organisms. The host organisms which are advantageously used are microorganisms such as fungi or yeasts, or plant cells, preferably plants or parts thereof. Fungi, yeasts or plants are preferably used, especially preferably plants, very especially preferably plants such as oil crops, which are high in lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassaya, pepper, *Tagetes, Solanacea* plants such as potato, tobacco, eggplant and tomato, *Vicia* species, pea, alfalfa, bushy plants (coffee, cacao, tea), *Salix* species, trees (oil palm, coconut), and perennial grasses and fodder crops. Especially preferred plants according to the invention are oil crops such as soybean, peanut, oilseed rape, canola, linseed, hemp, evening primrose, sunflower, safflower, trees (oil palm, coconut).

The invention furthermore relates to isolated nucleic acid sequences as described above coding for polypeptides having acyl-CoA:lysophospholipid-acyltransferase activity, wherein the acyl-CoA:lysophospholipid acyltransferases encoded by said nucleic acid sequences specifically convert $C_{16}$, $C_{18}$-, $C_{20}$- or $C_{22}$-fatty acids having at least one double bond in the fatty acid molecule.

Advantageous isolated nucleic acid sequences are sequences selected from the group consisting of:

a) a nucleic acid sequence having the sequence depicted in SEQ ID NO: 1, SEQ ID NO: 3, SEQ ID NO: 5 or SEQ ID NO: 7,
b) nucleic acid sequences which can be derived from the coding sequence comprised in SEQ ID NO: 1, SEQ ID NO: 3, SEQ ID NO: 5 or SEQ ID NO: 7 as a result of the degenerated genetic code
c) derivatives of the nucleic acid sequence depicted in SEQ ID NO: 1, SEQ ID NO: 3, SEQ ID NO: 5 or SEQ ID NO: 7 which code for polypeptides having the amino acid sequence depicted in SEQ ID NO: 2, SEQ ID NO: 4, SEQ ID NO: 6 or SEQ ID NO: 8 and are at least 40% homologous at the amino acid level to SEQ ID NO: 2, SEQ ID NO: 4, SEQ ID NO: 6 or SEQ ID NO: 8 and have an acyl-CoA:lysophospholipid-acyltransferase activity.

The abovementioned nucleic acids according to the invention are derived from organisms such as animals, ciliates, fungi, plants such as algae or dinoflagellates which are capable of synthesizing PUFAs.

In an advantageous embodiment, the term "nucleic acid (molecule)" as used in the present context additionally comprises the untranslated sequence at the 3' and at the 5' end of the coding gene region: at least 500, preferably 200, especially preferably 100 nucleotides of the sequence upstream of the 5' end of the coding region and at least 100, preferably 50, especially preferably 20 nucleotides of the sequence downstream of the 3' end of the coding gene region. An "isolated" nucleic acid molecule is separate from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences which are located at the 5' and 3' ends of the nucleic acid). In various embodiments, the isolated acyl-CoA:lysophospholipid acyltransferase molecule can comprise for example fewer than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived.

The nucleic acid molecules used in the process, for example a nucleic acid molecule with a nucleotide sequence of SEQ ID NO: 1, SEQ ID NO: 3, SEQ ID NO: 5 or SEQ ID NO: 7 or of a part thereof can be isolated using molecular-biological standard techniques and the sequence information provided herein. Also, for example a homologous sequence or homologous, conserved sequence regions can be identified at the DNA or amino acid level with the aid of comparative algorithms. They can be used as hybridization probe together with standard hybridization techniques (such as, for example, those described in Sambrook et al., Molecular Cloning: A Laboratory Manual. 2nd ed., Cold Spring Harbor Laboratory, Cold Spring Harbor Laboratory Press, Cold Spring Harbor, N.Y., 1989) for isolating further nucleic acid sequences which can be used in the process. Moreover, a nucleic acid molecule comprising a complete sequence of SEQ ID NO: 1, SEQ ID NO: 3, SEQ ID NO: 5 or SEQ ID NO: 7 or a part thereof can be isolated by polymerase chain reaction, where oligonucleotide primers which are based on this sequence or on parts thereof are used (for example a nucleic acid molecule comprising the complete sequence or part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for the amplification by means of polymerase chain reaction can be generated based on one of the sequences shown in SEQ ID NO: 1, SEQ ID NO: 3, SEQ ID NO: 5 or SEQ ID NO: 7 or with the aid of the amino acid sequences detailed in SEQ ID NO: 2, SEQ ID NO: 4, SEQ ID NO: 6 or SEQ ID NO: 8. A nucleic acid according to the invention can be amplified by standard PCR amplification techniques using cDNA or, alternatively, genomic DNA as template and suitable oligonucleotide primers. The nucleic acid amplified thus can be cloned into a suitable vector and characterized by means of DNA sequence analysis. Oligonucleotides which correspond to a desaturase nucleotide sequence can be generated by standard synthetic methods, for example using an automatic DNA synthesizer.

Homologs of the acyl-CoA:lysophospholipid acyltransferase nucleic acid sequences with the sequence SEQ ID NO: 1, SEQ ID NO: 3, SEQ ID NO: 5 or SEQ ID NO: 7 means, for example, allelic variants with at least approximately 40 to 60%, preferably at least approximately from 60 to 70%, more preferably at least approximately from 70 to 80%, 80% to 90% or 90 to 95% and even more preferably at least approximately 95%, 96%, 97%, 98%, 99% or more homology with a nucleotide sequence shown in SEQ ID NO: 1, SEQ ID NO: 3, SEQ ID NO: 5 or SEQ ID NO: 7 or its homologs, derivatives or analogs or parts thereof. Furthermore, isolated nucleic acid molecules of a nucleotide sequence which hybridize with one of the nucleotide sequences shown in SEQ ID NO: 1, SEQ ID NO: 3, SEQ ID NO: 5 or SEQ ID NO: 7 or with a part thereof, for example hybridized under stringent conditions. Allelic variants comprise in particular functional variants which can be obtained by deletion, insertion or substitution of nucleotides from/into the sequence detailed in SEQ ID NO: 1, SEQ ID NO: 3, SEQ ID NO: 5 or SEQ ID NO: 7, it being intended, however, that the enzyme activity of the resulting proteins which are synthesized is advantageously retained for the insertion of one or more genes. Proteins which retain the enzymatic activity of acyl-CoA:lysophospholipid acyltransferase, i.e. whose activity is essentially not reduced, means proteins with at least 10%, preferably 20%, especially preferably 30%, very especially preferably 40% of the original enzyme activity in comparison with the protein encoded by SEQ ID NO: 1, SEQ ID NO: 3, SEQ ID NO: 5 or SEQ ID NO: 7.

Homologs of SEQ ID NO: 1, SEQ ID NO: 3, SEQ ID NO: 5 or SEQ ID NO: 7 means for example also bacterial, fungal and plant homologs, truncated sequences, single-stranded DNA or RNA of the coding and noncoding DNA sequence.

Homologs of SEQ ID NO: 1, SEQ ID NO: 3, SEQ ID NO: 5 or SEQ ID NO: 7 also mean derivatives such as, for example, promoter variants. The promoters upstream of the nucleotide sequences detailed can be modified by one or more nucleotide exchanges, by insertion(s) and/or deletion(s) without the functionality or activity of the promoters being adversely affected, however. It is furthermore possible that the modification of the promoter sequence enhances their activity or that they are replaced entirely by more active promoters, including those from heterologous organisms.

The abovementioned nucleic acids and protein molecules with acyl-CoA:lysophospholipid acyltransferase activity which are involved in the metabolism of lipids and fatty acids, PUFA cofactors and enzymes or in the transport of lipophilic compounds across membranes are used in the process according to the invention for the modulation of the production of PUFAs in transgenic organisms, advantageously in plants, such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and *Tagetes*, *Solanaceae* plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the PUFAs or a reduction of undesired compounds (for example when the modulation of the metabolism of lipids and fatty acids, cofactors and enzymes leads to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since polyunsaturated fatty acids (=PUFAs) are not only incorporated into triacylglycerol but also into membrane lipids.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydratization reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press. Washington, D.C., pp. 612-636 and references cited therein; Lengeler et al. (Ed.) (1999) Biology of Procaryotes. Thieme: Stuttgart, New York, and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool. This is made possible by acyl-CoA:lysophospholipid acyltransferases. Moreover, these enzymes are capable of transferring the elongated fatty acids from the CoA esters back to the phospholipids. If appropriate, this reaction sequence can be followed repeatedly (see FIG. 10).

Examples of precursors for the biosynthesis of PUFAs are oleic acid, linoleic acid and linolenic acid. These $C_{18}$-carbon fatty acids must be elongated to $C_{20}$ and $C_{22}$ in order to obtain fatty acids of the eicosa and docosa chain type. With the aid of the acyl-CoA:lysophospholipid acyltransferases used in the process, advantageous in combination with desaturases such as Δ4-, Δ5-, Δ6- and Δ8-desaturases and/or Δ5-, Δ6-, Δ9-elongases, arachidonic acid, eicosapentaenoic acid, docosapentaenoic acid or docosahexaenoic acid and various other long-chain PUFAs can be obtained, extracted and employed in various applications regarding foodstuffs, feedstuffs, cosmetics or pharmaceuticals. Preferably $C_{18}$-, $C_{20}$- and/or $C_{22}$-fatty acids with at least two, advantageously at least three, four, five or six, double bonds in the fatty acid molecule can be prepared using the abovementioned enzymes, to give preferably $C_{20}$- or $C_{22}$-fatty acids with advantageously three, four or five double bonds in the fatty acid molecule. Desaturation may take place before or after elongation of the fatty acid in question. This is why the products of the desaturase activities and the further desaturation and elongation steps which are possible result in preferred PUFAs with a higher degree of desaturation, including a further elongation from $C_{20}$- to $C_{22}$-fatty acids, to fatty acids such as γ-linolenic acid, dihomo-γ-linolenic acid, arachidonic acid, stearidonic acid, eicosatetraenoic acid or eicosapentaenoic acid. Substrates of the acyl-CoA: lysophospholipid acyltransferases used in the process according to the invention are $C_{16}$-, $C_{18}$-, $C_{20}$- or $C_{22}$-fatty acids such as, for example, palmitic acid, palmitoleic acid, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid, arachidonic acid, eicosatetraenoic acid or eicosapentaenoic acid. The $C_{18}$-, $C_{20}$- or $C_{22}$-fatty acids with at least two double bonds in the fatty acid are obtained in the process according to the invention in the form of the free fatty acid or in the form of their esters, for example in the form of their glycerides.

The term "glyceride" is understood as meaning glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

Publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Guhnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of synthesizing themselves in sufficient quantity and must therefore take up additional quantities, although they can be synthesized readily by other organisms such as bacteria; for example, cats are no longer capable of synthesizing arachidonic acid.

The term "acyl-CoA:lysophospholipid acyltransferases" comprises for the purposes of the invention proteins which participate in the transfer of the fatty acids bound to phospholipids to the CoA-ester pool and vice versa and their homologs, derivatives and analogs. Phospholipids for the purposes of the invention are understood as meaning phosphatidylcholine, phosphatidylethanolamine, phosphatidylserine, phosphatidylglycerol and/or phosphatidylinositol, advantageously phosphatidylcholine. The terms acyl-CoA:lysophospholipid acyltransferase(s) comprise nucleic acid sequences which encode an acyl-CoA:lysophospholipid acyltransferase and part of which may be a coding region and likewise corresponding 5' and 3' untranslated sequence regions. The terms production or productivity are known in the art and encompass the concentration of the fermentation product (compounds of the formula I) which is formed within a specific period of time and in a specific fermentation volume (for example kg of product per hour per liter). The term production efficiency comprises the time required for obtaining a specific production quantity (for example the time required by the cell to establish a certain throughput rate of a fine chemical). The term yield or product/carbon yield is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained in a specific culture quantity over a specified period of time is increased. The terms biosynthesis or biosynthetic pathway are known in the art and comprise the synthesis of a compound, preferably an organic compound, by a cell from intermediates, for example in a multi-step and strongly regulated process. The terms catabolism or catabolic pathway are known in the art and comprise the cleavage of a compound, preferably of an organic compound, by a cell to give catabolites (in more general terms, smaller or less complex molecules), for example in a multi-step and strongly regulated process. The term metabolism is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

In a further embodiment, derivatives of the nucleic acid molecule according to the invention represented in SEQ ID NO: 1, SEQ ID NO: 3, SEQ ID NO: 5 or SEQ ID NO: 7 encode proteins with at least 40%, advantageously from approximately 50 to 60%, advantageously at least from approximately 60 to 70% and more preferably at least from approximately 70 to 80%, 80 to 90%, 90 to 95% and most preferably at least approximately 96%, 97%, 98%, 99% or more homology (=identity) with a complete amino acid sequence of SEQ ID NO: 2, SEQ ID NO: 4, SEQ ID NO: 6 or SEQ ID NO: 8. The homology was calculated over the entire amino acid or nucleic acid sequence region. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as a percentage were determined over the entire sequence region using the program BestFit and the following settings: Gap Weight: 8, Length Weight: 2.

Moreover, the invention comprises nucleic acid molecules which differ from one of the nucleotide sequences shown in SEQ ID NO: 1, SEQ ID NO: 3, SEQ ID NO: 5 or SEQ ID NO: 7 (and parts thereof) owing to the degeneracy of the genetic code and which thus encode the same acyl-CoA:lysophospholipid acyltransferase as those encoded by the nucleotide sequences shown in SEQ ID NO: 1, SEQ ID NO: 3, SEQ ID NO: 5 or SEQ ID NO: 7.

In addition to the acyl-CoA:lysophospholipid acyltransferase(s) shown in SEQ ID NO: 1, SEQ ID NO: 3, SEQ ID NO: 5 or SEQ ID NO: 7, the skilled worker will recognize that DNA sequence polymorphisms which lead to changes in the amino acid sequences of the acyl-CoA:lysophospholipid acyltransferase(s) may exist within a population. These genetic polymorphisms in the acyl-CoA:lysophospholipid acyltransferase gene may exist between individuals within a population owing to natural variation. These natural variants usually bring about a variance of 1 to 5% in the nucleotide sequence of the acyl-CoA:lysophospholipid acyltransferase gene. Each and every one of these nucleotide variations and resulting amino acid polymorphisms in the acyl-CoA:lysophospholipid acyltransferase which are the result of natural variation and do not modify the functional activity of acyl-CoA:lysophospholipid acyltransferases are to be encompassed by the invention.

Owing to their homology to the acyl-CoA:lysophospholipid acyltransferase nucleic acids disclosed here, nucleic acid molecules which are advantageous for the process according to the invention can be isolated following standard hybridization techniques under stringent hybridization conditions, using the sequences or part thereof as hybridization probe. In this context it is possible, for example, to use isolated nucleic acid molecules which are least 15 nucleotides in length and which hybridize under stringent conditions with the nucleic acid molecules which comprise a nucleotide sequence of SEQ ID NO: 1, SEQ ID NO: 3, SEQ ID NO: 5 or SEQ ID NO: 7. Nucleic acids with at least 25, 50, 100, 250 or more nucleotides can also be used. The term "hybridizes under stringent conditions" as used in the present context is intended to describe hybridization and washing conditions under which nucleotide sequences with at least 60% homology to one another usually remain hybridized with one another. Conditions are preferably such that sequences with at least approximately 65%, preferably at least approximately 70% and especially preferably at least 75% or more homology to one another usually remain hybridized to one another. These stringent conditions are known to the skilled worker and described, for example, in Current Protocols in Molecular Biology, John Wiley & Sons, N.Y. (1989), 6.3.1-6.3.6. A preferred nonlimiting example of stringent hybridization conditions is hybridizations in 6× sodium chloride/sodium citrate (=SSC) at approximately 45° C., followed by one or more washing steps in 0.2×SSC, 0.1% SDS at 50 to 65° C. The skilled worker knows that these hybridization conditions differ depending on the type of nucleic acid and, for example when organic solvents are present, regarding temperature and buffer concentration. Under "standard hybridization conditions", for example, the hybridization temperature is, depending on the type of nucleic acid, between 42° C. and 58° C. in aqueous buffer with a concentration of 0.1 to 5×SSC (pH 7.2). If organic solvent, for example 50% formamide, is present in the abovementioned buffer, the temperature under standard conditions is approximately 42° C. The hybridization conditions for DNA:DNA hybrids, for example, are 0.1×SSC and 20° C. to 45° C., preferably 30° C. to 45° C. The hybridization conditions for DNA:RNA hybrids are, for example, 0.1×SSC and 30° C. to 55° C., preferably 45° C. to 55° C. The abovementioned hybridization temperatures are determined by way of example for a nucleic acid with approximately 100 bp (=base pairs) in length and with a G+C content of 50% in the absence of formamide. The skilled worker knows how to determine the required hybridization conditions on the basis of the abovementioned textbooks or textbooks such as Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

In order to determine the percentage of homology (=identity) of two amino acid sequences (for example one of the sequences of SEQ ID NO: 2, SEQ ID NO: 4, SEQ ID NO: 6 or SEQ ID NO: 8) or of two nucleic acids (for example SEQ ID NO: 1, SEQ ID NO: 3, SEQ ID NO: 5 or SEQ ID NO: 7), the sequences are written one under the other for an optimal comparison (for example, gaps may be introduced into the sequence of a protein or of a nucleic acid in order to generate an optimal alignment with the other protein or the other nucleic acid). Then, the amino acid residues or nucleotides at the corresponding amino acid positions or nucleotide positions are compared. If a position in a sequence is occupied by the same amino acid residue or the same nucleotide as the corresponding position in the other sequence, then the molecules are homologous at this position (i.e. amino acid or nucleic acid "homology" as used in the present context corresponds to amino acid or nucleic acid "identity"). The percentage of homology between the two sequences is a function of the number of positions which the sequences share (i.e. % homology=number of identical positions/total number of positions×100). The terms homology and identity are therefore to be considered as synonymous.

An isolated nucleic acid molecule which encodes an acyl-CoA:lysophospholipid acyltransferase which is homologous to a protein sequence of SEQ ID NO: 2, SEQ ID NO: 4, SEQ ID NO: 6 or SEQ ID NO: 8 can be generated by introducing one or more nucleotide substitutions, additions or deletions in/into a nucleotide sequence of SEQ ID NO: 1, SEQ ID NO: 3, SEQ ID NO: 5 or SEQ ID NO: 7 so that one or more amino acid substitutions, additions or deletions are introduced in/into the protein which is encoded. Mutations in one of the sequences of SEQ ID NO: 1, SEQ ID NO: 3, SEQ ID NO: 5 or SEQ ID NO: 7 can be introduced by standard techniques such as site-specific mutagenesis and PCR-mediated mutagenesis. It is preferred to generate conservative amino acid substitutions in one or more of the predicted nonessential amino acid residues. In a "conservative amino acid substitution", the amino acid residue is replaced by an amino acid residue with a similar side chain. Families of amino acid residues with similar side chains have been defined in the art. These families comprise amino acids with basic side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in an acyl-CoA:lysophospholipid acyltransferase is thus preferably replaced by another amino acid residue from the same family of side chains. In another embodiment, the mutations can, alternatively, be introduced randomly over all or part of the sequence encoding the acyl-CoA:lysophospholipid acyltransferase, for example by saturation mutagenesis, and the resulting mutants can be screened by the herein-described acyl-CoA:lysophospholipid acyltransferase activity in order to identify mutants which have retained the acyl-CoA:lysophospholipid acyltransferase activity. Following the mutagenesis of one of the sequences of SEQ ID NO: 1, SEQ ID NO: 3, SEQ ID NO: 5 or SEQ ID NO: 7, the protein which is encoded can be expressed recombinantly, and the activity of the protein can be determined, for example using the tests described in the present text.

The present invention is illustrated in greater detail by the examples which follow, which are not to be construed as limiting. The content of all of the references, patent applications, patents and published patent applications cited in the present patent application is herewith incorporated by reference.

EXAMPLES

Example 1

General Methods a) General Cloning Methods:

Cloning methods such as, for example, restriction cleavages, agarose gel electrophoresis, purification of DNA fragments, transfer of nucleic acids to nitrocellulose and nylon membranes, linking of DNA fragments, transformation of *Escherichia coli* and yeast cells, cultivation of bacteria and sequence analysis of recombinant DNA were carried out as described in Sambrook et al. (1989) (Cold Spring Harbor Laboratory Press: ISBN 0-87969-309-6) or Kaiser, Michaelis and Mitchell (1994) "Methods in Yeast Genetics" (Cold Spring Harbor Laboratory Press: ISBN 0-87969-451-3).

b) Chemicals

Unless stated otherwise in the text, the chemicals used were obtained in analytical-grade quality from Fluka (Neu-Ulm, Germany), Merck (Darmstadt, Germany), Roth (Karlsruhe, Germany), Serva (Heidelberg, Germany) and Sigma (Deisenhofen, Germany). Solutions were prepared using purified, pyrogen-free water, referred to as $H_2O$ hereinbelow, from a Milli-Q Water System water purification system (Millipore, Eschborn, Germany). Restriction endonucleases, DNA-modifying enzymes and molecular-biological kits were obtained from AGS (Heidelberg, Germany), Amersham (Brunswick, Germany), Biometra (Gottingen, Germany), Boehringer (Mannheim, Germany), Genomed (Bad Oeynhausen, Germany), New England Biolabs (Schwalbach/Taunus, Germany), Novagen (Madison, Wis., USA), Perkin-Elmer (Weiterstadt, Germany), Pharmacia (Freiburg, Germany), Qiagen (Hilden, Germany) and Stratagene (Amsterdam, the Netherlands). Unless stated otherwise, they were used according to the manufacturer's instructions.

c) Cloning and Expression of Desaturases and Elongases

The *Escherichia coli* strain XL1 Blue MRF' kan (Stratagene) was used for subcloning Δ6-desaturase from *Physcomitrella patens*. This gene was functionally expressed using the *Saccharomyces cerevisiae* strain INVSc 1 (Invitrogen Co.), *E. coli* was cultured in Luria-Bertani broth (LB, Duchefa, Haarlem, the Netherlands) at 37° C. If necessary, ampicillin (100 mg/liter) was added and 1.5% (w/v) agar was added for solid LB media. *S. cerevisiae* was cultured at 30° C.

either in YPG medium or in complete minimal medium without uracil (CMdum; see in: Ausubel, F. M., Brent, R., Kingston, R. E., Moore, D. D., Seidman, J. G., Smith, J. A., Struhl, K., Albright, L. B., Coen, D. M., and Varki, A. (1995) Current Protocols in Molecular Biology, John Wiley & Sons, New York) with either 2% (w/v) raffinose or glucose. For solid media, 2% (w/v) Bacto™-Agar (Difco) were added. The plasmids used for cloning and expression are pUC18 (Pharmacia) and pYES2 (Invitrogen Co.).

d) Cloning and Expression of PUFA-Specific Desaturases and Elongases

For expression in plants, cDNA clones of SEQ ID NO: 9, 11 or 13 were modified so as for only the coding region to be amplified by means of polymerase chain reaction with the aid of two oligonucleotides. Care was taken here to observe a consensus sequence upstream of the start codon, for efficient translation. To this end, either the ATA or the AAA base sequence was chosen and inserted into the sequence upstream of the ATG [Kozak, M. (1986) Point mutations define a sequence flanking the AUG initiator codon that modulates translation by eukaryotic ribosomes, Cell 44, 283-2929]. In addition, a restriction cleavage site was introduced upstream of this consensus triplet, which must be compatible with the cleavage site of the target vector into which the fragment is to be cloned and with the aid of which gene expression is to be carried out in microorganisms or plants.

The PCR reaction was carried out in a thermocycler (Biometra), using plasmid DNA as template and Pfu DNA polymerase (Stratagene) and the following temperature program: 3 min at 96° C., followed by 30 cycles of 30 s at 96° C., 30 s at 55° C. and 2 min at 72° C., 1 cycle of 10 min at 72° C. and stop at 4° C. The annealing temperature was varied depending on the oligonucleotides chosen. A synthesis time of about one minute per kilobase pair of DNA has to be taken as starting point. Other parameters which influence the PCR, such as, for example, Mg ions, salt, DNA polymerase etc., are familiar to the skilled worker in the field and may be varied as required.

The correct size of the amplified DNA fragment was confirmed by means of agarose-TBE gel electrophoresis. The amplified DNA was extracted from the gel using the QIAquick gel extraction kit (QIAGEN) and ligated into the SmaI restriction site of the dephosphorylated pUC18 vector, using the Sure Clone Ligations Kit (Pharmacia), resulting in the pUC derivatives. After transformation of E. coli XL1 Blue MRF' kan a DNA minipreparation [Riggs, M. G., & McLachlan, A. (1986) A simplified screening procedure for large numbers of plasmid mini-preparation. BioTechniques 4, 310-313] of ampicillin-resistant transformants was carried out, and positive clones were identified by means of BamHI restriction analysis. The sequence of the cloned PCR product was confirmed by means of resequencing using the ABI PRISM Big Dye Terminator Cycle Sequencing Ready Reaction Kit (Perkin-Elmer, Weiterstadt, Germany).

e) Transformation of *Agrobacterium*

Unless described otherwise, *Agrobacterium*-mediated plant transformation was carried out with the aid of an *Agrobacterium tumefaciens* strain, as by Deblaere et al. (1984, Nucl. Acids Res. 13, 4777-4788).

f) Plant Transformation

Unless described otherwise, *Agrobacterium*-mediated plant transformation was carried out using standard transformation and regeneration techniques (Gelvin, Stanton B., Schilperoort, Robert A., Plant Molecular Biology Manual, 2nd ed., Dordrecht: Kluwer Academic Publ., 1995, in Sect., Ringbuc Zentrale Signatur: BT11-P ISBN 0-7923-2731-4; Glick, Bernard R., Thompson, John E., Methods in Plant Molecular Biology and Biotechnology, Boca Raton: CRC Press, 1993, 360 S., ISBN 0-8493-5164-2).

According thereto, it is possible to transform, for example, oilseed rape by means of cotyledon or hypocotyl transformation (Moloney et al., Plant Cell 8 (1989) 238-242; De Block et al., Plant Physiol. 91 (1989) 694-701). The use of antibiotics for the selection of *agrobacteria* and plants depends on the binary vector used for transformation and the *Agrobacterium* strain. Normally, oilseed rape is selected using kanamycin as selectable plant marker.

The transformation of soya may be carried out using, for example, a technique described in EP-A-0 0424 047 (Pioneer Hi-Bred International) or in EP-A-0 0397 687, U.S. Pat. No. 5,376,543, U.S. Pat. No. 5,169,770 (University Toledo).

The transformation of plants using particle bombardment, polyethylene glycol-mediated DNA uptake or via the silicon carbonate fiber technique is described, for example, by Freeling and Walbot "The maize handbook" (1993) ISBN 3-540-97826-7, Springer Verlag New York).

Unless described otherwise, *Agrobacterium*-mediated gene transfer into linseed (*Linum usitatissimum*) was carried out by the technique as described in Mlynarova et al. [(1994) Plant Cell Report 13:282-285].

g) Plasmids for Plant Transformation

Binary vectors based on the vectors pBinAR (Höfgen and Willmitzer, Plant Science 66 (1990) 221-230) or pGPTV (Becker et al. 1992, Plant Mol. Biol. 20:1195-1197) were used for plant transformation. The binary vectors which comprise the nucleic acids to be expressed are constructed by ligating the cDNA in sense orientation into the T-DNA. 5' of the cDNA, a plant promoter activates cDNA transcription. A polyadenylation sequence is located 3' of the cDNA. The binary vectors may carry different marker genes such as, for example, the acetolactate synthase gene (AHAS or ALS) [Ott et al., J. Mol. Biol. 1996, 263:359-360] which imparts a resistance to the imidazolinones or the nptII marker gene which codes for a kanamycin resistance imparted by neomycin phosphotransferase.

Tissue-specific expression of the nucleic acids can be achieved using a tissue-specific promoter. Unless described otherwise, the LeB4 or the USP promoter or the phaseolin promoter was cloned 5' of the cDNA. Terminators used were the NOS terminator and the OCS terminator (see FIG. 8). FIG. 8 depicts a vector map of the vector used for expression, pSUN3CeLPLAT.

It is also possible to use any other seed-specific promoter element such as, for example, the napin or arcelin promoter (Goossens et al. 1999, Plant Phys. 120(4):1095-1103 and Gerhardt et al. 2000, Biochimica et Biophysica Acta 1490(1-2):87-98).

The CaMV-35S promoter or a v-ATPase C1 promoter can be used for constitutive expression in the whole plant.

The nucleic acids used in the process which encode acyl-CoA:lysophospholipid acyltransferases; desaturases or elongases were cloned into a binary vector one after the other by constructing a plurality of expression cassettes, in order to mimic the metabolic pathway in plants.

Within an expression cassette, the protein to be expressed may be guided into a cellular compartment by using a signal peptide, for example for plastids, mitochondria or the endoplasmic reticulum (Kermode, Crit. Rev. Plant Sci. 15, 4 (1996) 285-423). The signal peptide is cloned 5' of and in frame with the cDNA in order to achieve the subcellular localization of the fusion protein.

Examples of multiexpression cassettes were disclosed in DE 102 19 203 and are given again below.

i.) Promoter-Terminator Cassettes

Expression cassettes consist of at least two functional units such as a promoter and a terminator. Further desired gene sequences such as targeting sequences, coding regions of genes or parts thereof etc. may be inserted between promoter and terminator. To construct the expression cassettes, promoters and terminators (USP promoter: Baeumlein et al., Mol Gen Genet, 1991, 225 (3):459-67); OCS terminator: Gielen et al. EMBO J. 3 (1984) 835ff.) were isolated with the aid of the polymerase chain reaction and tailor-made with flanking sequences of choice on the basis of synthetic oligonucleotides.

Examples of oligonucleotides which may be used are the following:

```
USP1 upstream (SEQ ID NO: 38):
-CCGGAATTCGGCGCGCCGAGCTCCTCGAGCAAATTTACACATTGCCA- USP2 upstream (SEQ ID NO: 39):
-CCGGAATTCGGCGCGCCGAGCTCCTCGAGCAAATTTACACATTGCCA- USP3 upstream (SEQ ID NO: 40):
-CCGGAATTCGGCGCGCCGAGCTCCTCGAGCAAATTTACACATTGCCA- USP1 downstream (SEQ ID NO: 41):
-AAAACTGCAGGCGGCCGCCCACCGCGGTGGGCTGGCTATGAAGAAATT- USP2 downstream (SEQ ID NO: 42):
-CGCGGATCCGCTGGCTATGAAGAAATT- USP3 downstream (SEQ ID NO: 43):
-TCCCCCGGGATCGATGCCGGCAGATCTGCTGGCTATGAAGAAATT- OCS1 upstream (SEQ ID NO: 44):
-AAAACTGCAGTCTAGAAGGCCTCCTGCTTTAATGAGATAT- OCS2 upstream (SEQ ID NO: 45):
-CGCGGATCCGATATCGGGCCCGCTAGCGTTAACCCTGCTTTAATGAGAT
AT- OCS3 upstream (SEQ ID NO: 46):
-TCCCCCGGGCCATGGCCTGCTTTAATGAGATAT- OCS1 downstream (SEQ ID NO: 47):
-CCCAAGCTTGGCGCGCCGAGCTCGAATTCGTCGACGGACAATCAGTAAA
TTGA- OCS2 downstream (SEQ ID NO: 48):
-CCCAAGCTTGGCGCGCCGAGCTCGAATTCGTCGACGGACAATCAGTAAA
TTGA- OCS3 downstream (SEQ ID NO: 49):
-CCCAAGCTTGGCGCGCCGAGCTCGTCGACGGACAATCAGTAAATTGA-
```

The methods are known to the skilled worker in the field and are well known from the literature.

In a first step, a promoter and a terminator were amplified via PCR. The terminator was then cloned into a recipient plasmid and, in a second step, the promoter was inserted upstream of the terminator. As a result, an expression cassette was cloned into the basic plasmid. The plasmids pUT1, 2 and 3 were thus generated on the basis of the pUC19 plasmid.

The corresponding constructs or plasmids are defined in SEQ ID NO: 15, 16 to 17. They comprise the USP promoter and the OCS terminator. Based on these plasmids, the construct pUT12 was generated by cutting pUT1 by means of SalI/ScaI and pUT2 by means of XhoI/ScaI. The fragments comprising the expression cassettes were ligated and transformed into E. coli XL1 blue MRF. After isolating ampicillin-resistant colonies, DNA was prepared and those clones which comprise two expression cassettes were identified by restriction analysis. The XhoI/SalI ligation of compatible ends has eliminated here the two cleavage sites, XhoI and SalI, between the expression cassettes. The resulting plasmid, pUT12, is indicated in SEQ ID NO: 18. Subsequently, pUT12 was cut again by means of SalI/ScaI and pUT3 was cut by means of XhoI/ScaI. The fragments comprising the expression cassettes were ligated and transformed into E. coli XL1 blue MRF. After isolation from ampicillin-resistant colonies, DNA was again prepared, and those clones which comprise three expression cassettes were identified by restriction analysis. In this manner, a set of multiexpression cassettes was produced which can be utilized for insertion of desired DNA and which is described in table 1 and which moreover can incorporate further expression cassettes.

Said cassettes comprise the following elements:

TABLE 1

| PUC19 derivative | Cleavage sites upstream of the USP promoter | Multiple cloning cleavage sites | Cleavage sites downstream of the OCS terminator |
| --- | --- | --- | --- |
| PUT1 | EcoRI/AscI/SacI/XhoI | BstXI/NotI/PstI/XbaI/StuI | SalI/EcoRI/SacI/AscI/HindIII |
| PUT2 | EcoRI/AscI/SacI/XhoI | BamHI/EcoRV/ApaI/NheI/HpaI | SalI/EcoRI/SacI/AscI/HindIII |
| PUT3 | EcoRI/AscI/SacI/XhoI | BglII/NaeI/ClaI/SmaI/NcoI | SalI/SacI/AscI/HindIII |
| PUT12 double expression cassette | EcoRI/AscI/SacI/XhoI | BstXI/NotI/PstI/XbaI/StuI and BamHI/EcoRV/ApaI/NheI/HpaI | SalI/EcoRI/SacI/AscI/HindIII |
| PUT123 triple expression cassette | EcoRI/AscI/SacI/XhoI | 1. BstXI/NotI/PstI/XbaI/StuI and 2. BamHI/EcoRV/ApaI/NheI/HpaI and 3. BglII/NaeI/ClaI/SmaI/NcoI | SalI/SacI/AscI/HindIII |

Furthermore, further multiexpression cassettes may be generated, as described and as specified in more detail in table 2, with the aid of the
i) USP promoter or with the aid of the
ii) 700 base pair 3' fragment of the LeB4 promoter or with the aid of the
iii) DC3 promoter and employed for seed-specific gene expression.

The DC3 promoter is described in Thomas, Plant Cell 1996, 263:359-368 and consists merely of the region from −117 to +26, which is why it therefore constitutes one of the smallest known seed-specific promoters. The expression cassettes may comprise several copies of the same promoter or else be constructed via three different promoters.

Advantageously used polylinker- or polylinker-terminator-polylinkers can be found in the sequences SEQ ID NO: 23 to 25.

TABLE 2

Multiple expression cassettes

| Plasmid name of the pUC19 derivative | Cleavage sites upstream of the particular promoter | Multiple cloning cleavage sites | Cleavage sites downstream of the OCS terminator |
|---|---|---|---|
| pUT1 (pUC19 with USP-OCS1) | EcoRI/AscI/SacI/XhoI | (1) BstXI/NotI/PstI/XbaI/StuI | SalI/EcoRI/SacI/AscI/HindIII |
| PDCT (pUC19 with DC3-OCS) | EcoRI/AscI/SacI/XhoI | (2) BamHI/EcoRV/ApaI/NheI/HpaI | SalI/EcoRI/SacI/AscI/HindIII |
| PleBT (pUC19 with LeB4(700)-OCS) | EcoRI/AscI/SacI/XhoI | (3) BglII/NaeI/ClaI/SmaI/NcoI | SalI/SacI/AscI/HindIII |
| PUD12 (pUC 19 with USP-OCS1 and with DC3-OCS) | EcoRI/AscI/SacI/XhoI | (1) BstXI/NotI/PstI/XbaI/StuI and (2) BamHI/EcoRV/ApaI/NheI/HpaI | SalI/EcoRI/SacI/AscI/HindIII |
| PUDL123 Triple expression cassette (pUC19 with USP/DC3 and LeB4-700) | EcoRI/AscI/SacI/XhoI | (1) BstXI/NotI/PstI/XbaI/StuI and (2) BamHI/(EcoRV*)/ApaI/NheI/HpaI and (3) BglII/NaeI/ClaI/SmaI/NcoI | SalI/SacI/AscI/HindIII |

*EcoRV cleavage site cuts in the 700 base pair fragment of the LeB4 promoter (LeB4-700)

Further promoters for multigene constructs can be generated analogously, in particular by using the
a) 2.7 kB fragment of the LeB4 promoter or with the aid of the
b) phaseolin promoter or with the aid of the
c) constitutive v-ATPase c1 promoter.

It may be particularly desirable to use further particularly suitable promoters for constructing seed-specific multiexpression cassettes, such as, for example, the napin promoter or the arcelin-5 promoter.

Further vectors which can be utilized in plants and which have one or two or three promoter-terminator expression cassettes can be found in the sequences SEQ ID NO: 26 to SEQ ID NO: 31.

ii.) Generation of expression constructs which comprise promoter, terminator and desired gene sequence for the expression of Pufa genes in plant expression cassettes.

The Δ6-elongase Pp_PSE1 is first inserted into the first cassette in pUT123 via BstXI and XbaI. Then, the moss Δ6-desaturase (Pp_des6) is inserted via BamHI/NaeI into the second cassette and, finally, the Phaeodactylum Δ5-desaturase (Pt_des5) is inserted via BglII/NcoI into the third cassette (see SEQ ID NO: 19). The triple construct is named pARA1. Taking into consideration sequence-specific restriction cleavage sites, further expression cassettes, as set out in table 3 and referred to as pARA2, pARA3 and pARA4, may be generated.

TABLE 3

Combinations of desaturases and elongases

| Gene plasmid | Δ6-Desaturase | Δ5-Desaturase | Δ6-Elongase |
|---|---|---|---|
| pARA1 | Pp_des6 | Pt_des5 | Pp_PSE1 |
| pARA2 | Pt_des6 | Pt_des5 | Pp_PSE1 |
| pARA3 | Pt_des6 | Ce_des5 | Pp_PSE1 |
| PARA4 | Ce_des6 | Ce_des5 | Ce_PSE1 | des5 = PUFA-specific Δ5-desaturase
des6 = PUFA-specific Δ6-desaturase

TABLE 3-continued

Combinations of desaturases and elongases

| Gene plasmid | Δ6-Desaturase | Δ5-Desaturase | Δ6-Elongase |
|---|---|---|---|

PSE = PUFA-specific Δ6-elongase
Pt_des5 = Δ5-desaturase from *Phaeodactylum tricornutum*
Pp_des6 or Pt_des6 = Δ6-desaturase from *Physcomitrella patens* or *Phaeodactylum tricornutum*
Pp = *Physcomitrella patens*,
Pt = *Phaeodactylum tricornutum*
Pp_PSE1 = Δ6-elongase from *Physcomitrella patens*
Pt_PSE1 = Δ6-elongase from *Phaeodactylum tricornutum*
Ce_des5 = Δ5-desaturase from *Caenorhabditis elegans* (Genbank Acc. No. AF078796)
Ce_des6 = Δ6-desaturase from *Caenorhabditis elegans* (Genbank Acc. No. AF031477, bases 11-1342)
Ce_PSE1 = Δ6-elongase from *Caenorhabditis elegans* (Genbank Acc. No. AF244356, bases 1-867)

Further desaturases or elongase gene sequences may also be inserted into the expression cassettes of the type described, such as, for example, Genbank Acc. No. AF231981, NM_013402, AF206662, AF268031, AF226273, AF110510 or AF110509.

iii.) transfer of expression cassettes into vectors for the transformation of *Agrobacterium tumefaciens* and for the transformation of plants The constructs thus generated were inserted into the binary vector pGPTV by means of AscI. For this purpose, the multiple cloning sequence was extended by an AscI cleavage site. For this purpose, the polylinker was synthesized de novo in the form of two double-stranded oligonucleotides, with an additional AscI DNA sequence being inserted. The oligonucleotide was inserted into the pGPTV vector by means of EcoRI and HindIII. The cloning techniques required are known to the skilled worker and may readily be found in the literature as described in example 1.

The nucleic acid sequences for Δ5-desaturase (SEQ ID NO: 13), Δ6-desaturase (SEQ ID NO: 9) and Δ6-elongase (SEQ ID NO: 11), which were used for the experiments described below, were the sequences from *Physcomitrella patens* and *Phaeodactylum tricornutum*. The corresponding amino acid sequences are the sequences SEQ ID NO: 10, SEQ ID NO: 12 and SEQ ID NO: 14. A vector which comprises all of the abovementioned genes is indicated in SEQ ID NO: 19. The corresponding amino acid sequences of the genes can be found in SEQ ID NO: 20, SEQ ID NO: 21 and SEQ ID NO: 22.

Example 2

Cloning and Characterization of the CeLPLATs a) Database Search

The ceLPLATs (=acyl-CoA:lysophospholipid acyltransferase from *Caenorhabditis elegans*) were identified by sequence comparisons with known LPA-ATs. The search was restricted to the nematode genome (*Caenorhabditis elegans*) with the aid of the BLAST-Psi algorithm (Altschul et al., J. Mol. Biol. 1990, 215: 403-410), since this organism synthesizes LCPUFAs. The probe employed in the sequence comparison was an LPAAT protein sequence from *Mus musculus* (MsLPAAT Accession No. NP_061350). LPLAT catalyzes, by a reversible transferase reaction, the ATP-independent synthesis of acyl-CoAs from phospholipids with the aid of CoA as cofactor (Yamashita et al., J. Biol. Chem. 2001, 20: 26745-26752). Sequence comparisons enabled two putative ceLPLAT sequences to be identified (Accession No. T06E8.1 and F59F4.4). The identified sequences are most similar to each other and to MsLPAATs (FIG. 1). The alignment was generated using the Clustal program.

b) Cloning of the CeLPLATs

Primer pairs were synthesized on the basis of the ceLPLAT nucleic acid sequences (table 1) and the corresponding cDNAs were isolated from a *C. elegans* cDNA library by means of PCR processes. The respective primer pairs were selected so as to carry, apart from the start codon, the yeast consensus sequence for high-efficiency translation (Kozak, Cell 1986, 44:283-292). The LPLAT cDNAs were amplified in each case using 2 μl of cDNA-library solution as template, 200 μM dNTPs, 2.5 U of "proof-reading" pfu polymerase and 50 μmol of each primer in a total volume of 50 μl. The conditions for the PCR were as follows: first denaturation at 95° C. for 5 minutes, followed by 30 cycles at 94° C. for 30 seconds, 58° C. for one minute and 72° C. for 2 minutes, and a final extension step at 72° C. for 10 minutes. The sequence of the LPLAT cDNAs was confirmed by DNA sequencing.

TABLE 4

Nucleotide sequences of the PCR primers for cloning CeLPLATs

| Primer | | | Nucleotide sequence |
|---|---|---|---|
| 5' T06E8.1f* | (SEQ ID NO: 50) | 5' ACATAATGGAGAACTTCTGGTCGATCGTC 3' |
| 3' T06E8.1r* | (SEQ ID NO: 51) | 5' TTACTCAGATTTCTTCCCGTCTTT 3' |
| 5' F59F4.4f* | (SEQ ID NO: 52) | 5' ACATAATGACCTTCCTAGCCATATTA 3' |
| 3' F59F4.4r* | (SEQ ID NO: 53) | 5' TGAGATATTCAAATTGGCGGCTTC 3' |

*f: forward, r: reverse

Example 3

Analysis of the Effect of the Recombinant Proteins on Production of the Desired Product a) Possible Preparation Methods The effect of genetic modification in fungi, algae, ciliates or, as described in the examples hereinabove, on the production of the polyunsaturated fatty acids in yeasts, or in plants may be determined by growing the modified microorganisms or the modified plant under suitable conditions (such as those described above) and studying the medium and/or the cellular components for increased production of the lipids or fatty acids. These analytical techniques are known to the skilled worker and comprise spectroscopy, thin layer chromatography, various types of staining methods, enzymic and microbiological methods and analytical chromatography such as high-performance liquid chromatography (see, for example, Ullmann, Encyclopedia of Industrial Chemistry, vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, vol. 17; Rehm et al. (1993) Biotechnology, vol. 3, chapter III: "Product recovery and purification", pp. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, vol. B3; chapter 11, pp. 1-27, VCH: Weinheim; and Dechow, F. J. (1989) Separation and purification techniques in biotechnology, Noyes Publications).

Apart from the abovementioned methods for detecting fatty acids in yeasts, plant lipids are extracted from plant material as described by Cahoon et al. (1999) Proc. Natl. Acad. Sci. USA 96 (22):12935-12940, and Browse et al. (1986) Analytic Biochemistry 152:141-145. The qualitative and quantitative analysis of lipids or fatty acids is described in Christie, William W., Advances in Lipid Methodology, Ayr/Scotland: Oily Press (Oily Press Lipid Library; 2); Christie, William W., Gas Chromatography and Lipids. A Practical Guide-Ayr, Scotland: Oily Press, 1989, Repr. 1992, IX, 307 S. (Oily Press Lipid Library; 1); "Progress in Lipid Research, Oxford: Pergamon Press, 1 (1952) 16 (1977) under the title.: Progress in the Chemistry of Fats and Other Lipids CODEN.

Thus, fatty acids or triacylglycerol (=TAG, abbreviations indicated in brackets) may be analyzed, for example, by means of fatty acid methyl esters (=FAME), gas liquid chromatography-mass spectrometry (=GC-MS) or thin layer chromatography (TLC).

Unequivocal proof for the presence of fatty acid products may be obtained by means of analyzing recombinant organisms following standard analytical procedures: GC, GC-MS or TLC, as variously described by Christie and references therein (1997, in: Advances on Lipid Methodology, fourth ed.: Christie, Oily Press, Dundee, 119-169; 1998, Gaschromatographie-Massenspektrometrie-Verfahren [Gas chromatography-mass spectrometry methods], Lipide 33:343-353).

The plant material to be analyzed may for this purpose be disrupted either by sonification, glass milling, liquid nitrogen and grinding or via other applicable processes. After the material has been disrupted, it is then centrifuged. The sediment is then resuspended in distilled water, heated at 100° C. for 10 min, cooled on ice and centrifuged again, followed by extraction in 0.5 M sulfuric acid in methanol containing 2% dimethoxypropane for 1 h at 90° C., leading to hydrolyzed oil and lipid compounds which result in transmethylated lipids. These fatty acid methyl esters may then be extracted in petroleum ether and finally be subjected to GC analysis using a capillary column (Chrompack, WCOT Fused Silica, CP-Wax-52 CB, 25 µm, 0.32 mm), with a temperature gradient of between 170° C. and 240° C. for 20 min and at 240° C. for 5 min. The identity of the resulting fatty acid methyl esters can be defined using standards available from commercial sources (i.e. Sigma).

In the case of fatty acids for which no standards are available, the identity may be shown via derivatization and subsequent GC-MS analysis. For example, the localization of triple-bond fatty acids is shown via GC-MS after derivatization with 4,4-dimethoxyoxazoline derivatives (Christie, 1998, see above).

b) Fatty Acid Analysis in Plants

Total fatty acids were extracted from plant seeds and analyzed by means of gas chromatography.

The seeds were taken up with 1% sodium methoxide in methanol and incubated at RT (approx. 22° C.) for 20 min. This was followed by washing with NaCl solution and taking up the FAMEs in 0.3 ml of heptane.

The samples were fractionated on a ZEBRON-ZB Wax capillary column (30 m, 0.32 mm, 0.25 µm; Phenomenex) in a Hewlett Packard 6850 gas chromatograph with flame ionization detector. The oven temperature was programmed from 70° C. (hold for 1 min) to 200° C. at a rate of 20° C./min, then to 250° C. (hold for 5 min) at a rate of 5° C./min and finally to 260° C. at a rate of 5° C./min. The carrier gas used was nitrogen (4.5 ml/min at 70° C.). The fatty acids were identified by comparison with retention times of FAME standards (SIGMA).

Example 4

Functional Characterization of CeLPLATs in Yeast a) Heterologous Expression in *Saccharomyces cerevisiae*

To characterize the function of the *C. elegans* CeLPLATs, the open reading frames of the particular cDNAs were cloned downstream of the galactose-inducible GAL1 promoter of pYes2.1Topo, using the pYes2.1TOPO TA Expression Kit (Invitrogen), resulting in pYes2-T06E8.1 and pYes2-F59F4.4.

Since expression of the CeLPLATs should result in an efficient exchange of the acyl substrates, the double construct pESCLeu-PpD6-Pse1 which includes the open reading frames of a Δ6-desaturase (PpD6) and a Δ6-elongase (PSE1) from *Physcomitrella patens* (see DE 102 19 203) was also prepared. The nucleic acid sequence of said Δ6-desaturase (PpD6) and said Δ6-elongase (Pse1) are indicated in each case in SEQ ID NO: 9 and SEQ ID NO: 11. The corresponding amino acid sequences can be found in SEQ ID NO. 10 and SEQ ID NO: 12.

The *Saccharomyces cerevisiae* strains C13ABYS86 (protease-deficient) and INVSc1 were transformed simultaneously with the vectors pYes2-T06E8.1 and pESCLeu-PpD6-Pse1 and, respectively, pYes2-F59F4.4 and pESCLeu-PpD6-Pse1 by means of a modified PEG/lithium acetate protocol. The control used was a yeast which was transformed with the pESCLeu-PpD6-Pse1 vector and the empty vector pYes2. The transformed yeasts were selected on complete minimal medium (CMdum) agar plates containing 2% glucose but no uracil or leucine. After selection, 4 transformants, two pYes2-T06E8.1/pESCLeu-PpD6-Pse1 and two pYes2-F59F4.4/pESCLeu-PpD6-Pse1 and one pESCLeu-PpD6-Pse1/pYes2 were selected for further functional expression. The experiments described were also carried out in the yeast strain INVSc1.

In order to express the CeLPLATs, precultures of in each case 2 ml of CMdum liquid medium containing 2% (w/v) raffinose but no uracil or leucine were first inoculated with the selected transformants and incubated at 30° C., 200 rpm, for 2 days. 5 ml of CMdum liquid medium (without uracil and leucine) containing 2% raffinose, 1% (v/v) Tergitol NP-40 and 250 µM linoleic acid ($18:2^{\Delta 9,12}$) or linolenic acid ($18:3^{\Delta 9,12,15}$) were then inoculated with the precultures to an $OD_{600}$ of 0.08. Expression was induced at an $OD_{600}$ of 0.2-0.4 by adding 2% (w/v) galactose. The cultures were incubated at 20° C. for a further 48 h.

Fatty Acid Analysis

The yeast cells from the main cultures were harvested by centrifugation (100×g, 10 min, 20° C.) and washed with 100 mM $NaHCO_3$, pH 8.0 in order to remove residual medium and fatty acids. Fatty acid methyl esters (FAMEs) were prepared from the yeast cell sediments by acidic methanolysis. For this, the cell sediments were incubated with 2 ml of 1N methanolic sulfuric acid and 2% (v/v) dimethoxypropane at 80° C. for 1 h. Extraction of the FAMES was carried out by extracting twice with petroleum ether (PE). Nonderivatized fatty acids were removed by washing the organic phases in each case once with 2 ml of 100 mM $NaHCO_3$, pH 8.0 and 2 ml of distilled water. The PE phases were subsequently dried with $Na_2SO_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph with flame ionization detector. The conditions for the GLC analysis were as follows: the oven temperature was programmed from 50° C. to 250° C. at a rate of 5° C./min and finally at 250° C. (hold) for 10 min. The signals were identified by comparing the retention times with those of corresponding fatty acid standards (Sigma).

Acyl-CoA Analysis

The acyl-CoA analysis was carried out as described in Larson and Graham (2001; Plant Journal 25: 115-125).

Expression Analysis

FIGS. 2 A and B and FIGS. 3 A and B depict the fatty acid profiles of transgenic C13ABYS86 yeasts fed with $18:2^{\Delta 9,12}$ and $18:3^{\Delta 9,12,15}$, respectively. The substrates fed can be detected in large amounts in all transgenic yeasts. All four transgenic yeasts display synthesis of $18:3^{\Delta 6,9,12}$ and $20:3^{\Delta 8,11,14}$ and, respectively, $18:4^{\Delta 6,9,12,15}$ and $20:4^{\Delta 8,11,14,17}$, the products of the Δ6-desaturase and Δ6-elongase reactions, meaning that the genes PpD6 and Pse1 were able to be functionally expressed.

FIG. 2 depicts, as described above, the fatty acid profiles of transgenic C13ABYS86 S. cerevisiae cells. The fatty acid methyl esters were synthesized by acidic methanolysis of intact cells which had been transformed either with the pES-CLeu-PpD6-Pse1/pYes2 (A) or with the pYes2-T06E8.1/pESCLeu-PpD6-Pse1 (B) vectors. The yeasts were cultured in minimal medium in the presence of $18:2^{\Delta 9,12}$. The fatty acid methyl esters were subsequently analyzed by GLC.

In the control yeasts transformed with the pESCLeu-PpD6-Pse1/pYes2 vectors, the proportion of $20:3^{\Delta 8,11,14}$ to which $18:3^{\Delta 6,9,12}$ is elongated by Pse1 is substantially lower than in the yeasts which additionally express LPLAT T06E8.1. In fact, elongation of $18:3^{\Delta 6,9,12}$ and $18:4^{\Delta 6,9,12,15}$ was improved by 100-150% by additional expression of CeLPLAT (T06E8.1) (FIG. 4). This significant increase in the LCPUFA content can be explained only as follows: the exogenously fed fatty acids ($18:2^{\Delta 9,12}$ and $18:3^{\Delta 9,12,15}$, respectively) are first incorporated into phospholipids and desaturated there by Δ6-desaturase to give $18:3^{\Delta 6,9,12}$ and $18:4^{\Delta 6,9,12,15}$. Only after reequilibration with the acyl-CoA pool, $18:3^{\Delta 6,9,12}$ and $18:4^{\Delta 6,9,12,15}$ can be elongated by the elongase to give $20:3^{\Delta 8,11,14}$- and $20:4^{\Delta 8,11,14,17}$-CoA, respectively and then incorporated again into the lipids. LPLAT T06E8.1 is capable of converting the Δ6-desaturated acyl groups very efficiently back to CoA thioesters. Interestingly, it was also possible to improve the elongation of the fed fatty acids $18:2^{\Delta 9,12}$ and $18:3^{\Delta 9,12,15}$. (FIGS. 2 A and B and FIGS. 3 A and B, respectively).

FIG. 3 indicates the fatty acid profiles of transgenic C13ABYS86 S. cerevisiae cells. Synthesis of the fatty acid methyl esters was carried out by acidic methanolysis of intact cells which had been transformed either with the vectors pESCLeu-PpD6-Pse1/pYes2 (A) or with the vectors pYes2-T06E8.1/pESCLeu-PpD6-Pse1 (B). The yeasts were cultured in minimal medium in the presence of $18:3^{\Delta 9,12,15}$. The fatty acid methyl esters were subsequently analyzed via GLC.

In contrast, expression of a different CeLPLAT (F59F4.4) has no influence on elongation (FIG. 4). F59F4.4 evidently does not encode an LPLAT. Thus, not every putative LPLAT nucleic acid sequence is enzymatically active in the reaction found according to the invention.

FIG. 4 indicates the elongation of exogenously applied $18:2^{\Delta 9,12}$ and $18:3^{\Delta 9,12,15}$, following their endogenous Δ6-desaturation (data of FIGS. 2 and 3). The exogenously fed fatty acids are first incorporated into phospholipids and desaturated there to give $18:3^{\Delta 8,9,12}$ and $18:4^{\Delta 6,9,12,15}$. Only after reequilibration with the acyl-CoA pool can $18:3^{\Delta 6,9,12}$ and $18:4^{\Delta 6,9,12,15}$ be elongated by the elongase to give $20:3^{\Delta 8,11,14}$- and $20:4^{\Delta 8,11,14,17}$-CoA, respectively, and then incorporated again into the lipids. LPLAT T06E8.1 is capable of converting the Δ6-desaturated acyl groups efficiently back to CoA-thioesters.

These results show that CeLPLAT (T06E8.1) after coexpression with Δ6-desaturase and Δ6-elongase, leads to efficient production of $C_{20}$-PUFAs. These results can be explained by the fact that CeLPLAT (T06E8.1) makes possible an efficient exchange of the newly synthesized fatty acids between lipids and the acyl-CoA pool (see FIG. 7).

FIG. 7 indicates the acyl-CoA composition of transgenic INVSc1 yeasts transformed with the pESCLeu PpD6Pse1/pYes2 (A) or pESCLeu-PpD6-Pse1/pYes2-T06E8.1 (B) vectors. The yeast cells were cultured in minimal medium without uracil and leucine in the presence of 250 μM $18:2^{\Delta 9,12}$. The acyl-CoA derivatives were analyzed via HPLC.

When using the yeast strain INVSc1 for coexpression of CeLPLAT (T06E8.1) together with PpD6 and Pse1, the following picture emerges: control yeasts expressing PpD6 and Pse1 comprise, as already shown when using the strain C13ABYS86, only small amounts of the elongation product ($20:3^{\Delta 8,11,14}$, with 18:2 feed) and $20:4^{\Delta 8,11,14,17}$, with 18:3 feed; see FIGS. 5 A and 6 A, respectively). Additional expression of CeLPLAT (T06E8.1) results in a marked increase in these elongation products (see FIGS. 5 B and 6 B). Table 6 indicates that additional expression of CeLPLAT surprisingly causes an 8 fold increase in the $20:3^{\Delta 8,11,14}$, (with 18:2 feed) and, respectively, the $20:4^{\Delta 8,11,14,17}$ (with 18.3 feed) content. It is also revealed that $C16:2^{\Delta 6,9}$ is also elongated more efficiently to give $C18:2^{\Delta 6,9}$.

TABLE 5

Fatty acid composition (in mol %) of transgenic yeasts transformed with the pESCLeu PpD6Pse1/pYes2 (PpD6 Pse1) or pESCLeu-PpD6-Pse1/pYes2-T06E8.1 (PpD6 Pse1 + T06E8) vectors.

| | Feeding with 250 μM $18:2^{\Delta 9,12}$ | | Feeding with 250 μM $18:3^{\Delta 9,12,15}$ | |
|---|---|---|---|---|
| Fatty acids | PpΔ6/Pse1 | PpΔ6/Pse1 + T06E8 | PpΔ6/Pse1 | PpΔ6/Pse1 + T06E8 |
| 16:0 | 15.31 ± 1.36 | 15.60 ± 1.36 | 12.20 ± 0.62 | 16.25 ± 1.85 |
| $16:1^{\Delta 9}$ | 23.22 ± 2.16 | 15.80 ± 3.92 | 17.61 ± 1.05 | 14.58 ± 1.93 |
| 18:0 | 5.11 ± 0.63 | 7.98 ± 1.28 | 5.94 ± 0.71 | 7.52 ± 0.89 |
| $18:1^{\Delta 9}$ | 15.09 ± 0.59 | 16.01 ± 2.53 | 15.62 ± 0.34 | 15.14 ± 2.61 |
| $18:1^{\Delta 11}$ | 4.64 ± 1.09 | 11.80 ± 1.12 | 4.56 ± 0.18 | 13.07 ± 1.66 |
| $18:2^{\Delta 9,12}$ | 28.72 ± 3.25 | 14.44 ± 1.61 | — | — |
| $18:3^{\Delta 6,9,12}$ | 3.77 ± 0.41 | 4.72 ± 0.72 | — | — |
| $18:3^{\Delta 9,12,15}$ | — | — | 32.86 ± 1.20 | 14.14 ± 2.52 |
| $18:4^{\Delta 6,9,12,15}$ | — | — | 5.16 ± 1.04 | 3.31 ± 1.15 |
| $20:2^{\Delta 11,14}$ | 2.12 ± 0.86 | 4.95 ± 4.71 | — | — |
| $20:3^{\Delta 8,11,14}$ | 1.03 ± 0.14 | 8.23 ± 1.59 | — | — |
| $20:3^{\Delta 11,14,17}$ | — | — | 4.12 ± 1.54 | 6.95 ± 2.52 |
| $20:4^{\Delta 8,11,14,17}$ | — | — | 1.34 ± 0.28 | 8.70 ± 1.11 |

The yeast cells were cultured in minimal medium without uracil and leucine in the presence of 250 μM $18:2^{\Delta 9,12}$ or $18:3^{\Delta 9,12,15}$. The fatty acid methyl esters were obtained by acidic methanolysis of whole cells and analyzed via GLC. Each value indicates the average (n = 4) ± standard deviation.

The fatty acid profile of transgenic INVSc1 S. cerevisiae cells can be found in FIG. 5. The fatty acid methyl esters were synthesized by acidic methanolysis of intact cells which had been transformed either with the pESCLeu-PpD6-Pse1/pYes2 (A) or with the pYes2-T06E8.1/pESCLeu-PpD6-Pse1 (B) vectors. The yeasts were cultured in minimal medium in the presence of $18:2^{\Delta 9,12}$. The fatty acid methyl esters were subsequently analyzed via GLC.

FIG. 6 depicts the fatty acid profiles of transgenic INVSc1 S. cerevisiae cells. The fatty acid methyl esters were synthesized by acidic methanolysis of intact cells which had been transformed either with the pESCLeu-PpD6-Pse1/pYes2 (A) or with the pYes2-T06E8.1/pESCLeu-PpD6-Pse1 (B) vectors. The yeasts were cultured in minimal medium in the presence of $18:3^{\Delta,12,15}$. The fatty acid methyl esters were subsequently analyzed via GLC.

A measure for the efficiency of LCPUFA biosynthesis in transgenic yeast is the quotient of the content of the desired Δ6-elongation product after Δ6-desaturation ($20:3^{\Delta 8,11,14}$ and $20:4^{\Delta 8,11,14,17}$, respectively) to the content of fatty acid fed in ($18:2^{\Delta 9,12}$ and $18:3^{\Delta 9,12,15}$, respectively). This quotient is 0.04 in INVSc1 control yeasts expressing PpD6 and Pse1, and 0.60 in yeasts expressing CeLPLAT in addition to PpD6 and Pse1. In other words: the content of desired Δ6-elongation product after Δ6-desaturation with coexpression of CeLPLAT is 60% of the content of the fatty acid fed in each case. In control yeasts, this content is only approx. 4%, meaning a 15 fold increase in the efficiency of LCPUFA biosynthesis in transgenic yeast due to coexpression of LPLAT.

Interestingly, coexpression of CeLPLAT causes not only an increase in the elongation products mentioned, $20:3^{\Delta 8,11,14}$ and $20:4^{\Delta 8,11,14,17}$, but also an increase in the $20:3^{\Delta 8,11,14}:20:2^{\Delta 11,14}$ ratio and the $20:4^{\Delta 8,11,14,17}:20:3^{\Delta 11,14,17}$ ratio, respectively. This means that, in the presence of LPLAT, Δ6-elongase preferably uses polyunsaturated fatty acids ($18:3^{\Delta 6,9,12}$ and $18:4^{\Delta 6,9,12,15}$) as substrate, while no distinct substrate specificity is discernible in the absence of LPLAT ($18:2^{\Delta 9,12}$ and $18:3^{\Delta 9,12,15}$ are also elongated). The reason for this may be protein-protein interactions between Δ6-elongase, Δ6-desaturase and LPLAT or posttranslational modifications (partial proteolysis, for example). This will also explain why the above-described rise in Δ6-elongation products with coexpression of Δ6-desaturase, Δ6-elongase and LPLAT is smaller when a protease-deficient yeast strain is used.

Acyl-CoA analyses of transgenic INVSc1 yeasts fed with $18:2^{\Delta 9,12}$ gave the following result: no $18:3^{\Delta 6,9,12}$-CoA and $20:3^{\Delta 8,11,14}$-CoA is detectable in control yeasts expressing PpD6 and Pse1, indicating that neither the substrate ($18:3^{\Delta 6,9,12}$-CoA) nor the product ($20:3^{\Delta 8,11,14}$-CoA) of Δ6-elongase is present in detectable amounts in control yeasts. This suggests that the transfer of $18:3^{\Delta 6,9,12}$ from membrane lipids into the acyl-CoA pool does not take place or does not take place correctly, meaning that there is hardly any substrate available for the Δ6-elongase present, and this in turn explains the low elongation product content in control yeasts. INVSc1 yeasts which express CeLPLAT in addition to PpD6 and Pse1 and which had been fed with $18:2^{\Delta 9,12}$ have substantial amounts of $20:3^{\Delta 8,11,14}$-CoA but not of $18:3^{\Delta 6,9,12}$-CoA. This indicates that LPLAT transfers $18:3^{\Delta 6,9,12}$ from the membrane lipids to the acyl-CoA pool very efficiently. $18:3^{\Delta 6,9,12}$-CoA is then elongated by Δ6-elongase so that $20:3^{\Delta 8,11,14}$-CoA but not any $18:3^{\Delta 6,9,12}$-CoA is detectable.

b) Functional Characterization of the CeLPLATs in Transgenic Plants

Expression of Functional CeLPLAT in Transgenic Plants

DE 102 19 203 describes transgenic plants whose seed oil comprises small amounts of ARA and EPA, due to seed-specific expression of functional genes coding for Δ6-desaturase, Δ6-elongase and Δ5-desaturase. The vector exploited for transformation of these plants can be found in SEQ ID NO: 19. In order to increase the content of these LCPUFAs, the gene CeLPLAT (T06E8.1) was additionally expressed in seeds in the transgenic plants mentioned.

For this purpose, the coding region of CeLPLAT was amplified via PCR.

Table 6 indicates the primers used for cloning another CeLPLAT clone into binary vectors.

TABLE 6

Nucleotide sequences of the PCR primers for cloning CeLPLAT (T06E8.1) into the binary vector pSUN3

| Primer | Nucleotide sequence |
|---|---|
| ARe503f* (SEQ ID NO: 54) | 5' TTAAGCGCGGCCGCATGGAGAACTTCTGGTCG 3' |
| ARe504r* (SEQ ID NO: 55) | 5' ACCTCGGCGGCCGCCCTTTTACTCAGATTTC 3' |

*f: forward, r: reverse

The PCR product was cloned into a pENTRY vector between USP promoter and OCS terminator. The expression cassette was then cloned into the binary pSUN300 vectors. The vector obtained was referred to as pSUN3CeLPLAT (FIG. 8). In addition, the CeLPLAT coding regions were amplified and cloned between LegB4 promoter and OCS terminator. This vector was referred to as pGPTVCeLPLAT (FIG. 9A).

In addition, the CeLPLAT coding regions were amplified via PCR and cloned between LegB4 promoter and OCS terminator. The PCR primers used for this were selected so as for an efficient Kozak sequence to be introduced into the PCR product. Moreover, the CeLPLAT DNA sequence was modified so as to adapt to the codon usage of higher plants.

The following primers were used for the PCR:

```
Forward primer (SEQ ID NO: 56):
5'-ACATAATGGAGAACTTCTGGTCTATTGTTGTGTTTTTTCTA-3'

Reverse primer (SEQ ID NO: 57):
5'-CTAGCTAGCTTACTCAGATTTCTTCCCGTCTTTTGTTTCTC-3'
```

The PCR product was cloned into the cloning vector pCR Script and cloned via the restriction enzymes XmaI and SacI into the vector pGPTV LegB4-700. The resulting plasmid was referred to as pGPTV LegB4-700+T06E8.1 (FIG. 9A).

The same PCR product was in addition cloned into a multigene expression vector which already comprised the genes for a Phaeodactylum tricornutum delta-6-desaturase (SEQ ID NO: 32, amino acid sequence SEQ ID NO: 33) and a P. patens delta-6-elongase. The resulting plasmid was referred to as pGPTV USP/OCS-1,2,3 PSE1 (Pp)+D6-Des(Pt)+2AT (T06E8-1) (FIG. 9B). The sequences of the vector and of the genes can be found in SEQ ID NO: 34, SEQ ID NO: 35, SEQ ID NO: 36 and SEQ ID NO: 37. The Phaeodactylum tricornutum Δ6-desaturase extends from nucleotide 4554 to 5987 in SEQ ID NO: 34. The *Physcomitrella patens* Δ6-elongase extends from nucleotide 1026 to 1898 and that of *Caenorhabditis elegans* LPLAT extends from nucleotide 2805 to 3653 in SEQ ID NO: 34.

Tobacco plants were cotransformed with the pSUN3CeLPLAT vector and the vector described in DE 102 19 203 and SEQ ID NO: 19, which comprises genes coding for Δ6-desaturase, Δ6-elongase and Δ5-desaturase, with transgenic plants being selected using kanamycin.

Tobacco plants were moreover transformed with the pGPTV USP/OCS-1,2,3 PSE1(Pp)+D6-Des(Pt)+2AT (T06E8-1) vector [see SEQ ID NO: 34, SEQ ID NO: 35, SEQ ID NO: 36 and SEQ ID NO: 37].

Linseed was transformed with the pSUN3CeLPLAT vector. The resulting transgenic plants were crossed with those transgenic linseed plants which already comprised small amounts of ARA and EPA, owing to functional gene expression of Δ6-desaturase, Δ6-elongase and Δ5-desaturase.

Linseed was furthermore transformed with the pGPTV LegB4-700+T06E8.1 vector. The resulting transgenic plants were crossed with those transgenic linseed plants which already comprised small amounts of ARA and EPA, owing to functional expression of Δ6-desaturase, Δ6-elongase and Δ5-desaturase.

The seeds of transgenic tobacco and linseed plants were, as described hereinbefore [example 3b)], studied for increased LCPUFAs contents.

The function of acyl-CoA:lysophopholipid acyltransferase (LPLAT) can be deduced from the studies presented herein as depicted in FIG. 10. The biosynthetic pathway of LCPUFAS is thus as follows.

Desaturases catalyze the introduction of double bonds into lipid-coupled fatty acids (sn2-acyl-phosphatidylcholine), while the elongases exclusively catalyze the elongation of coenzyme A-esterified fatty acids (acyl-CoAs). According to this mechanism, the alternating action of desaturases and elongases requires continuous exchange of acyl substrates between phospholipids and acyl-CoA pool and thus the existence of an additional activity which converts the acyl substrates to the substrate form required in each case, i.e. lipids (for desaturases) or CoA thioesters (for elongases). This exchange between acyl-CoA pool and phospholipids is made possible by LCPUFA-specific LPLAT. The biosynthesis of ARA (A) takes place analogously to that of EPA (B), but with the difference that, in the case of EPA, a Δ15-desaturation takes place upstream of the Δ6-desaturation so that α18:3-PC acts as a substrate for Δ6-desaturase. The biosynthesis of DHA requires a further exchange between phospholipids and acyl-CoA pool via LPLAT: $20:5^{\Delta 5,8,11,14,17}$ is transferred from the phospholipids pool to the CoA pool and, after Δ5-elongation, $22:5^{\Delta 7,10,13,16,19}$ is transferred from the CoA pool to the phospholipids pool and finally converted by Δ4-desaturase to give DHA. The same applies to the exchange in the biosynthetic pathway using Δ8-desaturase, Δ9-elongase and Δ5-desaturase.

Equivalents

Many equivalents of the specific embodiments of the invention described herein can be identified or found by the skilled worker by using merely routine experiments. These equivalents are intended to be within the scope of the patent claims.

We claim:

1. A fatty acid composition comprising polyunsaturated C18-fatty acids with at least two double bonds and polyunsaturated C20- and/or C22-fatty acids with at least two double bonds, wherein said fatty acid composition is prepared by a process comprising:
   (a) introducing and expressing in an organism at least one nucleic acid coding for a polypeptide having acyl-CoA:lysophospholipid-acyltransferase activity,
   (b) culturing and harvesting said organism, and
   (c) isolating a fatty acid composition from said organism, wherein the nucleic acid coding for a polypeptide having acyl-CoA:lysophospholipid-acyltransferase activity comprises a nucleotide sequence selected from the group consisting of:
   (i) the nucleotide sequence of SEQ ID NO: 1,
   (ii) a nucleotide sequence having at least 90% identity to the nucleotide sequence of SEQ ID NO: 1,
   (iii) a nucleotide sequence encoding the polypeptide sequence of SEQ ID NO: 2, and
   (iv) a nucleotide sequence encoding a polypeptide having at least 90% identity to the polypeptide sequence of SEQ ID NO: 2,
   and wherein the fatty acid composition comprises higher content of polyunsaturated C20- and/or C22-fatty acids as compared to a fatty acid composition isolated from a corresponding control organism without expressing said nucleic acid.

2. The fatty acid composition of claim 1, wherein the organism is a plant.

3. An oil composition or a lipid composition comprising the fatty acid composition of claim 2.

4. A process for producing a fatty acid composition comprising:
   (a) introducing and expressing into a plant at least one nucleic acid coding for a polypeptide having acyl-CoA:lysophospholipid-acyltransferase activity,
   (b) culturing and harvesting said plant, and
   (c) isolating a fatty acid composition from said plant, wherein the nucleic acid coding for a polypeptide having acyl-CoA:lysophospholipid-acyltransferase activity comprises a nucleotide sequence selected from the group consisting of:
   (i) the nucleotide sequence of SEQ ID NO: 1,
   (ii) a nucleotide sequence having at least 90% identity to the nucleotide sequence of SEQ ID NO: 1,
   (iii) a nucleotide sequence encoding the polypeptide sequence of SEQ ID NO: 2, and
   (iv) a nucleotide sequence encoding a polypeptide having at least 90% identity to the polypeptide sequence of SEQ ID NO: 2.

5. The process of claim 4, wherein the fatty acid composition are isolated from said plant by pressing or extracting the plant, parts of the plant, or organs of the plant.

6. The process of claim 5, wherein the parts of the plants are leaf, stem, seeds, root, tubers, anthers, fibers, root hairs, stalks, embryos, calli, cotyledons, petioles, harvested material, plant tissue, reproductive tissue, or cell cultures.

7. The process of claim 5, wherein the parts of the plant are plant seeds, and wherein the seeds are previously comminuted, steamed or roasted.

8. The process of claim 7, wherein the plant seeds are pressed or extracted with a solvent.

9. The process of claim 4, wherein the fatty acid composition are isolated from said plant by cold-beating or cold-pressing.

10. The process of claim 4, wherein the process further comprises introducing additional nucleic acid sequences into said plant, wherein the additional nucleic acid sequences code for polypeptides of the fatty acid or lipid metabolism selected from the group consisting of acyl-CoA-dehydrogenase(s), acyl-ACP[=acyl carrier protein] desaturase(s), acyl-ACP thioesterase(s), fatty acid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases and fatty acid elongase(s).

11. The process of claim 4, wherein the process further comprises introducing additional nucleic acid sequences into the plant, wherein the additional nucleic acid sequences code for polypeptides selected from the group consisting of Δ4-desaturase, Δ5-desaturase, Δ6-desaturase, Δ8-desaturase, Δ9-desaturase, Δ12-desaturase, Δ5-elongase, Δ6-elongase and Δ9-elongase.

12. The process of claim 4, wherein the polypeptide having acyl-CoA:lysophospholipid acyltransferase activity uses C16-, C18-, C20- or C22-fatty acids as substrate.

13. The fatty acid composition of claim 1, further comprising polyunsaturated C16-fatty acids and polyunsaturated C18-, C20- and/or C22-fatty acids having at least three double bonds.

14. The fatty acid composition of claim 1, comprising at least two polyunsaturated fatty acids selected from the group consisting of dihomo-γ-linolenic acid, arachidonic acid, eicosapentaenoic acid, docosapentaenoic acid, and docosahexaenoic acid.

15. The fatty acid composition of claim 1, wherein the polypeptide having acyl-CoA:lysophospholipid-acyltransferase activity uses C16-, C18-, C20- or C22-fatty acids as substrate.

16. The fatty acid composition of claim 1, wherein the nucleic acid coding for a polypeptide having acyl-CoA:lysophospholipid-acyltransferase activity comprises:
   (a) a nucleotide sequence having at least 95% identity to the nucleotide sequence of SEQ ID NO: 1; or
   (b) a nucleotide sequence encoding a polypeptide having at least 95% identity to the polypeptide sequence of SEQ ID NO: 2.

17. The fatty acid composition of claim 1, wherein at least one additional nucleic acid sequence coding for a polypeptide selected from the group consisting of acyl-CoA-dehydrogenase(s), acyl-ACP[=acyl carrier protein] desaturase(s), acyl-ACP thioesterase(s), fatty acid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases and fatty acid elongase(s) is further introduced and expressed in the organism.

18. The fatty acid composition of claim 1, wherein at least one additional nucleic acid sequence coding for a polypeptide selected from the group consisting of Δ4-desaturase, Δ5-desaturase, Δ6-desaturase, Δ8-desaturase, Δ9-desaturase, Δ12-desaturase, Δ5-elongase, Δ6-elongase and Δ9-elongase is further introduced and expressed in the organism.

19. A fatty acid composition obtained from a plant comprising polyunsaturated C18-, C20- and C22-fatty acids with at least two double bonds, wherein said plant expresses at least one heterologous nucleic acid encoding a polypeptide having acyl-CoA:lysophospholipid- acyltransferase activity, wherein said at least one heterologous nucleic acid comprises a nucleotide sequence selected from the group consisting of:

(i) the nucleotide sequence of SEQ ID NO: 1,
(ii) a nucleotide sequence having at least 90% identity to the nucleotide sequence of SEQ ID NO: 1,
(iii) a nucleotide sequence encoding the polypeptide sequence of SEQ ID NO: 2, and
(iv) a nucleotide sequence encoding a polypeptide having at least 90% identity to the polypeptide sequence of SEQ ID NO: 2,
and wherein said fatty acid composition comprises higher content of polyunsaturated C20- and C22-fatty acids as compared to a fatty acid composition isolated from a corresponding control plant without expressing said heterologous nucleic acid.

20. The fatty acid composition of claim 19, comprising eicosapentaenoic acid (EPA) and arachidonic acid (ARA), wherein the ratio of EPA:ARA is at least 1:2.

* * * * *

SEQUENCE LISTING

```
<160> NUMBER OF SEQ ID NOS: 59

<210> SEQ ID NO 1
<211> LENGTH: 849
<212> TYPE: DNA
<213> ORGANISM: Caenorhabditis elegans
<220> FEATURE:
<221> NAME/KEY: CDS
<222> LOCATION: (1)..(849)
<223> OTHER INFORMATION: Acyl-CoA:lysophospholipid acyltransferase

<400> SEQUENCE: 1 atg gag aac ttc tgg tcg atc gtc gtg ttt ttt cta ctc tca att ctc      48
Met Glu Asn Phe Trp Ser Ile Val Val Phe Phe Leu Leu Ser Ile Leu
1               5                   10                  15 ttc att tta tat aac ata tcg aca gta tgc cac tac tat atg cgg att      96
Phe Ile Leu Tyr Asn Ile Ser Thr Val Cys His Tyr Tyr Met Arg Ile
            20                  25                  30 tcg ttt tat tac ttc aca att tta ttg cat gga atg gaa gtt tgt gtt     144
Ser Phe Tyr Tyr Phe Thr Ile Leu Leu His Gly Met Glu Val Cys Val
        35                  40                  45 aca atg atc cct tct tgg cta aat ggg aag ggt gct gat tac gtg ttt     192
Thr Met Ile Pro Ser Trp Leu Asn Gly Lys Gly Ala Asp Tyr Val Phe
    50                  55                  60 cac tcg ttt ttc tat tgg tgt aaa tgg act ggt gtt cat aca aca gtc     240
His Ser Phe Phe Tyr Trp Cys Lys Trp Thr Gly Val His Thr Thr Val
65                  70                  75                  80 tat gga tat gaa aaa aca caa gtt gaa ggt ccg gct gta gtt att tgt     288
Tyr Gly Tyr Glu Lys Thr Gln Val Glu Gly Pro Ala Val Val Ile Cys
                85                  90                  95
```

```
aat cat cag agt tct ctc gac att cta tcg atg gca tca atc tgg ccg      336
Asn His Gln Ser Ser Leu Asp Ile Leu Ser Met Ala Ser Ile Trp Pro
        100                 105                 110 aag aat tgt gtt gta atg atg aaa cga att ctt gcc tat gtt cca ttc      384
Lys Asn Cys Val Val Met Met Lys Arg Ile Leu Ala Tyr Val Pro Phe
        115                 120                 125 ttc aat ctc gga gcc tac ttt tcc aac aca atc ttc atc gat cga tat      432
Phe Asn Leu Gly Ala Tyr Phe Ser Asn Thr Ile Phe Ile Asp Arg Tyr
        130                 135                 140 aac cgt gaa cgt gcg atg gct tca gtt gat tat tgt gca tct gaa atg      480
Asn Arg Glu Arg Ala Met Ala Ser Val Asp Tyr Cys Ala Ser Glu Met
145                 150                 155                 160 aag aac aga aat ctt aaa ctt tgg gta ttt ccg gaa gga aca aga aat      528
Lys Asn Arg Asn Leu Lys Leu Trp Val Phe Pro Glu Gly Thr Arg Asn
                165                 170                 175 cgt gaa gga ggg ttc att cca ttc aag aaa gga gca ttc aat att gca      576
Arg Glu Gly Gly Phe Ile Pro Phe Lys Lys Gly Ala Phe Asn Ile Ala
                180                 185                 190 gtt cgt gcg cag att ccc att att cca gtt gta ttc tca gac tat cgg      624
Val Arg Ala Gln Ile Pro Ile Ile Pro Val Val Phe Ser Asp Tyr Arg
                195                 200                 205 gat ttc tac tca aag cca ggc cga tat ttc aag aat gat gga gaa gtt      672
Asp Phe Tyr Ser Lys Pro Gly Arg Tyr Phe Lys Asn Asp Gly Glu Val
210                 215                 220 gtt att cga gtt ctg gat gcg att cca aca aaa ggg ctc act ctt gat      720
Val Ile Arg Val Leu Asp Ala Ile Pro Thr Lys Gly Leu Thr Leu Asp
225                 230                 235                 240 gac gtc agc gag ttg tct gat atg tgt cgg gac gtt atg ttg gca gcc      768
Asp Val Ser Glu Leu Ser Asp Met Cys Arg Asp Val Met Leu Ala Ala
                245                 250                 255 tat aag gaa gtt act cta gaa gct cag caa cga aat gcg aca cgg cgt      816
Tyr Lys Glu Val Thr Leu Glu Ala Gln Gln Arg Asn Ala Thr Arg Arg
                260                 265                 270 gga gaa aca aaa gac ggg aag aaa tct gag taa                          849
Gly Glu Thr Lys Asp Gly Lys Lys Ser Glu
                275                 280

<210> SEQ ID NO 2
<211> LENGTH: 282
<212> TYPE: PRT
<213> ORGANISM: Caenorhabditis elegans

<400> SEQUENCE: 2

Met Glu Asn Phe Trp Ser Ile Val Val Phe Phe Leu Leu Ser Ile Leu
1               5                   10                  15

Phe Ile Leu Tyr Asn Ile Ser Thr Val Cys His Tyr Tyr Met Arg Ile
            20                  25                  30

Ser Phe Tyr Tyr Phe Thr Ile Leu Leu His Gly Met Glu Val Cys Val
        35                  40                  45

Thr Met Ile Pro Ser Trp Leu Asn Gly Lys Gly Ala Asp Tyr Val Phe
    50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Val Ile Cys
                85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125
```

```
Phe Asn Leu Gly Ala Tyr Phe Ser Asn Thr Ile Phe Ile Asp Arg Tyr
        130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Pro Val Val Phe Ser Asp Tyr Arg
        195                 200                 205

Asp Phe Tyr Ser Lys Pro Gly Arg Tyr Phe Lys Asn Asp Gly Glu Val
        210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
        275                 280

<210> SEQ ID NO 3
<211> LENGTH: 849
<212> TYPE: DNA
<213> ORGANISM: Caenorhabditis elegans
<220> FEATURE:
<221> NAME/KEY: CDS
<222> LOCATION: (1)..(849)
<223> OTHER INFORMATION: Acyl-CoA:lysophospholipid acyltransferase

<400> SEQUENCE: 3 atg gag aac ttc tgg tcg atc gtc gtg ttt ttt cta ctc tca att ctc      48
Met Glu Asn Phe Trp Ser Ile Val Val Phe Phe Leu Leu Ser Ile Leu
1               5                   10                  15 ttc att tta tat aac ata tcg aca gta tgc cac tac tat atg cgg att      96
Phe Ile Leu Tyr Asn Ile Ser Thr Val Cys His Tyr Tyr Met Arg Ile
            20                  25                  30 tcg ttt tat tac ttc aca att tta ttg cat gga atg gaa gtt tgt gtt     144
Ser Phe Tyr Tyr Phe Thr Ile Leu Leu His Gly Met Glu Val Cys Val
        35                  40                  45 aca atg atc cct tct tgg cta aat ggg aag ggt gct gat tac gtg ttt     192
Thr Met Ile Pro Ser Trp Leu Asn Gly Lys Gly Ala Asp Tyr Val Phe
    50                  55                  60 cac tcg ttt ttc tat tgg tgt aaa tgg act ggt gtt cat aca aca gtc     240
His Ser Phe Phe Tyr Trp Cys Lys Trp Thr Gly Val His Thr Thr Val
65                  70                  75                  80 tat gga tat gaa aaa aca caa gtt gaa ggt ccg gct gta gtt att tgt     288
Tyr Gly Tyr Glu Lys Thr Gln Val Glu Gly Pro Ala Val Val Ile Cys
                85                  90                  95 aat cat cag agt tct ctc gac att cta tcg atg gca tca atc tgg ccg     336
Asn His Gln Ser Ser Leu Asp Ile Leu Ser Met Ala Ser Ile Trp Pro
            100                 105                 110 aag aat tgt gtt gta atg atg aaa cga att ctt gcc tat gtt cca ttc     384
Lys Asn Cys Val Val Met Met Lys Arg Ile Leu Ala Tyr Val Pro Phe
        115                 120                 125 ttc aat ctc gga gcc tac ttt tcc aac aca atc ttc atc gat cga tat     432
Phe Asn Leu Gly Ala Tyr Phe Ser Asn Thr Ile Phe Ile Asp Arg Tyr
    130                 135                 140 aac cgt gaa cgt gcg atg gct tca gtt gat tat tgt gca tct gaa atg     480
Asn Arg Glu Arg Ala Met Ala Ser Val Asp Tyr Cys Ala Ser Glu Met
```

```
Asn Arg Glu Arg Ala Met Ala Ser Val Asp Tyr Cys Ala Ser Glu Met
145                 150                 155                 160 aag aac aga aat ctt aaa ctt tgg gta tct ccg gaa gga aca aga aat    528
Lys Asn Arg Asn Leu Lys Leu Trp Val Ser Pro Glu Gly Thr Arg Asn
                165                 170                 175 cgt gaa gga ggg ttc att cca ttc aag aaa gga gca ttc aat att gca    576
Arg Glu Gly Gly Phe Ile Pro Phe Lys Lys Gly Ala Phe Asn Ile Ala
            180                 185                 190 gtt cgt gcg cag att ccc att att cca gtt gta ttc tca gac tat cgg    624
Val Arg Ala Gln Ile Pro Ile Ile Pro Val Val Phe Ser Asp Tyr Arg
        195                 200                 205 gat ttc tac tca aag cca ggc cga tat ttc aag aat gat gga gaa gtt    672
Asp Phe Tyr Ser Lys Pro Gly Arg Tyr Phe Lys Asn Asp Gly Glu Val
    210                 215                 220 gtt att cga gtt ctg gat gcg att cca aca aaa ggg ctc act ctt gat    720
Val Ile Arg Val Leu Asp Ala Ile Pro Thr Lys Gly Leu Thr Leu Asp
225                 230                 235                 240 gac gtc agc gag ttg tct gat atg tgt cgg gac gtt atg ttg gca gcc    768
Asp Val Ser Glu Leu Ser Asp Met Cys Arg Asp Val Met Leu Ala Ala
                245                 250                 255 tat aag gaa gtt act cta gaa gct cag caa cga aat gcg aca cgg cgt    816
Tyr Lys Glu Val Thr Leu Glu Ala Gln Gln Arg Asn Ala Thr Arg Arg
                260                 265                 270 gga gaa aca aaa gac ggg aag aaa tct gag taa                        849
Gly Glu Thr Lys Asp Gly Lys Lys Ser Glu
            275                 280

<210> SEQ ID NO 4
<211> LENGTH: 282
<212> TYPE: PRT
<213> ORGANISM: Caenorhabditis elegans

<400> SEQUENCE: 4

Met Glu Asn Phe Trp Ser Ile Val Val Phe Leu Leu Ser Ile Leu
1               5                   10                  15

Phe Ile Leu Tyr Asn Ile Ser Thr Val Cys His Tyr Tyr Met Arg Ile
                20                  25                  30

Ser Phe Tyr Tyr Phe Thr Ile Leu Leu His Gly Met Glu Val Cys Val
            35                  40                  45

Thr Met Ile Pro Ser Trp Leu Asn Gly Lys Gly Ala Asp Tyr Val Phe
    50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Val Ile Cys
                85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
    130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Ser Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Ile Pro Val Val Phe Ser Asp Tyr Arg
```

```
                         195                 200                 205
Asp Phe Tyr Ser Lys Pro Gly Arg Tyr Phe Lys Asn Asp Gly Glu Val
        210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
        275                 280

<210> SEQ ID NO 5
<211> LENGTH: 849
<212> TYPE: DNA
<213> ORGANISM: Caenorhabditis elegans
<220> FEATURE:
<221> NAME/KEY: CDS
<222> LOCATION: (1)..(849)
<223> OTHER INFORMATION: Acyl-CoA:lysophospholipid acyltransferase

<400> SEQUENCE: 5 atg gag aac ttc tgg tcg atc gtc gtg ttt ttt cta ctc tca att ctc      48
Met Glu Asn Phe Trp Ser Ile Val Val Phe Phe Leu Leu Ser Ile Leu
1               5                  10                  15 ttc att tta tat aac ata tcg aca gta tgc cac tac tat gtg cgg att      96
Phe Ile Leu Tyr Asn Ile Ser Thr Val Cys His Tyr Tyr Val Arg Ile
            20                  25                  30 tcg ttt tat tac ttc aca att tta ttg cat gga atg gaa gtt tgt gtt     144
Ser Phe Tyr Tyr Phe Thr Ile Leu Leu His Gly Met Glu Val Cys Val
        35                  40                  45 aca atg atc cct tct tgg cta aat ggg aag ggt gct gat tac gtg ttt     192
Thr Met Ile Pro Ser Trp Leu Asn Gly Lys Gly Ala Asp Tyr Val Phe
    50                  55                  60 cac tcg ttt ttc tat tgg tgt aaa tgg act ggt gtt cat aca aca gtc     240
His Ser Phe Phe Tyr Trp Cys Lys Trp Thr Gly Val His Thr Thr Val
65                  70                  75                  80 tat gga tat gaa aaa aca caa gtt gaa ggt ccg gct gta gtt att tgt     288
Tyr Gly Tyr Glu Lys Thr Gln Val Glu Gly Pro Ala Val Val Ile Cys
                85                  90                  95 aat cat cag agt tct ctc gac att cta tcg atg gca tca atc tgg ccg     336
Asn His Gln Ser Ser Leu Asp Ile Leu Ser Met Ala Ser Ile Trp Pro
            100                 105                 110 aag aat tgt gtt gta atg atg aaa cga att ctt gcc tat gtt cca ttc     384
Lys Asn Cys Val Val Met Met Lys Arg Ile Leu Ala Tyr Val Pro Phe
        115                 120                 125 ttc aat ctc gga gcc tac ttt tcc aac aca atc ttc atc gat cga tat     432
Phe Asn Leu Gly Ala Tyr Phe Ser Asn Thr Ile Phe Ile Asp Arg Tyr
    130                 135                 140 aac cgt gaa cgt gcg atg gct tca gtt gat tat tgt gca tct gaa atg     480
Asn Arg Glu Arg Ala Met Ala Ser Val Asp Tyr Cys Ala Ser Glu Met
145                 150                 155                 160 aag aac aga aat ctt aaa ctt tgg gta ttt ccg gaa gga aca aga aat     528
Lys Asn Arg Asn Leu Lys Leu Trp Val Phe Pro Glu Gly Thr Arg Asn
                165                 170                 175 cgt gaa gga ggg ttc att cca ttc aag aaa gga gca ttc aat att gca     576
Arg Glu Gly Gly Phe Ile Pro Phe Lys Lys Gly Ala Phe Asn Ile Ala
            180                 185                 190 gtt cgt gcg cag att ccc att att cca gtt gta ttc tca gac tat cgg     624
Val Arg Ala Gln Ile Pro Ile Ile Pro Val Val Phe Ser Asp Tyr Arg
        195                 200                 205
```

```
gat ttc tac tca aag cca ggc cga tat ttc aag aat gat gga gaa gtt      672
Asp Phe Tyr Ser Lys Pro Gly Arg Tyr Phe Lys Asn Asp Gly Glu Val
    210             215                 220 gtt att cga gtt ctg gat gcg att cca aca aaa ggg ctc act ctt gat      720
Val Ile Arg Val Leu Asp Ala Ile Pro Thr Lys Gly Leu Thr Leu Asp
225             230                 235                 240 gac gtc agc gag ttg tct gat atg tgt cgg gac gtt atg ttg gca gcc      768
Asp Val Ser Glu Leu Ser Asp Met Cys Arg Asp Val Met Leu Ala Ala
            245                 250                 255 tat aag gaa gtt act cta gaa gct cag caa cga aat gcg aca cgg cgt      816
Tyr Lys Glu Val Thr Leu Glu Ala Gln Gln Arg Asn Ala Thr Arg Arg
        260                 265                 270 gga gaa aca aaa gac ggg aag aaa tct gag taa                          849
Gly Glu Thr Lys Asp Gly Lys Lys Ser Glu
            275                 280
```

<210> SEQ ID NO 6
<211> LENGTH: 282
<212> TYPE: PRT
<213> ORGANISM: Caenorhabditis elegans

<400> SEQUENCE: 6

```
Met Glu Asn Phe Trp Ser Ile Val Val Phe Leu Leu Ser Ile Leu
1               5                   10                  15

Phe Ile Leu Tyr Asn Ile Ser Thr Val Cys His Tyr Tyr Val Arg Ile
            20                  25                  30

Ser Phe Tyr Tyr Phe Thr Ile Leu Leu His Gly Met Glu Val Cys Val
            35                  40                  45

Thr Met Ile Pro Ser Trp Leu Asn Gly Lys Gly Ala Asp Tyr Val Phe
        50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Ile Cys
                85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
    130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Pro Val Val Phe Ser Asp Tyr Arg
        195                 200                 205

Asp Phe Tyr Ser Lys Pro Gly Arg Tyr Phe Lys Asn Asp Gly Glu Val
    210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
            260                 265                 270
```

```
Gly Glu Thr Lys Asp Gly Lys Lys Ser Glu
            275                 280
```

<210> SEQ ID NO 7
<211> LENGTH: 849
<212> TYPE: DNA
<213> ORGANISM: Caenorhabditis elegans
<220> FEATURE:
<221> NAME/KEY: CDS
<222> LOCATION: (1)..(849)
<223> OTHER INFORMATION: Acyl-CoA:lysophospholipid acyltransferase

<400> SEQUENCE: 7

```
atg gag aac ttc tgg tcg atc gtc gtg ttt ttt cta ctc tca att ctc      48
Met Glu Asn Phe Trp Ser Ile Val Val Phe Phe Leu Leu Ser Ile Leu
1               5                   10                  15 ttc att tta tat aac ata tcg aca gta tgc cac tac tat atg cgg att      96
Phe Ile Leu Tyr Asn Ile Ser Thr Val Cys His Tyr Tyr Met Arg Ile
            20                  25                  30 tcg ttt tat tac ttc aca att tta ttg cat gga atg gaa gtt tgt gtt     144
Ser Phe Tyr Tyr Phe Thr Ile Leu Leu His Gly Met Glu Val Cys Val
        35                  40                  45 aca atg atc cct tct tgg cta aat ggg aag ggt gct gat tac gtg ttt     192
Thr Met Ile Pro Ser Trp Leu Asn Gly Lys Gly Ala Asp Tyr Val Phe
    50                  55                  60 cac tcg ttt ttc tat tgg tgt aaa tgg act ggt gtt cat aca aca gtc     240
His Ser Phe Phe Tyr Trp Cys Lys Trp Thr Gly Val His Thr Thr Val
65                  70                  75                  80 tat gga tat gaa aaa aca caa gtt gaa ggt ccg gcc gta gtt att tgt     288
Tyr Gly Tyr Glu Lys Thr Gln Val Glu Gly Pro Ala Val Val Ile Cys
                85                  90                  95 aat cat cag ggt tct ctc gac att cta tcg atg gca tca atc tgg ccg     336
Asn His Gln Gly Ser Leu Asp Ile Leu Ser Met Ala Ser Ile Trp Pro
            100                 105                 110 aag aat tgt gtt gta atg atg aaa cga att ctt gcc tat gtt cca ttc     384
Lys Asn Cys Val Val Met Met Lys Arg Ile Leu Ala Tyr Val Pro Phe
        115                 120                 125 ttc aat ctc gga gcc tac ttt tcc aac aca atc ttc atc gat cga tat     432
Phe Asn Leu Gly Ala Tyr Phe Ser Asn Thr Ile Phe Ile Asp Arg Tyr
    130                 135                 140 aac cgt gaa cgt gcg atg gct tca gtt gat tat tgt gca tct gaa atg     480
Asn Arg Glu Arg Ala Met Ala Ser Val Asp Tyr Cys Ala Ser Glu Met
145                 150                 155                 160 aag aac aga aat ctt aaa ctt tgg gta ttt ccg gaa gga aca aga aat     528
Lys Asn Arg Asn Leu Lys Leu Trp Val Phe Pro Glu Gly Thr Arg Asn
                165                 170                 175 cgt gaa gga ggg ttc att cca ttc aag aaa gga gca ttc aat att gca     576
Arg Glu Gly Gly Phe Ile Pro Phe Lys Lys Gly Ala Phe Asn Ile Ala
            180                 185                 190 gtt cgt gcg cag att ccc att att cca gtt gta ttc tca gac tat cgg     624
Val Arg Ala Gln Ile Pro Ile Ile Pro Val Val Phe Ser Asp Tyr Arg
        195                 200                 205 gat ttc tac tca aag cca ggc cga tat ttc aag aat gat gga gaa gtt     672
Asp Phe Tyr Ser Lys Pro Gly Arg Tyr Phe Lys Asn Asp Gly Glu Val
    210                 215                 220 gtt att cga gtt ctg gat gcg att cca aca aaa ggg ctc act ctt gat     720
Val Ile Arg Val Leu Asp Ala Ile Pro Thr Lys Gly Leu Thr Leu Asp
225                 230                 235                 240 gac gtc agc gag ttg tct gat atg tgt cgg gac gtt atg ttg gca gcc     768
Asp Val Ser Glu Leu Ser Asp Met Cys Arg Asp Val Met Leu Ala Ala
                245                 250                 255 tat aag gaa gtt act cta gaa gct cag caa cga aat gcg aca cgg cgt     816
```

```
Tyr Lys Glu Val Thr Leu Glu Ala Gln Gln Arg Asn Ala Thr Arg Arg
            260                 265                 270 gga aca aaa gac ggg aag aaa tct gag taa                              849
Gly Glu Thr Lys Asp Gly Lys Lys Ser Glu
            275                 280
```

<210> SEQ ID NO 8
<211> LENGTH: 282
<212> TYPE: PRT
<213> ORGANISM: Caenorhabditis elegans

<400> SEQUENCE: 8

```
Met Glu Asn Phe Trp Ser Ile Val Val Phe Leu Leu Ser Ile Leu
 1               5                  10                  15

Phe Ile Leu Tyr Asn Ile Ser Thr Val Cys His Tyr Tyr Met Arg Ile
                20                  25                  30

Ser Phe Tyr Tyr Phe Thr Ile Leu Leu His Gly Met Glu Val Cys Val
            35                  40                  45

Thr Met Ile Pro Ser Trp Leu Asn Gly Lys Gly Ala Asp Tyr Val Phe
        50                  55                  60

His Ser Phe Phe Tyr Trp Cys Lys Trp Thr Gly Val His Thr Thr Val
 65                  70                  75                  80

Tyr Gly Tyr Glu Lys Thr Gln Val Glu Gly Pro Ala Val Val Ile Cys
                85                  90                  95

Asn His Gln Gly Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
    130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Ile Pro Val Val Phe Ser Asp Tyr Arg
        195                 200                 205

Asp Phe Tyr Ser Lys Pro Gly Arg Tyr Phe Lys Asn Asp Gly Glu Val
    210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
        275                 280
```

<210> SEQ ID NO 9
<211> LENGTH: 1578
<212> TYPE: DNA
<213> ORGANISM: Physcomitrella patens
<220> FEATURE:
<221> NAME/KEY: CDS
<222> LOCATION: (1)..(1578)
<223> OTHER INFORMATION: Delta-6-desaturase

<400> SEQUENCE: 9

| | | | | | | | | | | | | | | | | |
|---|---|---|---|---|---|---|---|---|---|---|---|---|---|---|---|---|
| atg | gta | ttc | gcg | ggc | ggt | gga | ctt | cag | cag | ggc | tct | ctc | gaa | gaa | aac | 48 |
| Met | Val | Phe | Ala | Gly | Gly | Gly | Leu | Gln | Gln | Gly | Ser | Leu | Glu | Glu | Asn | |
| 1 | | | | 5 | | | | | 10 | | | | | 15 | | |
| atc | gac | gtc | gag | cac | att | gcc | agt | atg | tct | ctc | ttc | agc | gac | ttc | ttc | 96 |
| Ile | Asp | Val | Glu | His | Ile | Ala | Ser | Met | Ser | Leu | Phe | Ser | Asp | Phe | Phe | |
| | | | 20 | | | | | 25 | | | | | 30 | | | |
| agt | tat | gtg | tct | tca | act | gtt | ggt | tcg | tgg | agc | gta | cac | agt | ata | caa | 144 |
| Ser | Tyr | Val | Ser | Ser | Thr | Val | Gly | Ser | Trp | Ser | Val | His | Ser | Ile | Gln | |
| | | 35 | | | | | 40 | | | | | 45 | | | | |
| cct | ttg | aag | cgc | ctg | acg | agt | aag | aag | cgt | gtt | tcg | gaa | agc | gct | gcc | 192 |
| Pro | Leu | Lys | Arg | Leu | Thr | Ser | Lys | Lys | Arg | Val | Ser | Glu | Ser | Ala | Ala | |
| | 50 | | | | | 55 | | | | | 60 | | | | | |
| gtg | caa | tgt | ata | tca | gct | gaa | gtt | cag | aga | aat | tcg | agt | acc | cag | gga | 240 |
| Val | Gln | Cys | Ile | Ser | Ala | Glu | Val | Gln | Arg | Asn | Ser | Ser | Thr | Gln | Gly | |
| 65 | | | | 70 | | | | | 75 | | | | | 80 | | |
| act | gcg | gag | gca | ctc | gca | gaa | tca | gtc | gtg | aag | ccc | acg | aga | cga | agg | 288 |
| Thr | Ala | Glu | Ala | Leu | Ala | Glu | Ser | Val | Val | Lys | Pro | Thr | Arg | Arg | Arg | |
| | | | | 85 | | | | | 90 | | | | | 95 | | |
| tca | tct | cag | tgg | aag | aag | tcg | aca | cac | ccc | cta | tca | gaa | gta | gca | gta | 336 |
| Ser | Ser | Gln | Trp | Lys | Lys | Ser | Thr | His | Pro | Leu | Ser | Glu | Val | Ala | Val | |
| | | | 100 | | | | | 105 | | | | | 110 | | | |
| cac | aac | aag | cca | agc | gat | tgc | tgg | att | gtt | gta | aaa | aac | aag | gtg | tat | 384 |
| His | Asn | Lys | Pro | Ser | Asp | Cys | Trp | Ile | Val | Val | Lys | Asn | Lys | Val | Tyr | |
| | | 115 | | | | | 120 | | | | | 125 | | | | |
| gat | gtt | tcc | aat | ttt | gcg | gac | gag | cat | ccc | gga | gga | tca | gtt | att | agt | 432 |
| Asp | Val | Ser | Asn | Phe | Ala | Asp | Glu | His | Pro | Gly | Gly | Ser | Val | Ile | Ser | |
| | 130 | | | | | 135 | | | | | 140 | | | | | |
| act | tat | ttt | gga | cga | gac | ggc | aca | gat | gtt | ttc | tct | agt | ttt | cat | gca | 480 |
| Thr | Tyr | Phe | Gly | Arg | Asp | Gly | Thr | Asp | Val | Phe | Ser | Ser | Phe | His | Ala | |
| 145 | | | | 150 | | | | | 155 | | | | | 160 | | |
| gct | tct | aca | tgg | aaa | att | ctt | caa | gac | ttt | tac | att | ggt | gac | gtg | gag | 528 |
| Ala | Ser | Thr | Trp | Lys | Ile | Leu | Gln | Asp | Phe | Tyr | Ile | Gly | Asp | Val | Glu | |
| | | | | 165 | | | | | 170 | | | | | 175 | | |
| agg | gtg | gag | ccg | act | cca | gag | ctg | ctg | aaa | gat | ttc | cga | gaa | atg | aga | 576 |
| Arg | Val | Glu | Pro | Thr | Pro | Glu | Leu | Leu | Lys | Asp | Phe | Arg | Glu | Met | Arg | |
| | | | 180 | | | | | 185 | | | | | 190 | | | |
| gct | ctt | ttc | ctg | agg | gag | caa | ctt | ttc | aaa | agt | tcg | aaa | ttg | tac | tat | 624 |
| Ala | Leu | Phe | Leu | Arg | Glu | Gln | Leu | Phe | Lys | Ser | Ser | Lys | Leu | Tyr | Tyr | |
| | | 195 | | | | | 200 | | | | | 205 | | | | |
| gtt | atg | aag | ctg | ctc | acg | aat | gtt | gct | att | ttt | gct | gcg | agc | att | gca | 672 |
| Val | Met | Lys | Leu | Leu | Thr | Asn | Val | Ala | Ile | Phe | Ala | Ala | Ser | Ile | Ala | |
| | 210 | | | | | 215 | | | | | 220 | | | | | |
| ata | ata | tgt | tgg | agc | aag | act | att | tca | gcg | gtt | ttg | gct | tca | gct | tgt | 720 |
| Ile | Ile | Cys | Trp | Ser | Lys | Thr | Ile | Ser | Ala | Val | Leu | Ala | Ser | Ala | Cys | |
| 225 | | | | 230 | | | | | 235 | | | | | 240 | | |
| atg | atg | gct | ctg | tgt | ttc | caa | cag | tgc | gga | tgg | cta | tcc | cat | gat | ttt | 768 |
| Met | Met | Ala | Leu | Cys | Phe | Gln | Gln | Cys | Gly | Trp | Leu | Ser | His | Asp | Phe | |
| | | | | 245 | | | | | 250 | | | | | 255 | | |
| ctc | cac | aat | cag | gtg | ttt | gag | aca | cgc | tgg | ctt | aat | gaa | gtt | gtc | ggg | 816 |
| Leu | His | Asn | Gln | Val | Phe | Glu | Thr | Arg | Trp | Leu | Asn | Glu | Val | Val | Gly | |
| | | | 260 | | | | | 265 | | | | | 270 | | | |
| tat | gtg | atc | ggc | aac | gcc | gtt | ctg | ggg | ttt | agt | aca | ggg | tgg | tgg | aag | 864 |
| Tyr | Val | Ile | Gly | Asn | Ala | Val | Leu | Gly | Phe | Ser | Thr | Gly | Trp | Trp | Lys | |
| | | 275 | | | | | 280 | | | | | 285 | | | | |
| gag | aag | cat | aac | ctt | cat | cat | gct | gct | cca | aat | gaa | tgc | gat | cag | act | 912 |
| Glu | Lys | His | Asn | Leu | His | His | Ala | Ala | Pro | Asn | Glu | Cys | Asp | Gln | Thr | |
| | 290 | | | | | 295 | | | | | 300 | | | | | |
| tac | caa | cca | att | gat | gaa | gat | att | gat | act | ctc | ccc | ctc | att | gcc | tgg | 960 |
| Tyr | Gln | Pro | Ile | Asp | Glu | Asp | Ile | Asp | Thr | Leu | Pro | Leu | Ile | Ala | Trp | |
| 305 | | | | 310 | | | | | 315 | | | | | 320 | | |

```
agc aag gac ata ctg gcc aca gtt gag aat aag aca ttc ttg cga atc       1008
Ser Lys Asp Ile Leu Ala Thr Val Glu Asn Lys Thr Phe Leu Arg Ile
            325                 330                 335 ctc caa tac cag cat ctg ttc ttc atg ggt ctg tta ttt ttc gcc cgt       1056
Leu Gln Tyr Gln His Leu Phe Phe Met Gly Leu Leu Phe Phe Ala Arg
        340                 345                 350 ggt agt tgg ctc ttt tgg agc tgg aga tat acc tct aca gca gtg ctc       1104
Gly Ser Trp Leu Phe Trp Ser Trp Arg Tyr Thr Ser Thr Ala Val Leu
    355                 360                 365 tca cct gtc gac agg ttg ttg gag aag gga act gtt ctg ttt cac tac       1152
Ser Pro Val Asp Arg Leu Leu Glu Lys Gly Thr Val Leu Phe His Tyr
370                 375                 380 ttt tgg ttc gtc ggg aca gcg tgc tat ctt ctc cct ggt tgg aag cca       1200
Phe Trp Phe Val Gly Thr Ala Cys Tyr Leu Leu Pro Gly Trp Lys Pro
385                 390                 395                 400 tta gta tgg atg gcg gtg act gag ctc atg tcc ggc atg ctg ctg ggc       1248
Leu Val Trp Met Ala Val Thr Glu Leu Met Ser Gly Met Leu Leu Gly
            405                 410                 415 ttt gta ttt gta ctt agc cac aat ggg atg gag gtt tat aat tcg tct       1296
Phe Val Phe Val Leu Ser His Asn Gly Met Glu Val Tyr Asn Ser Ser
        420                 425                 430 aaa gaa ttc gtg agt gca cag atc gta tcc aca cgg gat atc aaa gga       1344
Lys Glu Phe Val Ser Ala Gln Ile Val Ser Thr Arg Asp Ile Lys Gly
    435                 440                 445 aac ata ttc aac gac tgg ttc act ggt ggc ctt aac agg caa ata gag       1392
Asn Ile Phe Asn Asp Trp Phe Thr Gly Gly Leu Asn Arg Gln Ile Glu
450                 455                 460 cat cat ctt ttc cca aca atg ccc agg cat aat tta aac aaa ata gca       1440
His His Leu Phe Pro Thr Met Pro Arg His Asn Leu Asn Lys Ile Ala
465                 470                 475                 480 cct aga gtg gag gtg ttc tgt aag aaa cac ggt ctg gtg tac gaa gac       1488
Pro Arg Val Glu Val Phe Cys Lys Lys His Gly Leu Val Tyr Glu Asp
            485                 490                 495 gta tct att gct acc ggc act tgc aag gtt ttg aaa gca ttg aag gaa       1536
Val Ser Ile Ala Thr Gly Thr Cys Lys Val Leu Lys Ala Leu Lys Glu
        500                 505                 510 gtc gcg gag gct gcg gca gag cag cat gct acc acc agt taa               1578
Val Ala Glu Ala Ala Ala Glu Gln His Ala Thr Thr Ser
    515                 520                 525

<210> SEQ ID NO 10
<211> LENGTH: 525
<212> TYPE: PRT
<213> ORGANISM: Physcomitrella patens

<400> SEQUENCE: 10

Met Val Phe Ala Gly Gly Leu Gln Gln Gly Ser Leu Glu Glu Asn
1               5                   10                  15

Ile Asp Val Glu His Ile Ala Ser Met Ser Leu Phe Ser Asp Phe Phe
            20                  25                  30

Ser Tyr Val Ser Ser Thr Val Gly Ser Trp Ser Val His Ser Ile Gln
        35                  40                  45

Pro Leu Lys Arg Leu Thr Ser Lys Lys Arg Val Ser Glu Ser Ala Ala
    50                  55                  60

Val Gln Cys Ile Ser Ala Glu Val Gln Arg Asn Ser Thr Gln Gly
65                  70                  75                  80

Thr Ala Glu Ala Leu Ala Glu Ser Val Val Lys Pro Thr Arg Arg
            85                  90                  95

Ser Ser Gln Trp Lys Lys Ser Thr His Pro Leu Ser Glu Val Ala Val
```

-continued

```
                100                 105                 110
His Asn Lys Pro Ser Asp Cys Trp Ile Val Lys Asn Lys Val Tyr
            115                 120                 125
Asp Val Ser Asn Phe Ala Asp Glu His Pro Gly Gly Ser Val Ile Ser
            130                 135                 140
Thr Tyr Phe Gly Arg Asp Gly Thr Asp Val Phe Ser Ser Phe His Ala
145                 150                 155                 160
Ala Ser Thr Trp Lys Ile Leu Gln Asp Phe Tyr Ile Gly Asp Val Glu
                165                 170                 175
Arg Val Glu Pro Thr Pro Glu Leu Leu Lys Asp Phe Arg Glu Met Arg
            180                 185                 190
Ala Leu Phe Leu Arg Glu Gln Leu Phe Lys Ser Ser Lys Leu Tyr Tyr
            195                 200                 205
Val Met Lys Leu Leu Thr Asn Val Ala Ile Phe Ala Ala Ser Ile Ala
            210                 215                 220
Ile Ile Cys Trp Ser Lys Thr Ile Ser Ala Val Leu Ala Ser Ala Cys
225                 230                 235                 240
Met Met Ala Leu Cys Phe Gln Gln Cys Gly Trp Leu Ser His Asp Phe
                245                 250                 255
Leu His Asn Gln Val Phe Glu Thr Arg Trp Leu Asn Glu Val Val Gly
            260                 265                 270
Tyr Val Ile Gly Asn Ala Val Leu Gly Phe Ser Thr Gly Trp Trp Lys
            275                 280                 285
Glu Lys His Asn Leu His Ala Ala Pro Asn Glu Cys Asp Gln Thr
            290                 295                 300
Tyr Gln Pro Ile Asp Glu Asp Ile Asp Thr Leu Pro Leu Ile Ala Trp
305                 310                 315                 320
Ser Lys Asp Ile Leu Ala Thr Val Glu Asn Lys Thr Phe Leu Arg Ile
                325                 330                 335
Leu Gln Tyr Gln His Leu Phe Phe Met Gly Leu Leu Phe Ala Arg
            340                 345                 350
Gly Ser Trp Leu Phe Trp Ser Trp Arg Tyr Thr Ser Thr Ala Val Leu
            355                 360                 365
Ser Pro Val Asp Arg Leu Leu Glu Lys Gly Thr Val Leu Phe His Tyr
370                 375                 380
Phe Trp Phe Val Gly Thr Ala Cys Tyr Leu Leu Pro Gly Trp Lys Pro
385                 390                 395                 400
Leu Val Trp Met Ala Val Thr Glu Leu Met Ser Gly Met Leu Leu Gly
                405                 410                 415
Phe Val Phe Val Leu Ser His Asn Gly Met Glu Val Tyr Asn Ser Ser
                420                 425                 430
Lys Glu Phe Val Ser Ala Gln Ile Val Ser Thr Arg Asp Ile Lys Gly
            435                 440                 445
Asn Ile Phe Asn Asp Trp Phe Thr Gly Gly Leu Asn Arg Gln Ile Glu
            450                 455                 460
His His Leu Phe Pro Thr Met Pro Arg His Asn Leu Asn Lys Ile Ala
465                 470                 475                 480
Pro Arg Val Glu Val Phe Cys Lys Lys His Gly Leu Val Tyr Glu Asp
                485                 490                 495
Val Ser Ile Ala Thr Gly Thr Cys Lys Val Leu Lys Ala Leu Lys Glu
            500                 505                 510
Val Ala Glu Ala Ala Ala Glu Gln His Ala Thr Thr Ser
            515                 520                 525
```

-continued

<210> SEQ ID NO 11
<211> LENGTH: 1192
<212> TYPE: DNA
<213> ORGANISM: Physcomitrella patens
<220> FEATURE:
<221> NAME/KEY: CDS
<222> LOCATION: (58)..(930)
<223> OTHER INFORMATION: Delta-6-elongase

<400> SEQUENCE: 11

```
ctgcttcgtc tcatcttggg ggtgtgattc gggagtgggt tgagttggtg gagcgca          57 atg gag gtc gtg gag aga ttc tac ggt gag ttg gat ggg aag gtc tcg        105
Met Glu Val Val Glu Arg Phe Tyr Gly Glu Leu Asp Gly Lys Val Ser
1               5                   10                  15 cag ggc gtg aat gca ttg ctg ggt agt ttt ggg gtg gag ttg acg gat        153
Gln Gly Val Asn Ala Leu Leu Gly Ser Phe Gly Val Glu Leu Thr Asp
            20                  25                  30 acg ccc act acc aaa ggc ttg ccc ctc gtt gac agt ccc aca ccc atc        201
Thr Pro Thr Thr Lys Gly Leu Pro Leu Val Asp Ser Pro Thr Pro Ile
        35                  40                  45 gtc ctc ggt gtt tct gta tac ttg act att gtc att gga ggg ctt ttg        249
Val Leu Gly Val Ser Val Tyr Leu Thr Ile Val Ile Gly Gly Leu Leu
50                  55                  60 tgg ata aag gcc agg gat ctg aaa ccg cgc gcc tcg gag cca ttt ttg        297
Trp Ile Lys Ala Arg Asp Leu Lys Pro Arg Ala Ser Glu Pro Phe Leu
65                  70                  75                  80 ctc caa gct ttg gtg ctt gtg cac aac ctg ttc tgt ttt gcg ctc agt        345
Leu Gln Ala Leu Val Leu Val His Asn Leu Phe Cys Phe Ala Leu Ser
                85                  90                  95 ctg tat atg tgc gtg ggc atc gct tat cag gct att acc tgg cgg tac        393
Leu Tyr Met Cys Val Gly Ile Ala Tyr Gln Ala Ile Thr Trp Arg Tyr
            100                 105                 110 tct ctc tgg ggc aat gca tac aat cct aaa cat aaa gag atg gcg att        441
Ser Leu Trp Gly Asn Ala Tyr Asn Pro Lys His Lys Glu Met Ala Ile
        115                 120                 125 ctg gta tac ttg ttc tac atg tct aag tac gtg gaa ttc atg gat acc        489
Leu Val Tyr Leu Phe Tyr Met Ser Lys Tyr Val Glu Phe Met Asp Thr
    130                 135                 140 gtt atc atg ata ctg aag cgc agc acc agg caa ata agc ttc ctc cac        537
Val Ile Met Ile Leu Lys Arg Ser Thr Arg Gln Ile Ser Phe Leu His
145                 150                 155                 160 gtt tat cat cat tct tca att tcc ctc att tgg tgg gct att gct cat        585
Val Tyr His His Ser Ser Ile Ser Leu Ile Trp Trp Ala Ile Ala His
                165                 170                 175 cac gct cct ggc ggt gaa gca tat tgg tct gcg gct ctg aac tca gga        633
His Ala Pro Gly Gly Glu Ala Tyr Trp Ser Ala Ala Leu Asn Ser Gly
            180                 185                 190 gtg cat gtt ctc atg tat gcg tat tac ttg ttg gct gcc tgc ctt cga        681
Val His Val Leu Met Tyr Ala Tyr Tyr Leu Leu Ala Ala Cys Leu Arg
        195                 200                 205 agt agc cca aag tta aaa aat aag tac ctt ttt tgg ggc agg tac ttg        729
Ser Ser Pro Lys Leu Lys Asn Lys Tyr Leu Phe Trp Gly Arg Tyr Leu
    210                 215                 220 aca caa ttc caa atg ttc cag ttt atg ctg aac tta gtg cag gct tac        777
Thr Gln Phe Gln Met Phe Gln Phe Met Leu Asn Leu Val Gln Ala Tyr
225                 230                 235                 240 tac gac atg aaa acg aat gcg cca tat cca caa tgg ctg atc aag att        825
Tyr Asp Met Lys Thr Asn Ala Pro Tyr Pro Gln Trp Leu Ile Lys Ile
                245                 250                 255 ttg ttc tac tac atg atc tcg ttg ctg ttt ctt ttc ggc aat ttt tac        873
Leu Phe Tyr Tyr Met Ile Ser Leu Leu Phe Leu Phe Gly Asn Phe Tyr
```

```
                   260                 265                 270
gta caa aaa tac atc aaa ccc tct gac gga aag caa aag gga gct aaa        921
Val Gln Lys Tyr Ile Lys Pro Ser Asp Gly Lys Gln Lys Gly Ala Lys
            275                 280                 285 act gag tga gctgtatcaa gccatagaaa ctctattatg ttagaacctg                970
Thr Glu
    290 aagttggtgc tttcttatct ccacttatct tttaagcagc atcagttttg aaatgatgtg     1030 tgggcgtggt ctgcaagtag tcatcaatat aatcggcctg agcacttcag atggattgtt     1090 agaacatgag taaaagcggt tattacggtg tttattttgt accaaatcac cgcacgggtg     1150 aattgaaata tttcagattt gatcaatttc atctgaaaaa aa                        1192

<210> SEQ ID NO 12
<211> LENGTH: 290
<212> TYPE: PRT
<213> ORGANISM: Physcomitrella patens

<400> SEQUENCE: 12

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285
```

-continued

Thr Glu
    290

<210> SEQ ID NO 13
<211> LENGTH: 1410
<212> TYPE: DNA
<213> ORGANISM: Phaeodactylum tricornutum
<220> FEATURE:
<221> NAME/KEY: CDS
<222> LOCATION: (1)..(1410)
<223> OTHER INFORMATION: Delta-5-desaturase

<400> SEQUENCE: 13

```
atg gct ccg gat gcg gat aag ctt cga caa cgc cag acg act gcg gta      48
Met Ala Pro Asp Ala Asp Lys Leu Arg Gln Arg Gln Thr Thr Ala Val
1               5                   10                  15 gcg aag cac aat gct gct acc ata tcg acg cag gaa cgc ctt tgc agt      96
Ala Lys His Asn Ala Ala Thr Ile Ser Thr Gln Glu Arg Leu Cys Ser
            20                  25                  30 ctg tct tcg ctc aaa ggc gaa gaa gtc tgc atc gac gga atc atc tat     144
Leu Ser Ser Leu Lys Gly Glu Glu Val Cys Ile Asp Gly Ile Ile Tyr
        35                  40                  45 gac ctc caa tca ttc gat cat ccc ggg ggt gaa acg atc aaa atg ttt     192
Asp Leu Gln Ser Phe Asp His Pro Gly Gly Glu Thr Ile Lys Met Phe
    50                  55                  60 ggt ggc aac gat gtc act gta cag tac aag atg att cac ccg tac cat     240
Gly Gly Asn Asp Val Thr Val Gln Tyr Lys Met Ile His Pro Tyr His
65                  70                  75                  80 acc gag aag cat ttg gaa aag atg aag cgt gtc ggc aag gtg acg gat     288
Thr Glu Lys His Leu Glu Lys Met Lys Arg Val Gly Lys Val Thr Asp
                85                  90                  95 ttc gtc tgc gag tac aag ttc gat acc gaa ttt gaa cgc gaa atc aaa     336
Phe Val Cys Glu Tyr Lys Phe Asp Thr Glu Phe Glu Arg Glu Ile Lys
            100                 105                 110 cga gaa gtc ttc aag att gtg cga cga ggc aag gat ttc ggt act ttg     384
Arg Glu Val Phe Lys Ile Val Arg Arg Gly Lys Asp Phe Gly Thr Leu
        115                 120                 125 gga tgg ttc ttc cgt gcg ttt tgc tac att gcc att ttc ttc tac ctg     432
Gly Trp Phe Phe Arg Ala Phe Cys Tyr Ile Ala Ile Phe Phe Tyr Leu
    130                 135                 140 cag tac cat tgg gtc acc acg gga acc tct tgg ctg ctg gcc gtg gcc     480
Gln Tyr His Trp Val Thr Thr Gly Thr Ser Trp Leu Leu Ala Val Ala
145                 150                 155                 160 tac gga atc tcc caa gcg atg att ggc atg aat gtc cag cac gat gcc     528
Tyr Gly Ile Ser Gln Ala Met Ile Gly Met Asn Val Gln His Asp Ala
                165                 170                 175 aac cac ggg gcc acc tcc aag cgt ccc tgg gtc aac gac atg cta ggc     576
Asn His Gly Ala Thr Ser Lys Arg Pro Trp Val Asn Asp Met Leu Gly
            180                 185                 190 ctc ggt gcg gat ttt att ggt ggt tcc aag tgg ctc tgg cag gaa caa     624
Leu Gly Ala Asp Phe Ile Gly Gly Ser Lys Trp Leu Trp Gln Glu Gln
        195                 200                 205 cac tgg acc cac cac gct tac acc aat cac gcc gag atg gat ccc gat     672
His Trp Thr His His Ala Tyr Thr Asn His Ala Glu Met Asp Pro Asp
    210                 215                 220 agc ttt ggt gcc gaa cca atg ctc cta ttc aac gac tat ccc ttg gat     720
Ser Phe Gly Ala Glu Pro Met Leu Leu Phe Asn Asp Tyr Pro Leu Asp
225                 230                 235                 240 cat ccc gct cgt acc tgg cta cat cgc ttt caa gca ttc ttt tac atg     768
His Pro Ala Arg Thr Trp Leu His Arg Phe Gln Ala Phe Phe Tyr Met
                245                 250                 255 ccc gtc ttg gct gga tac tgg ttg tcc gct gtc ttc aat cca caa att     816
```

```
ccc gtc ctc gcc ggc tac tgg ctg tcc gcg gtc ttc aac ccg caa atc          816
Pro Val Leu Ala Gly Tyr Trp Leu Ser Ala Val Phe Asn Pro Gln Ile
                260                 265                 270 ctt gac ctc cag caa cgc ggc gca ctt tcc gtc ggt atc cgt ctc gac          864
Leu Asp Leu Gln Gln Arg Gly Ala Leu Ser Val Gly Ile Arg Leu Asp
            275                 280                 285 aac gct ttc att cac tcg cga cgc aag tat gcg gtt ttc tgg cgg gct          912
Asn Ala Phe Ile His Ser Arg Arg Lys Tyr Ala Val Phe Trp Arg Ala
        290                 295                 300 gtg tac att gcg gtg aac gtg att gct ccg ttt tac aca aac tcc ggc          960
Val Tyr Ile Ala Val Asn Val Ile Ala Pro Phe Tyr Thr Asn Ser Gly
305                 310                 315                 320 ctc gaa tgg tcc tgg cgt gtc ttt gga aac atc atg ctc atg ggt gtg         1008
Leu Glu Trp Ser Trp Arg Val Phe Gly Asn Ile Met Leu Met Gly Val
                325                 330                 335 gcg gaa tcg ctc gcg ctg gcg gtc ctg ttt tcg ttg tcg cac aat ttc         1056
Ala Glu Ser Leu Ala Leu Ala Val Leu Phe Ser Leu Ser His Asn Phe
            340                 345                 350 gaa tcc gcg gat cgc gat ccg acc gcc cca ctg aaa aag acg gga gaa         1104
Glu Ser Ala Asp Arg Asp Pro Thr Ala Pro Leu Lys Lys Thr Gly Glu
        355                 360                 365 cca gtc gac tgg ttc aag aca cag gtc gaa act tcc tgc act tac ggt         1152
Pro Val Asp Trp Phe Lys Thr Gln Val Glu Thr Ser Cys Thr Tyr Gly
370                 375                 380 gga ttc ctt tcc ggt tgc ttc acg gga ggt ctc aac ttt cag gtt gaa         1200
Gly Phe Leu Ser Gly Cys Phe Thr Gly Gly Leu Asn Phe Gln Val Glu
385                 390                 395                 400 cac cac ttg ttc cca cgc atg agc agc gct tgg tat ccc tac att gcc         1248
His His Leu Phe Pro Arg Met Ser Ser Ala Trp Tyr Pro Tyr Ile Ala
            405                 410                 415 ccc aag gtc cgc gaa att tgc gcc aaa cac ggc gtc cac tac gcc tac         1296
Pro Lys Val Arg Glu Ile Cys Ala Lys His Gly Val His Tyr Ala Tyr
        420                 425                 430 tac ccg tgg atc cac caa aac ttt ctc tcc acc gtc cgc tac atg cac         1344
Tyr Pro Trp Ile His Gln Asn Phe Leu Ser Thr Val Arg Tyr Met His
    435                 440                 445 gcg gcc ggg acc ggt gcc aac tgg cgc cag atg gcc aga gaa aat ccc         1392
Ala Ala Gly Thr Gly Ala Asn Trp Arg Gln Met Ala Arg Glu Asn Pro
450                 455                 460 ttg acc gga cgg gcg taa                                                  1410
Leu Thr Gly Arg Ala
465
```

<210> SEQ ID NO 14
<211> LENGTH: 469
<212> TYPE: PRT
<213> ORGANISM: Phaeodactylum tricornutum

<400> SEQUENCE: 14

```
Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
                20                  25                  30

Leu Ser Ser Leu Lys Gly Glu Glu Val Cys Ile Asp Gly Ile Ile Tyr
            35                  40                  45

Asp Leu Gln Ser Phe Asp His Pro Gly Gly Glu Thr Ile Lys Met Phe
        50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95
```

```
Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
            115                 120                 125

Gly Trp Phe Phe Arg Ala Phe Cys Tyr Ile Ala Ile Phe Phe Tyr Leu
130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
            165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
            195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
            245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
            275                 280                 285

Asn Ala Phe Ile His Ser Arg Arg Lys Tyr Ala Val Phe Trp Arg Ala
290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
            325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
            355                 360                 365

Pro Val Asp Trp Phe Lys Thr Gln Val Glu Thr Ser Cys Thr Tyr Gly
            370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
            405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
            435                 440                 445

Ala Ala Gly Thr Gly Ala Asn Trp Arg Gln Met Ala Arg Glu Asn Pro
            450                 455                 460

Leu Thr Gly Arg Ala
465

<210> SEQ ID NO 15
<211> LENGTH: 3598
<212> TYPE: DNA
<213> ORGANISM: artificial sequence
<220> FEATURE:
<221> NAME/KEY: misc_feature
```

<222> LOCATION: (1)..(3598)
<223> OTHER INFORMATION: The sequence is a plant promoter-terminator expression cassette in vector pUC19

<400> SEQUENCE: 15

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg  cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cggcgcgccg agctcctcga   420
gcaaatttac acattgccac taaacgtcta aacccttgta atttgttttt gttttactat   480
gtgtgttatg tatttgattt gcgataaatt tttatatttg gtactaaatt tataacacct   540
tttatgctaa cgtttgccaa cacttagcaa tttgcaagtt gattaattga ttctaaatta   600
tttttgtctt ctaaatacat atactaatca actggaaatg taaatatttg ctaatatttc   660
tactatagga gaattaaagt gagtgaatat ggtaccacaa ggtttggaga tttaattgtt   720
gcaatgctgc atggatggca tatacaccaa acattcaata attcttgagg ataataatgg   780
taccacacaa gatttgaggt gcatgaacgt cacgtggaca aaaggtttag taattttca    840
agacaacaat gttaccacac acaagttttg aggtgcatgc atggatgccc tgtggaaagt   900
ttaaaaatat tttggaaatg atttgcatgg aagccatgtg taaaaccatg acatccactt   960
ggaggatgca ataatgaaga aaactacaaa tttacatgca actagttatg catgtagtct  1020
atataatgag gattttgcaa tactttcatt catacacact cactaagttt tacacgatta  1080
taatttcttc atagccagcc caccgcggtg ggcggccgcc tgcagtctag aaggcctcct  1140
gctttaatga gatatgcgag acgcctatga tcgcatgata tttgctttca attctgttgt  1200
gcacgttgta aaaacctga  gcatgtgtag ctcagatcct taccgccggt ttcggttcat  1260
tctaatgaat atatcacccg ttactatcgt attttatga  ataatattct ccgttcaatt  1320
tactgattgt ccgtcgacga attcgagctc ggcgcgccaa gcttggcgta atcatggtca  1380
tagctgtttc ctgtgtgaaa ttgttatccg ctcacaattc cacacaacat acgagccgga  1440
agcataaagt gtaaagcctg gggtgcctaa tgagtgagct aactcacatt aattgcgttg  1500
cgctcactgc ccgctttcca gtcgggaaac ctgtcgtgcc agctgcatta atgaatcggc  1560
caacgcgcgg ggagaggcgg tttgcgtatt gggcgctctt ccgcttcctc gctcactgac  1620
tcgctgcgct cggtcgttcg gctgcggcga gcggtatcag ctcactcaaa ggcggtaata  1680
cggttatcca cagaatcagg ggataacgca ggaaagaaca tgtgagcaaa aggccagcaa  1740
aaggccagga accgtaaaaa ggccgcgttg ctggcgtttt tccataggct ccgcccccct  1800
gacgagcatc acaaaaatcg acgctcaagt cagaggtggc gaaacccgac aggactataa  1860
agataccagg cgtttccccc tggaagctcc ctcgtgcgct ctcctgttcc gaccctgccg  1920
cttaccggat acctgtccgc ctttctccct tcgggaagcg tggcgctttc tcatagctca  1980
cgctgtaggt atctcagttc ggtgtaggtc gttcgctcca agctgggctg tgtgcacgaa  2040
ccccccgttc agcccgaccg ctgcgcctta tccggtaact atcgtcttga gtccaacccg  2100
gtaagacacg acttatcgcc actggcagca gccactggta acaggattag cagagcgagg  2160
tatgtaggcg gtgctacaga gttcttgaag tggtggccta actacggcta cactagaagg  2220
```

```
acagtatttg gtatctgcgc tctgctgaag ccagttacct tcggaaaaag agttggtagc    2280
tcttgatccg gcaaacaaac caccgctggt agcggtggtt tttttgtttg caagcagcag    2340
attacgcgca gaaaaaaagg atctcaagaa gatcctttga tcttttctac ggggtctgac    2400
gctcagtgga acgaaaactc acgttaaggg attttggtca tgagattatc aaaaaggatc    2460
ttcacctaga tccttttaaa ttaaaaatga agttttaaat caatctaaag tatatatgag    2520
taaacttggt ctgacagtta ccaatgctta atcagtgagg cacctatctc agcgatctgt    2580
ctatttcgtt catccatagt tgcctgactc cccgtcgtgt agataactac gatacgggag    2640
ggcttaccat ctggccccag tgctgcaatg ataccgcgag acccacgctc accggctcca    2700
gatttatcag caataaacca gccagccgga agggccgagc gcagaagtgg tcctgcaact    2760
ttatccgcct ccatccagtc tattaattgt tgccgggaag ctagagtaag tagttcgcca    2820
gttaatagtt tgcgcaacgt tgttgccatt gctacaggca tcgtggtgtc acgctcgtcg    2880
tttggtatgg cttcattcag ctccggttcc aacgatcaa  ggcgagttac atgatccccc    2940
atgttgtgca aaaaagcggt tagctccttc ggtcctccga tcgttgtcag aagtaagttg    3000
gccgcagtgt tatcactcat ggttatggca gcactgcata attctcttac tgtcatgcca    3060
tccgtaagat gcttttctgt gactggtgag tactcaacca agtcattctg agaatagtgt    3120
atgcggcgac cgagttgctc ttgcccggcg tcaatacggg ataataccgc gccacatagc    3180
agaactttaa aagtgctcat cattggaaaa cgttcttcgg ggcgaaaact ctcaaggatc    3240
ttaccgctgt tgagatccag ttcgatgtaa cccactcgtg cacccaactg atcttcagca    3300
tcttttactt tcaccagcgt ttctgggtga gcaaaaacag gaaggcaaaa tgccgcaaaa    3360
aagggaataa gggcgacacg gaaatgttga atactcatac tcttcctttt tcaatattat    3420
tgaagcattt atcagggtta ttgtctcatg agcggataca tatttgaatg tatttagaaa    3480
aataaacaaa tagggttcc gcgcacattt ccccgaaaag tgccacctga cgtctaagaa    3540
accattatta tcatgacatt aacctataaa aataggcgta tcacgaggcc ctttcgtc     3598

<210> SEQ ID NO 16
<211> LENGTH: 3590
<212> TYPE: DNA
<213> ORGANISM: artificial sequence
<220> FEATURE:
<221> NAME/KEY: misc_feature
<222> LOCATION: (1)..(3590)
<223> OTHER INFORMATION: The sequence is a plant promoter-terminator
      expression cassette in vector pUC19

<400> SEQUENCE: 16
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggcgcgccg agctcctcga     420
gcaaatttac acattgccac taaacgtcta aacccttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta     600 ttttttgtctt ctaaatacat atactaatca actggaaatg taaatatttg ctaatatttc    660
```

```
tactatagga gaattaaagt gagtgaatat ggtaccacaa ggtttggaga tttaattgtt    720
gcaatgctgc atggatggca tatacaccaa acattcaata attcttgagg ataataatgg    780
taccacacaa gatttgaggt gcatgaacgt cacgtggaca aaaggtttag taattttttca   840 agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct   1020
atataatgag gattttgcaa tactttcatt catacacact cactaagttt tacacgatta   1080
taatttcttc atagccagcg gatccgatat cgggcccgct agcgttaacc ctgctttaat   1140
gagatatgcg agacgcctat gatcgcatga tatttgcttt caattctgtt gtgcacgttg   1200
taaaaaacct gagcatgtgt agctcagatc cttaccgccg gtttcggttc attctaatga   1260
atatatcacc cgttactatc gtattttat gaataatatt ctccgttcaa tttactgatt    1320
gtccgtcgac gaattcgagc tcggcgcgcc aagcttggcg taatcatggt catagctgtt   1380
tcctgtgtga aattgttatc cgctcacaat tccacacaac atacgagccg aagcataaa    1440 gtgtaaagcc tggggtgcct aatgagtgag ctaactcaca ttaattgcgt tgcgctcact   1500
gcccgctttc cagtcgggaa acctgtcgtg ccagctgcat taatgaatcg gccaacgcgc   1560
ggggagaggc ggtttgcgta ttgggcgctc ttccgcttcc tcgctcactg actcgctgcg   1620
ctcggtcgtt cggctgcggc gagcggtatc agctcactca aaggcggtaa tacggttatc   1680
cacagaatca ggggataacg caggaaagaa catgtgagca aaaggccagc aaaaggccag   1740
gaaccgtaaa aaggccgcgt tgctggcgtt tttccatagg ctccgccccc ctgacgagca   1800
tcacaaaaat cgacgctcaa gtcagaggtg gcgaaacccg acaggactat aaagatacca   1860
ggcgtttccc cctggaagct ccctcgtgcg ctctcctgtt ccgaccctgc cgcttaccgg   1920
atacctgtcc gcctttctcc cttcgggaag cgtggcgctt tctcatagct cacgctgtag   1980
gtatctcagt tcggtgtagg tcgttcgctc caagctgggc tgtgtgcacg aaccccccgt   2040
tcagcccgac cgctgcgcct tatccggtaa ctatcgtctt gagtccaacc cggtaagaca   2100
cgacttatcg ccactggcag cagccactgg taacaggatt agcagagcga ggtatgtagg   2160
cggtgctaca gagttcttga agtggtggcc taactacggc tacactagaa ggacagtatt   2220
tggtatctgc gctctgctga agccagttac cttcggaaaa agagttggta gctcttgatc   2280
cggcaaacaa accaccgctg gtagcggtgg tttttttgtt tgcaagcagc agattacgcg   2340
cagaaaaaaa ggatctcaag aagatccttt gatcttttct acggggtctg acgctcagtg   2400
gaacgaaaac tcacgttaag ggattttggt catgagatta tcaaaaagga tcttcaccta   2460 gatccttta aattaaaaat gaagttttaa atcaatctaa agtatatatg agtaaacttg    2520
gtctgacagt taccaatgct taatcagtga ggcacctatc tcagcgatct gtctatttcg   2580
ttcatccata gttgcctgac tccccgtcgt gtagataact acgatacggg agggcttacc   2640
atctggcccc agtgctgcaa tgataccgcg agacccacgc tcaccggctc cagatttatc   2700
agcaataaac cagccagccg aagggccga gcgcagaagt ggtcctgcaa ctttatccgc    2760
ctccatccag tctattaatt gttgccggga agctagagta agtagttcgc cagttaatag   2820
tttgcgcaac gttgttgcca ttgctacagg catcgtggtg tcacgctcgt cgtttggtat   2880
ggcttcattc agctccggtt cccaacgatc aaggcgagtt acatgatccc ccatgttgtg   2940
caaaaaagcg gttagctcct tcggtcctcc gatcgttgtc agaagtaagt tggccgcagt   3000
gttatcactc atggttatgg cagcactgca taattctctt actgtcatgc catccgtaag   3060
```

```
atgcttttct gtgactggtg agtactcaac caagtcattc tgagaatagt gtatgcggcg    3120
accgagttgc tcttgcccgg cgtcaatacg ggataatacc gcgccacata gcagaacttt    3180
aaaagtgctc atcattggaa aacgttcttc ggggcgaaaa ctctcaagga tcttaccgct    3240
gttgagatcc agttcgatgt aacccactcg tgcacccaac tgatcttcag catcttttac    3300
tttcaccagc gtttctgggt gagcaaaaac aggaaggcaa aatgccgcaa aaagggaat     3360 aagggcgaca cggaaatgtt gaatactcat actcttcctt tttcaatatt attgaagcat    3420
ttatcagggt tattgtctca tgagcggata catatttgaa tgtatttaga aaaataaaca    3480 aatagggtt ccgcgcacat ttccccgaaa agtgccacct gacgtctaag aaaccattat     3540
tatcatgaca ttaacctata aaaataggcg tatcacgagg ccctttcgtc                3590
```

<210> SEQ ID NO 17
<211> LENGTH: 3584
<212> TYPE: DNA
<213> ORGANISM: artificial sequence
<220> FEATURE:
<221> NAME/KEY: misc_feature
<222> LOCATION: (1)..(3584)
<223> OTHER INFORMATION: The sequence is a plant promoter-terminator
      expression cassette in vector pUC19

<400> SEQUENCE: 17

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cggcgcgccg agctcctcga    420
gcaaatttac acattgccac taaacgtcta aacccttgta atttgttttt gttttactat    480
gtgtgttatg tatttgattt gcgataaatt tttatatttg gtactaaatt tataacacct    540
tttatgctaa cgtttgccaa cacttagcaa tttgcaagtt gattaattga ttctaaatta    600
tttttgtctt ctaaatacat atactaatca actggaaatg taaatatttg ctaatatttc    660
tactatagga gaattaaagt gagtgaatat ggtaccacaa ggtttggaga tttaattgtt    720
gcaatgctgc atggatggca tataccaa acattcaata attcttgagg ataataatgg     780
taccacacaa gatttgaggt gcatgaacgt cacgtggaca aaaggtttag taattttttca   840 agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct    1020
atataatgag gatttttgcaa tactttcatt catacacact cactaagttt tacacgatta    1080
taatttcttc atagccagca gatctgccgg catcgatccc gggccatggc ctgctttaat    1140
gagatatgcg agacgcctat gatcgcatga tatttgcttt caattctgtt gtgcacgttg    1200
taaaaaacct gagcatgtgt agctcagatc cttaccgccg gtttcggttc attctaatga    1260
atatatcacc cgttactatc gtatttttat gaataatatt ctccgttcaa tttactgatt    1320
gtccgtcgac gagctcggcg cgccaagctt ggcgtaatca tggtcatagc tgtttcctgt    1380
gtgaaattgt tatccgctca caattccaca caacatacga gccggaagca taaagtgtaa    1440
```

```
agcctggggt gcctaatgag tgagctaact cacattaatt gcgttgcgct cactgcccgc      1500
tttccagtcg ggaaacctgt cgtgccagct gcattaatga atcggccaac gcgcggggag      1560
aggcggtttg cgtattgggc gctcttccgc ttcctcgctc actgactcgc tgcgctcggt      1620
cgttcggctg cggcgagcgg tatcagctca ctcaaaggcg gtaatacggt tatccacaga      1680
atcaggggat aacgcaggaa agaacatgtg agcaaaaggc cagcaaaagg ccaggaaccg      1740
taaaaaggcc gcgttgctgg cgtttttcca taggctccgc cccectgacg agcatcacaa      1800 aaatcgacgc tcaagtcaga ggtggcgaaa cccgacagga ctataaagat accaggcgtt      1860
tccccctgga agctccctcg tgcgctctcc tgttccgacc ctgccgctta ccggatacct      1920
gtccgccttt ctcccttcgg gaagcgtggc gctttctcat agctcacgct gtaggtatct      1980
cagttcggtg taggtcgttc gctccaagct gggctgtgtg cacgaacccc ccgttcagcc      2040
cgaccgctgc gccttatccg gtaactatcg tcttgagtcc aacccggtaa gacacgactt      2100
atcgccactg gcagcagcca ctggtaacag gattagcaga gcgaggtatg taggcggtgc      2160
tacagagttc ttgaagtggt ggcctaacta cggctacact agaaggacag tatttggtat      2220
ctgcgctctg ctgaagccag ttaccttcgg aaaaagagtt ggtagctctt gatccggcaa      2280
acaaaccacc gctggtagcg gtggtttttt tgtttgcaag cagcagatta cgcgcagaaa      2340
aaaaggatct caagaagatc ctttgatctt ttctacgggg tctgacgctc agtggaacga      2400
aaactcacgt taagggattt tggtcatgag attatcaaaa aggatcttca cctagatcct      2460
tttaaattaa aaatgaagtt ttaaatcaat ctaaagtata tatgagtaaa cttggtctga      2520
cagttaccaa tgcttaatca gtgaggcacc tatctcagcg atctgtctat ttcgttcatc      2580
catagttgcc tgactccccg tcgtgtagat aactacgata cgggagggct taccatctgg      2640
ccccagtgct gcaatgatac cgcgagaccc acgctcaccg gctccagatt tatcagcaat      2700
aaaccagcca gccggaaggg ccgagcgcag aagtggtcct gcaactttat ccgcctccat      2760
ccagtctatt aattgttgcc gggaagctag agtaagtagt tcgccagtta atagtttgcg      2820
caacgttgtt gccattgcta caggcatcgt ggtgtcacgc tcgtcgtttg gtatggcttc      2880
attcagctcc ggttcccaac gatcaaggcg agttacatga tcccccatgt tgtgcaaaaa      2940
agcggttagc tccttcggtc ctccgatcgt tgtcagaagt aagttggccg cagtgttatc      3000
actcatggtt atggcagcac tgcataattc tcttactgtc atgccatccg taagatgctt      3060
ttctgtgact ggtgagtact caaccaagtc attctgagaa tagtgtatgc ggcgaccgag      3120
ttgctcttgc ccggcgtcaa tacgggataa taccgcgcca catagcagaa ctttaaaagt      3180
gctcatcatt ggaaaacgtt cttcggggcg aaaactctca aggatcttac cgctgttgag      3240
atccagttcg atgtaaccca ctcgtgcacc caactgatct tcagcatctt ttactttcac      3300
cagcgtttct gggtgagcaa aaacaggaag gcaaaatgcc gcaaaaaagg gaataagggc      3360
gacacggaaa tgttgaatac tcatactctt ccttttcaa tattattgaa gcatttatca      3420
gggttattgt ctcatgagcg gatacatatt tgaatgtatt tagaaaaata aacaaatagg      3480
ggttccgcgc acatttcccc gaaaagtgcc acctgacgtc taagaaacca ttattatcat      3540
gacattaacc tataaaaata ggcgtatcac gaggcccttt cgtc                       3584
```

<210> SEQ ID NO 18
<211> LENGTH: 4507
<212> TYPE: DNA
<213> ORGANISM: artificial sequence
<220> FEATURE:
<221> NAME/KEY: misc_feature
<222> LOCATION: (1)..(4507)

<223> OTHER INFORMATION: The sequence is a plant promoter-terminator expression cassette in vector pUC19

<400> SEQUENCE: 18

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cggcgcgccg agctcctcga   420
gcaaatttac acattgccac taaacgtcta aaccccttgta atttgttttt gttttactat   480
gtgtgttatg tatttgattt gcgataaatt tttatatttg gtactaaatt tataacacct   540
tttatgctaa cgtttgccaa cacttagcaa tttgcaagtt gattaattga ttctaaatta   600
tttttgtctt ctaaatacat atactaatca actggaaatg taaatatttg ctaatatttc   660
tactatagga gaattaaagt gagtgaatat ggtaccacaa ggtttggaga tttaattgtt   720
gcaatgctgc atggatggca tatacaccaa acattcaata attcttgagg ataataatgg   780
taccacacaa gatttgaggt gcatgaacgt cacgtggaca aaaggtttag taattttca   840
agacaacaat gttaccacac acaagttttg aggtgcatgc atggatgccc tgtggaaagt   900
ttaaaaatat tttggaaatg atttgcatgg aagccatgtg taaaaccatg acatccactt   960
ggaggatgca ataatgaaga aaactacaaa tttacatgca actagttatg catgtagtct  1020
atataatgag gattttgcaa tactttcatt catacacact cactaagttt tacacgatta  1080
taattctcc atagccagcc caccgcggtg gcggccgcc tgcagtctag aaggcctcct  1140
gctttaatga gatatgcgag acgcctatga tcgcatgata tttgctttca attctgttgt  1200
gcacgttgta aaaaacctga gcatgtgtag ctcagatcct taccgccggt ttcggttcat  1260
tctaatgaat atatcacccg ttactatcgt attttttatga ataatattct ccgttcaatt  1320
tactgattgt ccgtcgagca aatttacaca ttgccactaa acgtctaaac ccttgtaatt  1380
tgttttttgtt ttactatgtg tgttatgtat ttgatttgcg ataaattttt atatttggta  1440
ctaaattttat aacacctttt atgctaacgt ttgccaacac ttagcaattt gcaagttgat  1500
taattgattc taaattattt ttgtcttcta aatacatata ctaatcaact ggaaatgtaa  1560
atatttgcta atatttctac tataggagaa ttaaagtgag tgaatatggt accacaaggt  1620
ttggagattt aattgttgca atgctgcatg gatggcatat acaccaaaca ttcaataatt  1680
cttgaggata ataatggtac cacacaagat ttgaggtgca tgaacgtcac gtggacaaaa  1740
ggtttagtaa ttttcaaga caacaatgtt accacacaca agttttgagg tgcatgcatg  1800
gatgccctgt ggaaagttta aaaatatttt ggaaatgatt tgcatggaag ccatgtgtaa  1860
aaccatgaca tccacttgga ggatgcaata atgaagaaaa ctacaaattt acatgcaact  1920
agttatgcat gtagtctata taatgaggat tttgcaatac tttcattcat acacactcac  1980
taagttttac acgattataa tttcttcata gccagcggat ccgatatcgg gcccgctagc  2040
gttaaccctg ctttaatgag atatgcgaga cgcctatgat cgcatgatat ttgctttcaa  2100
ttctgttgtg cacgttgtaa aaaacctgag catgtgtagc tcagatcctt accgccggtt  2160
tcggttcatt ctaatgaata tatcacccgt tactatcgta tttttatgaa taatattctc  2220
cgttcaattt actgattgtc cgtcgacgaa ttcgagctcg gcgcgccaag cttggcgtaa  2280
```

-continued

```
tcatggtcat agctgtttcc tgtgtgaaat tgttatccgc tcacaattcc acacaacata    2340
cgagccggaa gcataaagtg taaagcctgg ggtgcctaat gagtgagcta actcacatta    2400
attgcgttgc gctcactgcc cgctttccag tcgggaaacc tgtcgtgcca gctgcattaa    2460
tgaatcggcc aacgcgcggg gagaggcggt ttgcgtattg ggcgctcttc cgcttcctcg    2520
ctcactgact cgctgcgctc ggtcgttcgg ctgcggcgag cggtatcagc tcactcaaag    2580
gcggtaatac ggttatccac agaatcaggg gataacgcag gaaagaacat gtgagcaaaa    2640
ggccagcaaa aggccaggaa ccgtaaaaag gccgcgttgc tggcgttttt ccataggctc    2700
cgcccccctg acgagcatca caaaaatcga cgctcaagtc agaggtggcg aaacccgaca    2760
ggactataaa gataccaggc gtttccccct ggaagctccc tcgtgcgctc tcctgttccg    2820
accctgccgc ttaccggata cctgtccgcc tttctccctt cgggaagcgt ggcgctttct    2880
catagctcac gctgtaggta tctcagttcg gtgtaggtcg ttcgctccaa gctgggctgt    2940
gtgcacgaac cccccgttca gcccgaccgc tgcgccttat ccggtaacta tcgtcttgag    3000
tccaacccgg taagacacga cttatcgcca ctggcagcag ccactggtaa caggattagc    3060
agagcgaggt atgtaggcgg tgctacagag ttcttgaagt ggtggcctaa ctacggctac    3120
actagaagga cagtatttgg tatctgcgct ctgctgaagc cagttacctt cggaaaaaga    3180
gttggtagct cttgatccgg caaacaaacc accgctggta gcggtggttt ttttgtttgc    3240
aagcagcaga ttacgcgcag aaaaaaagga tctcaagaag atcctttgat cttttctacg    3300
gggtctgacg ctcagtggaa cgaaaactca cgttaaggga ttttggtcat gagattatca    3360
aaaaggatct tcacctagat ccttttaaat taaaaatgaa gttttaaatc aatctaaagt    3420
atatatgagt aaacttggtc tgacagttac caatgcttaa tcagtgaggc acctatctca    3480
gcgatctgtc tatttcgttc atccatagtt gcctgactcc ccgtcgtgta gataactacg    3540
atacgggagg gcttaccatc tggccccagt gctgcaatga taccgcgaga cccacgctca    3600
ccggctccag atttatcagc aataaaccag ccagccggaa gggccgagcg cagaagtggt    3660
cctgcaactt tatccgcctc catccagtct attaattgtt gccgggaagc tagagtaagt    3720
agttcgccag ttaatagttt gcgcaacgtt gttgccattg ctacaggcat cgtggtgtca    3780
cgctcgtcgt ttggtatggc ttcattcagc tccggttccc aacgatcaag gcgagttaca    3840
tgatccccca tgttgtgcaa aaaagcggtt agctccttcg gtcctccgat cgttgtcaga    3900
agtaagttgg ccgcagtgtt atcactcatg gttatggcag cactgcataa ttctcttact    3960
gtcatgccat ccgtaagatg cttttctgtg actggtgagt actcaaccaa gtcattctga    4020
gaatagtgta tgcggcgacc gagttgctct tgcccggcgt caatacggga taataccgcg    4080
ccacatagca gaactttaaa agtgctcatc attggaaaac gttcttcggg gcgaaaactc    4140
tcaaggatct taccgctgtt gagatccagt tcgatgtaac ccactcgtgc acccaactga    4200
tcttcagcat cttttacttt caccagcgtt tctgggtgag caaaaacagg aaggcaaaat    4260
gccgcaaaaa agggaataag ggcgacacgg aaatgttgaa tactcatact cttcctttt    4320 caatattatt gaagcattta tcagggttat tgtctcatga gcggatacat atttgaatgt    4380
atttagaaaa ataaacaaat aggggttccg cgcacatttc cccgaaaagt gccacctgac    4440
gtctaagaaa ccattattat catgacatta acctataaaa ataggcgtat cacgaggccc    4500
tttcgtc                                                              4507
```

<210> SEQ ID NO 19
<211> LENGTH: 17752

-continued

```
<212> TYPE: DNA
<213> ORGANISM: Phaeodactylum tricornutum, Physcomitrella patens
<220> FEATURE:
<221> NAME/KEY: CDS
<222> LOCATION: (11543)..(12415)
<223> OTHER INFORMATION: Delta-6-elongase
<220> FEATURE:
<221> NAME/KEY: CDS
<222> LOCATION: (13313)..(14890)
<223> OTHER INFORMATION: Delta-6-desaturase
<220> FEATURE:
<221> NAME/KEY: CDS
<222> LOCATION: (15791)..(17200)
<223> OTHER INFORMATION: Delta-5-desaturase

<400> SEQUENCE: 19
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt gggggttcag cagccggcgc     480
tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg cgatggcgcg cgcatccatg     660
ccggcacgcg accgggcgca ccgcagatgg aaacggccga cgcgcagctt cgcttcctct     720
gcgaggcggg tttttcggcc ggggacgccg tcaatgcgct gatgacaatc agctacttca     780
ctgttggggc cgtgcttgag gagcaggccg gcgacagcga tgccggcgag cgcggcggca     840
ccgttgaaca ggctccgctc tcgccgctgt tgcgggccgc gatagacgcc ttcgacgaag     900
ccggtccgga cgcagcgttc gagcagggac tcgcggtgat tgtcgatgga ttggcgaaaa     960
ggaggctcgt tgtcaggaac gttgaaggac cgagaaaggg tgacgattga tcaggaccgc    1020
tgccggagcg caacccactc actacagcag agccatgtag acaacatccc ctccccctttt    1080
ccaccgcgtc agacgcccgt agcagcccgc tacgggcttt tcatgccct gccctagcgt     1140
ccaagcctca cggccgcgct cggcctctct ggcggccttc tggcgctctt ccgcttcctc    1200
gctcactgac tcgctgcgct cggtcgttcg gctgcggcga gcggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttt    1560
ccgctgcata accctgcttc gggtcatta tagcgatttt tcggtatat ccatccttttt    1620
tcgcacgata tacaggattt tgccaaaggg ttcgtgtaga ctttccttgg tgtatccaac    1680
ggcgtcagcc gggcaggata ggtgaagtag gcccacccgc gagcgggtgt tccttcttca    1740
ctgtcccctta ttcgcacctg gcggtgctca acgggaatcc tgctctgcga ggctggccgg    1800
ctaccgccgg cgtaacagat gagggcaagc ggatggctga tgaaaccaag ccaaccagga    1860
agggcagccc acctatcaag gtgtactgcc ttccagacga acgaagagcg attgaggaaa    1920
```

```
aggcggcggc ggccggcatg agcctgtcgg cctacctgct ggccgtcggc cagggctaca    1980
aaatcacggg cgtcgtggac tatgagcacg tccgcgagct ggcccgcatc aatggcgacc    2040
tgggccgcct gggcggcctg ctgaaactct ggctcaccga cgacccgcgc acggcgcggt    2100
tcggtgatgc cacgatcctc gccctgctgg cgaagatcga agagaagcag gacgagcttg    2160
gcaaggtcat gatgggcgtg gtccgcccga gggcagagcc atgactttt tagccgctaa    2220
aacggccggg gggtgcgcgt gattgccaag cacgtcccca tgcgctccat caagaagagc    2280
gacttcgcgg agctggtgaa gtacatcacc gacgagcaag gcaagaccga gcgcctttgc    2340
gacgctcacc gggctggttg ccctcgccgc tgggctggcg gccgtctatg ccctgcaaa     2400
cgcgccagaa acgccgtcga agccgtgtgc gagacaccgc ggccgccggc gttgtggata    2460
cctcgcggaa aacttggccc tcactgacag atgaggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca gcctggggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt ctttttaacct gcttttaaac caatattat     2880
aaaccttgtt tttaaccagg gctgcgccct gtgcgcgtga ccgcgcacgc cgaagggggg    2940
tgcccccct tctcgaaccc tcccggcccg ctaacgcggg cctcccatcc ccccagggc      3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga ccttttacaga attactctat gaagcgccat atttaaaaag   3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgg taaaacagc cagcgctggc     4020
gcgatttagc cccgacatag ccccactgtt cgtccatttc cgcgcagacg atgacgtcac    4080
tgcccggctg tatgcgcgag gttaccgact gcggcctgag tttttttaagt gacgtaaaat   4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgttta cggcagtgag agcagagata gcgctgatgt ccggcggtgc ttttgccgtt     4320
```

```
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggtttta gaatgcaagg aacagtgaat tggagttcgt    4560
cttgttataa ttagcttctt ggggtatctt taaatactgt agaaaagagg aaggaaataa    4620
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga agctgcctg ttccaaaggt cctgcacttt     4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcgggcaat    5700 cccgcaagga gggtgaatga atcggacgtt tgaccgaaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa cgacacggc    6180 ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca cccctatcgg    6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atggagaag taccgcaagc tgtcgccgac     6660
ggcccgacgg atgttcgact atttcagctc gcaccgggag ccgtacccgc tcaagctgga    6720
```

```
aaccttccgc ctcatgtgcg gatcggattc cacccgcgtg aagaagtggc gcgagcaggt    6780
cggcgaagcc tgcgaagagt tgcgaggcag cggcctggtg gaacacgcct gggtcaatga    6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc aacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcggcgtcg cagcgggcct ggcggggggcg    7680 gtttccatgg cgttcggaac cgtgctgacc cgcaagtggc aacctcccgt gcctctgctc    7740
acctttaccg cctggcaact gcggccggga ggacttctgc tcgttccagt agctttagtg    7800
tttgatccgc caatcccgat gcctacagga accaatgttc tcggcctggc gtggctcggc    7860
ctgatcggag cggtttaac ctacttcctt tggttccggg ggatctcgcg actcgaacct    7920
acagttgttt ccttactggg cttttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt tgtgccgag ctgccggtcg gggagctgtt ggctggctgg    8460
tggcaggata tattgtggtg taaacaaatt gacgcttaga caacttaata acacattgcg    8520
gacgttttta atgtactggg gtggtttttc ttttcaccag tgagacgggc aacagctgat    8580 tgccccttcac cgcctggccc tgagagagtt gcagcaagcg gtccacgctg gtttgcccca    8640
gcaggcgaaa atcctgtttg atggtggttc cgaaatcggc aaaatcccctt ataaatcaaa    8700 agaatagccc gagataggggt tgagtgttgt tccagtttgg aacaagagtc cactattaaa    8760
gaacgtggac tccaacgtca aagggcgaaa aaccgtctat cagggcgatg gcccactacg    8820
tgaaccatca cccaaatcaa gttttttggg gtcgaggtgc cgtaaagcac taaatcggaa    8880
ccctaaaggg agccccgat ttagagcttg acggggaaag ccggcgaacg tggcgagaaa    8940
ggaagggaag aaagcgaaag gagcgggcgc cattcaggct gcgcaactgt tgggaagggc    9000
gatcggtgcg ggcctcttcg ctattacgcc agctggcgaa aggggggatgt gctgcaaggc    9060 gattaagttg ggtaacgcca gggttttccc agtcacgacg ttgtaaaacg acggccagtg    9120
```

```
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcggggatc cgtcgaagct     9360 agcttgggtc ccgctcagaa gaactcgtca agaaggcgat agaaggcgat gcgctgcgaa    9420
tcgggagcgg cgataccgta aagcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
agttcggctg gcgcgagccc ctgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga tactttctcg    9840
gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata ccgcgctgc ctcgtcctgc agttcattca gggcaccgga caggtcggtc     10020
ttgacaaaaa gaaccgggcg cccctgcgct gacagccgga acacggcggc atcagagcag    10080
ccgattgtct gttgtgccca gtcatagccg aatagcctct ccacccaagc ggccggagaa    10140
cctgcgtgca atccatcttg ttcaatccaa gctcccatgg gcctcgact agagtcgaga     10200 tctggattga gagtgaatat gagactctaa ttggataccg aggggaattt atggaacgtc    10260
agtggagcat ttttgacaag aaatatttgc tagctgatag tgaccttagg cgacttttga    10320
acgcgcaata atggtttctg acgtatgtgc ttagctcatt aaactccaga aacccgcggc    10380
tgagtggctc cttcaacgtt gcggttctgt cagttccaaa cgtaaaacgg cttgtcccgc    10440
gtcatcggcg ggggtcataa cgtgactccc ttaattctcc gctcatgatc ttgatcccct    10500
gcgccatcag atccttggcg gcaagaaagc catccagttt actttgcagg gcttcccaac    10560
cttaccagag ggcgccccag ctggcaattc cggttcgctt gctgtccata aaaccgccca    10620
gtctagctat cgccatgtaa gcccactgca agctacctgc tttctctttg cgcttgcgtt    10680
ttcccttgtc cagatagccc agtagctgac attcatccgg ggtcagcacc gtttctgcgg    10740
actggctttc tacgtgttcc gcttccttta gcagcccttg cgccctgagt gcttgcggca    10800
gcgtgaagct tgcatgcctg caggtcgacg gcgcgccgag ctcctcgagc aaatttacac    10860
attgccacta aacgtctaaa cccttgtaat tgttttttgt tttactatgt gtgttatgta    10920
tttgatttgc gataaatttt tatatttggt actaaattta taacacccttt tatgctaacg    10980 tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata taccaaaac attcaataat tcttgaggat aataatggta ccacacaaga     11220
tttgaggtgc atgaacgtca cgtggacaaa aggtttagta attttttcaag acaacaatgt   11280 taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagttta cacgattata atttcttcat      11520
```

-continued

```
agccagccca ccgcggtgga aa atg gag gtc gtg gag aga ttc tac ggt gag      11572
                        Met Glu Val Val Glu Arg Phe Tyr Gly Glu
                         1               5                  10 ttg gat ggg aag gtc tcg cag ggc gtg aat gca ttg ctg ggt agt ttt      11620
Leu Asp Gly Lys Val Ser Gln Gly Val Asn Ala Leu Leu Gly Ser Phe
             15                  20                  25 ggg gtg gag ttg acg gat acg ccc act acc aaa ggc ttg ccc ctc gtt      11668
Gly Val Glu Leu Thr Asp Thr Pro Thr Thr Lys Gly Leu Pro Leu Val
                 30                  35                  40 gac agt ccc aca ccc atc gtc ctc ggt gtt tct gta tac ttg act att      11716
Asp Ser Pro Thr Pro Ile Val Leu Gly Val Ser Val Tyr Leu Thr Ile
             45                  50                  55 gtc att gga ggg ctt ttg tgg ata aag gcc agg gat ctg aaa ccg cgc      11764
Val Ile Gly Gly Leu Leu Trp Ile Lys Ala Arg Asp Leu Lys Pro Arg
 60                  65                  70 gcc tcg gag cca ttt ttg ctc caa gct ttg gtg ctt gtg cac aac ctg      11812
Ala Ser Glu Pro Phe Leu Leu Gln Ala Leu Val Leu Val His Asn Leu
 75                  80                  85                  90 ttc tgt ttt gcg ctc agt ctg tat atg tgc gtg ggc atc gct tat cag      11860
Phe Cys Phe Ala Leu Ser Leu Tyr Met Cys Val Gly Ile Ala Tyr Gln
                 95                 100                 105 gct att acc tgg cgg tac tct ctc tgg ggc aat gca tac aat cct aaa      11908
Ala Ile Thr Trp Arg Tyr Ser Leu Trp Gly Asn Ala Tyr Asn Pro Lys
                110                 115                 120 cat aaa gag atg gcg att ctg gta tac ttg ttc tac atg tct aag tac      11956
His Lys Glu Met Ala Ile Leu Val Tyr Leu Phe Tyr Met Ser Lys Tyr
                125                 130                 135 gtg gaa ttc atg gat acc gtt atc atg ata ctg aag cgc agc acc agg      12004
Val Glu Phe Met Asp Thr Val Ile Met Ile Leu Lys Arg Ser Thr Arg
140                 145                 150 caa ata agc ttc ctc cac gtt tat cat cat tct tca att tcc ctc att      12052
Gln Ile Ser Phe Leu His Val Tyr His His Ser Ser Ile Ser Leu Ile
155                 160                 165                 170 tgg tgg gct att gct cat cac gct cct ggc ggt gaa gca tat tgg tct      12100
Trp Trp Ala Ile Ala His His Ala Pro Gly Gly Glu Ala Tyr Trp Ser
                175                 180                 185 gcg gct ctg aac tca gga gtg cat gtt ctc atg tat gcg tat tac ttc      12148
Ala Ala Leu Asn Ser Gly Val His Val Leu Met Tyr Ala Tyr Tyr Phe
                190                 195                 200 ttg gct gcc tgc ctt cga agt agc cca aag tta aaa aat aag tac ctt      12196
Leu Ala Ala Cys Leu Arg Ser Ser Pro Lys Leu Lys Asn Lys Tyr Leu
                205                 210                 215 ttt tgg ggc agg tac ttg aca caa ttc caa atg ttc cag ttt atg ctg      12244
Phe Trp Gly Arg Tyr Leu Thr Gln Phe Gln Met Phe Gln Phe Met Leu
220                 225                 230 aac tta gtg cag gct tac tac gac atg aaa acg aat gcg cca tat cca      12292
Asn Leu Val Gln Ala Tyr Tyr Asp Met Lys Thr Asn Ala Pro Tyr Pro
235                 240                 245                 250 caa tgg ctg atc aag att ttg ttc tac tac atg atc tcg ttg ctg ttt      12340
Gln Trp Leu Ile Lys Ile Leu Phe Tyr Tyr Met Ile Ser Leu Leu Phe
                255                 260                 265 ctt ttc ggc aat ttt tac gta caa aaa tac atc aaa ccc tct gac gga      12388
Leu Phe Gly Asn Phe Tyr Val Gln Lys Tyr Ile Lys Pro Ser Asp Gly
                270                 275                 280 aag caa aag gga gct aaa act gag tga tctagaaggc ctcctgcttt            12435
Lys Gln Lys Gly Ala Lys Thr Glu
                285                 290 aatgagatat gcgagacgcc tatgatcgca tgatatttgc tttcaattct gttgtgcacg    12495
ttgtaaaaaa cctgagcatg tgtagctcag atccttaccg ccggtttcgg ttcattctaa    12555
```

-continued

```
tgaatatatc accegttact atcgtatttt tatgaataat attctccgtt caatttactg    12615
attgtccgtc gagcaaattt acacattgcc actaaacgtc taaacccttg taatttgttt    12675
ttgttttact atgtgtgtta tgtatttgat ttgcgataaa tttttatatt tggtactaaa    12735
tttataacac cttttatgct aacgtttgcc aacacttagc aatttgcaag ttgattaatt    12795
gattctaaat tattttgtc ttctaaatac atatactaat caactggaaa tgtaaatatt     12855
tgctaatatt tctactatag gagaattaaa gtgagtgaat atggtaccac aaggtttgga    12915
gatttaattg ttgcaatgct gcatggatgg catatacacc aaacattcaa taattcttga    12975
ggataataat ggtaccacac aagatttgag gtgcatgaac gtcacgtgga caaaaggttt    13035
agtaattttt caagacaaca atgttaccac acacaagttt tgaggtgcat gcatggatgc    13095
cctgtggaaa gtttaaaaat attttggaaa tgatttgcat ggaagccatg tgtaaaacca    13155
tgacatccac ttggaggatg caataatgaa gaaaactaca aatttacatg caactagtta    13215
tgcatgtagt ctatataatg aggattttgc aatactttca ttcatacaca ctcactaagt    13275
tttacacgat tataatttct tcatagccag cggatcc atg gta ttc gcg ggc ggt     13330
                                         Met Val Phe Ala Gly Gly
                                                         295
```

```
gga ctt cag cag ggc tct ctc gaa gaa aac atc gac gtc gag cac att    13378
Gly Leu Gln Gln Gly Ser Leu Glu Glu Asn Ile Asp Val Glu His Ile
        300                 305                 310 gcc agt atg tct ctc ttc agc gac ttc ttc agt tat gtg tct tca act    13426
Ala Ser Met Ser Leu Phe Ser Asp Phe Phe Ser Tyr Val Ser Ser Thr
    315                 320                 325 gtt ggt tcg tgg agc gta cac agt ata caa cct ttg aag cgc ctg acg    13474
Val Gly Ser Trp Ser Val His Ser Ile Gln Pro Leu Lys Arg Leu Thr
330                 335                 340 agt aag aag cgt gtt tcg gaa agc gct gcc gtg caa tgt ata tca gct    13522
Ser Lys Lys Arg Val Ser Glu Ser Ala Ala Val Gln Cys Ile Ser Ala
345                 350                 355                 360 gaa gtt cag aga aat tcg agt acc cag gga act gcg gag gca ctc gca    13570
Glu Val Gln Arg Asn Ser Ser Thr Gln Gly Thr Ala Glu Ala Leu Ala
            365                 370                 375 gaa tca gtc gtg aag ccc acg aga cga agg tca tct cag tgg aag aag    13618
Glu Ser Val Val Lys Pro Thr Arg Arg Arg Ser Ser Gln Trp Lys Lys
        380                 385                 390 tcg aca cac ccc cta tca gaa gta gca gta cac aac aag cca agc gat    13666
Ser Thr His Pro Leu Ser Glu Val Ala Val His Asn Lys Pro Ser Asp
    395                 400                 405 tgc tgg att gtt gta aaa aac aag gtg tat gat gtt tcc aat ttt gcg    13714
Cys Trp Ile Val Val Lys Asn Lys Val Tyr Asp Val Ser Asn Phe Ala
410                 415                 420 gac gag cat ccc gga gga tca gtt att agt act tat ttt gga cga gac    13762
Asp Glu His Pro Gly Gly Ser Val Ile Ser Thr Tyr Phe Gly Arg Asp
425                 430                 435                 440 ggc aca gat gtt ttc tct agt ttt cat gca gct tct aca tgg aaa att    13810
Gly Thr Asp Val Phe Ser Ser Phe His Ala Ala Ser Thr Trp Lys Ile
            445                 450                 455 ctt caa gac ttt tac att ggt gac gtg gag agg gtg gag ccg act cca    13858
Leu Gln Asp Phe Tyr Ile Gly Asp Val Glu Arg Val Glu Pro Thr Pro
        460                 465                 470 gag ctg ctg aaa gat ttc cga gaa atg aga gct ctt ttc ctg agg gag    13906
Glu Leu Leu Lys Asp Phe Arg Glu Met Arg Ala Leu Phe Leu Arg Glu
    475                 480                 485 caa ctt ttc aaa agt tcg aaa ttg tac tat gtt atg aag ctg ctc acg    13954
Gln Leu Phe Lys Ser Ser Lys Leu Tyr Tyr Val Met Lys Leu Leu Thr
490                 495                 500
```

```
aat gtt gct att ttt gct gcg agc att gca ata ata tgt tgg agc aag    14002
Asn Val Ala Ile Phe Ala Ala Ser Ile Ala Ile Ile Cys Trp Ser Lys
505                 510                 515                 520 act att tca gcg gtt ttg gct tca gct tgt atg atg gct ctg tgt ttc    14050
Thr Ile Ser Ala Val Leu Ala Ser Ala Cys Met Met Ala Leu Cys Phe
                525                 530                 535 caa cag tgc gga tgg cta tcc cat gat ttt ctc cac aat cag gtg ttt    14098
Gln Gln Cys Gly Trp Leu Ser His Asp Phe Leu His Asn Gln Val Phe
            540                 545                 550 gag aca cgc tgg ctt aat gaa gtt gtc ggg tat gtg atc ggc aac gcc    14146
Glu Thr Arg Trp Leu Asn Glu Val Val Gly Tyr Val Ile Gly Asn Ala
        555                 560                 565 gtt ctg ggg ttt agt aca ggg tgg tgg aag gag aag cat aac ctt cat    14194
Val Leu Gly Phe Ser Thr Gly Trp Trp Lys Glu Lys His Asn Leu His
    570                 575                 580 cat gct gct cca aat gaa tgc gat cag act tac caa cca att gat gaa    14242
His Ala Ala Pro Asn Glu Cys Asp Gln Thr Tyr Gln Pro Ile Asp Glu
585                 590                 595                 600 gat att gat act ctc ccc ctc att gcc tgg agc aag gac ata ctg gcc    14290
Asp Ile Asp Thr Leu Pro Leu Ile Ala Trp Ser Lys Asp Ile Leu Ala
                605                 610                 615 aca gtt gag aat aag aca ttc ttg cga atc ctc caa tac cag cat ctg    14338
Thr Val Glu Asn Lys Thr Phe Leu Arg Ile Leu Gln Tyr Gln His Leu
            620                 625                 630 ttc ttc atg ggt ctg tta ttt ttc gcc cgt ggt agt tgg ctc ttt tgg    14386
Phe Phe Met Gly Leu Leu Phe Phe Ala Arg Gly Ser Trp Leu Phe Trp
        635                 640                 645 agc tgg aga tat acc tct aca gca gtg ctc tca cct gtc gac agg ttg    14434
Ser Trp Arg Tyr Thr Ser Thr Ala Val Leu Ser Pro Val Asp Arg Leu
    650                 655                 660 ttg gag aag gga act gtt ctg ttt cac tac ttt tgg ttc gtc ggg aca    14482
Leu Glu Lys Gly Thr Val Leu Phe His Tyr Phe Trp Phe Val Gly Thr
665                 670                 675                 680 gcg tgc tat ctt ctc cct ggt tgg aag cca tta gta tgg atg gcg gtg    14530
Ala Cys Tyr Leu Leu Pro Gly Trp Lys Pro Leu Val Trp Met Ala Val
                685                 690                 695 act gag ctc atg tcc ggc atg ctg ctg ggc ttt gta ttt gta ctt agc    14578
Thr Glu Leu Met Ser Gly Met Leu Leu Gly Phe Val Phe Val Leu Ser
            700                 705                 710 cac aat ggg atg gag gtt tat aat tcg tct aaa gaa ttc gtg agt gca    14626
His Asn Gly Met Glu Val Tyr Asn Ser Ser Lys Glu Phe Val Ser Ala
        715                 720                 725 cag atc gta tcc aca cgg gat atc aaa gga aac ata ttc aac gac tgg    14674
Gln Ile Val Ser Thr Arg Asp Ile Lys Gly Asn Ile Phe Asn Asp Trp
    730                 735                 740 ttc act ggt ggc ctt aac agg caa ata gag cat cat ctt ttc cca aca    14722
Phe Thr Gly Gly Leu Asn Arg Gln Ile Glu His His Leu Phe Pro Thr
745                 750                 755                 760 atg ccc agg cat aat tta aac aaa ata gca cct aga gtg gag gtg ttc    14770
Met Pro Arg His Asn Leu Asn Lys Ile Ala Pro Arg Val Glu Val Phe
                765                 770                 775 tgt aag aaa cac ggt ctg gtg tac gaa gac gta tct att gct acc ggc    14818
Cys Lys Lys His Gly Leu Val Tyr Glu Asp Val Ser Ile Ala Thr Gly
            780                 785                 790 act tgc aag gtt ttg aaa gca ttg aag gaa gtc gcg gag gct gcg gca    14866
Thr Cys Lys Val Leu Lys Ala Leu Lys Glu Val Ala Glu Ala Ala Ala
        795                 800                 805 gag cag cat gct acc acc agt taa gctagcgtta accctgcttt aatgagatat   14920
Glu Gln His Ala Thr Thr Ser
        810                 815
```

-continued

```
gcgagacgcc tatgatcgca tgatatttgc tttcaattct gttgtgcacg ttgtaaaaaa    14980
cctgagcatg tgtagctcag atccttaccg ccggtttcgg ttcattctaa tgaatatatc    15040
acccgttact atcgtatttt tatgaataat attctccgtt caatttactg attgtccgtc    15100
gagcaaattt acacattgcc actaaacgtc taaacccttg taatttgttt ttgttttact    15160
atgtgtgtta tgtatttgat ttgcgataaa tttttatatt tggtactaaa tttataacac    15220
cttttatgct aacgtttgcc aacacttagc aatttgcaag ttgattaatt gattctaaat    15280 tattttttgtc ttctaaatac atatactaat caactggaaa tgtaaatatt tgctaatatt   15340
tctactatag gagaattaaa gtgagtgaat atggtaccac aaggtttgga gatttaattg    15400
ttgcaatgct gcatggatgg catatacacc aaacattcaa taattcttga ggataataat    15460
ggtaccacac aagatttgag gtgcatgaac gtcacgtgga caaaaggttt agtaattttt    15520
caagacaaca atgttaccac acacaagttt tgaggtgcat gcatggatgc cctgtggaaa    15580
gtttaaaaat attttggaaa tgatttgcat ggaagccatg tgtaaaacca tgacatccac    15640
ttggaggatg caataatgaa gaaaactaca aatttacatg caactagtta tgcatgtagt    15700
ctatataatg aggattttgc aatacttttca ttcatacaca ctcactaagt tttacacgat    15760
tataatttct tcatagccag cagatctaaa atg gct ccg gat gcg gat aag ctt    15814
                                  Met Ala Pro Asp Ala Asp Lys Leu
                                                  820 cga caa cgc cag acg act gcg gta gcg aag cac aat gct gct acc ata     15862
Arg Gln Arg Gln Thr Thr Ala Val Ala Lys His Asn Ala Ala Thr Ile
    825                 830                 835 tcg acg cag gaa cgc ctt tgc agt ctg tct tcg ctc aaa ggc gaa gaa     15910
Ser Thr Gln Glu Arg Leu Cys Ser Leu Ser Ser Leu Lys Gly Glu Glu
840                 845                 850                 855 gtc tgc atc gac gga atc atc tat gac ctc caa tca ttc gat cat ccc     15958
Val Cys Ile Asp Gly Ile Ile Tyr Asp Leu Gln Ser Phe Asp His Pro
                860                 865                 870 ggg ggt gaa acg atc aaa atg ttt ggt ggc aac gat gtc act gta cag     16006
Gly Gly Glu Thr Ile Lys Met Phe Gly Gly Asn Asp Val Thr Val Gln
            875                 880                 885 tac aag atg att cac ccg tac cat acc gag aag cat ttg gaa aag atg     16054
Tyr Lys Met Ile His Pro Tyr His Thr Glu Lys His Leu Glu Lys Met
        890                 895                 900 aag cgt gtc ggc aag gtg acg gat ttc gtc tgc gag tac aag ttc gat     16102
Lys Arg Val Gly Lys Val Thr Asp Phe Val Cys Glu Tyr Lys Phe Asp
    905                 910                 915 acc gaa ttt gaa cgc gaa atc aaa cga gaa gtc ttc aag att gtg cga     16150
Thr Glu Phe Glu Arg Glu Ile Lys Arg Glu Val Phe Lys Ile Val Arg
920                 925                 930                 935 cga ggc aag gat ttc ggt act ttg gga tgg ttc ttc cgt gcg ttt tgc     16198
Arg Gly Lys Asp Phe Gly Thr Leu Gly Trp Phe Phe Arg Ala Phe Cys
                940                 945                 950 tac att gcc att ttc ttc tac ctg cag tac cat tgg gtc acc acg gga     16246
Tyr Ile Ala Ile Phe Phe Tyr Leu Gln Tyr His Trp Val Thr Thr Gly
            955                 960                 965 acc tct tgg ctg ctg gcc gtg gcc tac gga atc tcc caa gcg atg att     16294
Thr Ser Trp Leu Leu Ala Val Ala Tyr Gly Ile Ser Gln Ala Met Ile
        970                 975                 980 ggc atg aat gtc cag cac gat gcc aac cac ggg gcc acc tcc aag cgt     16342
Gly Met Asn Val Gln His Asp Ala Asn His Gly Ala Thr Ser Lys Arg
    985                 990                 995 ccc tgg gtc aac gac atg cta ggc ctc ggt gcg gat ttt att ggt         16387
Pro Trp Val Asn Asp Met Leu Gly Leu Gly Ala Asp Phe Ile Gly
1000                1005                1010
```

| | | |
|---|---|---|
| ggt tcc aag tgg ctc tgg cag gaa caa cac tgg acc cac cac gct<br>Gly Ser Lys Trp Leu Trp Gln Glu Gln His Trp Thr His His Ala<br>1015                          1020                            1025 | | 16432 |
| tac acc aat cac gcc gag atg gat ccc gat agc ttt ggt gcc gaa<br>Tyr Thr Asn His Ala Glu Met Asp Pro Asp Ser Phe Gly Ala Glu<br>1030                          1035                            1040 | | 16477 |
| cca atg ctc cta ttc aac gac tat ccc ttg gat cat ccc gct cgt<br>Pro Met Leu Leu Phe Asn Asp Tyr Pro Leu Asp His Pro Ala Arg<br>1045                          1050                            1055 | | 16522 |
| acc tgg cta cat cgc ttt caa gca ttc ttt tac atg ccc gtc ttg<br>Thr Trp Leu His Arg Phe Gln Ala Phe Phe Tyr Met Pro Val Leu<br>1060                          1065                            1070 | | 16567 |
| gct gga tac tgg ttg tcc gct gtc ttc aat cca caa att ctt gac<br>Ala Gly Tyr Trp Leu Ser Ala Val Phe Asn Pro Gln Ile Leu Asp<br>1075                          1080                            1085 | | 16612 |
| ctc cag caa cgc ggc gca ctt tcc gtc ggt atc cgt ctc gac aac<br>Leu Gln Gln Arg Gly Ala Leu Ser Val Gly Ile Arg Leu Asp Asn<br>1090                          1095                            1100 | | 16657 |
| gct ttc att cac tcg cga cgc aag tat gcg gtt ttc tgg cgg gct<br>Ala Phe Ile His Ser Arg Arg Lys Tyr Ala Val Phe Trp Arg Ala<br>1105                          1110                            1115 | | 16702 |
| gtg tac att gcg gtg aac gtg att gct ccg ttt tac aca aac tcc<br>Val Tyr Ile Ala Val Asn Val Ile Ala Pro Phe Tyr Thr Asn Ser<br>1120                          1125                            1130 | | 16747 |
| ggc ctc gaa tgg tcc tgg cgt gtc ttt gga aac atc atg ctc atg<br>Gly Leu Glu Trp Ser Trp Arg Val Phe Gly Asn Ile Met Leu Met<br>1135                          1140                            1145 | | 16792 |
| ggt gtg gcg gaa tcg ctc gcg ctg gcg gtc ctg ttt tcg ttg tcg<br>Gly Val Ala Glu Ser Leu Ala Leu Ala Val Leu Phe Ser Leu Ser<br>1150                          1155                            1160 | | 16837 |
| cac aat ttc gaa tcc gcg gat cgc gat ccg acc gcc cca ctg aaa<br>His Asn Phe Glu Ser Ala Asp Arg Asp Pro Thr Ala Pro Leu Lys<br>1165                          1170                            1175 | | 16882 |
| aag acg gga gaa cca gtc gac tgg ttc aag aca cag gtc gaa act<br>Lys Thr Gly Glu Pro Val Asp Trp Phe Lys Thr Gln Val Glu Thr<br>1180                          1185                            1190 | | 16927 |
| tcc tgc act tac ggt gga ttc ctt tcc ggt tgc ttc acg gga ggt<br>Ser Cys Thr Tyr Gly Gly Phe Leu Ser Gly Cys Phe Thr Gly Gly<br>1195                          1200                            1205 | | 16972 |
| ctc aac ttt cag gtt gaa cac cac ttg ttc cca cgc atg agc agc<br>Leu Asn Phe Gln Val Glu His His Leu Phe Pro Arg Met Ser Ser<br>1210                          1215                            1220 | | 17017 |
| gct tgg tat ccc tac att gcc ccc aag gtc cgc gaa att tgc gcc<br>Ala Trp Tyr Pro Tyr Ile Ala Pro Lys Val Arg Glu Ile Cys Ala<br>1225                          1230                            1235 | | 17062 |
| aaa cac ggc gtc cac tac gcc tac tac ccg tgg atc cac caa aac<br>Lys His Gly Val His Tyr Ala Tyr Tyr Pro Trp Ile His Gln Asn<br>1240                          1245                            1250 | | 17107 |
| ttt ctc tcc acc gtc cgc tac atg cac gcg gcc ggg acc ggt gcc<br>Phe Leu Ser Thr Val Arg Tyr Met His Ala Ala Gly Thr Gly Ala<br>1255                          1260                            1265 | | 17152 |
| aac tgg cgc cag atg gcc aga gaa aat ccc ttg acc gga cgg gcg<br>Asn Trp Arg Gln Met Ala Arg Glu Asn Pro Leu Thr Gly Arg Ala<br>1270                          1275                            1280 | | 17197 |
| taa agatctgccg gcatcgatcc cgggccatgg cctgctttaa tgagatatgc | | 17250 |
| gagacgccta tgatcgcatg atatttgctt tcaattctgt tgtgcacgtt gtaaaaaacc | | 17310 |
| tgagcatgtg tagctcagat ccttaccgcc ggtttcggtt cattctaatg aatatatcac | | 17370 |
| ccgttactat cgtattttta tgaataatat tctccgttca atttactgat tgtccgtcga | | 17430 |

```
cgagctcggc gcgcctctag aggatcgatg aattcagatc ggctgagtgg ctccttcaac    17490
gttgcggttc tgtcagttcc aaacgtaaaa cggcttgtcc cgcgtcatcg gcggggtca    17550 taacgtgact cccttaattc tccgctcatg atcagattgt cgtttccgc cttcagttta    17610 aactatcagt gtttgacagg atatattggc gggtaaacct aagagaaaag agcgtttatt    17670
agaataatcg gatatttaaa agggcgtgaa aaggtttatc cttcgtccat ttgtatgtgc    17730
atgccaacca cagggttccc ca                                            17752
```

<210> SEQ ID NO 20
<211> LENGTH: 290
<212> TYPE: PRT
<213> ORGANISM: Phaeodactylum tricornutum, Physcomitrella patens

<400> SEQUENCE: 20

```
Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
                20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290
```

<210> SEQ ID NO 21

<211> LENGTH: 525
<212> TYPE: PRT
<213> ORGANISM: Phaeodactylum tricornutum, Physcomitrella patens

<400> SEQUENCE: 21

```
Met Val Phe Ala Gly Gly Leu Gln Gln Gly Ser Leu Glu Asn
1               5                   10                  15

Ile Asp Val Glu His Ile Ala Ser Met Ser Leu Phe Ser Asp Phe Phe
                20                  25                  30

Ser Tyr Val Ser Ser Thr Val Gly Ser Trp Ser Val His Ser Ile Gln
                35                  40                  45

Pro Leu Lys Arg Leu Thr Ser Lys Lys Arg Val Ser Glu Ser Ala Ala
    50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
                100                 105                 110

His Asn Lys Pro Ser Asp Cys Trp Ile Val Lys Asn Lys Val Tyr
                115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
                180                 185                 190

Ala Leu Phe Leu Arg Glu Gln Leu Phe Lys Ser Ser Lys Leu Tyr Tyr
                195                 200                 205

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
                260                 265                 270

Tyr Val Ile Gly Asn Ala Val Leu Gly Phe Ser Thr Gly Trp Trp Lys
                275                 280                 285

Glu Lys His Asn Leu His Ala Ala Pro Asn Glu Cys Asp Gln Thr
290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Phe Phe Ala Arg
                340                 345                 350

Gly Ser Trp Leu Phe Trp Ser Trp Arg Tyr Thr Ser Thr Ala Val Leu
                355                 360                 365

Ser Pro Val Asp Arg Leu Leu Glu Lys Gly Thr Val Leu Phe His Tyr
    370                 375                 380

Phe Trp Phe Val Gly Thr Ala Cys Tyr Leu Leu Pro Gly Trp Lys Pro
385                 390                 395                 400
```

```
Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
            420                 425                 430

Lys Glu Phe Val Ser Ala Gln Ile Val Ser Thr Arg Asp Ile Lys Gly
        435                 440                 445

Asn Ile Phe Asn Asp Trp Phe Thr Gly Gly Leu Asn Arg Gln Ile Glu
450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Glu Gln His Ala Thr Thr Ser
        515                 520                 525

<210> SEQ ID NO 22
<211> LENGTH: 469
<212> TYPE: PRT
<213> ORGANISM: Phaeodactylum tricornutum, Physcomitrella patens

<400> SEQUENCE: 22

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255
```

```
Pro Val Leu Ala Gly Tyr Trp Leu Ser Ala Val Phe Asn Pro Gln Ile
        260                 265                 270

Leu Asp Leu Gln Gln Arg Gly Ala Leu Ser Val Gly Ile Arg Leu Asp
    275                 280                 285

Asn Ala Phe Ile His Ser Arg Arg Lys Tyr Ala Val Phe Trp Arg Ala
290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465

<210> SEQ ID NO 23
<211> LENGTH: 26
<212> TYPE: DNA
<213> ORGANISM: artificial sequence
<220> FEATURE:
<221> NAME/KEY: misc_feature
<222> LOCATION: (1)..(26)
<223> OTHER INFORMATION: polylinker sequence

<400> SEQUENCE: 23
gaattcggcg cgccgagctc ctcgag                                          26

<210> SEQ ID NO 24
<211> LENGTH: 265
<212> TYPE: DNA
<213> ORGANISM: artificial sequence
<220> FEATURE:
<221> NAME/KEY: misc_feature
<222> LOCATION: (1)..(265)
<223> OTHER INFORMATION: polylinker-terminator-polylinkers sequence

<400> SEQUENCE: 24
ccaccgcggt gggcggccgc ctgcagtcta gaaggcctcc tgctttaatg agatatgcga    60
gacgcctatg atcgcatgat atttgctttc aattctgttg tgcacgttgt aaaaaacctg   120
agcatgtgta gctcagatcc ttaccgccgg tttcggttca ttctaatgaa tatatcaccc   180
gttactatcg tattttatg aataatattc tccgttcaat ttactgattg tccgtcgacg   240
aattcgagct cggcgcgcca agctt                                         265
```

```
<210> SEQ ID NO 25
<211> LENGTH: 257
<212> TYPE: DNA
<213> ORGANISM: artificial sequence
<220> FEATURE:
<221> NAME/KEY: misc_feature
<222> LOCATION: (1)..(257)
<223> OTHER INFORMATION: polylinker-terminator-polylinkers sequence

<400> SEQUENCE: 25
ggatccgata tcgggcccgc tagcgttaac cctgctttaa tgagatatgc gagacgccta    60
tgatcgcatg atatttgctt tcaattctgt tgtgcacgtt gtaaaaaacc tgagcatgtg   120
tagctcagat ccttaccgcc ggtttcggtt cattctaatg aatatatcac ccgttactat   180 cgtatttta tgaataatat tctccgttca atttactgat tgtccgtcga cgaattcgag   240
ctcggcgcgc caagctt                                                   257

<210> SEQ ID NO 26
<211> LENGTH: 5410
<212> TYPE: DNA
<213> ORGANISM: artificial sequence
<220> FEATURE:
<221> NAME/KEY: misc_feature
<222> LOCATION: (1)..(5410)
<223> OTHER INFORMATION: plant expression vector with one
      promoter-terminator expression cassette

<400> SEQUENCE: 26
ttttggaaat gatttgcatg gaagccatgt gtaaaaccat gacatccact tggaggatgc    60
aataatgaag aaaactacaa atttacatgc aactagttat gcatgtagtc tatataatga   120
ggattttgca atactttcat tcatacacac tcactaagtt ttacacgatt ataatttctt   180
catagccagc ggatccgata tcgggcccgc tagcgttaac cctgctttaa tgagatatgc   240
gagacgccta tgatcgcatg atatttgctt tcaattctgt tgtgcacgtt gtaaaaaacc   300
tgagcatgtg tagctcagat ccttaccgcc ggtttcggtt cattctaatg aatatatcac   360
ccgttactat cgtatttta tgaataatat tctccgttca atttactgat tgtccgtcga   420
gcaaatttac acattgccac taaacgtcta aaccccttgta atttgttttt gttttactat   480
gtgtgttatg tatttgattt gcgataaatt tttatatttg gtactaaatt tataacacct   540
tttatgctaa cgtttgccaa cacttagcaa tttgcaagtt gattaattga ttctaaatta   600 ttttttgtctt ctaaatacat atactaatca actggaaatg taaatatttg ctaatatttc   660
tactatagga gaattaaagt gagtgaatat ggtaccacaa ggtttggaga tttaattgtt   720
gcaatgctgc atggatggca tatacaccaa acattcaata attcttgagg ataataatgg   780
taccacacaa gatttgaggt gcatgaacgt cacgtggaca aaaggtttag taattttca   840 agacaacaat gttaccacac acaagttttg aggtgcatgc atggatgccc tgtggaaagt   900
ttaaaaatat tttggaaatg atttgcatgg aagccatgtg taaaaccatg acatccactt   960
ggaggatgca ataatgaaga aaactacaaa tttacatgca actagttatg catgtagtct  1020
atataatgag gattttgcaa tactttcatt catacacact cactaagttt tacacgatta  1080
taatttcttc atagccagca gatctgccgg catcgatccc gggccatggc ctgctttaat  1140
gagatatgcg agacgcctat gatcgcatga tatttgcttt caattctgtt gtgcacgttg  1200
taaaaaacct gagcatgtgt agctcagatc cttaccgccg gtttcggttc attctaatga  1260
atatatcacc cgttactatc gtattttat gaataatatt ctccgttcaa tttactgatt  1320
gtccgtcgac gagctcggcg cgccaagctt ggcgtaatca tggtcatagc tgtttcctgt  1380
```

```
gtgaaattgt tatccgctca caattccaca caacatacga gccggaagca taaagtgtaa    1440
agcctggggt gcctaatgag tgagctaact cacattaatt gcgttgcgct cactgcccgc    1500
tttccagtcg ggaaacctgt cgtgccagct gcattaatga atcggccaac gcgcggggag    1560
aggcggtttg cgtattgggc gctcttccgc ttcctcgctc actgactcgc tgcgctcggt    1620
cgttcggctg cggcgagcgg tatcagctca ctcaaaggcg gtaatacggt tatccacaga    1680 atcagggga taacgcagga agaacatgtg agcaaaaggc cagcaaaagg ccaggaaccg    1740
taaaaaggcc gcgttgctgg cgttttccca taggctccgc cccctgacg agcatcacaa    1800 aaatcgacgc tcaagtcaga ggtggcgaaa cccgacagga ctataaagat accaggcgtt    1860
tccccctgga agctccctcg tgcgctctcc tgttccgacc ctgccgctta ccggatacct    1920
gtccgccttt ctcccttcgg gaagcgtggc gctttctcat agctcacgct gtaggtatct    1980
cagttcggtg taggtcgttc gctccaagct gggctgtgtg cacgaacccc ccgttcagcc    2040
cgaccgctgc gccttatccg gtaactatcg tcttgagtcc aacccggtaa gacacgactt    2100
atcgccactg gcagcagcca ctggtaacag gattagcaga gcgaggtatg taggcggtgc    2160
tacagagttc ttgaagtggt ggcctaacta cggctacact agaaggacag tatttggtat    2220
ctgcgctctg ctgaagccag ttaccttcgg aaaaagagtt ggtagctctt gatccggcaa    2280
acaaaccacc gctggtagcg gtggtttttt tgtttgcaag cagcagatta cgcgcagaaa    2340
aaaaggatct caagaagatc ctttgatctt ttctacgggg tctgacgctc agtggaacga    2400
aaactcacgt taagggattt tggtcatgag attatcaaaa aggatcttca cctagatcct    2460
tttaaattaa aaatgaagtt ttaaatcaat ctaaagtata tatgagtaaa cttggtctga    2520
cagttaccaa tgcttaatca gtgaggcacc tatctcagcg atctgtctat ttcgttcatc    2580
catagttgcc tgactccccg tcgtgtagat aactacgata cgggagggct taccatctgg    2640
ccccagtgct gcaatgatac cgcgagaccc acgctcaccg gctccagatt tatcagcaat    2700
aaaccagcca gccggaaggg ccgagcgcag aagtggtcct gcaactttat ccgcctccat    2760
ccagtctatt aattgttgcc gggaagctag agtaagtagt tcgccagtta atagtttgcg    2820
caacgttgtt gccattgcta caggcatcgt ggtgtcacgc tcgtcgtttg gtatggcttc    2880
attcagctcc ggttcccaac gatcaaggcg agttacatga tcccccatgt tgtgcaaaaa    2940
agcggttagc tccttcggtc ctccgatcgt tgtcagaagt aagttggccg cagtgttatc    3000
actcatggtt atggcagcac tgcataattc tcttactgtc atgccatccg taagatgctt    3060
ttctgtgact ggtgagtact caaccaagtc attctgagaa tagtgtatgc ggcgaccgag    3120
ttgctcttgc ccggcgtcaa tacgggataa taccgcgcca catagcagaa ctttaaaagt    3180
gctcatcatt ggaaaacgtt cttcggggcg aaaactctca aggatcttac cgctgttgag    3240
atccagttcg atgtaaccca ctcgtgcacc caactgatct tcagcatctt ttactttcac    3300
cagcgtttct gggtgagcaa aaacaggaag gcaaaatgcc gcaaaaaagg gaataagggc    3360
gacacggaaa tgttgaatac tcatactctt cctttttcaa tattattgaa gcatttatca    3420
gggttattgt ctcatgagcg gatacatatt tgaatgtatt tagaaaaata aacaaatagg    3480
ggttccgcgc acatttcccc gaaaagtgcc acctgacgtc taagaaacca ttattatcat    3540
gacattaacc tataaaaata ggcgtatcac gaggcccttt cgtctcgcgc gtttcggtga    3600
tgacggtgaa aacctctgac acatgcagct cccggagacg gtcacagctt gtctgtaagc    3660
ggatgccggg agcagacaag cccgtcaggg cgcgtcagcg ggtgttggcg ggtgtcgggg    3720
ctggcttaac tatgcggcat cagagcagat tgtactgaga gtgcaccata tgcggtgtga    3780
```

```
aataccgcac agatgcgtaa ggagaaaata ccgcatcagg cgccattcgc cattcaggct    3840
gcgcaactgt tgggaagggc gatcggtgcg ggcctcttcg ctattacgcc agctggcgaa    3900 aggggatgt gctgcaaggc gattaagttg ggtaacgcca gggttttccc agtcacgacg     3960
ttgtaaaacg acggccagtg aattcggcgc gccgagctcc tcgagcaaat ttacacattg    4020
ccactaaacg tctaaaccct tgtaatttgt ttttgtttta ctatgtgtgt tatgtatttg    4080
atttgcgata aattttata tttggtacta aatttataac accttttatg ctaacgtttg     4140
ccaacactta gcaatttgca agttgattaa ttgattctaa attattttg tcttctaaat     4200 acatatacta atcaactgga aatgtaaata tttgctaata tttctactat aggagaatta    4260
aagtgagtga atatggtacc acaaggtttg gagatttaat tgttgcaatg ctgcatggat    4320
ggcatataca ccaaacattc aataattctt gaggataata atggtaccac acaagatttg    4380
aggtgcatga acgtcacgtg gacaaaaggt ttagtaattt ttcaagacaa caatgttacc    4440
acacacaagt tttgaggtgc atgcatggat gccctgtgga aagtttaaaa atattttgga    4500
aatgatttgc atggaagcca tgtgtaaaac catgacatcc acttggagga tgcaataatg    4560
aagaaaacta caaatttaca tgcaactagt tatgcatgta gtctatataa tgaggatttt    4620
gcaatacttt cattcataca cactcactaa gttttacacg attataattt cttcatagcc    4680
agcccaccgc ggtgggcggc cgcctgcagt ctagaaggcc tcctgcttta atgagatatg    4740
cgagacgcct atgatcgcat gatatttgct ttcaattctg ttgtgcacgt tgtaaaaaac    4800
ctgagcatgt gtagctcaga tccttaccgc cggtttcggt tcattctaat gaatatatca    4860
cccgttacta tcgtattttt atgaataata ttctccgttc aatttactga ttgtccgtcg    4920
agcaaattta cacattgcca ctaaacgtct aaacccttgt aatttgtttt tgttttacta    4980
tgtgtgttat gtatttgatt tgcgataaat ttttatattt ggtactaaat ttataacacc    5040
ttttatgcta acgttgcca acacttagca atttgcaagt tgattaattg attctaaatt     5100 attttttgtct tctaaataca tatactaatc aactggaaat gtaaatattt gctaatattt    5160
ctactatagg agaattaaag tgagtgaata tggtaccaca aggtttggag atttaattgt    5220
tgcaatgctg catggatggc atatacacca aacattcaat aattcttgag gataataatg    5280
gtaccacaca agatttgagg tgcatgaacg tcacgtggac aaaaggttta gtaatttttc    5340
aagacaacaa tgttaccaca cacaagtttt gaggtgcatg catggatgcc ctgtggaaag    5400
tttaaaaata                                                           5410
```

<210> SEQ ID NO 27
<211> LENGTH: 12093
<212> TYPE: DNA
<213> ORGANISM: artificial sequence
<220> FEATURE:
<221> NAME/KEY: misc_feature
<222> LOCATION: (1)..(12093)
<223> OTHER INFORMATION: plant expression vector with one
      promoter-terminator expression cassette

<400> SEQUENCE: 27

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga    300 ttcttatca ctgataagtt ggtggacata ttatgtttat cagtgataaa gtgtcaagca     360
```

```
tgacaaagtt gcagccgaat acagtgatcc gtgccgccct ggacctgttg aacgaggtcg    420
gcgtagacgg tctgacgaca cgcaaactgg cggaacggtt gggggttcag cagccggcgc    480
tttactggca cttcaggaac aagcgggcgc tgctcgacgc actggccgaa gccatgctgg    540
cggagaatca tacgcattcg gtgccgagag ccgacgacga ctggcgctca tttctgatcg    600
ggaatgcccg cagcttcagg caggcgctgc tcgcctaccg cgatggcgcg cgcatccatg    660
ccggcacgcg accgggcgca ccgcagatgg aaacggccga cgcgcagctt cgcttcctct    720
gcgaggcggt ttttcggcc ggggacgccg tcaatgcgct gatgacaatc agctacttca    780 ctgttgggc cgtgcttgag gagcaggccg cgacagcga tgccggcgag cgcggcggca    840
ccgttgaaca ggctccgctc tcgccgctgt tgcgggccgc gatagacgcc ttcgacgaag    900
ccggtccgga cgcagcgttc gagcagggac tcgcggtgat tgtcgatgga ttggcgaaaa    960
ggaggctcgt tgtcaggaac gttgaaggac cgagaaaggg tgacgattga tcaggaccgc   1020
tgccggagcg caacccactc actacagcag agccatgtag acaacatccc ctccccttt    1080 ccaccgcgtc agacgcccgt agcagcccgc tacgggcttt ttcatgccct gccctagcgt   1140
ccaagcctca cggccgcgct cggcctctct ggcggccttc tggcgctctt ccgcttcctc   1200
gctcactgac tcgctgcgct cggtcgttcg gctgcggcga gcggtatcag ctcactcaaa   1260
ggcggtaata cggttatcca cagaatcagg ggataacgca ggaaagaaca tgtgagcaaa   1320
aggccagcaa aaggccagga accgtaaaaa ggccgcgttg ctggcgtttt tccataggct   1380 ccgccccct gacgagcatc acaaaaatcg acgctcaagt cagaggtggc gaaacccgac   1440
aggactataa agataccagg cgtttccccc tggaagctcc ctcgtgcgct ctcctgttcc   1500
gaccctgccg cttaccggat acctgtccgc ctttctccct cgggaagcg tggcgctttt   1560 ccgctgcata accctgcttc ggggtcatta tagcgatttt ttcggtatat ccatcctttt   1620
tcgcacgata tacaggattt tgccaaaggg ttcgtgtaga cttccttgg tgtatccaac   1680 ggcgtcagcc gggcaggata ggtgaagtag gcccacccgc gagcgggtgt tccttcttca   1740
ctgtccctta ttcgcacctg gcggtgctca acgggaatcc tgctctgcga ggctggccgg   1800
ctaccgccgg cgtaacagat gagggcaagc ggatggctga tgaaaccaag ccaaccagga   1860
agggcagccc acctatcaag gtgtactgcc ttccagacga acgaagagcg attgaggaaa   1920
aggcggcggc ggccggcatg agcctgtcgg cctacctgct ggccgtcggc cagggctaca   1980
aaatcacggg cgtcgtggac tatgagcacg tccgcgagct ggcccgcatc aatggcgacc   2040
tgggccgcct gggcggcctg ctgaaactct ggctcaccga cgacccgcgc acggcgcggt   2100
tcggtgatgc cacgatcctc gccctgctgg cgaagatcga agagaagcag gacgagcttg   2160
gcaaggtcat gatgggcgtg gtccgcccga gggcagagcc atgactttt tagccgctaa   2220 aacggccggg gggtgcgcgt gattgccaag cacgtcccca tgcgctccat caagaagagc   2280
gacttcgcgg agctggtgaa gtacatcacc gacgagcaag gcaagaccga gcgcctttgc   2340
gacgctcacc gggctggttg ccctcgccgc tgggctggcg gccgtctatg gccctgcaaa   2400
cgcgccagaa acgcgtcga agccgtgtgc gagacaccgc ggccgccggc gttgtggata   2460
cctcgcggaa aacttggccc tcactgacag atgaggggcg gacgttgaca cttgaggggc   2520
cgactcaccc ggcgcggcgt tgacagatga ggggcaggct cgatttcggc cggcgacgtg   2580
gagctggcca gcctcgcaaa tcggcgaaaa cgcctgattt tacgcgagtt tcccacagat   2640
gatgtggaca agcctgggga taagtgccct gcggtattga cacttgaggg gcgcgactac   2700
tgacagatga ggggcgcgat ccttgacact tgaggggcag agtgctgaca gatgagggc   2760
```

```
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaaggggg    2940 tgccccccct tctcgaaccc tcccggcccg ctaacgcggg cctcccatcc ccccaggggc    3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttacc ttgggcattc ttggcatagt ggtcgcgggt gccgtgctcg     3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagc ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa acaactttga    4500
aaaagctgtt ttctggtatt taaggtttta gaatgcaagg aacagtgaat tggagttcgt    4560
cttgttataa ttagcttctt ggggtatctt taaatactgt agaaagagg aaggaaataa     4620 taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccaccatgat gtgtgaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
```

```
cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc cacccgcgtg aagaagtggc gcgagcaggt    6780
cggcgaagcc tgcgaagagt tgcgaggcag cggcctggtg gaaacgcct gggtcaatga    6840 tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
```

```
ccgatacgat tgatggcggt cctgggggct atttgcggaa ctgcgggcgt ggcgctgttg   7620
gtgttgacac caaacgcagc gctagatcct gtcggcgtcg cagcgggcct ggcggggggcg   7680 gtttccatgg cgttcggaac cgtgctgacc cgcaagtggc aacctcccgt gcctctgctc   7740
acctttaccg cctggcaact ggcggccgga ggacttctgc tcgttccagt agctttagtg   7800
tttgatccgc caatcccgat gcctacagga accaatgttc tcggcctggc gtggctcggc   7860
ctgatcggag cgggtttaac ctacttcctt tggttccggg ggatctcgcg actcgaacct   7920
acagttgttt ccttactggg cttttctcagc cccagatctg gggtcgatca gccggggatg   7980
catcaggccg acagtcggaa cttcgggtcc ccgacctgta ccattcggtg agcaatggat   8040 agggagttg atatcgtcaa cgttcacttc taaagaaata gcgccactca gcttcctcag   8100
cggctttatc cagcgatttc ctattatgtc ggcatagttc tcaagatcga cagcctgtca   8160
cggttaagcg agaaatgaat aagaaggctg ataattcgga tctctgcgag ggagatgata   8220
tttgatcaca ggcagcaacg ctctgtcatc gttacaatca acatgctacc ctccgcgaga   8280
tcatccgtgt ttcaaacccg gcagcttagt tgccgttctt ccgaatagca tcggtaacat   8340
gagcaaagtc tgccgcctta caacggctct cccgctgacg ccgtcccgga ctgatgggct   8400
gcctgtatcg agtggtgatt ttgtgccgag ctgccggtcg gggagctgtt ggctggctgg   8460
tggcaggata tattgtggtg taaacaaatt gacgcttaga caacttaata acacattgcg   8520
gacgttttta atgtactggg gtggtttttc ttttcaccag tgagacgggc aacagctgat   8580
tgcccttcac cgcctggccc tgagagagtt gcagcaagcg gtccacgctg gtttgcccca   8640
gcaggcgaaa atcctgtttg atggtggttc cgaaatcggc aaaatcccct taaatcaaa   8700 agaatagccc gagatagggt tgagtgttgt tccagtttgg aacaagagtc cactattaaa   8760
gaacgtggac tccaacgtca aagggcgaaa accgtctat cagggcgatg gcccactacg   8820
tgaaccatca cccaaatcaa gttttttggg gtcgaggtgc cgtaaagcac taaatcggaa   8880
ccctaaaggg agcccccgat ttagagcttg acggggaaag ccggcgaacg tggcgagaaa   8940
ggaagggaag aaagcgaaag gagcgggcgc cattcaggct gcgcaactgt tgggaagggc   9000
gatcggtgcg ggcctcttcg ctattacgcc agctggcgaa aggggggatgt gctgcaaggc   9060 gattaagttg ggtaacgcca gggttttccc agtcacgacg ttgtaaaacg acggccagtg   9120
aattaattcc catcttgaaa gaaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300
tgtgtaatac ataaattgat gatatagcta gcttagctca tcgggggatc cgtcgaagct   9360
agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg cgcgagcccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga ctctttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
```

```
agccacgata gccgcgctgc ctcgtcctgc agttcattca gggcaccgga caggtcggtc    10020
ttgacaaaaa gaaccgggcg cccctgcgct gacagccgga acacggcggc atcagagcag    10080
ccgattgtct gttgtgccca gtcatagccg aatagcctct ccacccaagc ggccggagaa    10140
cctgcgtgca atccatcttg ttcaatccaa gctcccatgg gccctcgact agagtcgaga    10200
tctggattga gagtgaatat gagactctaa ttggataccg aggggaattt atggaacgtc    10260
agtggagcat ttttgacaag aaatatttgc tagctgatag tgaccttagg cgacttttga    10320
acgcgcaata atggtttctg acgtatgtgc ttagctcatt aaactccaga aacccgcggc    10380
tgagtggctc cttcaacgtt gcggttctgt cagttccaaa cgtaaaacgg cttgtcccgc    10440
gtcatcggcg ggggtcataa cgtgactccc ttaattctcc gctcatgatc ttgatccccT    10500
gcgccatcag atccttggcg gcaagaaagc catccagttt actttgcagg gcttcccaac    10560
cttaccagag ggcgccccag ctggcaattc cggttcgctt gctgtccata aaaccgccca    10620
gtctagctat cgccatgtaa gcccactgca agctacctgc tttctctttg cgcttgcgtt    10680
ttcccttgtc cagatagccc agtagctgac attcatccgg ggtcagcacc gtttctgcgg    10740
actggctttc tacgtgttcc gcttcctttA gcagcccttg cgccctgagt gcttgcggca    10800
gcgtgaagct tgcatgcctg caggtcgacg gcgcgccgag ctcctcgagc aaatttacac    10860
attgccacta aacgtctaaa cccttgtaat ttgttttTgt tttactatgt gtgttatgta    10920
tttgatttgc gataaatttt tatatttggt actaaattta taacacccttt tatgctaacg    10980 tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata taccaaaac attcaataat tcttgaggat aataatggta ccacacaaga    11220
tttgaggtgc atgaacgtca cgtggacaaa aggtttagta atttttcaag acaacaatgt    11280
taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagccca ccgcggtggg cggccgcctg cagtctagaa ggcctcctgc tttaatgaga    11580
tatgcgagac gcctatgatc gcatgatatt tgctttcaat tctgttgtgc acgttgtaaa    11640
aaacctgagc atgtgtagct cagatcctta ccgccggttt cggttcattc taatgaatat    11700
atcacccgtt actatcgtat ttttatgaat aatattctcc gttcaattta ctgattgtcc    11760
gtcgacgaat tcgagctcgg cgcgcctcta gaggatcgat gaattcagat cggctgagtg    11820
gctccttcaa cgttgcggtt ctgtcagttc caaacgtaaa acggcttgtc ccgcgtcatc    11880
ggcgggggtc ataacgtgac tcccttaatt ctccgctcat gatcagattg tcgtttcccg    11940
ccttcagttt aaactatcag tgtttgacag gatatattgg cgggtaaacc taagagaaaa    12000
gagcgtttat tagaataatc ggatatttaa aagggcgtga aaaggtttat ccttcgtcca    12060
tttgtatgtg catgccaacc acagggttcc cca                                12093
```

<210> SEQ ID NO 28
<211> LENGTH: 12085
<212> TYPE: DNA
<213> ORGANISM: artificial sequence
<220> FEATURE:
<221> NAME/KEY: misc_feature
<222> LOCATION: (1)..(12085)
<223> OTHER INFORMATION: plant expression vector with one
      promoter-terminator expression cassette

<400> SEQUENCE: 28

| | | | | | |
|---|---|---|---|---|---|
| gatctggcgc | cggccagcga | gacgagcaag | attggccgcc | gcccgaaacg | atccgacagc | 60 |
| gcgcccagca | caggtgcgca | ggcaaattgc | accaacgcat | acagcgccag | cagaatgcca | 120 |
| tagtgggcgg | tgacgtcgtt | cgagtgaacc | agatcgcgca | ggaggcccgg | cagcaccggc | 180 |
| ataatcaggc | cgatgccgac | agcgtcgagc | gcgacagtgc | tcagaattac | gatcaggggt | 240 |
| atgttgggtt | tcacgtctgg | cctccggacc | agcctccgct | ggtccgattg | aacgcgcgga | 300 |
| ttctttatca | ctgataagtt | ggtggacata | ttatgtttat | cagtgataaa | gtgtcaagca | 360 |
| tgacaaagtt | gcagccgaat | acagtgatcc | gtgccgccct | ggacctgttg | aacgaggtcg | 420 |
| gcgtagacgg | tctgacgaca | cgcaaactgg | cggaacggtt | gggggttcag | cagccggcgc | 480 |
| tttactggca | cttcaggaac | aagcgggcgc | tgctcgacgc | actggccgaa | gccatgctgg | 540 |
| cggagaatca | tacgcattcg | gtgccgagag | ccgacgacga | ctggcgctca | tttctgatcg | 600 |
| ggaatgcccg | cagcttcagg | caggcgctgc | tcgcctaccg | cgatgcgcg | cgcatccatg | 660 |
| ccggcacgcg | accgggcgca | ccgcagatgg | aaacggccga | cgcgcagctt | cgcttcctct | 720 |
| gcgaggcggg | tttttcggcc | ggggacgccg | tcaatgcgct | gatgacaatc | agctacttca | 780 |
| ctgttgggc | cgtgcttgag | gagcaggccg | gcgacagcga | tgccggcgag | cgcggcggca | 840 |
| ccgttgaaca | ggctccgctc | tcgccgctgt | tgcgggccgc | gatagacgcc | ttcgacgaag | 900 |
| ccggtccgga | cgcagcgttc | gagcagggac | tcgcggtgat | tgtcgatgga | ttggcgaaaa | 960 |
| ggaggctcgt | tgtcaggaac | gttgaaggac | cgagaaaggg | tgacgattga | tcaggaccgc | 1020 |
| tgccggagcg | caacccactc | actacagcag | agccatgtag | acaacatccc | ctccccctttt | 1080 |
| ccaccgcgtc | agacgcccgt | agcagcccgc | tacgggcttt | ttcatgccct | gcctagcgt | 1140 |
| ccaagcctca | cggccgcgct | cggcctctct | ggcggccttc | tggcgctctt | ccgcttcctc | 1200 |
| gctcactgac | tcgctgcgct | cggtcgttcg | gctgcggcga | gcggtatcag | ctcactcaaa | 1260 |
| ggcggtaata | cggttatcca | cagaatcagg | ggataacgca | ggaaagaaca | tgtgagcaaa | 1320 |
| aggccagcaa | aaggccagga | accgtaaaaa | ggccgcgttg | ctggcgtttt | tccataggct | 1380 |
| ccgcccccct | gacgagcatc | acaaaaatcg | acgctcaagt | cagaggtggc | gaaacccgac | 1440 |
| aggactataa | agataccagg | cgtttccccc | tggaagctcc | ctcgtgcgct | ctcctgttcc | 1500 |
| gaccctgccg | cttaccggat | acctgtccgc | ctttctccct | tcgggaagcg | tggcgctttt | 1560 |
| ccgctgcata | accctgcttc | ggggtcatta | tagcgatttt | ttcggtatat | ccatcctttt | 1620 |
| tcgcacgata | tacaggattt | tgccaaaggg | ttcgtgtaga | ctttccttgg | tgtatccaac | 1680 |
| ggcgtcagcc | gggcaggata | ggtgaagtag | gcccacccgc | gagcgggtgt | tccttcttca | 1740 |
| ctgtcccttta | ttcgcacctg | gcggtgctca | acgggaatcc | tgctctgcga | ggctggccgg | 1800 |
| ctaccgccgg | cgtaacagat | gagggcaagc | ggatggctga | tgaaaccaag | ccaaccagga | 1860 |
| agggcagccc | acctatcaag | gtgtactgcc | ttccagacga | acgaagagcg | attgaggaaa | 1920 |
| aggcggcggc | ggccggcatg | agcctgtcgg | cctacctgct | ggccgtcggc | cagggctaca | 1980 |
| aaatcacggg | cgtcgtggac | tatgagcacg | tccgcgagct | ggcccgcatc | aatgcgacc | 2040 |
| tgggccgcct | gggcggcctg | ctgaaactct | ggctcaccga | cgacccgcgc | acggcgcggt | 2100 |
| tcggtgatgc | cacgatcctc | gccctgctgg | cgaagatcga | agagaagcag | gacgagcttg | 2160 |
| gcaaggtcat | gatgggcgtg | gtccgcccga | gggcagagcc | atgacttttt | tagccgctaa | 2220 |

```
aacggccggg gggtgcgcgt gattgccaag cacgtcccca tgcgctccat caagaagagc    2280
gacttcgcgg agctggtgaa gtacatcacc gacgagcaag gcaagaccga gcgcctttgc    2340
gacgctcacc gggctggttg ccctcgccgc tgggctggcg gccgtctatg gccctgcaaa    2400
cgcgccagaa acgccgtcga agccgtgtgc gagacaccgc ggccgccggc gttgtggata    2460
cctcgcggaa aacttggccc tcactgacag atgaggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca gcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaaggggg    2940 tgccccccct tctcgaaccc tcccggcccg ctaacgcggg cctcccatcc ccccaggggc    3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840 gcagcttttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260 ccatgttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggttta gaatgcaagg aacagtgaat tggagttcgt    4560
cttgttataa ttagcttctt ggggtatctt taaatactgt agaaaagagg aaggaaataa    4620
```

-continued

```
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataagggga ccacctatga tgtggaacgg    4800
gaaaaggaca tgatgctatg gctggaagga agctgcctg ttccaaaggt cctgcacttt     4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttaaa gacggaaaag     5160 cccgaagagg aacttgtctt tcccacggc gacctgggag acagcaacat ctttgtgaaa     5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340 ctatttttg acttactggg gatcaagcct gattgggaga aaataaaata ttatattta     5400 ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg ataccaagt acgaaagga     5580 cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtaccccgc tcaagctgga    6720 aaccttccgc ctcatgtgcg gatcggattc cacccgcgtg aagaagtggc gcgagcaggt    6780
cggcgaagcc tgcgaagagt tgcgaggcag cggcctggtg gaacacgcct gggtcaatga    6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
```

-continued

```
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc aacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggggct atttgcggaa ctgcgggcgt ggcgctgttg    7620
gtgttgacac caaacgcagc gctagatcct gtcggcgtcg cagcgggcct ggcggggggcg    7680 gtttccatgg cgttcggaac cgtgctgacc cgcaagtggc aacctcccgt gcctctgctc    7740 accttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520
gacgttttta atgtactggg gtggtttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatcccct ataaatcaaa    8700
agaatagccc gagatagggt tgagtgttgt tccagttttgg aacaagagtc cactattaaa    8760
gaacgtggac tccaacgtca aagggcgaaa aaccgtctat cagggcgatg cccactacg    8820 tgaaccatca cccaaatcaa gtttttttggg gtcgaggtgc cgtaaagcac taaatcggaa    8880
ccctaaaggg agcccccgat ttagagcttg acggggaaag ccggcgaacg tggcgagaaa    8940
ggaagggaag aaagcgaaag gagcgggcgc cattcaggct cgcaactgt gggaagggc     9000 gatcggtgcg ggcctcttcg ctattacgcc agctggcgaa aggggatgt gctgcaaggc     9060 gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcggggggatc cgtcgaagct    9360 agcttgggtc ccgctcagaa gaactcgtca agaaggcgat agaaggcgat gcgctgcgaa    9420
```

```
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg cccctgcgct gacagccgga acacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg aggggaattt atggaacgtc  10260
agtggagcat ttttgacaag aaatatttgc tagctgatag tgaccttagg cgacttttga  10320
acgcgcaata atggtttctg acgtatgtgc ttagctcatt aaactccaga aacccgcggc  10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgcccag ctggcaattc cggttcgctt gctgtccata aaaccgccca  10620
gtctagctat cgccatgtaa gcccactgca agctacctgc tttctctttg cgcttgcgtt  10680
ttcccttgtc cagatagccc agtagctgac attcatccgg ggtcagcacc gtttctgcgg  10740
actggctttc tacgtgttcc gcttcctta gcagcccttg cgccctgagt gcttgcggca  10800
gcgtgaagct tgcatgcctg caggtcgacg gcgcgccgag ctcctcgagc aaatttacac  10860
attgccacta aacgtctaaa cccttgtaat ttgtttttgt tttactatgt gtgttatgta  10920
tttgatttgc gataaatttt tatatttggt actaaattta taacacccttt tatgctaacg  10980
tttgccaaca cttagcaatt tgcaagttga ttaattgatt ctaaattatt tttgtcttct  11040
aaatacatat actaatcaac tggaaatgta aatatttgct aatatttcta ctataggaga  11100
attaaagtga gtgaatatgg taccacaagg tttggagatt taattgttgc aatgctgcat  11160
ggatggcata tacaccaaac attcaataat tcttgaggat aataatggta ccacacaaga  11220
tttgaggtgc atgaacgtca cgtggacaaa aggtttagta attttttcaag acaacaatgt  11280
taccacacac aagttttgag gtgcatgcat ggatgccctg tggaaagttt aaaaatattt  11340
tggaaatgat ttgcatggaa gccatgtgta aaaccatgac atccacttgg aggatgcaat  11400
aatgaagaaa actacaaatt tacatgcaac tagttatgca tgtagtctat ataatgagga  11460
ttttgcaata ctttcattca tacacactca ctaagtttta cacgattata atttcttcat  11520
agccagcgga tccgatatcg ggcccgctag cgttaaccct gctttaatga gatatgcgag  11580
acgcctatga tcgcatgata tttgctttca attctgttgt gcacgttgta aaaacctga  11640
gcatgtgtag ctcagatcct taccgccggt ttcggttcat tctaatgaat atatcacccg  11700
ttactatcgt atttttatga ataatattct ccgttcaatt tactgattgt ccgtcgacga  11760
attcgagctc ggcgcgcctc tagaggatcg atgaattcag atcggctgag tggctccttc  11820
```

```
aacgttgcgg ttctgtcagt tccaaacgta aaacggcttg tcccgcgtca tcggcggggg    11880
tcataacgtg actcccttaa ttctccgctc atgatcagat tgtcgtttcc cgccttcagt    11940
ttaaactatc agtgtttgac aggatatatt ggcgggtaaa cctaagagaa aagagcgttt    12000
attagaataa tcggatattt aaagggcgt  gaaaaggttt atccttcgtc catttgtatg    12060
tgcatgccaa ccacagggtt cccca                                          12085
```

<210> SEQ ID NO 29
<211> LENGTH: 12079
<212> TYPE: DNA
<213> ORGANISM: artificial sequence
<220> FEATURE:
<221> NAME/KEY: misc_feature
<222> LOCATION: (1)..(12079)
<223> OTHER INFORMATION: plant expression vector with one
      promoter-terminator expression cassette

<400> SEQUENCE: 29

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt ggggggttcag cagccggcgc     480 tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg cgatggcgcg cgcatccatg     660
ccggcacgcg accgggcgca ccgcagatgg aaacggccga cgcgcagctt cgcttcctct     720
gcgaggcggg ttttcggcc ggggacgccg tcaatgcgct gatgacaatc agctacttca     780
ctgttggggc cgtgcttgag gagcaggccg gcgacagcga tgccggcgag cgcggcggca     840
ccgttgaaca ggctccgctc tcgccgctgt tgcgggccgc gatagacgcc ttcgacgaag     900
ccggtccgga cgcagcgttc gagcagggac tcgcggtgat tgtcgatgga ttggcgaaaa     960
ggaggctcgt tgtcaggaac gttgaaggac cgagaaaggg tgacgattga tcaggaccgc    1020
tgccggagcg caacccactc actacagcag agccatgtag acaacatccc ctccccctt     1080 ccaccgcgtc agacgcccgt agcagcccgc tacgggcttt ttcatgccct gccctagcgt    1140
ccaagcctca cggccgcgct cggcctctct ggcggccttc tggcgctctt ccgcttcctc    1200
gctcactgac tcgctgcgct cggtcgttcg gctgcggcga gcggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttt    1560
ccgctgcata accctgcttc ggggtcatta tagcgatttt tcggtatat ccatccttt      1620 tcgcacgata tacaggattt tgccaaaggg ttcgtgtaga ctttccttgg tgtatccaac    1680
ggcgtcagcc gggcaggata ggtgaagtag gcccacccgc gagcgggtgt tccttcttca    1740
```

```
ctgtcccttattcgcacctggcggtgctcaacgggaatcctgctctgcgaggctggccgg      1800
ctaccgccggcgtaacagatgagggcaagcggatggctgatgaaaccaagccaaccagga      1860
agggcagcccacctatcaaggtgtactgccttccagacgaacgaagagcgattgaggaaa      1920
aggcggcggcggccggcatgagcctgtcggcctacctgctggccgtcggcagggctaca      1980
aaatcacgggcgtcgtggactatgagcacgtccgcgagctggcccgcatcaatggcgacc      2040
tgggccgcctgggcggcctgctgaaactctggctcaccgacgacccgcgcacggcgcggt      2100
tcggtgatgccacgatcctcgccctgctggcgaagatcgaagagaagcaggacgagcttg      2160
gcaaggtcatgatgggcgtgtccgcccgagggcagagccatgacttttttagccgctaa      2220
aacggccgggggtgcgcgtgattgccaagcacgtcccccatgcgctccatcaagaagagc      2280
gacttcgcggagctggtgaagtacatcaccgacgagcaagcaagaccgagcgcctttgc      2340
gacgctcaccgggctggttgccctcgccgctgggctggcgccgtctatggccctgcaaa      2400
cgcgccagaaacgcgtcgaagccgtgtgcgagacaccgcggccgccggcgttgtggata      2460
cctcgcggaaaacttggccctcactgacagatgaggggcggacgttgacacttgaggggc      2520
cgactcaccgggcgcggcgttgacagatgaggggcaggctcgatttcggccggcgacgtg      2580
gagctggccagcctcgcaaatcggcgaaaacgcctgatttacgcgagttcccacagat      2640
gatgtggacaagcctgggataagtgccctgcggtattgacacttgagggcgcgactac      2700
tgacagatgaggggcgcgatccttgacactgaggggcagagtgctgacagatgaggggc      2760
gcacctattgacatttgagggctgtccacaggcagaaaatccagcatttgcaagggttt      2820
ccgcccgttttcggccaccgctaacctgtcttttaacctgcttttaaaccaatatttat      2880
aaaccttgttttaaccaggctgcgccctgtgcgcgtgaccgcgcacgcgaagggggg      2940
tgccccccctctcgaacccctccggcccgctaacgcgggcctcccatccccaggggc      3000
tgcgccctcggccgcgaacggcctcacccaaaaatggcagcgctggcagtccttgcca      3060
ttgccgggatcggggcagtaacgggatgggcgatcagcccgagcgcgacgcccggaagca      3120
ttgacgtgccgcaggtgctggcatcgacatcagcgaccaggtgccgggcagtgagggcg      3180
gcggcctgggtggcggcctgcccttcacttcggccgtcggggcattcacggacttcatgg      3240
cggggccggcaattttaccttgggcattcttggcatagtggtcgcgggtgccgtgctcg      3300
tgttcggggtgcgataaaccagcgaaccatttgaggtgataggtaagattataccgag      3360
gtatgaaaacgagaattggacctttacagaattactctatgaagcgccatatttaaaaag      3420
ctaccaagacgaagaggatgaagaggatgaggaggcagattgccttgaatatattgacaa      3480
tactgataagataatatatcttttatatagaagatatcgccgtatgtaaggatttcaggg      3540
ggcaaggcataaggcagcgcgcttatcaatatatctatagaatgggcaaagcataaaaact      3600
tgcatggactaatgcttgaaacccaggacaataaccttatagcttgtaaattctatcata      3660
attgggtaatgactccaacttattgatagtgttttatgttcagataatgccgatgactt      3720
tgtcatgcagctccaccgatttgagaacacagcgacttccgtcccagccgtgccaggt      3780
gctgcctcagattcaggttatgccgctcaattcgctgcgtatatcgcttgctgattacgt      3840
gcagcttccttcaggcggattcatacagcgccagccatccgtcatccatatccaccca      3900
cgtcaaagggtgacagcaggctcataagacgccccagcgcgcctagtgcgttcaccga      3960
atacgtgcgcaacaaccgtcttccggagactgtcatacgcgtaaaacagcagcgctggc      4020
gcgatttagccccgacatagccccactgttcgtccatttcgcgcagacgatgacgtcac      4080
tgccccggctgtatgcgcgaggttaccgactgcggcctgagttttttaagtgacgtaaaat      4140
```

```
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga     4500 aaaagctgtt ttctggtatt taaggtttta gaatgcaagg aacagtgaat tggagttcgt    4560
cttgttataa ttagcttctt ggggtatctt taaatactgt agaaagagg aaggaaataa     4620 taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgaaggaa    5580 cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag     6060 cgaggccaag caggccgcgt tgctgaaaca cacgaagcag cagatcaagg aaatgcagct    6120
ttccttgttc gatattgcgc cgtggccgga cacgatgcga gcgatgccaa cgacacggc     6180 ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttgagtac gcgaagcgca ccctatcgg      6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
```

```
ggaccgtggc aagaaaacgt cccgttgcca ggtcctgatc gacgaggaaa tcgtcgtgct   6600
gtttgctggc gaccactaca cgaaattcat atgggagaag taccgcaagc tgtcgccgac   6660
ggcccgacgg atgttcgact atttcagctc gcaccgggag ccgtacccgc tcaagctgga   6720
aaccttccgc ctcatgtgcg gatcggattc cacccgcgtg aagaagtggc gcgagcaggt   6780
cggcgaagcc tgcgaagagt tgcgaggcag cggcctggtg gaaacgcgcct gggtcaatga   6840 tgacctggtg cattgcaaac gctagggcct tgtggggtca gttccggctg ggggttcagc   6900
agccagcgct ttactggcat ttcaggaaca agcgggcact gctcgacgca cttgcttcgc   6960
tcagtatcgc tcgggacgca cggcgcgctc tacgaactgc cgataaacag aggattaaaa   7020
ttgacaattg tgattaaggc tcagattcga cggcttggag cggccgacgt gcaggatttc   7080
cgcgagatcc gattgtcggc cctgaagaaa gctccagaga tgttcgggtc cgtttacgag   7140
cacgaggaga aaaagcccat ggaggcgttc gctgaacggt tgcgagatgc cgtggcattc   7200
ggcgcctaca tcgacggcga gatcattggg ctgtcggtct tcaaacagga ggacggcccc   7260
aaggacgctc acaaggcgca tctgtccggc gttttcgtgg agcccgaaca gcgaggccga   7320
ggggtcgccg gtatgctgct gcgggcgttg ccggcgggtt tattgctcgt gatgatcgtc   7380
cgacagattc aacgggaat ctggtggatg cgcatcttca tcctcggcgc acttaatatt   7440
tcgctattct ggagcttgtt gtttatttcg gtctaccgcc tgccgggcgg ggtcgcggcg   7500
acggtaggcg ctgtgcagcc gctgatggtc gtgttcatct ctgccgctct gctaggtagc   7560
ccgatacgat tgatgcgggt cctgggggct atttgcggaa ctgcgggcgt ggcgctgttg   7620
gtgttgacac caaacgcagc gctagatcct gtcggcgtcg cagcgggcct ggcgggggcg   7680
gtttccatgg cgttcggaac cgtgctgacc cgcaagtggc aacctcccgt gcctctgctc   7740
acctttaccg cctggcaact ggcggccgga ggacttctgc tcgttccagt agctttagtg   7800
tttgatccgc caatcccgat gcctacagga accaatgttc tcggcctggc gtggctcggc   7860
ctgatcggag cgggtttaac ctacttcctt tggttccggg ggatctcgcg actcgaacct   7920
acagttgttt ccttactggg cttctcagc cccagatctg gggtcgatca gccggggatg   7980
catcaggccg acagtcggaa cttcgggtcc ccgacctgta ccattcggtg agcaatggat   8040 agggagttg atatcgtcaa cgttcacttc taaagaaata gcgccactca gcttcctcag   8100
cggctttatc cagcgatttc ctattatgtc ggcatagttc tcaagatcga cagcctgtca   8160
cggttaagcg agaaatgaat aagaaggctg ataattcgga tctctgcgag ggagatgata   8220
tttgatcaca ggcagcaacg ctctgtcatc gttacaatca acatgctacc ctccgcgaga   8280
tcatccgtgt ttcaaacccg gcagcttagt tgccgttctt ccgaatagca tcggtaacat   8340
gagcaaagtc tgccgcctta caacggctct cccgctgacg ccgtcccgga ctgatgggct   8400
gcctgtatcg agtggtgatt ttgtgccgag ctgccggtcg gggagctgtt ggctggctgg   8460
tggcaggata tattgtggtg taaacaaatt gacgcttaga caacttaata acacattgcg   8520
gacgttttta atgtactggg gtggtttttc ttttcaccag tgagacgggc aacagctgat   8580
tgcccttcac cgcctggccc tgagagagtt gcagcaagcg gtccacgctg gtttgcccca   8640
gcaggcgaaa atcctgtttg atggtggttc cgaaatcggc aaaatcccttt ataaatcaaa   8700 agaatagccc gagatagggt tgagtgttgt tccagtttgg aacaagagtc cactattaaa   8760
gaacgtggac tccaacgtca aagggcgaaa aaccgtctat cagggcgatg gcccactacg   8820
tgaaccatca cccaaatcaa gttttttggg gtcgaggtgc cgtaaagcac taaatcggaa   8880
ccctaaaggg agccccgat ttagagcttg acggggaaag ccggcgaacg tggcgagaaa   8940
```

```
ggaagggaag aaagcgaaag gagcgggcgc cattcaggct gcgcaactgt tgggaagggc    9000
gatcggtgcg ggcctcttcg ctattacgcc agctggcgaa aggggatgt gctgcaaggc    9060 gattaagttg ggtaacgcca gggttttccc agtcacgacg ttgtaaaacg acggccagtg   9120
aattaattcc catcttgaaa gaaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300
tgtgtaatac ataaattgat gatatagcta gcttagctca tcgggggatc cgtcgaagct   9360
agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg cgcgagccc ctgatgctct tcgtccagat catcctgatc gacaagaccg    9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg cccctgcgct gacagccgga acacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg aggggaattt atggaacgtc  10260
agtggagcat ttttgacaag aaatatttgc tagctgatag tgaccttagg cgactttgga  10320
acgcgcaata atggtttctg acgtatgtgc ttagctcatt aaactccaga aacccgcggc  10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgccccag ctggcaattc cggttcgctt gctgtccata aaaccgccca  10620
gtctagctat cgccatgtaa gcccactgca agctacctgc tttctctttg cgcttgcgtt  10680
ttcccttgtc cagatagccc agtagctgac attcatccgg ggtcagcacc gtttctgcgg  10740
actggctttc tacgtgttcc gcttccttta gcagcccttg cgccctgagt gcttgcggca  10800
gcgtgaagct tgcatgcctg caggtcgacg gcgcgccgag ctcctcgagc aaatttacac  10860
attgccacta aacgtctaaa cccttgtaat ttgttttgt tttactatgt gtgttatgta   10920
tttgatttgc gataaatttt tatatttggt actaaattta taacacctt tatgctaacg   10980 tttgccaaca cttagcaatt tgcaagttga ttaattgatt ctaaattatt tttgtcttct  11040
aaatacatat actaatcaac tggaaatgta aatatttgct aatatttcta ctataggaga  11100
attaaagtga gtgaatatgg taccacaagg tttggagatt taattgttgc aatgctgcat  11160
ggatggcata taccaaaac attcaataat tcttgaggat aataatggta ccacacaaga   11220
tttgaggtgc atgaacgtca cgtggacaaa aggtttagta attttcaag acaacaatgt    11280 taccacacac aagttttgag gtgcatgcat ggatgccctg tggaaagttt aaaaatattt  11340
```

```
tggaaatgat tgcatggaa gccatgtgta aaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagcaga tctgccggca tcgatcccgg gccatggcct gctttaatga gatatgcgag    11580
acgcctatga tcgcatgata tttgctttca attctgttgt gcacgttgta aaaaacctga    11640
gcatgtgtag ctcagatcct taccgccggt ttcggttcat tctaatgaat atatcacccg    11700
ttactatcgt attttatga ataatattct ccgttcaatt tactgattgt ccgtcgacga    11760
gctcggcgcg cctctagagg atcgatgaat tcagatcggc tgagtggctc cttcaacgtt    11820
gcggttctgt cagttccaaa cgtaaaacgg cttgtcccgc gtcatcggcg ggggtcataa    11880
cgtgactccc ttaattctcc gctcatgatc agattgtcgt ttcccgcctt cagtttaaac    11940
tatcagtgtt tgacaggata tattggcggg taaacctaag agaaagagc gtttattaga    12000 ataatcggat atttaaaagg gcgtgaaaag gtttatcctt cgtccatttg tatgtgcatg    12060
ccaaccacag ggttcccca                                                12079
```

<210> SEQ ID NO 30
<211> LENGTH: 13002
<212> TYPE: DNA
<213> ORGANISM: artificial sequence
<220> FEATURE:
<221> NAME/KEY: misc_feature
<222> LOCATION: (1)..(13002)
<223> OTHER INFORMATION: plant expression vector with two
      promoter-terminator expression cassettes

<400> SEQUENCE: 30

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt gggggttcag cagccggcgc     480
tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg catggcgcg cgcatccatg     660 ccggcacgcg accgggcgca ccgcagatgg aaacggccga cgcgcagctt cgcttcctct     720
gcgaggcggg ttttcggcc ggggacgccg tcaatgcgct gatgacaatc agctacttca     780 ctgttgggc cgtgcttgag gagcaggccg gcgacagcga tgccggcgag gcggcggca     840 ccgttgaaca ggctccgctc tcgcgcgtgt gcgggccgc gatagacgcc ttcgacgaag     900
ccggtccgga cgcagcgttc gagcagggac tcgcggtgat tgtcgatgga ttggcgaaaa     960
ggaggctcgt tgtcaggaac gttgaaggac cgagaaaggg tgacgattga tcaggaccgc    1020
tgccggagcg caacccactc actacagcag agccatgtag acaacatccc ctccccctt    1080 ccaccgcgtc agacgcccgt agcagccgc tacgggcttt tcatgccct gcctagcgt     1140 ccaagcctca cggccgcgct cggcctctct ggcggccttc tggcgctctt ccgcttcctc    1200
```

-continued

```
gctcactgac tcgctgcgct cggtcgttcg gctgcggcga gcggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttt    1560
ccgctgcata accctgcttc ggggtcatta tagcgatttt ttcggtatat ccatcctttt    1620
tcgcacgata tacaggattt tgccaaaggg ttcgtgtaga cttccttgg tgtatccaac    1680 ggcgtcagcc gggcaggata ggtgaagtag gcccacccgc gagcgggtgt tccttcttca    1740
ctgtccctta ttcgcacctg gcggtgctca acgggaatcc tgctctgcga ggctggccgg    1800
ctaccgccgg cgtaacagat gagggcaagc ggatggctga tgaaaccaag ccaaccagga    1860
agggcagccc acctatcaag gtgtactgcc ttccagacga acgaagagcg attgaggaaa    1920
aggcggcggc ggccggcatg agcctgtcgg cctacctgct ggccgtcggc cagggctaca    1980
aaatcacggg cgtcgtggac tatgagcacg tccgcgagct ggcccgcatc aatggcgacc    2040
tgggccgcct gggcggcctg ctgaaactct ggctcaccga cgacccgcgc acggcgcggt    2100
tcggtgatgc cacgatcctc gccctgctgg cgaagatcga agagaagcag gacgagcttg    2160
gcaaggtcat gatgggcgtg gtccgcccga gggcagagcc atgactttt tagccgctaa    2220 aacggccggg gggtgcgcgt gattgccaag cacgtcccca tgcgctccat caagaagagc    2280
gacttcgcgg agctggtgaa gtacatcacc gacgagcaag gcaagaccga gcgcctttgc    2340
gacgctcacc gggctggttg ccctcgccgc tgggctggcg gccgtctatg gccctgcaaa    2400
cgcgccagaa acgccgtcga agccgtgtgc gagacaccgc ggccgccggc gttgtggata    2460
cctcgcggaa aacttggccc tcactgacag atgaggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca agcctgggga taagtgccct gcggtattga cacttgaggg gcgcgactac    2700
tgacagatga ggggcgcgat ccttgacact tgagggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaagggggg    2940 tgcccccct tctcgaaccc tcccggcccg ctaacgcggg cctcccatcc ccccagggc    3000 tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
```

```
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg atttttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggtttta gaatgcaagg aacagtgaat ggagttcgt    4560 cttgttataa ttagcttctt ggggtatctt taaatactgt agaaagagg aaggaaataa    4620 taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt tcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatattta    5400 ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg ataccaagt acgagaagga    5580 cggccagacg gtctacggga ccgacttcat gccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgccgcg ccatcggccg ccgtggagcg    5940
ttcgcgtcgt ctcgaacagg aggcggcagg tttggcgaag tcgatgacca tcgacacgcg    6000
```

| | |
|---|---:|
| aggaactatg acgaccaaga agcgaaaaac cgccggcgag gacctggcaa aacaggtcag | 6060 |
| cgaggccaag caggccgcgt tgctgaaaca cacgaagcag cagatcaagg aaatgcagct | 6120 |
| ttccttgttc gatattgcgc cgtggccgga cacgatgcga gcgatgccaa acgacacggc | 6180 |
| ccgctctgcc ctgttcacca cgcgcaacaa gaaaatcccg cgcgaggcgc tgcaaaacaa | 6240 |
| ggtcattttc cacgtcaaca aggacgtgaa gatcacctac accggcgtcg agctgcgggc | 6300 |
| cgacgatgac gaactggtgt ggcagcaggt gttggagtac gcgaagcgca ccctatcgg | 6360 |
| cgagccgatc accttcacgt tctacgagct tgccaggac ctgggctggt cgatcaatgg | 6420 |
| ccggtattac acgaaggccg aggaatgcct gtcgcgccta caggcgacgg cgatgggctt | 6480 |
| cacgtccgac cgcgttgggc acctggaatc ggtgtcgctg ctgcaccgct tccgcgtcct | 6540 |
| ggaccgtggc aagaaaacgt cccgttgcca ggtcctgatc gacgaggaaa tcgtcgtgct | 6600 |
| gtttgctggc gaccactaca cgaaattcat atgggagaag taccgcaagc tgtcgccgac | 6660 |
| ggcccgacgg atgttcgact atttcagctc gcaccgggag ccgtacccgc tcaagctgga | 6720 |
| aaccttccgc ctcatgtgcg gatcggattc cacccgcgtg aagaagtggc gcgagcaggt | 6780 |
| cggcgaagcc tgcgaagagt tgcgaggcag cggcctggtg aacacgcct gggtcaatga | 6840 |
| tgacctggtg cattgcaaac gctagggcct tgtggggtca gttccggctg ggggttcagc | 6900 |
| agccagcgct ttactggcat ttcaggaaca agcgggcact gctcgacgca cttgcttcgc | 6960 |
| tcagtatcgc tcgggacgca cggcgcgctc tacgaactgc cgataaacag aggattaaaa | 7020 |
| ttgacaattg tgattaaggc tcagattcga cggcttggag cggccgacgt gcaggatttc | 7080 |
| cgcgagatcc gattgtcggc cctgaagaaa gctccagaga tgttcgggtc cgtttacgag | 7140 |
| cacgaggaga aaaagcccat ggaggcgttc gctgaacggt tgcgagatgc cgtggcattc | 7200 |
| ggcgcctaca tcgacggcga gatcattggg ctgtcggtct tcaaacagga ggacggcccc | 7260 |
| aaggacgctc acaaggcgca tctgtccggc gttttcgtgg agcccgaaca gcgaggccga | 7320 |
| ggggtcgccg gtatgctgct gcgggcgttg ccggcgggtt tattgctcgt gatgatcgtc | 7380 |
| cgacagattc caacgggaat ctggtggatg cgcatcttca tcctcggcgc acttaatatt | 7440 |
| tcgctattct ggagcttgtt gtttatttcg gtctaccgcc tgccgggcgg ggtcgcggcg | 7500 |
| acggtaggcg ctgtgcagcc gctgatggtc gtgttcatct ctgccgctct gctaggtagc | 7560 |
| ccgatacgat tgatgcgcgt cctggggggct atttgcggaa ctgcgggcgt ggcgctgttg | 7620 |
| gtgttgacac caaacgcagc gctagatcct gtcggcgtcg cagcggggcct ggcgggggcg | 7680 |
| gtttccatgg cgttcggaac cgtgctgacc cgcaagtggc aacctcccgt gcctctgctc | 7740 |
| acctttaccg cctggcaact ggcggccgga ggacttctgc tcgttccagt agctttagtg | 7800 |
| tttgatccgc caatcccgat gcctacagga accaatgttc tcggcctggc gtggctcggc | 7860 |
| ctgatcggag cgggtttaac ctacttcctt tggttccggg ggatctcgcg actcgaacct | 7920 |
| acagttgttt ccttactggg cttttctcagc cccagatctg gggtcgatca gccggggatg | 7980 |
| catcaggccg acagtcggaa cttcgggtcc ccgacctgta ccattcggtg agcaatggat | 8040 |
| agggagttga atatcgtcaa cgttcacttc taaagaaata gcgccactca gcttcctcag | 8100 |
| cggctttatc cagcgatttc ctattatgtc ggcatagttc tcaagatcga cagcctgtca | 8160 |
| cggttaagcg agaaatgaat aagaaggctg ataattcgga tctctgcgag ggagatgata | 8220 |
| tttgatcaca ggcagcaacg ctctgtcatc gttacaatca acatgctacc ctccgcgaga | 8280 |
| tcatccgtgt ttcaaacccg gcagcttagt tgccgttctt ccgaatagca tcggtaacat | 8340 |
| gagcaaagtc tgccgcctta caacggctct cccgctgacg ccgtcccgga ctgatgggct | 8400 |

```
gcctgtatcg agtggtgatt tgtgccgag ctgccggtcg gggagctgtt ggctggctgg   8460
tggcaggata tattgtggtg taaacaaatt gacgcttaga caacttaata acacattgcg   8520
gacgttttta atgtactggg gtggtttttc ttttcaccag tgagacgggc aacagctgat   8580
tgcccttcac cgcctggccc tgagagagtt gcagcaagcg gtccacgctg gtttgcccca   8640
gcaggcgaaa atcctgtttg atggtggttc cgaaatcggc aaaatccctt ataaatcaaa   8700
agaatagccc gagatagggt tgagtgttgt tccagtttgg aacaagagtc cactattaaa   8760
gaacgtggac tccaacgtca aagggcgaaa aaccgtctat cagggcgatg gcccactacg   8820
tgaaccatca cccaaatcaa gttttttggg gtcgaggtgc cgtaaagcac taaatcggaa   8880
ccctaaaggg agcccccgat ttagagcttg acggggaaag ccggcgaacg tggcgagaaa   8940
ggaagggaag aaagcgaaag gagcgggcgc cattcaggct gcgcaactgt tgggaagggc   9000
gatcggtgcg ggcctcttcg ctattacgcc agctggcgaa aggggggatgt gctgcaaggc   9060 gattaagttg ggtaacgcca gggttttccc agtcacgacg ttgtaaaacg acggccagtg   9120
aattaattcc catcttgaaa gaaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300 tgtgtaaatac ataaattgat gatatagcta gcttagctca tcgggggatc cgtcgaagct   9360
agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg cgcgcgagcc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga ctttttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg cccctgcgct gacagccgga acacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg aggggaattt atggaacgtc  10260
agtggagcat ttttgacaag aaatatttgc tagctgatag tgaccttagg cgactttttga  10320 acgcgcaata atggtttctg acgtatgtgc ttagctcatt aaactccaga aacccgcggc  10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgccccag ctggcaattc cggttcgctt gctgtccata aaaccgccca  10620
gtctagctat cgccatgtaa gcccactgca agctacctgc tttctctttg cgcttgcgtt  10680
ttcccttgtc cagatagccc agtagctgac attcatccgg ggtcagcacc gtttctgcgg  10740
actggctttc tacgtgttcc gcttccttta gcagcccttg cgccctgagt gcttgcggca  10800
```

```
gcgtgaagct tgcatgcctg caggtcgacg gcgcgccgag ctcctcgagc aaatttacac   10860
attgccacta aacgtctaaa cccttgtaat ttgtttttgt tttactatgt gtgttatgta   10920
tttgatttgc gataaatttt tatatttggt actaaattta taacacccttt tatgctaacg  10980 tttgccaaca cttagcaatt tgcaagttga ttaattgatt ctaaattatt tttgtcttct   11040
aaatacatat actaatcaac tggaaatgta aatatttgct aatatttcta ctataggaga   11100
attaaagtga gtgaatatgg taccacaagg tttggagatt taattgttgc aatgctgcat   11160
ggatggcata taccaaaac attcaataat tcttgaggat aataatggta ccacacaaga    11220
tttgaggtgc atgaacgtca cgtggacaaa aggtttagta atttttcaag acaacaatgt   11280
taccacacac aagttttgag gtgcatgcat ggatgccctg tggaaagttt aaaaatattt    11340
tggaaatgat ttgcatggaa gccatgtgta aaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagccca ccgcggtggg cggccgcctg cagtctagaa ggcctcctgc tttaatgaga    11580
tatgcgagac gcctatgatc gcatgatatt tgctttcaat tctgttgtgc acgttgtaaa    11640
aaacctgagc atgtgtagct cagatcctta ccgccggttt cggttcattc taatgaatat    11700
atcacccgtt actatcgtat ttttatgaat aatattctcc gttcaattta ctgattgtcc    11760
gtcgagcaaa tttacacatt gccactaaac gtctaaaccc ttgtaatttg ttttttgtttt   11820 actatgtgtg ttatgtattt gatttgcgat aaatttttat atttggtact aaatttataa    11880 cacctttttat gctaacgttt gccaacactt agcaatttgc aagttgatta attgattcta   11940
aattattttt gtcttctaaa tacatatact aatcaactgg aaatgtaaat atttgctaat    12000
atttctacta taggagaatt aaagtgagtg aatatggtac cacaaggttt ggagatttaa    12060
ttgttgcaat gctgcatgga tgcatatac accaaacatt caataattct tgaggataat     12120
aatggtacca cacaagattt gaggtgcatg aacgtcacgt ggacaaaagg tttagtaatt    12180
tttcaagaca acaatgttac cacacacaag ttttgaggtg catgcatgga tgccctgtgg    12240 aaagttttaaa aatattttgg aaatgatttg catggaagcc atgtgtaaaa ccatgacatc    12300
cacttggagg atgcaataat gaagaaaact acaaatttac atgcaactag ttatgcatgt    12360
agtctatata tgaggatttt gcaatacttt cattcatac acactcacta agttttacac       12420
gattataatt tcttcatagc cagcggatcc gatatcgggc ccgctagcgt taaccctgct    12480
ttaatgagat atgcgagacg cctatgatcg catgatattt gctttcaatt ctgttgtgca    12540
cgttgtaaaa aacctgagca tgtgtagctc agatccttac cgccggtttc ggttcattct    12600
aatgaatata tcacccgtta ctatcgtatt tttatgaata atattctccg ttcaatttac    12660
tgattgtccg tcgacgaatt cgagctcggc gcgcctctag aggatcgatg aattcagatc    12720
ggctgagtgg ctccttcaac gttgcggttc tgtcagttcc aaacgtaaaa cggcttgtcc    12780
cgcgtcatcg gcgggggtca taacgtgact cccttaattc tccgctcatg atcagattgt    12840
cgtttcccgc cttcagttta aactatcagt gtttgacagg atatattggc gggtaaacct    12900
aagagaaaag agcgtttatt agaataatcg gatatttaaa agggcgtgaa aaggtttatc   12960
cttcgtccat ttgtatgtgc atgccaacca cagggttccc ca                      13002

<210> SEQ ID NO 31
<211> LENGTH: 13905
<212> TYPE: DNA
<213> ORGANISM: artificial sequence
<220> FEATURE:
```

-continued

<221> NAME/KEY: misc_feature
<222> LOCATION: (1)..(12085)
<223> OTHER INFORMATION: plant expression vector with three
      promoter-terminator expression cassettes

<400> SEQUENCE: 31

| | |
|---|---|
| gatctggcgc cggccagcga gacgagcaag attggccgcc gcccgaaacg atccgacagc | 60 |
| gcgcccagca caggtgcgca ggcaaattgc accaacgcat acagcgccag cagaatgcca | 120 |
| tagtgggcgg tgacgtcgtt cgagtgaacc agatcgcgca ggaggcccgg cagcaccggc | 180 |
| ataatcaggc cgatgccgac agcgtcgagc gcgacagtgc tcagaattac gatcaggggt | 240 |
| atgttgggtt tcacgtctgg cctccggacc agcctccgct ggtccgattg aacgcgcgga | 300 |
| ttctttatca ctgataagtt ggtggacata ttatgtttat cagtgataaa gtgtcaagca | 360 |
| tgacaaagtt gcagccgaat acagtgatcc gtgccgccct ggacctgttg aacgaggtcg | 420 |
| gcgtagacgg tctgacgaca cgcaaactgg cggaacggtt gggggttcag cagccggcgc | 480 |
| tttactggca cttcaggaac aagcgggcgc tgctcgacgc actggccgaa gccatgctgg | 540 |
| cggagaatca tacgcattcg gtgccgagag ccgacgacga ctggcgctca tttctgatcg | 600 |
| ggaatgcccg cagcttcagg caggcgctgc tcgcctaccg cgatggcgcg cgcatccatg | 660 |
| ccggcacgcg accgggcgca ccgcagatgg aaacggccga cgcgcagctt cgcttcctct | 720 |
| gcgaggcggg ttttcggcc ggggacgccg tcaatgcgct gatgacaatc agctacttca | 780 |
| ctgttggggc cgtgcttgag gagcaggccg gcgacagcga tgccggcgag cgcggcggca | 840 |
| ccgttgaaca ggctccgctc tcgccgctgt tgcgggccgc gatagacgcc ttcgacgaag | 900 |
| ccggtccgga cgcagcgttc gagcagggac tcgcggtgat tgtcgatgga ttggcgaaaa | 960 |
| ggaggctcgt tgtcaggaac gttgaaggac cgagaaaggg tgacgattga tcaggaccgc | 1020 |
| tgccggagcg caacccactc actacagcag agccatgtag acaacatccc ctccccccttt | 1080 |
| ccaccgcgtc agacgcccgt agcagcccgc tacgggcttt tcatgcccct gccctagcgt | 1140 |
| ccaagcctca cggccgcgct cggcctctct ggcggccttc tggcgctctt ccgcttcctc | 1200 |
| gctcactgac tcgctgcgct cggtcgttcg gctgcggcga gcggtatcag ctcactcaaa | 1260 |
| ggcggtaata cggttatcca cagaatcagg ggataacgca ggaaagaaca tgtgagcaaa | 1320 |
| aggccagcaa aaggccagga accgtaaaaa ggccgcgttg ctggcgtttt tccataggct | 1380 |
| ccgcccccct gacgagcatc acaaaaatcg acgctcaagt cagaggtggc gaaacccgac | 1440 |
| aggactataa agataccagg cgtttccccc tggaagctcc ctcgtgcgct ctcctgttcc | 1500 |
| gaccctgccg cttaccggat acctgtccgc ctttctccct tcgggaagcg tggcgctttt | 1560 |
| ccgctgcata accctgcttc gggtcatta tagcgatttt ttcggtatat ccatcctttt | 1620 |
| tcgcacgata tacaggattt tgccaaaggg ttcgtgtaga ctttccttgg tgtatccaac | 1680 |
| ggcgtcagcc gggcaggata ggtgaagtag gcccacccgc gagcgggtgt tccttcttca | 1740 |
| ctgtccctta ttcgcacctg gcggtgctca acgggaatcc tgctctgcga ggctggccgg | 1800 |
| ctaccgccgg cgtaacagat gagggcaagc ggatggctga tgaaaccaag ccaaccagga | 1860 |
| agggcagccc acctatcaag gtgtactgcc ttccagacga acgaagagcg attgaggaaa | 1920 |
| aggcggcggc ggccggcatg agcctgtcgg cctacctgct ggccgtcggc cagggctaca | 1980 |
| aaatcacggg cgtcgtggac tatgagcacg tccgcgagct ggcccgcatc aatgcgacc | 2040 |
| tgggccgcct gggcgccctg ctgaaactct ggctcaccga cgaccgcgc acggcgcggt | 2100 |
| tcggtgatgc cacgatcctc gccctgctgg cgaagatcga agagaagcag gacgagcttg | 2160 |
| gcaaggtcat gatgggcgtg gtccgcccga gggcagagcc atgactttt tagccgctaa | 2220 |

```
aacggccggg gggtgcgcgt gattgccaag cacgtcccca tgcgctccat caagaagagc    2280
gacttcgcgg agctggtgaa gtacatcacc gacgagcaag gcaagaccga gcgcctttgc    2340
gacgctcacc gggctggttg ccctcgccgc tgggctggcg gccgtctatg gccctgcaaa    2400
cgcgccagaa acgccgtcga agccgtgtgc gagacaccgc ggccgccggc gttgtggata    2460
cctcgcggaa aacttggccc tcactgacag atgaggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaaggggg    2940 tgccccccct tctcgaaccc tcccggcccg ctaacgcggg cctcccatcc ccccaggggc    3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840 gcagcttttcc cttcaggcgg gattcataca gcggccagcc atccgtcatc catatccacca    3900 cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag tttttttaagt gacgtaaaat    4140 cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga ggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggtttta gaatgcaagg aacagtgaat tggagttcgt    4560
cttgttataa ttagcttctt ggggtatctt taaatactgt agaaaagagg aaggaaataa    4620
```

```
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa agattatcg agctgtatgc ggagtgcatc     4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttttaaa gacggaaaag    5160 cccgaagagg aacttgtctt tcccacggc gacctggaga acagcaacat ctttgtgaaa      5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta     5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgccccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag     6060 cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg     6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccccgcgtg aagaagtggc gcgagcaggt   6780
cggcgaagcc tgcgaagagt tgcgaggcag cggcctggtg gaacacgcct gggtcaatga    6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
```

```
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcggcgtcg cagcgggcct ggcggggcg    7680 gtttccatgg cgttcggaac cgtgctgacc cgcaagtggc aacctccgt gcctctgctc    7740 acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg cttttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt tgtgccgag ctgccggtcg gggagctgtt ggctggctgg    8460
tggcaggata tattgtggtg taaacaaatt gacgcttaga caacttaata acacattgcg    8520
gacgttttta atgtactggg gtggttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagatagggt tgagtgttgt tccagtttgg aacaagagtc cactattaaa    8760
gaacgtggac tccaacgtca aagggcgaaa aaccgtctat cagggcgatg gcccactacg    8820
tgaaccatca cccaaatcaa gttttttggg gtcgaggtgc cgtaaagcac taaatcggaa    8880
ccctaaaggg agcccccgat ttagagcttg acggggaaag ccggcgaacg tggcgagaaa    8940
ggaagggaag aaagcgaaag gagcgggcgc cattcaggct gcgcaactgt gggaagggc    9000 gatcggtgcg ggcctcttcg ctattacgcc agctggcgaa aggggatgt gctgcaaggc    9060 gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcggggatc cgtcgaagct    9360 agcttgggtc ccgctcagaa gaactcgtca agaaggcgat agaaggcgat gcgctgcgaa    9420
```

```
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg cccctgcgct gacagccgga acacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg aggggaattt atggaacgtc  10260
agtggagcat ttttgacaag aaatatttgc tagctgatag tgaccttagg cgacttttga  10320
acgcgcaata atgtttctg acgtatgtgc ttagctcatt aaactccaga aacccgcggc  10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgcccag ctggcaattc cggttcgctt gctgtccata aaaccgccca  10620
gtctagctat cgccatgtaa gcccactgca agctacctgc tttctctttg cgcttgcgtt  10680
ttcccttgtc cagatagccc agtagctgac attcatccgg ggtcagcacc gtttctgcgg  10740
actggctttc tacgtgttcc gcttccttta gcagcccttg cgccctgagt gcttgcggca  10800
gcgtgaagct tgcatgcctg caggtcgacg gcgcgccgag ctcctcgagc aaatttacac  10860
attgccacta aacgtctaaa cccttgtaat tgttttttgt tttactatgt gtgttatgta  10920
tttgatttgc gataaatttt tatatttggt actaaattta taacacccttt tatgctaacg  10980 tttgccaaca cttagcaatt tgcaagttga ttaattgatt ctaaattatt tttgtcttct  11040
aaatacatat actaatcaac tggaaatgta aatatttgct aatatttcta ctataggaga  11100
attaaagtga gtgaatatgg taccacaagg tttggagatt taattgttgc aatgctgcat  11160
ggatggcata taccaaaac attcaataat tcttgaggat aataatggta ccacacaaga  11220
tttgaggtgc atgaacgtca cgtggacaaa aggtttagta attttttcaag acaacaatgt  11280 taccacacac aagttttgag gtgcatgcat ggatgccctg tggaaagttt aaaaatattt  11340
tggaaatgat ttgcatggaa gccatgtgta aaaccatgac atccacttgg aggatgcaat  11400
aatgaagaaa actacaaatt tacatgcaac tagttatgca tgtagtctat ataatgagga  11460
ttttgcaata ctttcattca tacacactca ctaagtttta cacgattata atttcttcat  11520
agccagccca ccgcggtggg cggccgcctg cagtctagaa ggcctcctgc tttaatgaga  11580
tatgcgagac gcctatgatc gcatgatatt tgctttcaat tctgttgtgc acgttgtaaa  11640
aaacctgagc atgtgtagct cagatcctta ccgccggttt cggttcattc taatgaatat  11700
atcacccgtt actatcgtat ttttatgaat aatattctcc gttcaattta ctgattgtcc  11760
gtcgagcaaa tttacacatt gccactaaac gtctaaaccc ttgtaatttg ttttttgtttt  11820
```

```
actatgtgtg ttatgtattt gatttgcgat aaattttat atttggtact aaatttataa    11880
caccttttat gctaacgttt gccaacactt agcaatttgc aagttgatta attgattcta    11940 aattatttt gtcttctaaa tacatatact aatcaactgg aaatgtaaat atttgctaat    12000
atttctacta taggagaatt aaagtgagtg aatatggtac cacaaggttt ggagatttaa    12060
ttgttgcaat gctgcatgga tggcatatac accaaacatt caataattct tgaggataat    12120
aatggtacca cacaagattt gaggtgcatg aacgtcacgt ggacaaaagg tttagtaatt    12180
tttcaagaca acaatgttac cacacacaag ttttgaggtg catgcatgga tgccctgtgg    12240
aaagtttaaa aatattttgg aaatgatttg catggaagcc atgtgtaaaa ccatgacatc    12300
cacttggagg atgcaataat gaagaaaact acaaatttac atgcaactag ttatgcatgt    12360
agtctatata atgaggattt tgcaatactt tcattcatac acactcacta agttttacac    12420
gattataatt tcttcatagc cagcggatcc gatatcgggc ccgctagcgt taaccctgct    12480
ttaatgagat atgcgagacg cctatgatcg catgatattt gctttcaatt ctgttgtgca    12540
cgttgtaaaa aacctgagca tgtgtagctc agatccttac cgccggtttc ggttcattct    12600
aatgaatata tcacccgtta ctatcgtatt tttatgaata atattctccg ttcaatttac    12660
tgattgtccg tcgagcaaat ttacacattg ccactaaacg tctaaaccct tgtaatttgt    12720
ttttgtttta ctatgtgtgt tatgtatttg atttgcgata aatttttata tttggtacta    12780
aatttataac acctttatg ctaacgtttg ccaacactta gcaatttgca agttgattaa    12840
ttgattctaa attattttg tcttctaaat acatatacta atcaactgga aatgtaaata    12900
tttgctaata tttctactat aggagaatta aagtgagtga atatggtacc acaaggtttg    12960
gagatttaat tgttgcaatg ctgcatggat ggcatataca ccaaacattc aataattctt    13020
gaggataata atggtaccac acaagatttg aggtgcatga acgtcacgtg gacaaaaggt    13080
ttagtaattt tcaagacaa caatgttacc acacacaagt tttgaggtgc atgcatggat    13140
gccctgtgga aagtttaaaa atattttgga aatgatttgc atggaagcca tgtgtaaaac    13200
catgacatcc acttggagga tgcaataatg aagaaaacta caaatttaca tgcaactagt    13260
tatgcatgta gtctatataa tgaggatttt gcaatacttt cattcataca cactcactaa    13320
gttttacacg attataattt cttcatagcc agcagatctg ccggcatcga tcccgggcca    13380
tggcctgctt taatgagata tgcgagacgc ctatgatcgc atgatatttg ctttcaattc    13440
tgttgtgcac gttgtaaaaa acctgagcat gtgtagctca gatccttacc gccggtttcg    13500
gttcattcta atgaatatat cacccgttac tatcgtattt ttatgaataa tattctccgt    13560
tcaatttact gattgtccgt cgacgagctc ggcgcgcctc tagaggatcg atgaattcag    13620
atcggctgag tggctccttc aacgttgcgg ttctgtcagt tccaaacgta aacggcttg    13680 tcccgcgtca tcggcggggg tcataacgtg actcccttaa ttctccgctc atgatcagat    13740
tgtcgtttcc cgccttcagt ttaaactatc agtgtttgac aggatatatt ggcgggtaaa    13800
cctaagagaa aagagcgttt attagaataa tcggatattt aaaagggcgt gaaaaggttt    13860
atccttcgtc catttgtatg tgcatgccaa ccacagggtt cccca                   13905
```

<210> SEQ ID NO 32
<211> LENGTH: 1443
<212> TYPE: DNA
<213> ORGANISM: Phaeodactylum tricornutum
<220> FEATURE:
<221> NAME/KEY: CDS
<222> LOCATION: (9)..(1442)
<223> OTHER INFORMATION: delta-6-desaturase

<400> SEQUENCE: 32

```
gatctaaa atg ggc aaa gga ggg gac gct cgg gcc tcg aag ggc tca acg          50
         Met Gly Lys Gly Gly Asp Ala Arg Ala Ser Lys Gly Ser Thr
         1               5                   10 gcg gct cgc aag atc agt tgg cag gaa gtc aag acc cac gcg tct ccg           98
Ala Ala Arg Lys Ile Ser Trp Gln Glu Val Lys Thr His Ala Ser Pro
15                  20                  25                  30 gag gac gcc tgg atc att cac tcc aat aag gtc tac gac gtg tcc aac          146
Glu Asp Ala Trp Ile Ile His Ser Asn Lys Val Tyr Asp Val Ser Asn
                35                  40                  45 tgg cac gaa cat ccc gga ggc gcc gtc att ttc acg cac gcc ggt gac          194
Trp His Glu His Pro Gly Gly Ala Val Ile Phe Thr His Ala Gly Asp
                50                  55                  60 gac atg acg gac att ttc gct gcc ttt cac gca ccc gga tcg cag tcg          242
Asp Met Thr Asp Ile Phe Ala Ala Phe His Ala Pro Gly Ser Gln Ser
            65                  70                  75 ctc atg aag aag ttc tac att ggc gaa ttg ctc ccg gaa acc acc ggc          290
Leu Met Lys Lys Phe Tyr Ile Gly Glu Leu Leu Pro Glu Thr Thr Gly
        80                  85                  90 aag gag ccg cag caa atc gcc ttt gaa aag ggc tac cgc gat ctg cgc          338
Lys Glu Pro Gln Gln Ile Ala Phe Glu Lys Gly Tyr Arg Asp Leu Arg
95                  100                 105                 110 tcc aaa ctc atc atg atg ggc atg ttc aag tcc aac aag tgg ttc tac          386
Ser Lys Leu Ile Met Met Gly Met Phe Lys Ser Asn Lys Trp Phe Tyr
                115                 120                 125 gtc tac aag tgc ctc agc aac atg gcc att tgg gcc gcc gcc tgt gct          434
Val Tyr Lys Cys Leu Ser Asn Met Ala Ile Trp Ala Ala Ala Cys Ala
            130                 135                 140 ctc gtc ttt tac tcg gac cgc ttc tgg gta cac ctg gcc agc gcc gtc          482
Leu Val Phe Tyr Ser Asp Arg Phe Trp Val His Leu Ala Ser Ala Val
        145                 150                 155 atg ctg gga aca ttc ttt cag cag tcg gga tgg ttg gca cac gac ttt          530
Met Leu Gly Thr Phe Phe Gln Gln Ser Gly Trp Leu Ala His Asp Phe
    160                 165                 170 ctg cac cac cag gtc ttc acc aag cgc aag cac ggg gat ctc gga gga          578
Leu His His Gln Val Phe Thr Lys Arg Lys His Gly Asp Leu Gly Gly
175                 180                 185                 190 ctc ttt tgg ggg aac ctc atg cag ggt tac tcc gta cag tgg tgg aaa          626
Leu Phe Trp Gly Asn Leu Met Gln Gly Tyr Ser Val Gln Trp Trp Lys
                195                 200                 205 aac aag cac aac gga cac cac gcc gtc ccc aac ctc cac tgc tcc tcc          674
Asn Lys His Asn Gly His His Ala Val Pro Asn Leu His Cys Ser Ser
            210                 215                 220 gca gtc gcg caa gat ggg gac ccg gac atc gat acc atg ccc ctt ctc          722
Ala Val Ala Gln Asp Gly Asp Pro Asp Ile Asp Thr Met Pro Leu Leu
        225                 230                 235 gcc tgg tcc gtc cag caa gcc cag tct tac cgg gaa ctc caa gcc gac          770
Ala Trp Ser Val Gln Gln Ala Gln Ser Tyr Arg Glu Leu Gln Ala Asp
    240                 245                 250 gga aag gat tcg ggt ttg gtc aag ttc atg atc cgt aac caa tcc tac          818
Gly Lys Asp Ser Gly Leu Val Lys Phe Met Ile Arg Asn Gln Ser Tyr
255                 260                 265                 270 ttt tac ttt ccc atc ttg ttg ctc gcc cgc ctg tcg tgg ttg aac gag          866
Phe Tyr Phe Pro Ile Leu Leu Leu Ala Arg Leu Ser Trp Leu Asn Glu
                275                 280                 285 tcc ttc aag tgc gcc ttt ggg ctt gga gct gcg tcg gag aac gct gct          914
Ser Phe Lys Cys Ala Phe Gly Leu Gly Ala Ala Ser Glu Asn Ala Ala
            290                 295                 300 ctc gaa ctc aag gcc aag ggt ctt cag tac ccc ctt ttg gaa aag gct          962
```

-continued

```
                Leu Glu Leu Lys Ala Lys Gly Leu Gln Tyr Pro Leu Leu Glu Lys Ala
                        305                 310                 315 ggc atc ctg ctg cac tac gct tgg atg ctt aca gtt tcg tcc ggc ttt    1010
Gly Ile Leu Leu His Tyr Ala Trp Met Leu Thr Val Ser Ser Gly Phe
320                 325                 330 gga cgc ttc tcg ttc gcg tac acc gca ttt tac ttt cta acc gcg acc    1058
Gly Arg Phe Ser Phe Ala Tyr Thr Ala Phe Tyr Phe Leu Thr Ala Thr
335                 340                 345                 350 gcg tcc tgt gga ttc ttg ctc gcc att gtc ttt ggc ctc ggc cac aac    1106
Ala Ser Cys Gly Phe Leu Leu Ala Ile Val Phe Gly Leu Gly His Asn
                355                 360                 365 ggc atg gcc acc tac aat gcc gac gcc cgt ccg gac ttc tgg aag ctc    1154
Gly Met Ala Thr Tyr Asn Ala Asp Ala Arg Pro Asp Phe Trp Lys Leu
        370                 375                 380 caa gtc acc acg act cgc aac gtc acg ggc gga cac ggt ttc ccc caa    1202
Gln Val Thr Thr Thr Arg Asn Val Thr Gly Gly His Gly Phe Pro Gln
    385                 390                 395 gcc ttt gtc gac tgg ttc tgt ggt ggc ctc cag tac caa gtc gac cac    1250
Ala Phe Val Asp Trp Phe Cys Gly Gly Leu Gln Tyr Gln Val Asp His
400                 405                 410 cac tta ttc ccc agc ctg ccc cga cac aat ctg gcc aag aca cac gca    1298
His Leu Phe Pro Ser Leu Pro Arg His Asn Leu Ala Lys Thr His Ala
415                 420                 425                 430 ctg gtc gaa tcg ttc tgc aag gag tgg ggt gtc cag tac cac gaa gcc    1346
Leu Val Glu Ser Phe Cys Lys Glu Trp Gly Val Gln Tyr His Glu Ala
                435                 440                 445 gac ctt gtg gac ggg acc atg gaa gtc ttg cac cat ttg ggc agc gtg    1394
Asp Leu Val Asp Gly Thr Met Glu Val Leu His His Leu Gly Ser Val
        450                 455                 460 gcc ggc gaa ttc gtc gtg gat ttt gta cgc gat gga ccc gcc atg taa a  1443
Ala Gly Glu Phe Val Val Asp Phe Val Arg Asp Gly Pro Ala Met
    465                 470                 475

<210> SEQ ID NO 33
<211> LENGTH: 477
<212> TYPE: PRT
<213> ORGANISM: Phaeodactylum tricornutum

<400> SEQUENCE: 33

Met Gly Lys Gly Gly Asp Ala Arg Ala Ser Lys Gly Ser Thr Ala Ala
1               5                   10                  15

Arg Lys Ile Ser Trp Gln Glu Val Lys Thr His Ala Ser Pro Glu Asp
                20                  25                  30

Ala Trp Ile Ile His Ser Asn Lys Val Tyr Asp Val Ser Asn Trp His
            35                  40                  45

Glu His Pro Gly Gly Ala Val Ile Phe Thr His Ala Gly Asp Asp Met
        50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Glu Thr Thr Gly Lys Glu
                85                  90                  95

Pro Gln Gln Ile Ala Phe Glu Lys Gly Tyr Arg Asp Leu Arg Ser Lys
            100                 105                 110

Leu Ile Met Met Gly Met Phe Lys Ser Asn Lys Trp Phe Tyr Val Tyr
        115                 120                 125

Lys Cys Leu Ser Asn Met Ala Ile Trp Ala Ala Cys Ala Leu Val
    130                 135                 140

Phe Tyr Ser Asp Arg Phe Trp Val His Leu Ala Ser Ala Val Met Leu
145                 150                 155                 160
```

```
Gly Thr Phe Phe Gln Gln Ser Gly Trp Leu Ala His Asp Phe Leu His
                165                 170                 175
His Gln Val Phe Thr Lys Arg Lys His Gly Asp Leu Gly Gly Leu Phe
            180                 185                 190
Trp Gly Asn Leu Met Gln Gly Tyr Ser Val Gln Trp Lys Asn Lys
        195                 200                 205
His Asn Gly His His Ala Val Pro Asn Leu His Cys Ser Ser Ala Val
    210                 215                 220
Ala Gln Asp Gly Asp Pro Asp Ile Asp Thr Met Pro Leu Leu Ala Trp
225                 230                 235                 240
Ser Val Gln Gln Ala Gln Ser Tyr Arg Glu Leu Gln Ala Asp Gly Lys
                245                 250                 255
Asp Ser Gly Leu Val Lys Phe Met Ile Arg Asn Gln Ser Tyr Phe Tyr
            260                 265                 270
Phe Pro Ile Leu Leu Leu Ala Arg Leu Ser Trp Leu Asn Glu Ser Phe
        275                 280                 285
Lys Cys Ala Phe Gly Leu Gly Ala Ala Ser Glu Asn Ala Ala Leu Glu
    290                 295                 300
Leu Lys Ala Lys Gly Leu Gln Tyr Pro Leu Leu Glu Lys Ala Gly Ile
305                 310                 315                 320
Leu Leu His Tyr Ala Trp Met Leu Thr Val Ser Ser Gly Phe Gly Arg
                325                 330                 335
Phe Ser Phe Ala Tyr Thr Ala Phe Tyr Phe Leu Thr Ala Thr Ala Ser
            340                 345                 350
Cys Gly Phe Leu Leu Ala Ile Val Phe Gly Leu Gly His Asn Gly Met
        355                 360                 365
Ala Thr Tyr Asn Ala Asp Ala Arg Pro Asp Phe Trp Lys Leu Gln Val
    370                 375                 380
Thr Thr Thr Arg Asn Val Thr Gly Gly His Gly Phe Pro Gln Ala Phe
385                 390                 395                 400
Val Asp Trp Phe Cys Gly Gly Leu Gln Tyr Gln Val Asp His His Leu
                405                 410                 415
Phe Pro Ser Leu Pro Arg His Asn Leu Ala Lys Thr His Ala Leu Val
            420                 425                 430
Glu Ser Phe Cys Lys Glu Trp Gly Val Gln Tyr His Glu Ala Asp Leu
        435                 440                 445
Val Asp Gly Thr Met Glu Val Leu His His Leu Gly Ser Val Ala Gly
    450                 455                 460
Glu Phe Val Val Asp Phe Val Arg Asp Gly Pro Ala Met
465                 470                 475

<210> SEQ ID NO 34
<211> LENGTH: 17061
<212> TYPE: DNA
<213> ORGANISM: Phaeodactylum tricornutum, Physcomitrella patens,
      Caenorhabditis elegans
<220> FEATURE:
<221> NAME/KEY: CDS
<222> LOCATION: (4554)..(5987)
<223> OTHER INFORMATION: Phaeodactylum tricornutum delta-6-desaturase
<220> FEATURE:
<221> NAME/KEY: CDS
<222> LOCATION: (2805)..(3653)
<223> OTHER INFORMATION: Caenorhabditis elegans LPLAT
<220> FEATURE:
<221> NAME/KEY: CDS
<222> LOCATION: (1026)..(1898)
<223> OTHER INFORMATION: Physcomitrella patens delta-6-elongase
```

<400> SEQUENCE: 34

```
tggggaaccc tgtggttggc atgcacatac aaatggacga aggataaacc ttttcacgcc       60 ctttttaaata tccgattatt ctaataaacg ctcttttctc ttaggtttac ccgccaatat     120
atcctgtcaa acactgatag tttaaactga aggcgggaaa cgacaatctg atcatgagcg     180
gagaattaag ggagtcacgt tatgaccccc gccgatgacg cgggacaagc cgttttacgt     240
ttggaactga cagaaccgca acgttgaagg agccactcag ccgatctgaa ttcatcgatc     300
ctctagaggc gcgccgagct cctcgagcaa atttacacat gccactaaa cgtctaaacc      360 cttgtaattt gttttgttt tactatgtgt gttatgtatt tgatttgcga taaattttta     420
tatttggtac taaatttata acaccttta tgctaacgtt tgccaacact tagcaatttg      480
caagttgatt aattgattct aaattatttt tgtcttctaa atacatatac taatcaactg     540
gaaatgtaaa tatttgctaa tatttctact ataggagaat taaagtgagt gaatatggta     600
ccacaaggtt tggagattta attgttgcaa tgctgcatgg atggcatata caccaaacat     660
tcaataattc ttgaggataa taatggtacc acacaagatt tgaggtgcat gaacgtcacg     720
tggacaaaag gtttagtaat ttttcaagac aacaatgtta ccacacacaa gttttgaggt     780
gcatgcatgg atgccctgtg gaaagtttaa aaatattttg gaaatgattt gcatggaagc     840
catgtgtaaa accatgacat ccacttggag gatgcaataa tgaagaaaac tacaaattta     900
catgcaacta gttatgcatg tagtctatat aatgaggatt ttgcaatact ttcattcata     960
cacactcact aagttttaca cgattataat ttcttcatag ccagcccacc gcggtgggcg    1020
```

```
gccgc atg gag gtc gtg gag aga ttc tac ggt gag ttg gat ggg aag gtc    1070
      Met Glu Val Val Glu Arg Phe Tyr Gly Glu Leu Asp Gly Lys Val
       1               5                  10                  15 tcg cag ggc gtg aat gca ttg ctg ggt agt ttt ggg gtg gag ttg acg       1118
Ser Gln Gly Val Asn Ala Leu Leu Gly Ser Phe Gly Val Glu Leu Thr
             20                  25                  30 gat acg ccc act acc aaa ggc ttg ccc ctc gtt gac agt ccc aca ccc       1166
Asp Thr Pro Thr Thr Lys Gly Leu Pro Leu Val Asp Ser Pro Thr Pro
         35                  40                  45 atc gtc ctc ggt gtt tct gta tac ttg act att gtc att gga ggg ctt      1214
Ile Val Leu Gly Val Ser Val Tyr Leu Thr Ile Val Ile Gly Gly Leu
     50                  55                  60 ttg tgg ata aag gcc agg gat ctg aaa ccg cgc gcc tcg gag cca ttt      1262
Leu Trp Ile Lys Ala Arg Asp Leu Lys Pro Arg Ala Ser Glu Pro Phe
 65                  70                  75 ttg ctc caa gct ttg gtg ctt gtg cac aac ctg ttc tgt ttt gcg ctc      1310
Leu Leu Gln Ala Leu Val Leu Val His Asn Leu Phe Cys Phe Ala Leu
80                  85                  90                  95 agt ctg tat atg tgc gtg ggc atc gct tat cag gct att acc tgg cgg      1358
Ser Leu Tyr Met Cys Val Gly Ile Ala Tyr Gln Ala Ile Thr Trp Arg
                100                 105                 110 tac tct ctc tgg ggc aat gca tac aat cct aaa cat aaa gag atg gcg      1406
Tyr Ser Leu Trp Gly Asn Ala Tyr Asn Pro Lys His Lys Glu Met Ala
            115                 120                 125 att ctg gta tac ttg ttc tac atg tct aag tac gtg gaa ttc atg gat      1454
Ile Leu Val Tyr Leu Phe Tyr Met Ser Lys Tyr Val Glu Phe Met Asp
        130                 135                 140 acc gtt atc atg ata ctg aag cgc agc acc agg caa ata agc ttc ctc      1502
Thr Val Ile Met Ile Leu Lys Arg Ser Thr Arg Gln Ile Ser Phe Leu
    145                 150                 155 cac gtt tat cat cat tct tca att tcc ctc att tgg tgg gct att gct      1550
His Val Tyr His His Ser Ser Ile Ser Leu Ile Trp Trp Ala Ile Ala
160                 165                 170                 175
```

-continued

| | |
|---|---|
| cat cac gct cct ggc ggt gaa gca tat tgg tct gcg gct ctg aac tca<br>His His Ala Pro Gly Gly Glu Ala Tyr Trp Ser Ala Ala Leu Asn Ser<br>               180                        185                     190 | 1598 |
| gga gtg cat gtt ctc atg tat gcg tat tac ttc ttg gct gcc tgc ctt<br>Gly Val His Val Leu Met Tyr Ala Tyr Tyr Phe Leu Ala Ala Cys Leu<br>        195                        200                    205 | 1646 |
| cga agt agc cca aag tta aaa aat aag tac ctt ttt tgg ggc agg tac<br>Arg Ser Ser Pro Lys Leu Lys Asn Lys Tyr Leu Phe Trp Gly Arg Tyr<br>210                        215                        220 | 1694 |
| ttg aca caa ttc caa atg ttc cag ttt atg ctg aac tta gtg cag gct<br>Leu Thr Gln Phe Gln Met Phe Gln Phe Met Leu Asn Leu Val Gln Ala<br>    225                        230                    235 | 1742 |
| tac tac gac atg aaa acg aat gcg cca tat cca caa tgg ctg atc aag<br>Tyr Tyr Asp Met Lys Thr Asn Ala Pro Tyr Pro Gln Trp Leu Ile Lys<br>240                        245                    250                255 | 1790 |
| att ttg ttc tac tac atg atc tcg ttg ctg ttt ctt ttc ggc aat ttt<br>Ile Leu Phe Tyr Tyr Met Ile Ser Leu Leu Phe Leu Phe Gly Asn Phe<br>                    260                    265                    270 | 1838 |
| tac gta caa aaa tac atc aaa ccc tct gac gga aag caa aag gga gct<br>Tyr Val Gln Lys Tyr Ile Lys Pro Ser Asp Gly Lys Gln Lys Gly Ala<br>        275                        280                    285 | 1886 |
| aaa act gag tga tctagaaggc ctcctgcttt aatgagatat gcgagacgcc<br>Lys Thr Glu<br>        290 | 1938 |
| tatgatcgca tgatatttgc tttcaattct gttgtgcacg ttgtaaaaaa cctgagcatg | 1998 |
| tgtagctcag atccttaccg ccggtttcgg ttcattctaa tgaatatatc acccgttact | 2058 |
| atcgtatttt tatgaataat attctccgtt caatttactg attgtccgtc gagcaaattt | 2118 |
| acacattgcc actaaacgtc taaacccttg taatttgttt ttgttttact atgtgtgtta | 2178 |
| tgtatttgat ttgcgataaa tttttatatt tggtactaaa tttataacac cttttatgct | 2238 |
| aacgtttgcc aacacttagc aatttgcaag ttgattaatt gattctaaat tattttttgtc | 2298 |
| ttctaaatac atatactaat caactggaaa tgtaaatatt tgctaatatt tctactatag | 2358 |
| gagaattaaa gtgagtgaat atggtaccac aaggtttgga gatttaattg ttgcaatgct | 2418 |
| gcatggatgg catatacacc aaacattcaa taattcttga ggataataat ggtaccacac | 2478 |
| aagatttgag gtgcatgaac gtcacgtgga caaaaggttt agtaattttt caagacaaca | 2538 |
| atgttaccac acacaagttt tgaggtgcat gcatggatgc cctgtggaaa gtttaaaaat | 2598 |
| attttggaaa tgatttgcat ggaagccatg tgtaaaacca tgacatccac ttggaggatg | 2658 |
| caataatgaa gaaaactaca aatttacatg caactagtta tgcatgtagt ctatataatg | 2718 |
| aggattttgc aatactttca ttcatacaca ctcactaagt tttacacgat tataaatttct | 2778 |
| tcatagccag cggatccgcc cacata atg gag aac ttc tgg tct att gtt gtg<br>                                       Met Glu Asn Phe Trp Ser Ile Val Val<br>                                                                295 | 2831 |
| ttt ttt cta ctc tca att ctc ttc att tta tat aac ata tcg aca gta<br>Phe Phe Leu Leu Ser Ile Leu Phe Ile Leu Tyr Asn Ile Ser Thr Val<br>300                        305                    310                    315 | 2879 |
| tgc cac tac tat atg cgg att tcg ttt tat tac ttc aca att tta ttg<br>Cys His Tyr Tyr Met Arg Ile Ser Phe Tyr Tyr Phe Thr Ile Leu Leu<br>                    320                    325                    330 | 2927 |
| cat gga atg gaa gtt tgt gtt aca atg atc cct tct tgg cta aat ggg<br>His Gly Met Glu Val Cys Val Thr Met Ile Pro Ser Trp Leu Asn Gly<br>        335                        340                    345 | 2975 |
| aag ggt gct gat tac gtg ttt cac tcg ttt ttc tat tgg tgt aaa tgg<br>Lys Gly Ala Asp Tyr Val Phe His Ser Phe Phe Tyr Trp Cys Lys Trp<br>350                        355                    360 | 3023 |

```
act ggt gtt cat aca aca gtc tat gga tat gaa aaa aca caa gtt gaa      3071
Thr Gly Val His Thr Thr Val Tyr Gly Tyr Glu Lys Thr Gln Val Glu
    365                 370                 375 ggt ccg gct gta gtt att tgt aat cat cag agt tct ctc gac att cta      3119
Gly Pro Ala Val Val Ile Cys Asn His Gln Ser Ser Leu Asp Ile Leu
380                 385                 390                 395 tcg atg gca tca atc tgg ccg aag aat tgt gtt gta atg atg aaa cga      3167
Ser Met Ala Ser Ile Trp Pro Lys Asn Cys Val Val Met Met Lys Arg
                400                 405                 410 att ctt gcc tat gtt cca ttc ttc aat ctc gga gcc tac ttt tcc aac      3215
Ile Leu Ala Tyr Val Pro Phe Phe Asn Leu Gly Ala Tyr Phe Ser Asn
            415                 420                 425 aca atc ttc atc gat cga tat aac cgt gaa cgt gcg atg gct tca gtt      3263
Thr Ile Phe Ile Asp Arg Tyr Asn Arg Glu Arg Ala Met Ala Ser Val
        430                 435                 440 gat tat tgt gca tct gaa atg aag aac aga aat ctt aaa ctt tgg gta      3311
Asp Tyr Cys Ala Ser Glu Met Lys Asn Arg Asn Leu Lys Leu Trp Val
    445                 450                 455 ttt ccg gaa gga aca aga aat cgt gaa gga ggg ttc att cca ttc aag      3359
Phe Pro Glu Gly Thr Arg Asn Arg Glu Gly Gly Phe Ile Pro Phe Lys
460                 465                 470                 475 aaa gga gca ttc aat att gca gtt cgt gcg cag att ccc att att cca      3407
Lys Gly Ala Phe Asn Ile Ala Val Arg Ala Gln Ile Pro Ile Ile Pro
                480                 485                 490 gtt gta ttc tca gac tat cgg gat ttc tac tca aag cca ggc cga tat      3455
Val Val Phe Ser Asp Tyr Arg Asp Phe Tyr Ser Lys Pro Gly Arg Tyr
            495                 500                 505 ttc aag aat gat gga gaa gtt gtt att cga gtt ctg gat gcg att cca      3503
Phe Lys Asn Asp Gly Glu Val Val Ile Arg Val Leu Asp Ala Ile Pro
        510                 515                 520 aca aaa ggg ctc act ctt gat gac gtc agc gag ttg tct gat atg tgt      3551
Thr Lys Gly Leu Thr Leu Asp Asp Val Ser Glu Leu Ser Asp Met Cys
    525                 530                 535 cgg gac gtt atg ttg gca gcc tat aag gaa gtt act cta gaa gct cag      3599
Arg Asp Val Met Leu Ala Ala Tyr Lys Glu Val Thr Leu Glu Ala Gln
540                 545                 550                 555 caa cga aat gcg aca cgg cgt gga gaa aca aaa gac ggg aag aaa tct      3647
Gln Arg Asn Ala Thr Arg Arg Gly Glu Thr Lys Asp Gly Lys Lys Ser
                560                 565                 570 gag taa gctagcgtta accctgcttt aatgagatat gcgagacgcc tatgatcgca      3703
Glu tgatatttgc tttcaattct gttgtgcacg ttgtaaaaaa cctgagcatg tgtagctcag   3763
atccttaccg ccggtttcgg ttcattctaa tgaatatatc acccgttact atcgtatttt   3823
tatgaataat attctccgtt caatttactg attgtccgtc gagcaaattt acacattgcc   3883
actaaacgtc taaaccccttg taatttgttt ttgttttact atgtgtgtta tgtatttgat   3943
ttgcgataaa ttttatatt tggtactaaa tttataacac ttttatgct aacgtttgcc    4003 aacacttagc aatttgcaag ttgattaatt gattctaaat tattttttgtc ttctaaatac  4063 atatactaat caactggaaa tgtaaatatt tgctaatatt tctactatag gagaattaaa   4123
gtgagtgaat atggtaccac aaggtttgga gatttaattg ttgcaatgct gcatggatgg   4183
catatacacc aaacattcaa taattcttga ggataataat ggtaccacac aagatttgag   4243
gtgcatgaac gtcacgtgga caaaaggttt agtaattttt caagcaacaa atgttaccac   4303
acacaagttt tgaggtgcat gcatggatgc cctgtggaaa gtttaaaaat attttggaaa   4363
tgatttgcat ggaagccatg tgtaaaacca tgacatccac ttggaggatg caataatgaa   4423
gaaaactaca aatttacatg caactagtta tgcatgtagt ctatataatg aggattttgc   4483
```

-continued

```
aatactttca ttcatacaca ctcactaagt tttacacgat tataatttct tcatagccag       4543
cagatctaaa atg ggc aaa gga ggg gac gct cgg gcc tcg aag ggc tca          4592
           Met Gly Lys Gly Gly Asp Ala Arg Ala Ser Lys Gly Ser
               575                 580                 585 acg gcg gct cgc aag atc agt tgg cag gaa gtc aag acc cac gcg tct        4640
Thr Ala Ala Arg Lys Ile Ser Trp Gln Glu Val Lys Thr His Ala Ser
                590                 595                 600 ccg gag gac gcc tgg atc att cac tcc aat aag gtc tac gac gtg tcc        4688
Pro Glu Asp Ala Trp Ile Ile His Ser Asn Lys Val Tyr Asp Val Ser
            605                 610                 615 aac tgg cac gaa cat ccc gga ggc gcc gtc att ttc acg cac gcc ggt        4736
Asn Trp His Glu His Pro Gly Gly Ala Val Ile Phe Thr His Ala Gly
        620                 625                 630 gac gac atg acg gac att ttc gct gcc ttt cac gca ccc gga tcg cag        4784
Asp Asp Met Thr Asp Ile Phe Ala Ala Phe His Ala Pro Gly Ser Gln
    635                 640                 645 tcg ctc atg aag aag ttc tac att ggc gaa ttg ctc ccg gaa acc acc        4832
Ser Leu Met Lys Lys Phe Tyr Ile Gly Glu Leu Leu Pro Glu Thr Thr
650                 655                 660                 665 ggc aag gag ccg cag caa atc gcc ttt gaa aag ggc tac cgc gat ctg        4880
Gly Lys Glu Pro Gln Gln Ile Ala Phe Glu Lys Gly Tyr Arg Asp Leu
                670                 675                 680 cgc tcc aaa ctc atc atg atg ggc atg ttc aag tcc aac aag tgg ttc        4928
Arg Ser Lys Leu Ile Met Met Gly Met Phe Lys Ser Asn Lys Trp Phe
            685                 690                 695 tac gtc tac aag tgc ctc agc aac atg gcc att tgg gcc gcc gcc tgt        4976
Tyr Val Tyr Lys Cys Leu Ser Asn Met Ala Ile Trp Ala Ala Ala Cys
        700                 705                 710 gct ctc gtc ttt tac tcg gac cgc ttc tgg gta cac ctg gcc agc gcc        5024
Ala Leu Val Phe Tyr Ser Asp Arg Phe Trp Val His Leu Ala Ser Ala
    715                 720                 725 gtc atg ctg gga aca ttc ttt cag cag tcg gga tgg ttg gca cac gac        5072
Val Met Leu Gly Thr Phe Phe Gln Gln Ser Gly Trp Leu Ala His Asp
730                 735                 740                 745 ttt ctg cac cac cag gtc ttc acc aag cgc aag cac ggg gat ctc gga        5120
Phe Leu His His Gln Val Phe Thr Lys Arg Lys His Gly Asp Leu Gly
                750                 755                 760 gga ctc ttt tgg ggg aac ctc atg cag ggt tac tcc gta cag tgg tgg        5168
Gly Leu Phe Trp Gly Asn Leu Met Gln Gly Tyr Ser Val Gln Trp Trp
            765                 770                 775 aaa aac aag cac aac gga cac cac gcc gtc ccc aac ctc cac tgc tcc        5216
Lys Asn Lys His Asn Gly His His Ala Val Pro Asn Leu His Cys Ser
        780                 785                 790 tcc gca gtc gcg caa gat ggg gac ccg gac atc gat acc atg ccc ctt        5264
Ser Ala Val Ala Gln Asp Gly Asp Pro Asp Ile Asp Thr Met Pro Leu
    795                 800                 805 ctc gcc tgg tcc gtc cag caa gcc cag tct tac cgg gaa ctc caa gcc        5312
Leu Ala Trp Ser Val Gln Gln Ala Gln Ser Tyr Arg Glu Leu Gln Ala
810                 815                 820                 825 gac gga aag gat tcg ggt ttg gtc aag ttc atg atc cgt aac caa tcc        5360
Asp Gly Lys Asp Ser Gly Leu Val Lys Phe Met Ile Arg Asn Gln Ser
                830                 835                 840 tac ttt tac ttt ccc atc ttg ttg ctc gcc cgc ctg tcg tgg ttg aac        5408
Tyr Phe Tyr Phe Pro Ile Leu Leu Leu Ala Arg Leu Ser Trp Leu Asn
            845                 850                 855 gag tcc ttc aag tgc gcc ttt ggg ctt gga gct gcg tcg gag aac gct        5456
Glu Ser Phe Lys Cys Ala Phe Gly Leu Gly Ala Ala Ser Glu Asn Ala
        860                 865                 870 gct ctc gaa ctc aag gcc aag ggt ctt cag tac ccc ctt ttg gaa aag        5504
```

```

Ala Leu Glu Leu Lys Ala Lys Gly Leu Gln Tyr Pro Leu Leu Glu Lys
    875                 880                 885 gct ggc atc ctg ctg cac tac gct tgg atg ctt aca gtt tcg tcc ggc     5552
Ala Gly Ile Leu Leu His Tyr Ala Trp Met Leu Thr Val Ser Ser Gly
890                 895                 900                 905 ttt gga cgc ttc tcg ttc gcg tac acc gca ttt tac ttt cta acc gcg     5600
Phe Gly Arg Phe Ser Phe Ala Tyr Thr Ala Phe Tyr Phe Leu Thr Ala
                910                 915                 920 acc gcg tcc tgt gga ttc ttg ctc gcc att gtc ttt ggc ctc ggc cac     5648
Thr Ala Ser Cys Gly Phe Leu Leu Ala Ile Val Phe Gly Leu Gly His
            925                 930                 935 aac ggc atg gcc acc tac aat gcc gac gcc cgt ccg gac ttc tgg aag     5696
Asn Gly Met Ala Thr Tyr Asn Ala Asp Ala Arg Pro Asp Phe Trp Lys
        940                 945                 950 ctc caa gtc acc acg act cgc aac gtc acg ggc gga cac ggt ttc ccc     5744
Leu Gln Val Thr Thr Thr Arg Asn Val Thr Gly Gly His Gly Phe Pro
    955                 960                 965 caa gcc ttt gtc gac tgg ttc tgt ggt ggc ctc cag tac caa gtc gac     5792
Gln Ala Phe Val Asp Trp Phe Cys Gly Gly Leu Gln Tyr Gln Val Asp
970                 975                 980                 985 cac cac tta ttc ccc agc ctg ccc cga cac aat ctg gcc aag aca cac     5840
His His Leu Phe Pro Ser Leu Pro Arg His Asn Leu Ala Lys Thr His
                990                 995                 1000 gca ctg gtc gaa tcg ttc tgc aag gag tgg ggt gtc cag tac cac         5885
Ala Leu Val Glu Ser Phe Cys Lys Glu Trp Gly Val Gln Tyr His
            1005                1010                1015 gaa gcc gac ctt gtg gac ggg acc atg gaa gtc ttg cac cat ttg         5930
Glu Ala Asp Leu Val Asp Gly Thr Met Glu Val Leu His His Leu
        1020                1025                1030 ggc agc gtg gcc ggc gaa ttc gtc gtg gat ttt gta cgc gat gga         5975
Gly Ser Val Ala Gly Glu Phe Val Val Asp Phe Val Arg Asp Gly
    1035                1040                1045 ccc gcc atg taa agatctgccg gcatcgatcc cgggccatgg cctgctttaa         6027
Pro Ala Met tgagatatgc gagacgccta tgatcgcatg atatttgctt tcaattctgt tgtgcacgtt   6087
gtaaaaaacc tgagcatgtg tagctcagat ccttaccgcc ggtttcggtt cattctaatg   6147
aatatatcac ccgttactat cgtattttta tgaataatat tctccgttca atttactgat   6207
tgtccgtcga cgagctcggc gcgccgtcga cctgcaggca tgcaagcttc acgctgccgc   6267
aagcactcag ggcgcaaggg ctgctaaagg aagcggaaca cgtagaaagc cagtccgcag   6327
aaacggtgct gacccggat gaatgtcagc tactgggcta tctggacaag gaaaacgca    6387 agcgcaaaga gaaagcaggt agcttgcagt gggcttacat ggcgatagct agactgggcg   6447
gttttatgga cagcaagcga accggaattg ccagctgggg cgccctctgg taaggttggg   6507
aagccctgca aagtaaactg gatggctttc ttgccgccaa ggatctgatg gcgcagggga   6567
tcaagatcat gagcggagaa ttaagggagt cacgttatga ccccgccga tgacgcggga    6627 caagccgttt tacgtttgga actgacagaa ccgcaacgtt gaaggagcca ctcagccgcg   6687
ggtttctgga gttaatgag ctaagcacat acgtcagaaa ccattattgc gcgttcaaaa    6747
gtcgcctaag gtcactatca gctagcaaat atttcttgtc aaaaatgctc cactgacgtt   6807
ccataaattc ccctcggtat ccaattagag tctcatattc actctcaatc cagatctcga   6867
ctctagtcga gggcccatgg gagcttggat tgaacaagat ggattgcacg caggttctcc   6927
ggccgcttgg gtggagaggc tattcggcta tgactgggca caacagacaa tcggctgctc   6987
tgatgccgcc gtgttccggc tgtcagcgca ggggcgcccg gttctttttg tcaagaccga   7047
```

```
cctgtccggt gccctgaatg aactgcagga cgaggcagcg cggctatcgt ggctggccac    7107
gacgggcgtt ccttgcgcag ctgtgctcga cgttgtcact gaagcgggaa gggactggct    7167
gctattgggc gaagtgccgg ggcaggatct cctgtcatct caccttgctc ctgccgagaa    7227
agtatccatc atggctgatg caatgcgcg gctgcatacg cttgatccgg ctacctgccc     7287
attcgaccac caagcgaaac atcgcatcga gcgagcacgt actcggatgg aagccggtct    7347
tgtcgatcag gatgatctgg acgaagagca tcagggctc cgccagccg aactgttcgc      7407
caggctcaag gcgcgcatgc ccgacggcga ggatctcgtc gtgacccatg gcgatgcctg    7467
cttgccgaat atcatggtgg aaaatggccg cttttctgga ttcatcgact gtggccggct    7527
gggtgtggcg gaccgctatc aggacatagc gttggctacc cgtgatattg ctgaagagct    7587
tggcggcgaa tgggctgacc gcttcctcgt gctttacggt atcgccgctc ccgattcgca    7647
gcgcatcgcc ttctatcgcc ttcttgacga gttcttctga gcgggaccca gctagcttc    7707
gacggatccc ccgatgagct aagctagcta tatcatcaat ttatgtatta cataaatat    7767
cgcactcagt ctttcatcta cggcaatgta ccagctgata taatcagtta ttgaaatatt    7827
tctgaattta aacttgcatc aataaattta tgttttgct tggactataa acctgactt     7887
gttattttat caataaatat ttaaactata tttctttcaa gatgggaatt aattcactgg    7947
ccgtcgtttt acaacgtcgt gactgggaaa accctggcgt tacccaactt aatcgccttg    8007
cagcacatcc cccttttcgcc agctggcgta atagcgaaga ggcccgcacc gatcgccctt    8067
cccaacagtt gcgcagcctg aatggcgccc gctcctttcg ctttcttccc ttcctttctc    8127
gccacgttcg ccggctttcc ccgtcaagct ctaaatcggg ggctcccttt agggttccga    8187
tttagtgctt tacggcacct cgaccccaaa aaacttgatt tgggtgatgg ttcacgtagt    8247
gggccatcgc cctgatagac ggttttttcgc cctttgacgt tggagtccac gttctttaat    8307
agtggactct tgttccaaac tggaacaaca ctcaaccct  tctcgggcta ttcttttgat    8367
ttataaggga ttttgccgat ttcggaacca ccatcaaaca ggattttcgc ctgctggggc    8427
aaaccagcgt ggaccgcttg ctgcaactct ctcagggcca ggcggtgaag gcaatcagc     8487
tgttgcccgt ctcactggtg aaaagaaaaa ccaccccagt acattaaaaa cgtccgcaat    8547
gtgttattaa gttgtctaag cgtcaatttg tttacaccac aatatatcct gccaccagcc    8607
agccaacagc tccccgaccg gcagctcggc acaaaatcac cactcgatac aggcagccca    8667
tcagtccggg acggcgtcag cgggagagcc gttgtaaggc ggcagacttt gctcatgtta    8727
ccgatgctat tcggaagaac ggcaactaag ctgccgggtt tgaaacacgg atgatctcgc    8787
ggagggtagc atgttgattg taacgatgac agagcgttgc tgcctgtgat caaatatcat    8847
ctccctcgca gagatccgaa ttatcagcct tcttattcat ttctcgctta accgtgacag    8907
gctgtcgatc ttgagaacta tgccgacata ataggaaatc gctggataaa gccgctgagg    8967
aagctgagtg gcgctatttc tttagaagtg aacgttgacg atatcaactc ccctatccat    9027
tgctcaccga atggtacagg tcgggaccc gaagttccga ctgtcggcct gatgcatccc     9087
cggctgatcg accccagatc tggggctgag aaagcccagt aaggaaacaa ctgtaggttc    9147
gagtcgcgag atccccggga accaaaggaa gtaggttaaa cccgctccga tcaggccgag    9207
ccacgccagg ccgagaacat tggttcctgt aggcatcggg attggcggat caaacactaa    9267
agctactgga acgagcagaa gtcctccggc cgccagttgc caggcggtaa aggtgagcag    9327
aggcacggga ggttgccact tgcgggtcag cacggttccg aacgcatgg aaaccgcccc     9387
cgccaggccc gctgcgacgc cgacaggatc tagcgctgcg tttggtgtca acaccaacag    9447
```

```
cgccacgccc gcagttccgc aaatagcccc caggaccgcc atcaatcgta tcgggctacc    9507
tagcagagcg gcagagatga acacgaccat cagcggctgc acagcgccta ccgtcgccgc    9567
gaccccgccc ggcaggcggt agaccgaaat aaacaacaag ctccagaata gcgaaatatt    9627
aagtgcgccg aggatgaaga tgcgcatcca ccagattccc gttggaatct gtcggacgat    9687
catcacgagc aataaacccg ccggcaacgc ccgcagcagc ataccggcga ccctcggcc     9747 tcgctgttcg ggctccacga aaacgccgga cagatgcgcc ttgtgagcgt ccttggggcc    9807
gtcctcctgt ttgaagaccg acagcccaat gatctcgccg tcgatgtagg cgccgaatgc    9867
cacggcatct cgcaaccgtt cagcgaacgc ctccatgggc tttttctcct cgtgctcgta    9927
aacggacccg aacatctctg gagctttctt cagggccgac aatcggatct cgcggaaatc    9987
ctgcacgtcg gccgctccaa gccgtcgaat ctgagcctta atcacaattg tcaattttaa   10047
tcctctgttt atcggcagtt cgtagagcgc gccgtgcgtc ccgagcgata ctgagcgaag   10107
caagtgcgtc gagcagtgcc cgcttgttcc tgaaatgcca gtaaagcgct ggctgctgaa   10167
cccccagccg gaactgaccc cacaaggccc tagcgtttgc aatgcaccag gtcatcattg   10227
acccaggcgt gttccaccag gccgctgcct cgcaactctt cgcaggcttc gccgacctgc   10287
tcgcgccact tcttcacgcg ggtggaatcc gatccgcaca tgaggcggaa ggtttccagc   10347
ttgagcgggt acggctcccg gtgcgagctg aaatagtcga acatccgtcg ggccgtcggc   10407
gacagcttgc ggtacttctc ccatatgaat ttcgtgtagt ggtcgccagc aaacagcacg   10467
acgatttcct cgtcgatcag gacctggcaa cgggacgttt tcttgccacg gtccaggacg   10527
cggaagcggt gcagcagcga caccgattcc aggtgcccaa cgcggtcgga cgtgaagccc   10587
atcgccgtcg cctgtaggcg cgacaggcat tcctcggcct tcgtgtaata ccggccattg   10647
atcgaccagc ccaggtcctg gcaaagctcg tagaacgtga aggtgatcgg ctcgccgata   10707
ggggtgcgct tcgcgtactc caacacctgc tgccacacca gttcgtcatc gtcggcccgc   10767
agctcgacgc cggtgtaggt gatcttcacg tccttgttga cgtggaaaat gaccttgttt   10827
tgcagcgcct cgcgcgggat tttcttgttg cgcgtggtga acagggcaga gcgggccgtg   10887
tcgtttggca tcgctcgcat cgtgtccggc cacggcgcaa tatcgaacaa ggaaagctgc   10947
atttccttga tctgctgctt cgtgtgtttc agcaacgcgg cctgcttggc ctcgctgacc   11007
tgttttgcca ggtcctcgcc ggcggttttt cgcttcttgg tcgtcatagt tcctcgcgtg   11067
tcgatggtca tcgacttcgc caaacctgcc gcctcctgtt cgagacgacg cgaacgctcc   11127
acggcggcca tggcgcggg cagggcaggg ggagccagtt gcacgctgtc gcgctcgatc   11187
ttggccgtag cttgctggac catcgagccg acggactgga aggtttcgcg gggcgcacgc   11247
atgacggtgc ggcttgcgat ggtttcggca tcctcggcgg aaaaccccgc gtcgatcagt   11307
tcttgcctgt atgccttccg gtcaaacgtc cgattcattc accctccttg cgggattgcc   11367
ccgactcacg ccggggcaat gtgcccttat tcctgatttg acccgcctgg tgccttggtg   11427
tccagataat ccaccttatc ggcaatgaag tcggtcccgt agaccgtctg gccgtccttc   11487
tcgtacttgg tattccgaat cttgcccctgc acgaatacca gcgacccctt gcccaaatac   11547
ttgccgtggg cctcggcctg agagccaaaa cacttgatgc ggaagaagtc ggtgcgctcc   11607
tgcttgtcgc cggcatcgtt gcgccacatc taggtactaa acaattcat ccagtaaaat    11667 ataatatttt attttctccc aatcaggctt gatccccagt aagtcaaaaa atagctcgac   11727
atactgttct tccccgatat cctccctgat cgaccggacg cagaaggcaa tgtcatacca   11787
cttgtccgcc ctgccgcttc tcccaagatc aataaagcca cttactttgc catctttcac   11847
```

```
aaagatgttg ctgtctccca ggtcgccgtg ggaaaagaca agttcctctt cgggcttttc    11907
cgtctttaaa aaatcataca gctcgcgcgg atctttaaat ggagtgtctt cttcccagtt    11967
ttcgcaatcc acatcggcca gatcgttatt cagtaagtaa tccaattcgg ctaagcggct    12027
gtctaagcta ttcgtatagg gacaatccga tatgtcgatg gagtgaaaga gcctgatgca    12087
ctccgcatac agctcgataa tcttttcagg gctttgttca tcttcatact cttccgagca    12147
aaggacgcca tcggcctcac tcatgagcag attgctccag ccatcatgcc gttcaaagtg    12207
caggaccttt ggaacaggca gctttccttc cagccatagc atcatgtcct tttcccgttc    12267
cacatcatag gtggtccctt tataccggct gtccgtcatt tttaaatata ggttttcatt    12327
ttctcccacc agcttatata ccttagcagg agacattcct tccgtatctt ttacgcagcg    12387 gtattttcg atcagttttt tcaattccgg tgatattctc attttagcca tttattattt      12447
ccttcctctt ttctacagta tttaaagata ccccaagaag ctaattataa caagacgaac    12507
tccaattcac tgttccttgc attctaaaac cttaaatacc agaaaacagc ttttcaaag      12567 ttgttttcaa agttggcgta taacatagta tcgacggagc cgattttgaa accacaatta    12627
tgggtgatgc tgccaactta ctgatttagt gtatgatggt gttttgagg tgctccagtg      12687 gcttctgtgt ctatcagctg tccctcctgt tcagctactg acggggtggt gcgtaacggc    12747
aaaagcaccg ccggacatca gcgctatctc tgctctcact gccgtaaaac atggcaactg    12807
cagttcactt acaccgcttc tcaacccggt acgcaccaga aaatcattga tatggccatg    12867
aatggcgttg gatgccgggc aacagcccgc attatgggcg ttggcctcaa cacgatttta    12927
cgtcacttaa aaaactcagg ccgcagtcgg taacctcgcg catacagccg ggcagtgacg    12987
tcatcgtctg cgcggaaatg gacgaacagt ggggctatgt cggggctaaa tcgcgccagc    13047
gctggctgtt ttacgcgtat gacagtctcc ggaagacggt tgttgcgcac gtattcggtg    13107
aacgcactat ggcgacgctg gggcgtctta tgagcctgct gtcacccttt gacgtggtga    13167 tatgatgac ggatggctgg ccgctgtatg aatcccgcct gaagggaaag ctgcacgtaa      13227
tcagcaagcg atatacgcag cgaattgagc ggcataacct gaatctgagg cagcacctgg    13287
cacggctggg acggaagtcg ctgtcgttct caaaatcggt ggagctgcat gacaaagtca    13347
tcgggcatta tctgaacata aaacactatc aataagttgg agtcattacc caattatgat    13407
agaatttaca agctataagg ttattgtcct gggtttcaag cattagtcca tgcaagtttt    13467
tatgctttgc ccattctata gatatattga taagcgcgct gcctatgcct tgccccctga    13527
aatccttaca tacggcgata tcttctatat aaaagatata ttatcttatc agtattgtca    13587
atatattcaa ggcaatctgc ctcctcatcc tcttcatcct cttcgtcttg gtagcttttt    13647
aaatatggcg cttcatagag taattctgta aaggtccaat tctcgttttc atacctcggt    13707
ataatcttac ctatcacctc aaatggttcg ctgggtttat cgcaccccg aacacgagca      13767 cggcacccgc gaccactatg ccaagaatgc ccaaggtaaa aattgccggc cccgccatga    13827
agtccgtgaa tgccccgacg gccgaagtga agggcaggcc gccacccagg ccgccgccct    13887 cactgccccgg cacctggtcg ctgaatgtcg atgccagcac ctgcggcacg tcaatgcttc   13947
cgggcgtcgc gctcgggctg atcgcccatc ccgttactgc cccgatcccg gcaatggcaa    14007
ggactgccag cgctgccatt tttggggtga ggccgttcgc ggccgagggg cgcagcccct    14067 gggggggatgg gaggcccgcg ttagcgggcc gggagggttc gagaagggg gcacccccc      14127 ttcggcgtgc gcggtcacgc gcacagggcg cagccctggt taaaaacaag gtttataaat    14187
attggtttaa aagcaggtta aaagacaggt tagcggtggc cgaaaaacgg gcggaaaccc    14247
```

```
ttgcaaatgc tggatttttct gcctgtggac agcccctcaa atgtcaatag gtgcgccct    14307
catctgtcag cactctgccc ctcaagtgtc aaggatcgcg cccctcatct gtcagtagtc    14367
gcgcccctca agtgtcaata ccgcagggca cttatcccca ggcttgtcca catcatctgt    14427
gggaaactcg cgtaaaatca ggcgttttcg ccgatttgcg aggctggcca gctccacgtc    14487
gccggccgaa atcgagcctg cccctcatct gtcaacgccg cgccgggtga gtcggcccct    14547
caagtgtcaa cgtccgcccc tcatctgtca gtgagggcca agttttccgc gaggtatcca    14607
caacgccggc ggccgcggtg tctcgcacac ggcttcgacg gcgtttctgg cgcgtttgca    14667
gggccataga cggccgccag cccagcgcg agggcaacca gcccggtgag cgtcgcaaag    14727
gcgctcggtc ttgccttgct cgtcggtgat gtacttcacc agctccgcga agtcgctctt    14787
cttgatggag cgcatgggga cgtgcttggc aatcacgcgc accccccggc cgttttagcg    14847
gctaaaaaag tcatggctct gccctcgggc ggaccacgcc catcatgacc ttgccaagct    14907
cgtcctgctt ctcttcgatc ttcgccagca gggcgaggat cgtggcatca ccgaaccgcg    14967
ccgtgcgcgg gtcgtcggtg agccagagtt tcagcaggcc gcccaggcgg cccaggtcgc    15027
cattgatgcg ggccagctcg cggacgtgct catagtccac gacgcccgtg attttgtagc    15087
cctggccgac ggccagcagg taggccgaca ggctcatgcc ggccgccgcc gccttttcct    15147
caatcgctct tcgttcgtct ggaaggcagt acaccttgat aggtgggctg cccttcctgg    15207
ttggcttggt ttcatcagcc atccgcttgc cctcatctgt tacgccggcg gtagccggcc    15267
agcctcgcag agcaggattc ccgttgagca ccgccaggtg cgaataaggg acagtgaaga    15327
aggaacaccc gctcgcgggt gggcctactt cacctatcct gcccggctga cgccgttgga    15387
tacaccaagg aaagtctaca cgaacccttt ggcaaaatcc tgtatatcgt gcgaaaaagg    15447
atggatatac cgaaaaaatc gctataatga ccccgaagca gggttatgca gcggaaaagc    15507
gccacgcttc ccgaagggag aaaggcggac aggtatccgg taagcggcag ggtcggaaca    15567
ggagagcgca cgagggagct ccaggggga acgcctggt atctttatag tcctgtcggg    15627
tttcgccacc tctgacttga gcgtcgattt ttgtgatgct cgtcaggggg cggagccta    15687
tggaaaaacg ccagcaacgc ggcctttta cggttcctgg cctttgctg ccttttgct    15747
cacatgttct ttcctgcgtt atcccctgat tctgtggata accgtattac cgcctttgag    15807
tgagctgata ccgctcgccg cagccgaacg accgagcgca gcgagtcagt gagcgaggaa    15867
gcggaagagc gccagaaggc cgccagagag gccgagcgcg gccgtgaggc ttggacgcta    15927
gggcagggca tgaaaagcc cgtagcgggc tgctacgggc gtctgacgcg gtggaaaggg    15987
ggagggatg ttgtctacat ggctctgctg tagtgagtgg gttgcgctcc ggcagcggtc    16047
ctgatcaatc gtcacccttt ctcggtcctt caacgttcct gacaacgagc ctccttttcg    16107
ccaatccatc gacaatcacc gcgagtccct gctcgaacgc tgcgtccgga ccggcttcgt    16167
cgaaggcgtc tatcgcggcc cgcaacagcg gcgagagcgg agcctgttca acggtgccgc    16227
cgcgctcgcc ggcatcgctg tcgccggcct gctcctcaag cacggcccca acagtgaagt    16287
agctgattgt catcagcgca ttgacggcgt ccccggccaa aaacccgcc tcgcagagga    16347
agcgaagctg cgcgtcggcc gtttccatct gcggtgcgcc cggtcgcgtg ccggcatgga    16407
tgcgcgcgca atcgcggtag gcgagcagcg cctgcctgaa gctgcgggca ttcccgatca    16467
gaaatgagcg ccagtcgtcg tcggctctcg gcaccgaatg cgtatgattc tccgccagca    16527
tggcttcggc cagtgcgtcg agcagcgccc gcttgttcct gaagtgccag taaagccgcg    16587
gctgctgaac ccccaaccgt tccgccagtt tgcgtgtcgt cagaccgtct acgccgacct    16647
```

```
cgttcaacag gtccagggcg gcacggatca ctgtattcgg ctgcaacttt gtcatgcttg    16707
acactttatc actgataaac ataatatgtc caccaactta tcagtgataa agaatccgcg    16767
cgttcaatcg gaccagcgga ggctggtccg gaggccagac gtgaaaccca acatacccct    16827
gatcgtaatt ctgagcactg tcgcgctcga cgctgtcggc atcggcctga ttatgccggt    16887
gctgccgggc ctcctgcgcg atctggttca ctcgaacgac gtcaccgccc actatggcat    16947
tctgctggcg ctgtatgcgt tggtgcaatt tgcctgcgca cctgtgctgg gcgcgctgtc    17007
ggatcgtttc gggcggcggc caatcttgct cgtctcgctg gccggcgcca gatc          17061
```

<210> SEQ ID NO 35
<211> LENGTH: 290
<212> TYPE: PRT
<213> ORGANISM: Phaeodactylum tricornutum, Physcomitrella patens,
      Caenorhabditis elegans

<400> SEQUENCE: 35

```
Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290
```

<210> SEQ ID NO 36
<211> LENGTH: 282
<212> TYPE: PRT
<213> ORGANISM: Phaeodactylum tricornutum, Physcomitrella patens, Caenorhabditis elegans

<400> SEQUENCE: 36

```
Met Glu Asn Phe Trp Ser Ile Val Phe Leu Leu Ser Ile Leu
1               5                   10                  15

Phe Ile Leu Tyr Asn Ile Ser Thr Val Cys His Tyr Met Arg Ile
            20                  25                  30

Ser Phe Tyr Tyr Phe Thr Ile Leu Leu His Gly Met Glu Val Cys Val
        35                  40                  45

Thr Met Ile Pro Ser Trp Leu Asn Gly Lys Gly Ala Asp Tyr Val Phe
50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Val Ile Cys
                85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Ile Pro Val Val Phe Ser Asp Tyr Arg
        195                 200                 205

Asp Phe Tyr Ser Lys Pro Gly Arg Tyr Phe Lys Asn Asp Gly Glu Val
210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
        275                 280
```

<210> SEQ ID NO 37
<211> LENGTH: 477
<212> TYPE: PRT
<213> ORGANISM: Phaeodactylum tricornutum, Physcomitrella patens, Caenorhabditis elegans

<400> SEQUENCE: 37

```
Met Gly Lys Gly Gly Asp Ala Arg Ala Ser Lys Gly Ser Thr Ala Ala
1               5                   10                  15

Arg Lys Ile Ser Trp Gln Glu Val Lys Thr His Ala Ser Pro Glu Asp
            20                  25                  30

Ala Trp Ile Ile His Ser Asn Lys Val Tyr Asp Val Ser Asn Trp His
        35                  40                  45
```

-continued

Glu His Pro Gly Gly Ala Val Ile Phe Thr His Ala Gly Asp Asp Met
 50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Thr Thr Gly Lys Glu
                 85                  90                  95

Pro Gln Gln Ile Ala Phe Glu Lys Gly Tyr Arg Asp Leu Arg Ser Lys
                100                 105                 110

Leu Ile Met Met Gly Met Phe Lys Ser Asn Lys Trp Phe Tyr Val Tyr
            115                 120                 125

Lys Cys Leu Ser Asn Met Ala Ile Trp Ala Ala Cys Ala Leu Val
130                 135                 140

Phe Tyr Ser Asp Arg Phe Trp Val His Leu Ala Ser Ala Val Met Leu
145                 150                 155                 160

Gly Thr Phe Phe Gln Gln Ser Gly Trp Leu Ala His Asp Phe Leu His
                165                 170                 175

His Gln Val Phe Thr Lys Arg Lys His Gly Asp Leu Gly Gly Leu Phe
            180                 185                 190

Trp Gly Asn Leu Met Gln Gly Tyr Ser Val Gln Trp Lys Asn Lys
            195                 200                 205

His Asn Gly His His Ala Val Pro Asn Leu His Cys Ser Ser Ala Val
210                 215                 220

Ala Gln Asp Gly Asp Pro Asp Ile Asp Thr Met Pro Leu Leu Ala Trp
225                 230                 235                 240

Ser Val Gln Gln Ala Gln Ser Tyr Arg Glu Leu Gln Ala Asp Gly Lys
                245                 250                 255

Asp Ser Gly Leu Val Lys Phe Met Ile Arg Asn Gln Ser Tyr Phe Tyr
            260                 265                 270

Phe Pro Ile Leu Leu Leu Ala Arg Leu Ser Trp Leu Asn Glu Ser Phe
            275                 280                 285

Lys Cys Ala Phe Gly Leu Gly Ala Ser Glu Asn Ala Ala Leu Glu
            290                 295                 300

Leu Lys Ala Lys Gly Leu Gln Tyr Pro Leu Leu Glu Lys Ala Gly Ile
305                 310                 315                 320

Leu Leu His Tyr Ala Trp Met Leu Thr Val Ser Ser Gly Phe Gly Arg
            325                 330                 335

Phe Ser Phe Ala Tyr Thr Ala Phe Tyr Phe Leu Thr Ala Thr Ala Ser
            340                 345                 350

Cys Gly Phe Leu Leu Ala Ile Val Phe Gly Leu Gly His Asn Gly Met
            355                 360                 365

Ala Thr Tyr Asn Ala Asp Ala Arg Pro Asp Phe Trp Lys Leu Gln Val
            370                 375                 380

Thr Thr Thr Arg Asn Val Thr Gly Gly His Gly Phe Pro Gln Ala Phe
385                 390                 395                 400

Val Asp Trp Phe Cys Gly Gly Leu Gln Tyr Gln Val Asp His His Leu
            405                 410                 415

Phe Pro Ser Leu Pro Arg His Asn Leu Ala Lys Thr His Ala Leu Val
            420                 425                 430

Glu Ser Phe Cys Lys Glu Trp Gly Val Gln Tyr His Glu Ala Asp Leu
            435                 440                 445

Val Asp Gly Thr Met Glu Val Leu His His Leu Gly Ser Val Ala Gly
450                 455                 460

Glu Phe Val Val Asp Phe Val Arg Asp Gly Pro Ala Met

<210> SEQ ID NO 38
<211> LENGTH: 47
<212> TYPE: DNA
<213> ORGANISM: artificial sequence
<220> FEATURE:
<221> NAME/KEY: misc_feature
<222> LOCATION: (1)..(47)
<223> OTHER INFORMATION: synthetic oligonucleotide

<400> SEQUENCE: 38
ccggaattcg gcgcgccgag ctcctcgagc aaatttacac attgcca      47

<210> SEQ ID NO 39
<211> LENGTH: 47
<212> TYPE: DNA
<213> ORGANISM: artificial sequence
<220> FEATURE:
<221> NAME/KEY: misc_feature
<222> LOCATION: (1)..(47)
<223> OTHER INFORMATION: synthetic oligonucleotide

<400> SEQUENCE: 39
ccggaattcg gcgcgccgag ctcctcgagc aaatttacac attgcca      47

<210> SEQ ID NO 40
<211> LENGTH: 47
<212> TYPE: DNA
<213> ORGANISM: artificial sequence
<220> FEATURE:
<221> NAME/KEY: misc_feature
<222> LOCATION: (1)..(47)
<223> OTHER INFORMATION: synthetic oligonucleotide

<400> SEQUENCE: 40
ccggaattcg gcgcgccgag ctcctcgagc aaatttacac attgcca      47

<210> SEQ ID NO 41
<211> LENGTH: 48
<212> TYPE: DNA
<213> ORGANISM: artificial sequence
<220> FEATURE:
<221> NAME/KEY: misc_feature
<222> LOCATION: (1)..(48)
<223> OTHER INFORMATION: synthetic oligonucleotide

<400> SEQUENCE: 41
aaaactgcag gcggccgccc accgcggtgg gctggctatg aagaaatt     48

<210> SEQ ID NO 42
<211> LENGTH: 27
<212> TYPE: DNA
<213> ORGANISM: artificial sequence
<220> FEATURE:
<221> NAME/KEY: misc_feature
<222> LOCATION: (1)..(27)
<223> OTHER INFORMATION: synthetic oligonucleotide

<400> SEQUENCE: 42
cgcggatccg ctggctatga agaaatt      27

<210> SEQ ID NO 43
<211> LENGTH: 45
<212> TYPE: DNA
<213> ORGANISM: artificial sequence
<220> FEATURE:
<221> NAME/KEY: misc_feature
<222> LOCATION: (1)..(45)

```
<223> OTHER INFORMATION: synthetic oligonucleotide

<400> SEQUENCE: 43
tcccccggga tcgatgccgg cagatctgct ggctatgaag aaatt            45

<210> SEQ ID NO 44
<211> LENGTH: 40
<212> TYPE: DNA
<213> ORGANISM: artificial sequence
<220> FEATURE:
<221> NAME/KEY: misc_feature
<222> LOCATION: (1)..(40)
<223> OTHER INFORMATION: synthetic oligonucleotide

<400> SEQUENCE: 44
aaaactgcag tctagaaggc ctcctgcttt aatgagatat                  40

<210> SEQ ID NO 45
<211> LENGTH: 51
<212> TYPE: DNA
<213> ORGANISM: artificial sequence
<220> FEATURE:
<221> NAME/KEY: misc_feature
<222> LOCATION: (1)..(51)
<223> OTHER INFORMATION: synthetic oligonucleotide

<400> SEQUENCE: 45
cgcggatccg atatcgggcc cgctagcgtt aaccctgctt taatgagata t     51

<210> SEQ ID NO 46
<211> LENGTH: 33
<212> TYPE: DNA
<213> ORGANISM: artificial sequence
<220> FEATURE:
<221> NAME/KEY: misc_feature
<222> LOCATION: (1)..(33)
<223> OTHER INFORMATION: synthetic oligonucleotide

<400> SEQUENCE: 46
tcccccgggc catggcctgc tttaatgaga tat                         33

<210> SEQ ID NO 47
<211> LENGTH: 53
<212> TYPE: DNA
<213> ORGANISM: artificial sequence
<220> FEATURE:
<221> NAME/KEY: misc_feature
<222> LOCATION: (1)..(53)
<223> OTHER INFORMATION: synthetic oligonucleotide

<400> SEQUENCE: 47
cccaagcttg gcgcgccgag ctcgaattcg tcgacggaca atcagtaaat tga   53

<210> SEQ ID NO 48
<211> LENGTH: 53
<212> TYPE: DNA
<213> ORGANISM: artificial sequence
<220> FEATURE:
<221> NAME/KEY: misc_feature
<222> LOCATION: (1)..(53)
<223> OTHER INFORMATION: synthetic oligonucleotide

<400> SEQUENCE: 48
cccaagcttg gcgcgccgag ctcgaattcg tcgacggaca atcagtaaat tga   53

<210> SEQ ID NO 49
<211> LENGTH: 47
<212> TYPE: DNA
```

```
<213> ORGANISM: artificial sequence
<220> FEATURE:
<221> NAME/KEY: misc_feature
<222> LOCATION: (1)..(47)
<223> OTHER INFORMATION: synthetic oligonucleotide

<400> SEQUENCE: 49
cccaagcttg gcgcgccgag ctcgtcgacg gacaatcagt aaattga            47

<210> SEQ ID NO 50
<211> LENGTH: 29
<212> TYPE: DNA
<213> ORGANISM: artificial sequence
<220> FEATURE:
<221> NAME/KEY: misc_feature
<222> LOCATION: (1)..(29)
<223> OTHER INFORMATION: synthetic oligonucleotide

<400> SEQUENCE: 50
acataatgga gaacttctgg tcgatcgtc                                29

<210> SEQ ID NO 51
<211> LENGTH: 24
<212> TYPE: DNA
<213> ORGANISM: artificial sequence
<220> FEATURE:
<221> NAME/KEY: misc_feature
<222> LOCATION: (1)..(24)
<223> OTHER INFORMATION: synthetic oligonucleotide

<400> SEQUENCE: 51
ttactcagat ttcttcccgt cttt                                     24

<210> SEQ ID NO 52
<211> LENGTH: 26
<212> TYPE: DNA
<213> ORGANISM: artificial sequence
<220> FEATURE:
<221> NAME/KEY: misc_feature
<222> LOCATION: (1)..(26)
<223> OTHER INFORMATION: synthetic oligonucleotide

<400> SEQUENCE: 52
acataatgac cttcctagcc atatta                                   26

<210> SEQ ID NO 53
<211> LENGTH: 24
<212> TYPE: DNA
<213> ORGANISM: artificial sequence
<220> FEATURE:
<221> NAME/KEY: misc_feature
<222> LOCATION: (1)..(24)
<223> OTHER INFORMATION: synthetic oligonucleotide

<400> SEQUENCE: 53
tcagatattc aaattggcgg cttc                                     24

<210> SEQ ID NO 54
<211> LENGTH: 32
<212> TYPE: DNA
<213> ORGANISM: artificial sequence
<220> FEATURE:
<221> NAME/KEY: misc_feature
<222> LOCATION: (1)..(32)
<223> OTHER INFORMATION: synthetic oligonucleotide

<400> SEQUENCE: 54
ttaagcgcgg ccgcatggag aacttctggt cg                            32
```

<210> SEQ ID NO 55
<211> LENGTH: 31
<212> TYPE: DNA
<213> ORGANISM: artificial sequence
<220> FEATURE:
<221> NAME/KEY: misc_feature
<222> LOCATION: (1)..(31)
<223> OTHER INFORMATION: synthetic oligonucleotide

<400> SEQUENCE: 55
acctcggcgg ccgccctttt actcagattt c                                    31

<210> SEQ ID NO 56
<211> LENGTH: 41
<212> TYPE: DNA
<213> ORGANISM: artificial sequence
<220> FEATURE:
<221> NAME/KEY: misc_feature
<222> LOCATION: (1)..(41)
<223> OTHER INFORMATION: synthetic oligonucleotide

<400> SEQUENCE: 56
acataatgga gaacttctgg tctattgttg tgttttttct a                         41

<210> SEQ ID NO 57
<211> LENGTH: 41
<212> TYPE: DNA
<213> ORGANISM: artificial sequence
<220> FEATURE:
<221> NAME/KEY: misc_feature
<222> LOCATION: (1)..(41)
<223> OTHER INFORMATION: synthetic oligonucleotide

<400> SEQUENCE: 57
ctagctagct tactcagatt tcttcccgtc ttttgtttct c                         41

<210> SEQ ID NO 58
<211> LENGTH: 285
<212> TYPE: PRT
<213> ORGANISM: Mus musculus

<400> SEQUENCE: 58

Met Glu Leu Trp Pro Gly Ala Trp Thr Ala Leu Leu Leu Leu Leu
1               5                   10                  15

Leu Leu Leu Ser Thr Leu Trp Phe Cys Ser Ser Ala Lys Tyr Phe
                20                  25                  30

Phe Lys Met Ala Phe Tyr Asn Gly Trp Ile Leu Phe Leu Ala Ile Leu
            35                  40                  45

Ala Ile Pro Val Cys Ala Val Arg Gly Arg Asn Val Glu Asn Met Lys
        50                  55                  60

Ile Leu Arg Leu Leu Leu His Ala Lys Tyr Leu Tyr Gly Ile Arg
65                  70                  75                  80

Val Glu Val Arg Gly Ala His His Phe Pro Pro Thr Gln Pro Tyr Val
                85                  90                  95

Val Val Ser Asn His Gln Ser Ser Leu Asp Leu Leu Gly Met Met Glu
            100                 105                 110

Val Leu Pro Asp Arg Cys Val Pro Ile Ala Lys Arg Glu Leu Leu Trp
        115                 120                 125

Ala Gly Ser Ala Gly Leu Ala Cys Trp Leu Ala Gly Ile Ile Phe Ile
    130                 135                 140

Asp Arg Lys Arg Thr Gly Asp Ala Ile Ser Val Met Ser Glu Val Ala
145                 150                 155                 160

```
Gln Thr Leu Leu Thr Gln Asp Val Arg Val Trp Val Phe Pro Glu Gly
                165                 170                 175

Thr Arg Asn His Asn Gly Ser Met Leu Pro Phe Lys Arg Gly Ala Phe
            180                 185                 190

His Leu Ala Val Gln Ala Gln Val Pro Ile Ile Pro Ile Val Met Ser
        195                 200                 205

Ser Tyr Gln Asp Phe Tyr Ser Lys Lys Glu Arg Arg Phe Thr Ser Pro
    210                 215                 220

Gly Arg Cys Gln Val Arg Val Leu Pro Pro Val Ser Thr Glu Gly Leu
225                 230                 235                 240

Thr Pro Asp Asp Val Pro Ala Leu Ala Asp Ser Val Arg His Ser Met
                245                 250                 255

Leu Thr Ile Phe Arg Glu Ile Ser Thr Asp Gly Leu Gly Gly Gly Asp
            260                 265                 270

Cys Leu Lys Lys Pro Gly Gly Ala Gly Glu Ala Arg Leu
        275                 280                 285

<210> SEQ ID NO 59
<211> LENGTH: 262
<212> TYPE: PRT
<213> ORGANISM: Caenorhabditis elegans

<400> SEQUENCE: 59

Met Thr Phe Leu Ala Ile Leu Phe Val Ile Ala Val Leu Leu Leu Leu
1               5                   10                  15

Ala Gln Leu Pro Val Ile Gly Phe Tyr Ile Arg Ala Val Tyr Phe Gly
                20                  25                  30

Met Cys Leu Ile Ile Gly Gly Phe Leu Gly Gly Leu Ala Ser Ile Pro
            35                  40                  45

Phe Gly Lys Ser Pro Asn Asn His Phe Arg Met Phe Lys Ile Phe Gln
    50                  55                  60

Ala Met Thr Trp Pro Met Gly Val Arg Phe Glu Leu Arg Asn Ser Glu
65                  70                  75                  80

Ile Leu His Asp Lys Lys Pro Tyr Ile Ile Ala Asn His Gln Ser
                85                  90                  95

Ala Leu Asp Val Leu Gly Met Ser Phe Ala Trp Pro Val Asp Cys Val
            100                 105                 110

Val Met Leu Lys Ser Ser Leu Lys Tyr Leu Pro Gly Phe Asn Leu Cys
        115                 120                 125

Ala Tyr Leu Cys Asp Ser Val Tyr Ile Asn Arg Phe Ser Lys Glu Lys
    130                 135                 140

Ala Leu Lys Thr Val Asp Thr Thr Leu His Glu Ile Val Thr Lys Lys
145                 150                 155                 160

Arg Lys Val Trp Ile Tyr Pro Glu Gly Thr Arg Asn Ala Glu Pro Glu
                165                 170                 175

Leu Leu Pro Phe Lys Lys Gly Ala Phe Ile Leu Ala Lys Gln Ala Lys
            180                 185                 190

Ile Pro Ile Val Pro Cys Val Phe Ser Ser His Lys Phe Phe Tyr Ser
        195                 200                 205

His Ala Glu Lys Arg Leu Thr Ser Gly Asn Cys Ile Ile Asp Ile Leu
    210                 215                 220

Pro Glu Val Asp Ser Ser Lys Phe Asp Ser Ile Asp Asp Leu Ser Ala
225                 230                 235                 240
```

-continued

```
His Cys Arg Lys Ile Met Gln Ala His Arg Glu Lys Leu Asp Ala Glu
                245                 250                 255
Ala Ala Asn Leu Asn Ile
            260
```